(12) United States Patent
Hackel et al.

(10) Patent No.: US 10,787,499 B2
(45) Date of Patent: Sep. 29, 2020

(54) EPCAM TARGETED POLYPEPTIDES, CONJUGATES THEREOF, AND METHODS OF USE THEREOF

(71) Applicant: REGENTS OF THE UNIVERSITY OF MINNESOTA, Minneapolis, MN (US)

(72) Inventors: Benjamin Hackel, Minneapolis, MN (US); Carston R. Wagner, Minneapolis, MN (US); Lawrence A. Stern, Minneapolis, MN (US); Clifford Csizmar, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

(21) Appl. No.: 15/895,834

(22) Filed: Feb. 13, 2018

(65) Prior Publication Data

US 2018/0251524 A1    Sep. 6, 2018

Related U.S. Application Data

(60) Provisional application No. 62/458,432, filed on Feb. 13, 2017.

(51) Int. Cl.
| | |
|---|---|
| *A61K 38/00* | (2006.01) |
| *C07K 14/78* | (2006.01) |
| *A61K 51/08* | (2006.01) |
| *A61K 47/64* | (2017.01) |
| *A61K 49/00* | (2006.01) |

(52) U.S. Cl.
CPC .......... *C07K 14/78* (2013.01); *A61K 47/6435* (2017.08); *A61K 49/0056* (2013.01); *A61K 51/08* (2013.01); *A61K 51/088* (2013.01); *C07K 2319/735* (2013.01)

(58) Field of Classification Search
None
See application file for complete search history.

(56) References Cited

U.S. PATENT DOCUMENTS

| 9,206,237 B2 | 12/2015 | Kimura et al. |
| 9,433,689 B2 | 9/2016 | Hackel et al. |
| 2005/0084913 A1 | 4/2005 | Punnonen et al. |
| 2007/0122406 A1 | 5/2007 | Chamberlain et al. |
| 2013/0079280 A1* | 3/2013 | Baca .................... C07K 14/001 514/9.3 |

FOREIGN PATENT DOCUMENTS

| EP | 2541249 A1 | 1/2013 |
| WO | 2013131001 A1 | 9/2013 |

OTHER PUBLICATIONS

Andersson, et al., "Phase I trial of EpCAM-targeting immunotoxin MOC31PE, alone and in combination with cyclosporin", Br J Cancer 113(11), 1548-1555 (2015).

Arcangeli, et al., "Balance of Anti-CD123 Chimeric Antigen Receptor Binding Affinity and Density for the Targeting of Acute Myeloid Leukemia.", Mol Ther 25(8), 1933-1945 (2017).
Carlson, et al., "Chemically controlled self-assembly of protein nanorings", J Am Chem Soc 128 (23), 7630-7638 (2006).
Caruso, et al., "Tuning Sensitivity of Car to EGFR Density Limits Recognition of Normal Tissue While Maintaining Potent Antitumor Activity.", Cancer Res 75, 3305-3518 (2015).
clinicaltrials.gov, https://clinicaltrials.gov/ct2/results?term=epcam &Search=Search, 4 pages, page last reviewed Jan. 2018.
Csizmar, et al., "Engineering Reversible Cell-Cell Interactions with Lipid Anchored Prosthetic Receptors", Bioconjug Chem 29(4), 1291-1301 (2018).
Drent, et al., "A Rational Strategy for Reducing On-Target Off-Tumor Effects of CD38-Chimeric Antigen Receptors by Affinity Optimization.", Mol Ther 25(8), 1946-1958 (2017).
Eder, et al., "68Ga-labelled recombinant antibody variants for immuno-PET imaging of solid tumours.", Eur J Nucl Med Mol Imaging 37(7), 1397-1407 (2010).
Gabrielse, et al., "Reversible re-programing of cell-cell interactions.", Angew Chem Int Ed 53(20), 5112-5116 (2014).
Goldberg, et al., "Engineering a targeted delivery platform using Centyrins.", Protein Eng Des Sel 29(12), 563-572 (2016).
Hackel, et al., "Designed hydrophilic and charge mutations of the fibronectin domain: towards tailored protein biodistribution.", Protein Engineering, Design & Selection 25(10), 639-647 (2012).
Hackel, et al., "Use of 64Cu-labeled Fibronectin Domain with EGFROverexpressing Tumor Xenograft: Molecular Imaging1.", Radiology 263(1), 179-188 (2012).
Iwasaki, et al., "A Fluorescent Imaging Probe Based on a Macrocyclic Scaffold That Binds to Cellular EpCAM.", J Mol Evol 81(5-6), 210-217 (2015).
Lim, et al., "Stable, high-affinity streptavidin monomer for protein labeling and monovalent biotin detection.", Biotechnol Bioeng 110(1), 57-67 (2013).
Liu, et al., "Affinity-Tuned ErbB2 or EGFR Chimeric Antigen Receptor T Cells Exhibit an Increased Therapeutic Index against Tumors in Mice.", Cancer Res 75, 3596-3607 (2015).
Martin-Killias, et al., "A Novel Fusion Toxin Derived from an EpCAM-Specific Designed Ankyrin Repeat Protein Has Potent Antitumor Activity", Clin Cancer Res 17(1), 100-110 (2011).
Natarajan, "A Novel Engineered Anti-CD20 Tracer Enables Early Time PET Imaging in a Humanized Transgenic Mouse Model of B-cell Non-Hodgkins Lymphoma.", Clinical Cancer Res 19(24), 6820-6829 (2013).

(Continued)

*Primary Examiner* — Thomas S Heard
(74) *Attorney, Agent, or Firm* — Viksnins Harris Padys Malen LLP

(57) ABSTRACT

Certain embodiments of the invention provide epithelial cell adhesion molecule (EpCAM) binding polypeptides, as well as conjugates and CSANs comprising such polypeptides. Additionally, certain embodiments of the invention also provide methods of using such polypeptides and compounds for molecular imaging and molecularly targeted therapies.

27 Claims, 34 Drawing Sheets
(28 of 34 Drawing Sheet(s) Filed in Color)
Specification includes a Sequence Listing.

(56) References Cited

OTHER PUBLICATIONS

Shah, et al., "In Vivo Evaluation of Site-Specifically PEGylated Chemically Self-Assembled Protein Nanostructures.", Mol Pharmaceutics 13(7), 2193-2203 (2016).
Shen, et al., "Prosthetic Antigen Receptors.", J Am Chem Soc 137, 10108-10111 (2015).
Stefan, et al., "DARPins recognizing the tumor-associated antigen EpCAM selected by phage and ribosome display and engineered for multivalency.", J Mol Biol 413(4), 826-843 (2011).
Stern, et al., "Titratable Avidity Reduction Enhances Affinity Discrimination in Mammalian Cellular Selections of Yeast-Displayed Ligands.", ACS Combinatorial Science 19(5), 315-323 (2017).
Van Driel, et al., "EpCAM as multi-tumour target for near-infrared fluorescence guided surgery", BMC Cancer 16, 884 (2016).
Went, et al., "Frequent EpCam protein expression in human carcinomas.", Hum Pathol 35(1), 122-128 (2004).
Zielonka, et al., "Shark Attack: high affinity binding proteins derived from shark vNAR domains by stepwise in vitro affinity maturation.", J Biotechnol 191(10), 236-245 (2014).

* cited by examiner

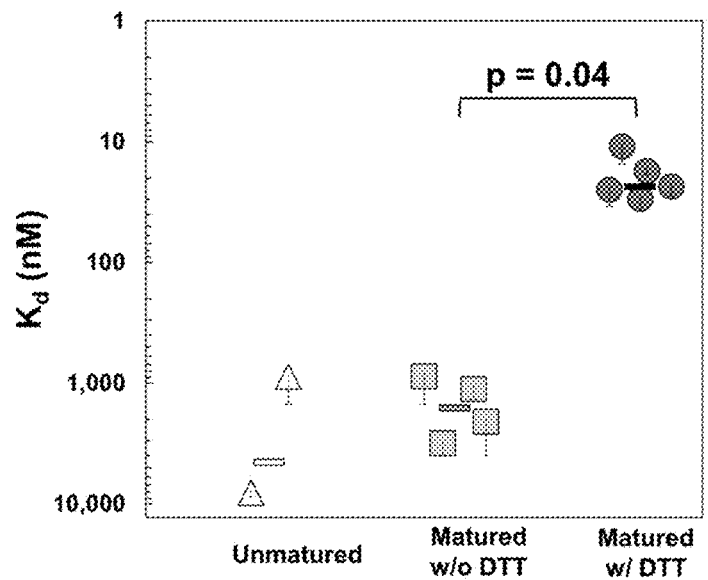
FIGURE 1D
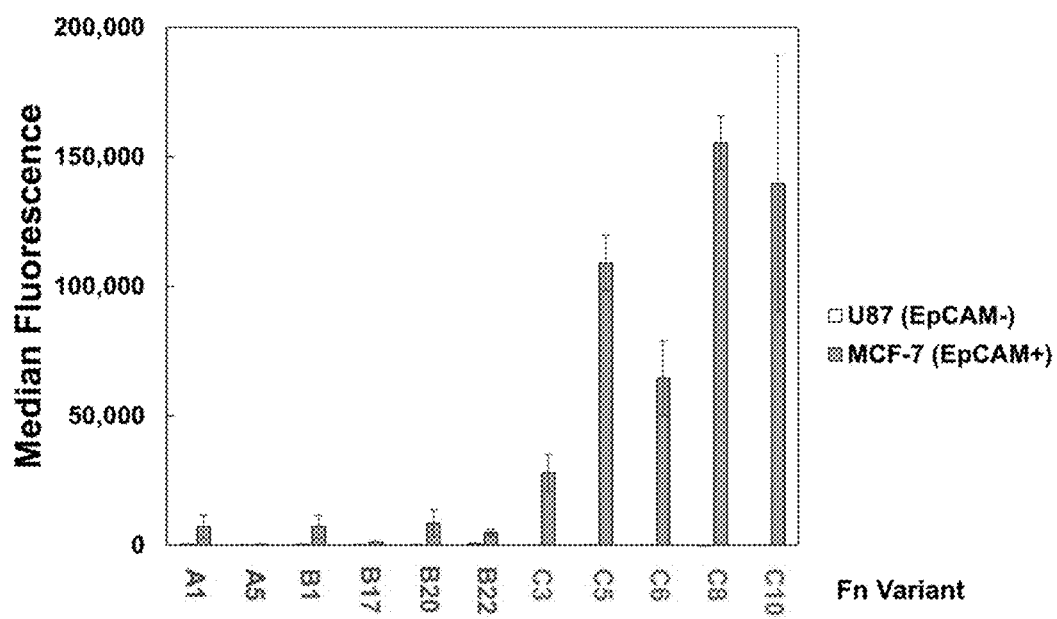

FIGURE 2

| Sequence Designation | 1  SSDSPRNLEVTNATPNSLTISW | 21  DYPNSASY | 32  VRITYGETGGNS | 41 | 51  PSQRFTVPGNTYM | 61  ATISGLKPGQDYTITVIAVT | 71 | 87  YRDNYSYSN | 91  PISINYRTEIDKPSQ | K_d (nM) |
|---|---|---|---|---|---|---|---|---|---|---|
| Consensus | SSDSPRNLEVTNATPNSLTISW | DYPNSASY | VRITYGETGGNS | | PSQRFTVPGNTYM | ATISGLKPGQDYTITVIAVT | | YRDNYSYSN | PISINYRTEIDKPSQ | |
| A1 | . . . . . . . . . . . . . . . . . . . . . | . . . . . . . . | . . . . . . . . . . . . | | . . . . . . . . . . . . . | . . . . . . . . . . R . D . . . . . . . | | . . . . S . . . . | . . . . . . . . . . . . . . . | 880±600 |
| A5 | . . . . . . . . . . . . . . . . . . . . . | . . . . . . . . | . . . . . . . . . . . . | | . . . . . . . . . . . . . | . . . . . . . . . . . . . . . . . . . . | | . . . . . W . . . | . . . . . . . . . . . . . . . | 8,100±700 |
| B1 | . . . . . . . . . . . . . . . . . . . . . | . . D Y T . . . | . . . . . . . . . . . . | | . . . . . . . . . . . . . | . . . . . . . . . . . . T . . . . . . . | | . . . . S . . . . | . . . . . . . . . . . . . . . | 880±600 |
| B17 | . . . . . . . . . . . . . . . . . . . . . | . . . . . . . . | . . . . . . T . . . . . | | . . . . . . . . . . . . . | . . . . . . . V . . R . . . . . . . . . | | . . . . S . L . . | . . . . . . . . . . . . . . . | 3,100±800 |
| B20 | . . . . . . . . . . . . . . . . . . . . . | . . N S . Y . . | . . . . . . . . . . . . | | . . . . . . . . . . . . . | . . . . . . . . . . . . . . . . . . . . | | . . . . S . L . . | . . . . . . . . . . . . . . . | 2,100±2,000 |
| B22 | . . . . . . . . . . . . . . . . . . . . . | . . . . . . . . | . . . . . . . . . . . . | | . . . . . . . . . . . . . | . . . . . . . . . . . E . . . . . . . . | | . . . . . . . . . | . . . . . . . . . . . . . . . | 1,100±200 |
| C3 | . . . . . . . . . . . . . . . . . . . . . | . . . . . . . . | . . . . . . . . . . . . | | . . . . . . . . . . . . . | . . . . . . . . . . . . . . . . . . . . | | . . . . S . L . . | . . . . . . . . . . . . . . . | 24±5 |
| C5 | . . . . . . . . S . . . . . . . . . . . . | . . . . . . . . | . . . . . . . . . . . . | | . . . . . L . S . . . . . | . . . . . . . . . . . . . . . . . . . . | | . . . . . . L . . | . . . S . . . . . . . . . . . | 17±1 |
| C6 | . . . . . . . . . . . . . . . . . . . . . | . . . . . . . . | . . . . . . . . . . . . | | . . . . . . . D . . . . . | . . . . . . . . . . . . . . . . . . . . | | . . . . . . SV . . | . . . V . . . . . . . . . . . | 30±8 |
| C8 | . . . . . . . . . . . . . . . . . . . . . | . . D . D F . . | . . . . . . . . . . . . | | . . . . . . . . . . . . . | . . . . . . . . . . . . . . . . . . . . | | . . . . . . L . . | . . . . . . . . . . . . . . . | 11±4 |
| C10 | . . . . . . . . . . . . . . . . . . . . . | . . . . . . . . | . . . . . . . . . . . . | | . . . . . . . S . . . . . | . . . . . . . . . . R . H T . . . . . . | | . . . . . . . . . | . . . . . . . . . . . . . . . | 25±9 |

FIGURE 7
```
Fn 3.4.5   SPRNLEVTNATPNSLTISWDNSNYASY--YRITYGETGGNSPSQELTVPGSTYNATISGLKPGQDYIITVYAV--TYRD
           +P+NL V+  T +S  +SWD+  +A Y  + I Y E+     +  LTVPGS  +  ++GLKPG +Y +++Y V    Y+D
Centyrin   APKNLVVSEVTEDSARLSWDDP-WAFYESFLIQYQESEKVGEAIVLTVPGSERSYDLTGLKPGTEYTVSIYGVHNVYKD
```
FIGURE 8
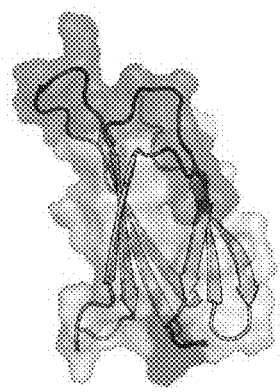
FIGURE 9
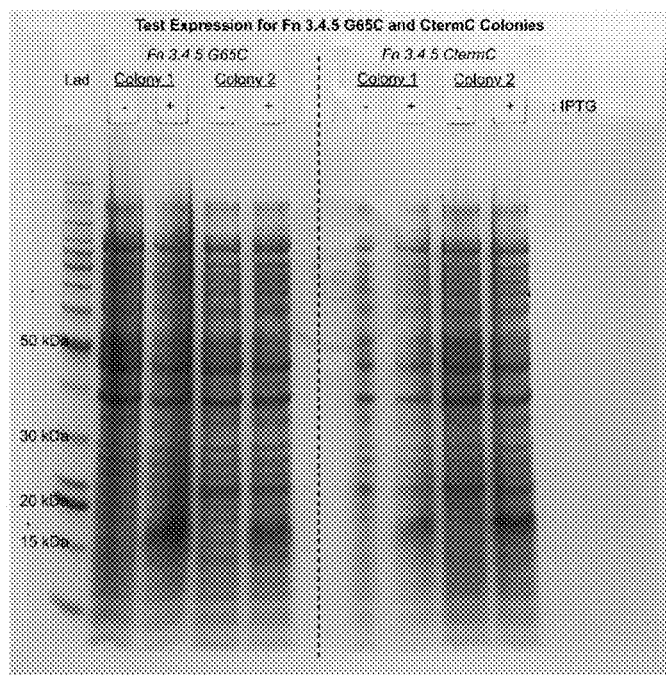

| Compound | MW | mg/mL | Molarity | Eq. | nmol | Amount | Phase |
|---|---|---|---|---|---|---|---|
| Fibronectin (clone: Fn_NT) | 12,050 | 0.308 | 25.5 | 1 | 40.8 | 1.6 mL | L |
| Tris(2-carboxyethyl)-phosphine HCl (TCEP) | 286.65 | 10 | 35 mM | 100 | 4,080 | 120 µL | L |
| NODAGA-maleimide | 497.21 | 10 | 20 mM | 100 | 4,080 | 205 µL | L |

FIGURE 17
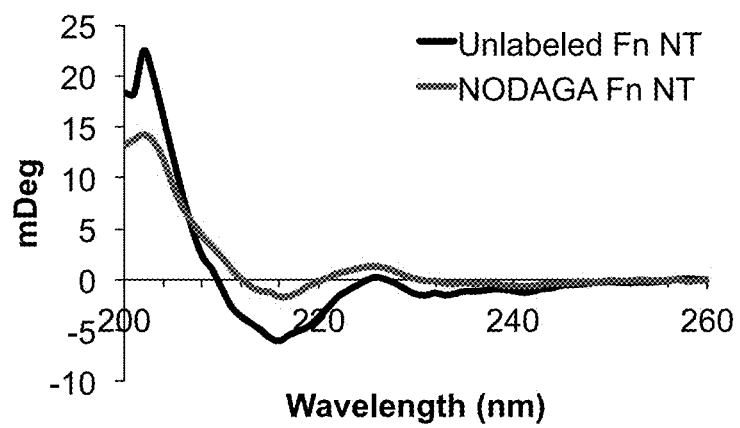
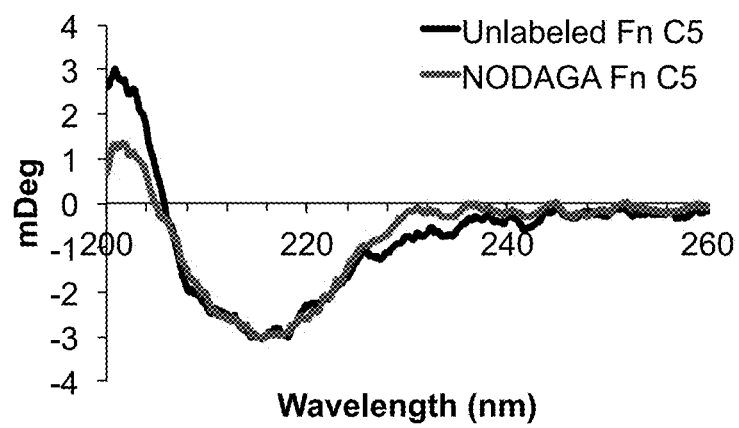

FIGURE 22
FIGURE 23
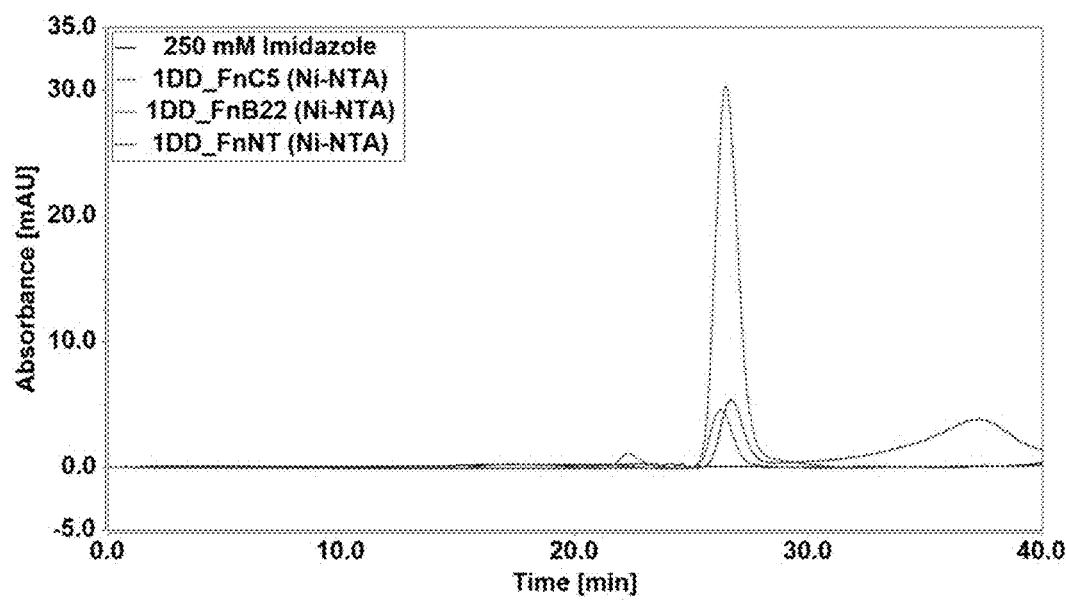
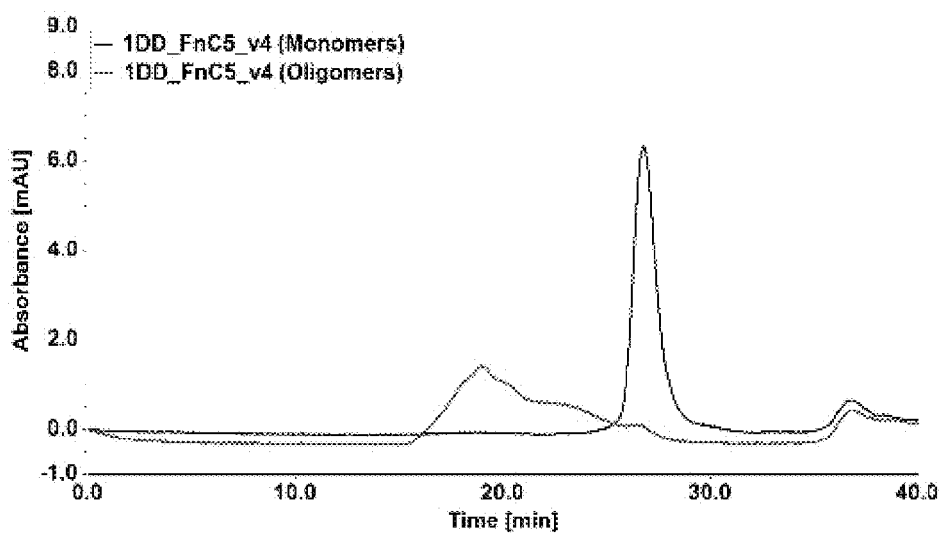

FIGURE 24
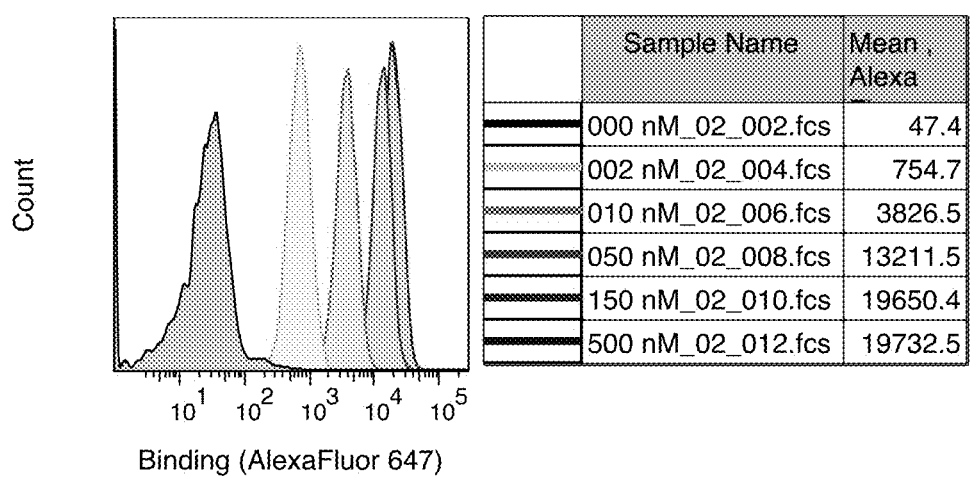
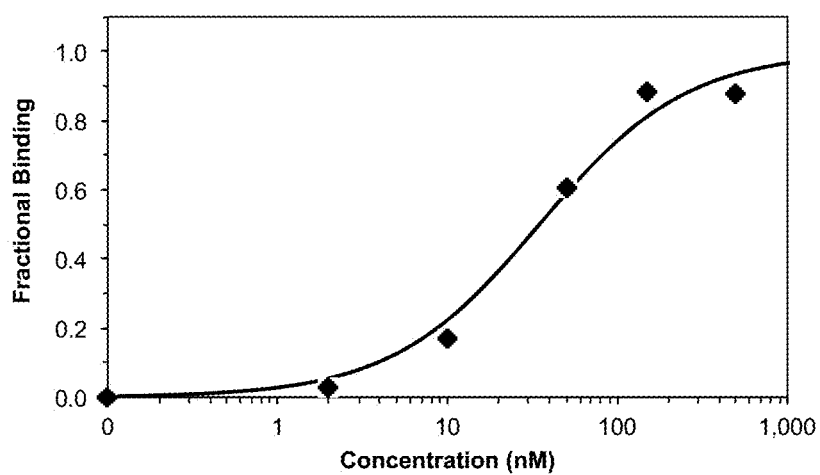

FIGURES 29A-C
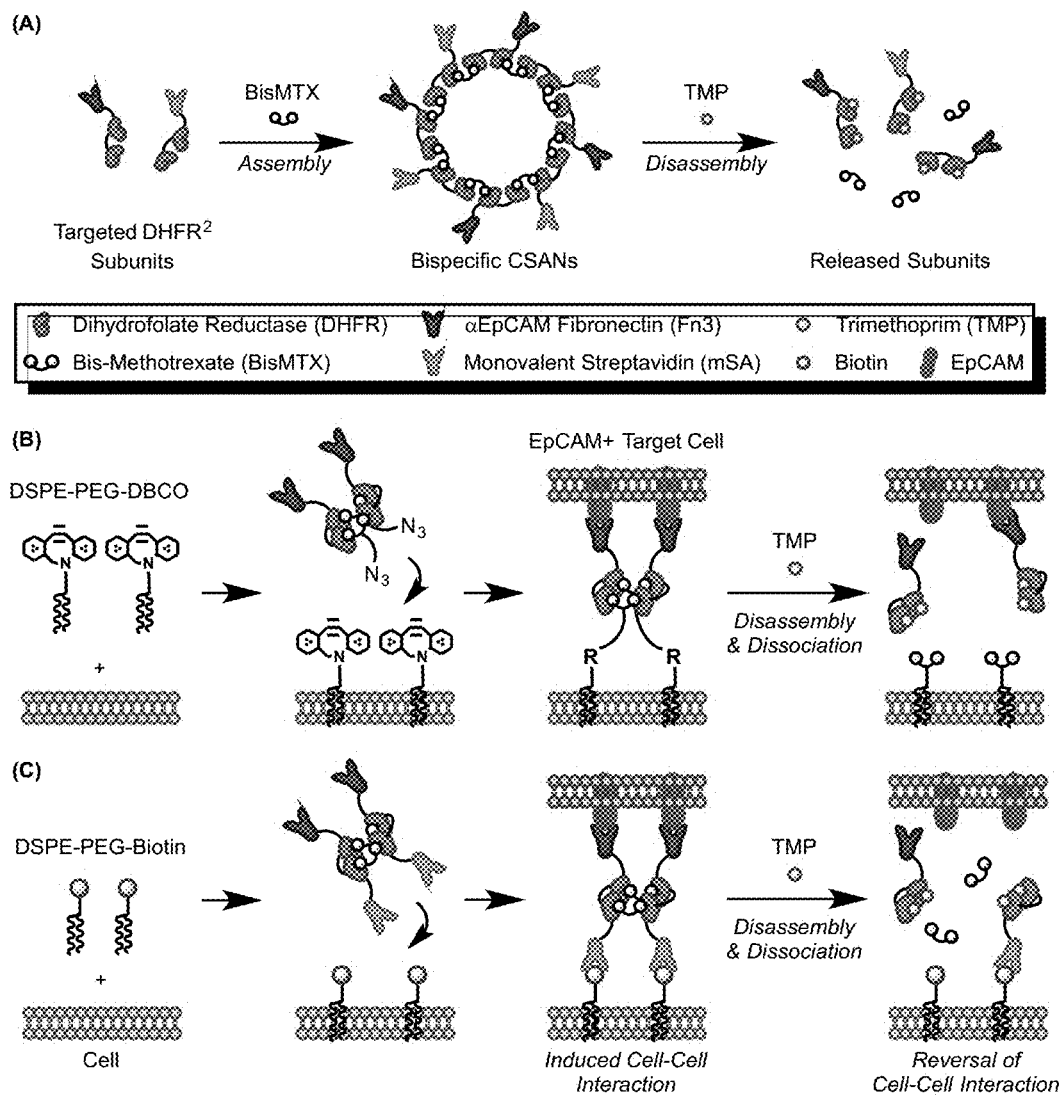

FIGURES 30A-H
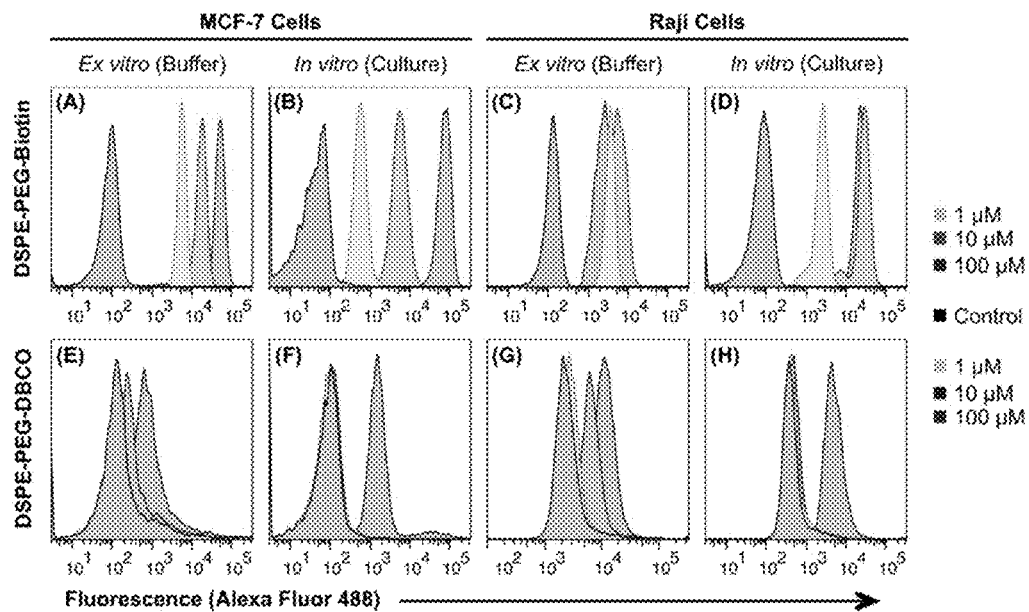
FIGURES 31A-D
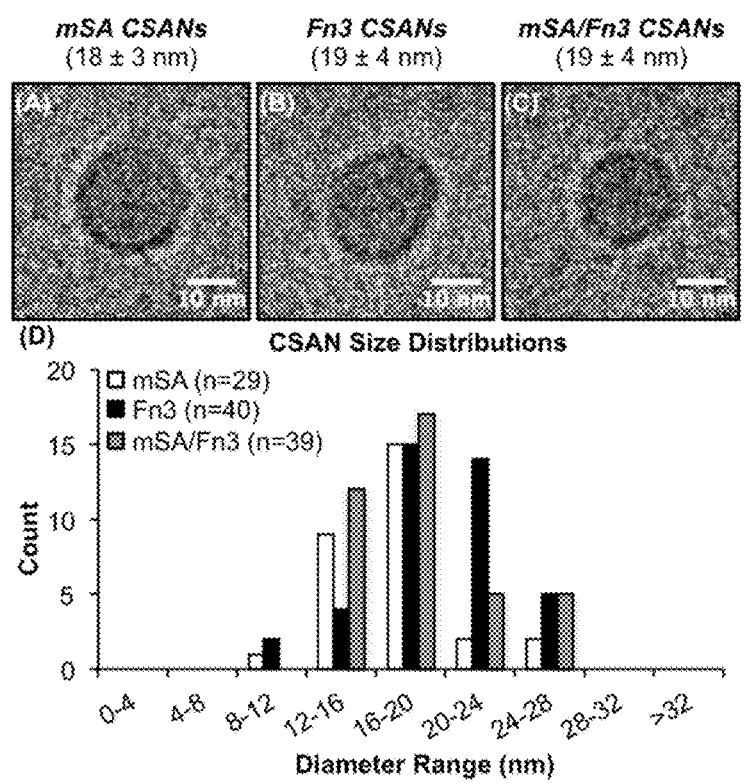

FIGURES 32A-E
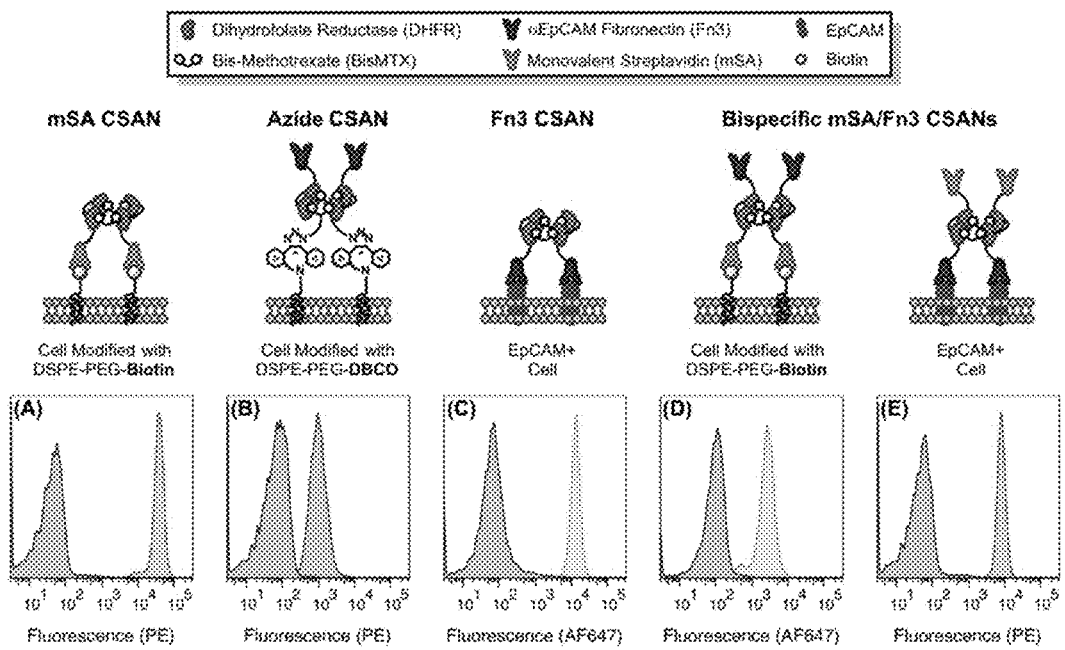
FIGURES 33A-D
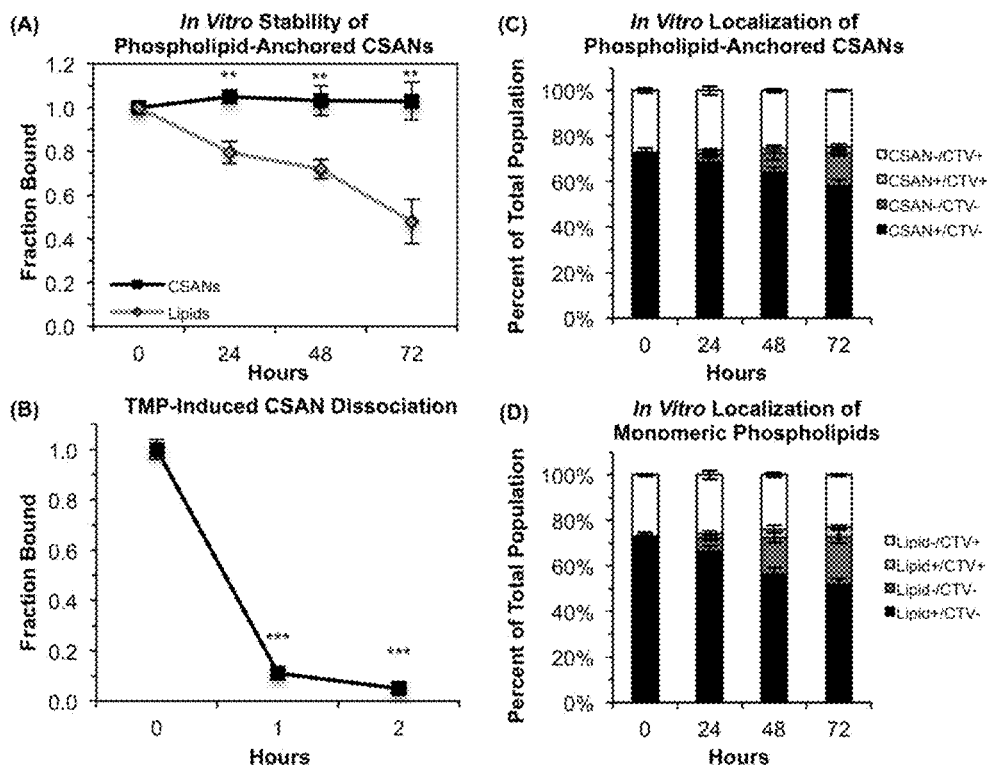

FIGURES 34A-F
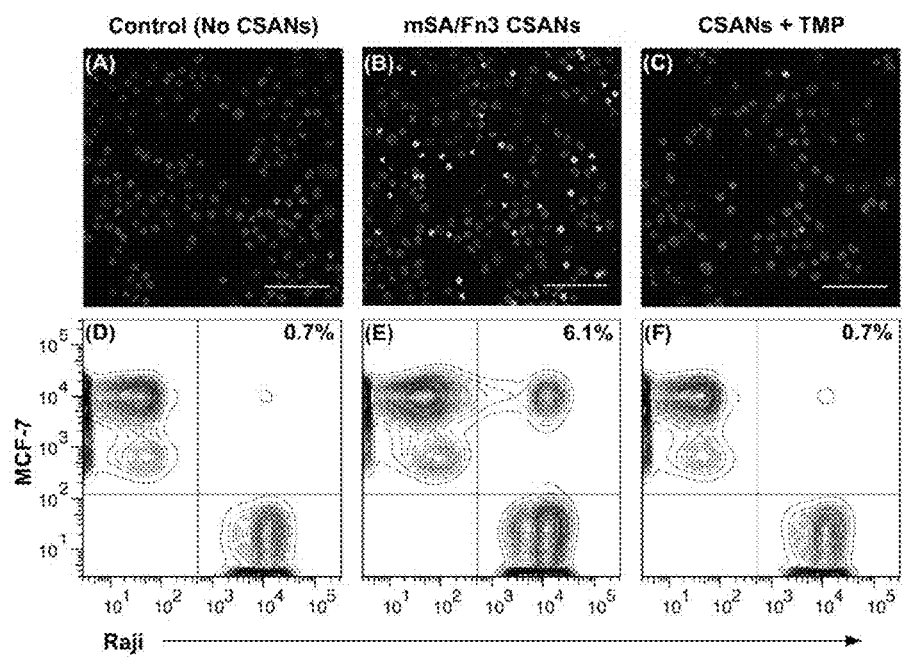
FIGURES 35A-D
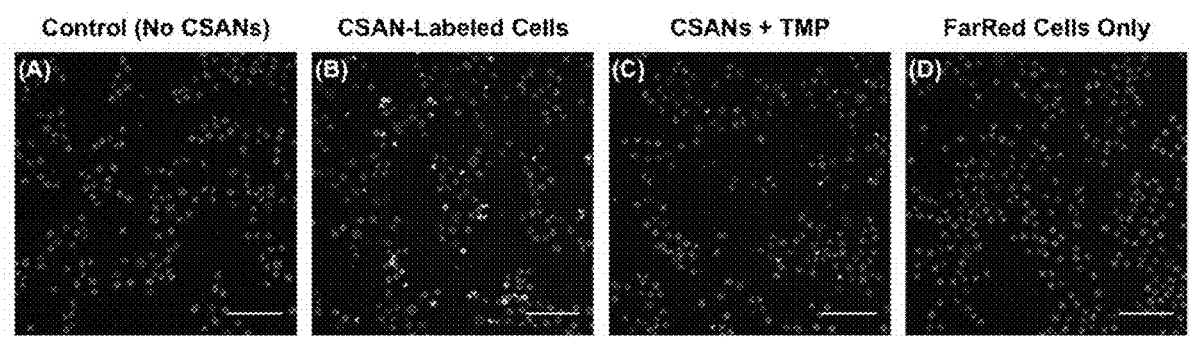

FIGURES 36A-B
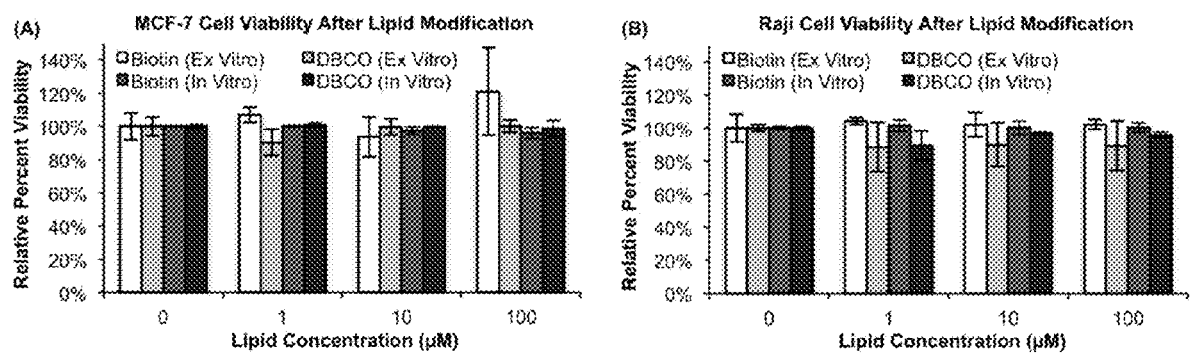
FIGURES 37A-B
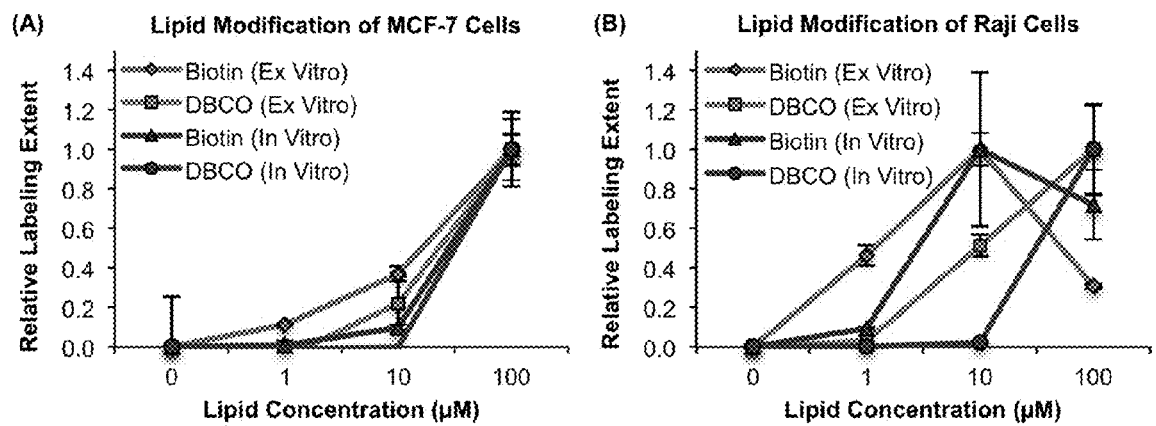

FIGURES 38A-B
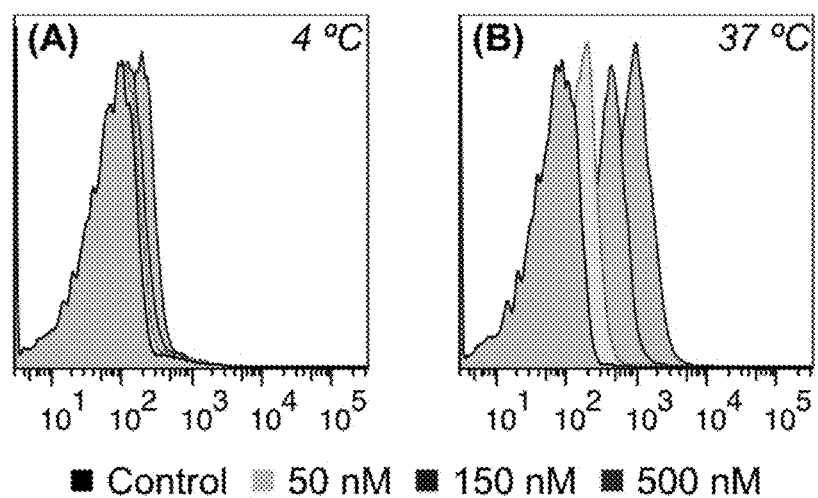
Azide/Fn3 CSANs Binding to DBCO-Modified Raji Cells

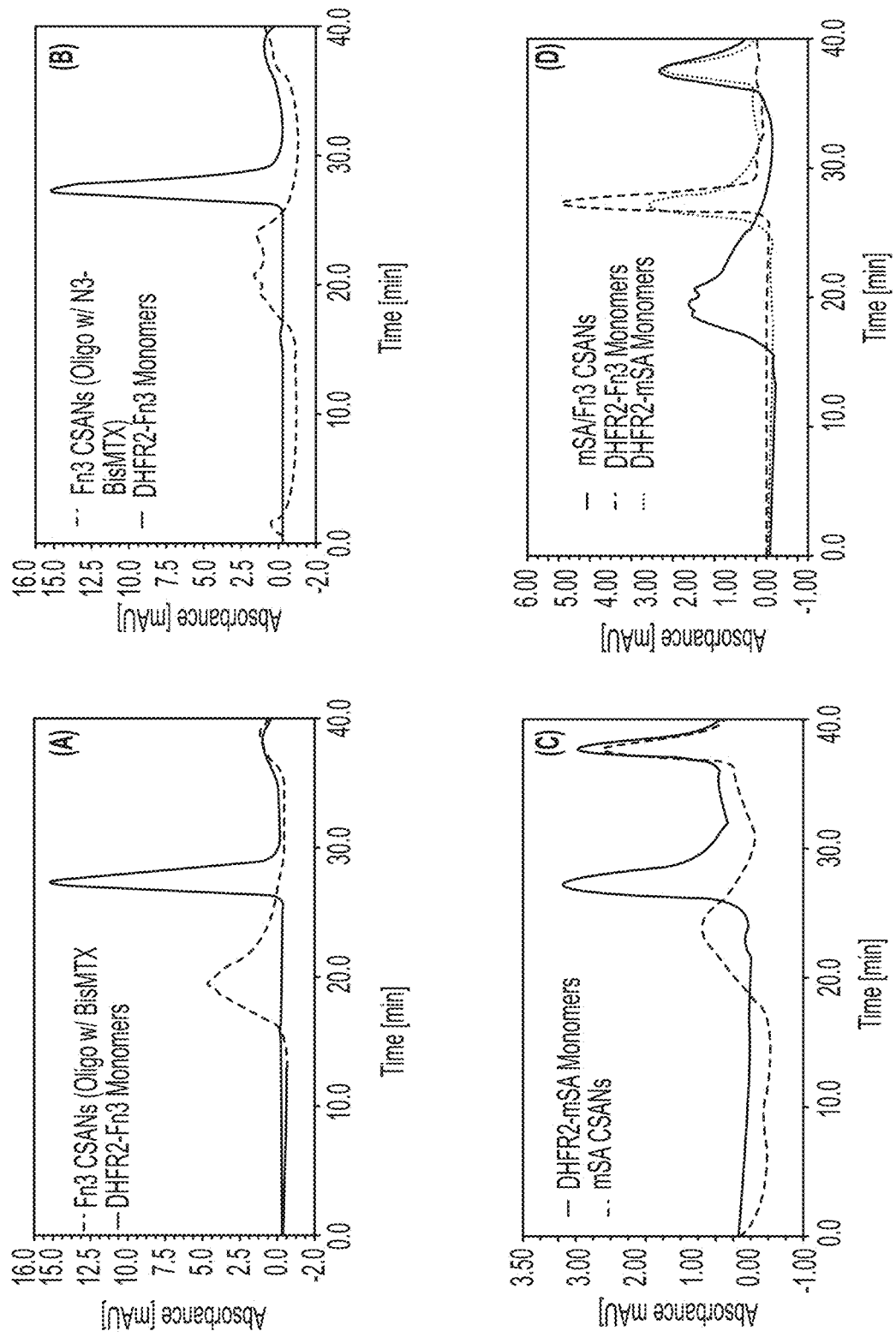
FIGURES 39A-D

FIGURES 40A-B
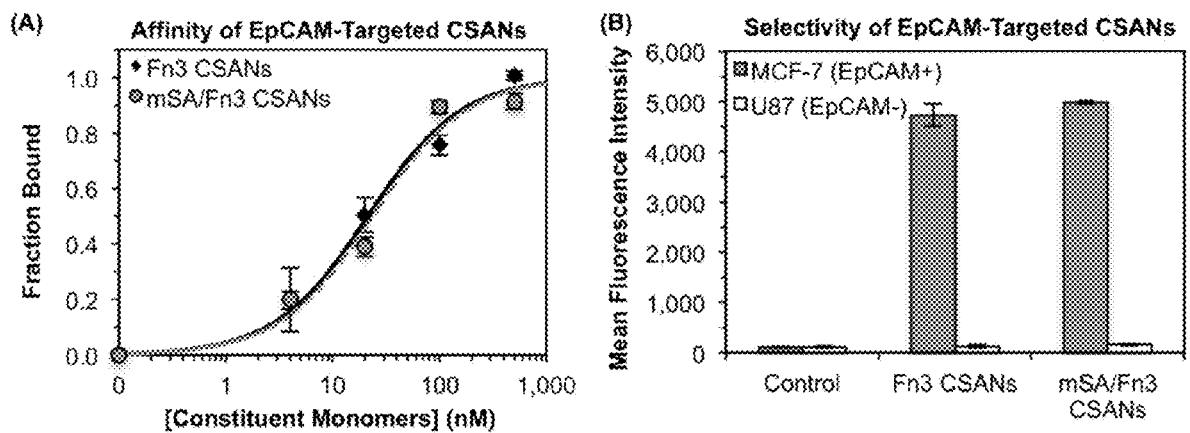
FIGURE 41A
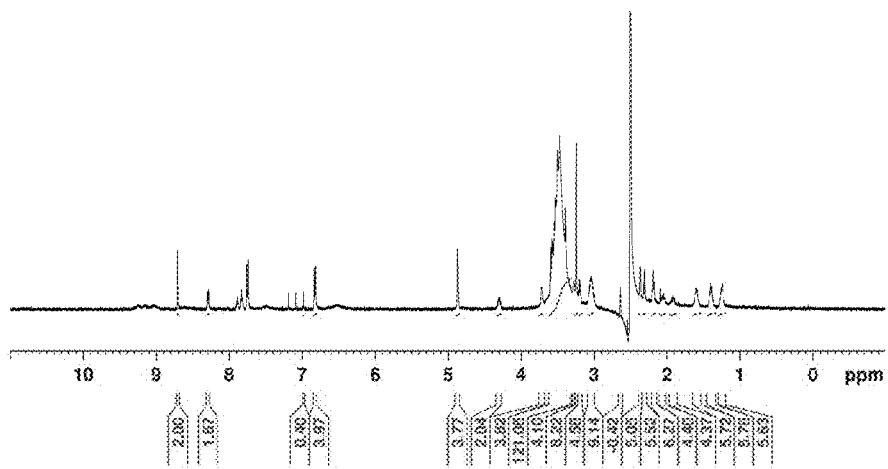

FIGURE 42
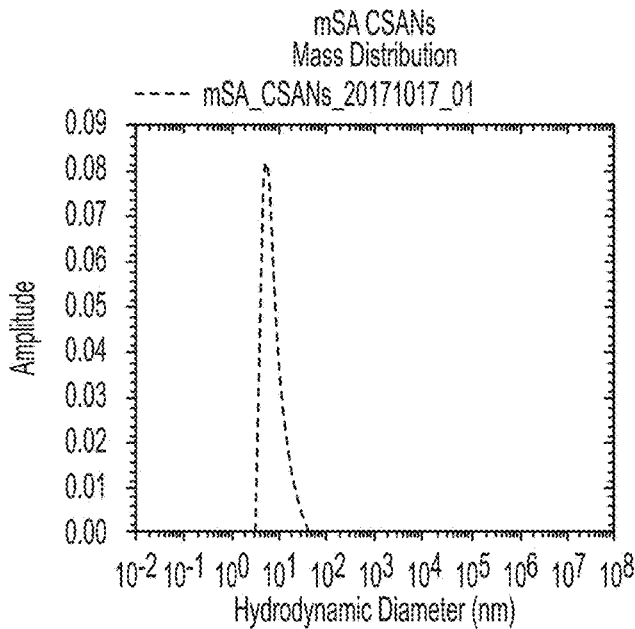
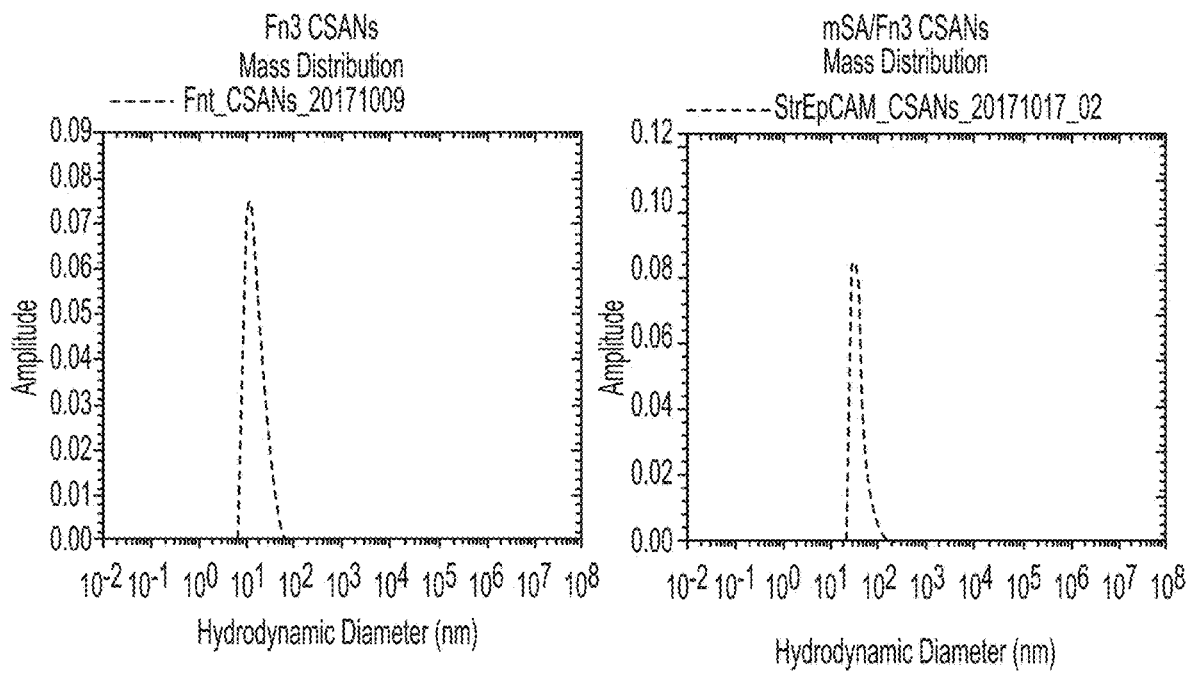
| Sample | Diameter (nm) | Dispersity |
|---|---|---|
| mSA CSANs | 17.2 ± 12.4 | 72.1% |
| Fn3 CSANs | 17.1 ± 10.4 | 61.0% |
| mSA/Fn3 CSANs | 16.8 ± 12.0 | 71.5% |

FIGURES 43A-B
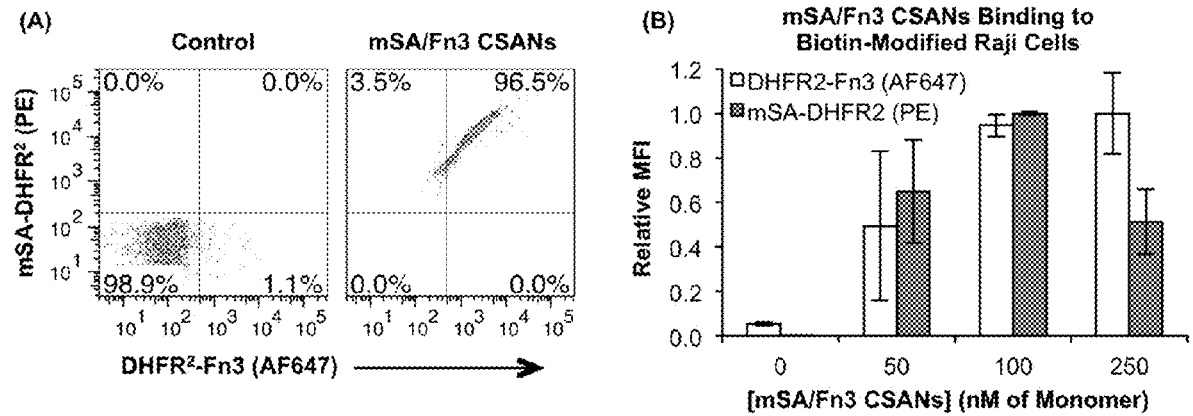
FIGURE 44
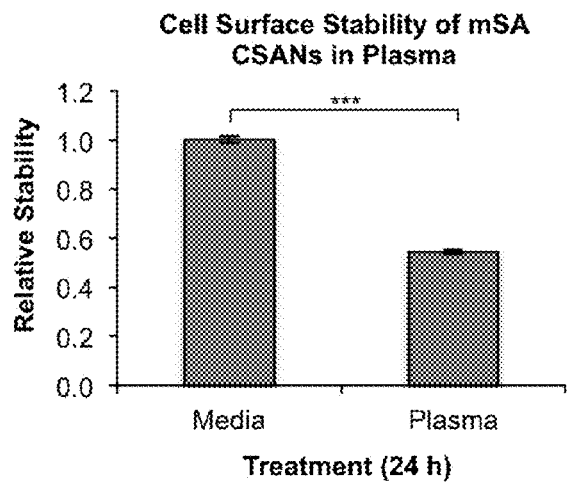

SEQUENCE LISTING

```
<160> NUMBER OF SEQ ID NOS: 70

<210> SEQ ID NO 1
<211> LENGTH: 101
<212> TYPE: PRT
<213> ORGANISM: Homo sapiens

<400> SEQUENCE: 1

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr Glu Ile
                85                  90                  95

Asp Lys Pro Ser Gln
            100
```

<210> SEQ ID NO 2
<211> LENGTH: 9
<212> TYPE: PRT
<213> ORGANISM: Homo sapiens

<400> SEQUENCE: 2

Asp Ala Pro Ala Val Thr Val Arg Tyr
1               5

<210> SEQ ID NO 3
<211> LENGTH: 5
<212> TYPE: PRT
<213> ORGANISM: Homo sapiens

<400> SEQUENCE: 3

Gly Ser Lys Ser Thr
1               5

<210> SEQ ID NO 4
<211> LENGTH: 11
<212> TYPE: PRT
<213> ORGANISM: Homo sapiens

<400> SEQUENCE: 4

Thr Gly Arg Gly Asp Ser Pro Ala Ser Ser Lys
1               5                   10

<210> SEQ ID NO 5
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Ser Ser Asp Ser Pro Arg Asn Leu Glu Val Thr Asn Ala Thr Pro Asn
1               5                   10                  15

Ser Leu Thr Ile Ser Trp Asp Ala Pro Ala Val Thr Val Arg Tyr Tyr
                20                  25                  30

Arg Ile Thr Tyr Gly Glu Thr Gly Gly Asn Ser Pro Ser Gln Glu Phe
            35                  40                  45

Thr Val Pro Gly Ser Lys Ser Thr Ala Thr Ile Ser Gly Leu Lys Pro
        50                  55                  60

Gly Gln Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr Glu Ile
                85                  90                  95

Asp Lys Pro Ser Gln
            100

<210> SEQ ID NO 6
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Ser Ser Asp Ser Pro Arg Asn Leu Glu Val Thr Asn Ala Thr Pro Asn
1               5                   10                  15

```
Ser Leu Thr Ile Ser Trp Asp Tyr Pro Asn Ser Ala Ser Tyr Tyr Arg
            20                  25                  30

Ile Thr Tyr Gly Glu Thr Gly Gly Asn Ser Pro Ser Gln Glu Phe Thr
        35                  40                  45

Val Pro Gly Asn Thr Tyr Asn Ala Thr Ile Ser Gly Leu Lys Pro Gly
    50                  55                  60

Gln Asp Tyr Ile Ile Thr Val Tyr Ala Val Thr Tyr Arg Asp Asn Tyr
65                  70                  75                  80

Ser Tyr Ser Asn Pro Ile Ser Ile Asn Tyr Arg Thr Glu Ile Asp Lys
                85                  90                  95

Pro Ser Gln

<210> SEQ ID NO 7
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Ser Ser Asp Ser Pro Arg Asn Leu Glu Val Thr Asn Ala Thr Pro Asn
1               5                   10                  15

Ser Leu Thr Ile Ser Trp Asp Tyr Pro Asn Ser Ala Ser Tyr Tyr Arg
            20                  25                  30

Ile Thr Tyr Gly Glu Thr Gly Gly Asn Ser Pro Ser Gln Glu Phe Thr
        35                  40                  45

Val Pro Gly Asn Thr Tyr Asn Ala Thr Ile Ser Gly Leu Arg Pro Asp
    50                  55                  60

Gln Asp Tyr Ile Ile Thr Val Tyr Ala Val Thr Ser Arg Asp Asn Tyr
65                  70                  75                  80

Ser Trp Ser Asn Pro Ile Ser Ile Asn Tyr Arg Thr Glu Ile Asp Lys
                85                  90                  95

Pro Ser Gln

<210> SEQ ID NO 8
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Ser Ser Asp Ser Pro Arg Asn Leu Glu Val Thr Asn Ala Thr Pro Asn
1               5                   10                  15

Ser Leu Thr Ile Ser Trp Asp Tyr Pro Asn Ser Ala Ser Tyr Tyr Arg
            20                  25                  30

Ile Thr Tyr Gly Glu Thr Gly Gly Asn Ser Pro Ser Gln Glu Phe Thr
        35                  40                  45

Val Pro Gly Asn Thr Tyr Asn Thr Thr Ile Ser Gly Leu Lys Pro Gly
    50                  55                  60

Gln Asp Tyr Thr Ile Thr Val Tyr Ala Val Thr Ser Arg Asp Asn Tyr
65                  70                  75                  80

Ser Tyr Leu Asn Pro Ile Ser Ile Asn Tyr Arg Thr Glu Ile Asp Lys
                85                  90                  95

Pro Ser Gln
```

```
<210> SEQ ID NO 9
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Ser Ser Asp Ser Pro Arg Asn Leu Glu Val Thr Asn Ala Thr Pro Asn
1               5                   10                  15

Ser Leu Thr Ile Ser Trp Asp Tyr Pro Asn Ser Ala Ser Tyr Tyr Arg
            20                  25                  30

Ile Thr Tyr Gly Glu Thr Gly Gly Asn Ser Pro Ser Gln Glu Phe Thr
        35                  40                  45

Val Pro Gly Asn Thr Tyr Asn Ala Thr Ile Ser Gly Leu Lys Pro Gly
50                  55                  60

Gln Asp Tyr Ile Ile Thr Val Tyr Ala Val Thr Ser Arg Asp Asn Tyr
65                  70                  75                  80

Ser Tyr Leu Asn Pro Ile Ser Ile Asn Tyr Arg Thr Glu Ile Asp Lys
                85                  90                  95

Pro Ser Gln

<210> SEQ ID NO 10
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Ser Ser Asp Ser Pro Arg Asn Leu Glu Val Thr Asn Ala Thr Pro Asn
1               5                   10                  15

Ser Leu Thr Ile Ser Trp Asp Asp Tyr Thr Ser Ala Ser Tyr Tyr Arg
            20                  25                  30

Ile Thr Tyr Gly Glu Thr Gly Gly Asn Ser Pro Ser Gln Glu Phe Thr
        35                  40                  45

Val Pro Gly Asn Thr Tyr Asn Ala Thr Val Ser Gly Leu Arg Pro Gly
50                  55                  60

Gln Asp Tyr Ile Ile Thr Val Tyr Ala Val Thr Tyr Arg Asp Asn Tyr
65                  70                  75                  80

Ser Tyr Ser Asn Pro Ile Ser Ile Asn Tyr Arg Thr Glu Ile Asp Lys
                85                  90                  95

Pro Ser Gln

<210> SEQ ID NO 11
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Ser Ser Asp Ser Pro Arg Asn Leu Glu Val Thr Asn Ala Thr Pro Asn
1               5                   10                  15

Ser Leu Thr Ile Ser Trp Asp Tyr Pro Asn Ser Ala Ser Tyr Tyr Arg
            20                  25                  30
```

Ile Thr Tyr Gly Glu Thr Gly Gly Asn Ser Pro Ser Gln Glu Phe Thr
            35                  40                  45

Val Pro Gly Asn Thr Tyr Asn Ala Thr Ile Ser Gly Leu Lys Pro Gly
    50                  55                  60

Gln Asp Tyr Ile Ile Thr Val Tyr Ala Val Thr Ser Arg Asp Asn Tyr
65                  70                  75                  80

Ser Tyr Ser Asn Leu Ile Ser Ile Asn Tyr Arg Thr Glu Ile Asp Lys
                85                  90                  95

Pro Ser Gln

<210> SEQ ID NO 12
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Ser Ser Asp Ser Pro Arg Asn Leu Glu Val Thr Asn Ala Thr Pro Asn
1               5                   10                  15

Ser Leu Thr Ile Ser Trp Asp Asn Ser Asn Tyr Ala Ser Tyr Tyr Arg
            20                  25                  30

Ile Thr Tyr Gly Glu Thr Gly Gly Asn Ser Pro Ser Gln Glu Leu Thr
            35                  40                  45

Val Pro Gly Ser Thr Tyr Asn Ala Thr Ile Ser Gly Leu Lys Pro Gly
    50                  55                  60

Gln Asp Tyr Ile Ile Thr Val Tyr Ala Val Thr Tyr Arg Asp Asn Tyr
65                  70                  75                  80

Ser Tyr Ser Asn Leu Ile Ser Ile Asn Tyr Arg Ser Glu Ile Asp Lys
                85                  90                  95

Pro Ser Gln

<210> SEQ ID NO 13
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Ser Ser Asp Ser Pro Arg Ser Leu Glu Val Thr Asn Ala Thr Pro Asn
1               5                   10                  15

Ser Leu Thr Ile Ser Trp Asp Tyr Pro Asn Ser Ala Ser Tyr Tyr Arg
            20                  25                  30

Ile Thr Tyr Gly Glu Thr Gly Gly Asn Ser Pro Ser Gln Glu Phe Thr
            35                  40                  45

Val Pro Gly Asp Thr Tyr Asn Ala Thr Ile Ser Gly Leu Glu Pro Gly
    50                  55                  60

Gln Asp Tyr Ile Ile Thr Val Tyr Ala Val Thr Tyr Arg Asp Asn Tyr
65                  70                  75                  80

Ser Tyr Ser Asn Ser Val Ser Ile Asn Tyr Arg Thr Glu Val Asp Lys
                85                  90                  95

Pro Ser Gln

<210> SEQ ID NO 14
<211> LENGTH: 99

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Ser Ser Asp Ser Pro Arg Asn Leu Glu Val Thr Asn Ala Thr Pro Asn
1               5                   10                  15

Ser Leu Thr Ile Ser Trp Asp Tyr Pro Asn Ser Ala Ser Tyr Tyr Arg
            20                  25                  30

Ile Thr Tyr Ser Glu Thr Gly Gly Asn Ser Pro Ser Gln Glu Phe Thr
            35                  40                  45

Val Pro Gly Asn Thr Tyr Asn Ala Thr Ile Ser Gly Leu Lys Pro Gly
    50                  55                  60

Gln Asp Tyr Ile Ile Thr Val Tyr Ala Val Thr Tyr Arg Asp Asn Tyr
65                  70                  75                  80

Ser Tyr Ser Asn Leu Ile Ser Ile Asn Tyr Arg Thr Glu Ile Asp Lys
                85                  90                  95

Pro Ser Gln

<210> SEQ ID NO 15
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Ser Ser Asp Ser Pro Arg Asn Leu Glu Val Thr Asn Ala Thr Pro Asn
1               5                   10                  15

Ser Leu Thr Ile Ser Trp Asp Asp Pro Asp Phe Ala Ser Tyr Tyr Arg
            20                  25                  30

Ile Thr Tyr Gly Glu Thr Gly Gly Ser Ser Pro Ser Gln Glu Phe Thr
            35                  40                  45

Val Pro Gly Asn Thr Tyr Ser Ala Thr Ile Ser Gly Leu Lys Pro Gly
    50                  55                  60

Arg Asp His Thr Ile Thr Val Tyr Ala Val Thr Tyr Arg Asp Asn Tyr
65                  70                  75                  80

Ser Tyr Ser Asn Pro Ile Ser Ile Asn Tyr Arg Thr Glu Ile Asp Lys
                85                  90                  95

Pro Ser Gln

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Asp Tyr Pro Asn Ser Ala Ser Tyr
1               5

<210> SEQ ID NO 17
<211> LENGTH: 5
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 17

Gly Asn Thr Tyr Asn
1               5

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Thr Tyr Arg Asp Asn Tyr Ser Tyr Ser Asn
1               5                   10

<210> SEQ ID NO 19
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Val Ser Asp Val Pro Arg Asp Leu Glu Val Val Ala Ala Thr Pro Thr
1               5                   10                  15

Ser Leu Leu Ile Ser Trp Asp Tyr Pro Asn Ser Ala Ser Tyr Tyr Arg
            20                  25                  30

Ile Thr Tyr Gly Glu Thr Gly Gly Asn Ser Pro Val Gln Glu Phe Thr
        35                  40                  45

Val Pro Gly Asn Thr Tyr Asn Ala Thr Ile Ser Gly Leu Arg Pro Asp
    50                  55                  60

Val Asp Tyr Ile Ile Thr Val Tyr Ala Val Thr Ser Arg Asp Asn Tyr
65                  70                  75                  80

Ser Trp Ser Asn Pro Ile Ser Ile Asn Tyr Arg Thr Glu Ile Asp Lys
                85                  90                  95

Pro Ser Gln

<210> SEQ ID NO 20
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Val Ser Asp Val Pro Arg Asp Leu Glu Val Val Ala Ala Thr Pro Thr
1               5                   10                  15

Ser Leu Leu Ile Ser Trp Asp Tyr Pro Asn Ser Ala Ser Tyr Tyr Arg
            20                  25                  30

Ile Thr Tyr Gly Glu Thr Gly Gly Asn Ser Pro Val Gln Glu Phe Thr
        35                  40                  45

Val Pro Gly Asn Thr Tyr Asn Ala Thr Ile Ser Gly Leu Lys Pro Gly
    50                  55                  60

Val Asp Tyr Ile Ile Thr Val Tyr Ala Val Thr Tyr Arg Asp Asn Tyr
65                  70                  75                  80
```

```
Ser Tyr Ser Asn Pro Ile Ser Ile Asn Tyr Arg Thr Glu Ile Asp Lys
                85                  90                  95

Pro Ser Gln

<210> SEQ ID NO 21
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Val Ser Asp Val Pro Arg Asp Leu Glu Val Val Ala Ala Thr Pro Thr
1               5                   10                  15

Ser Leu Leu Ile Ser Trp Asp Tyr Pro Asn Ser Ala Ser Tyr Tyr Arg
                20                  25                  30

Ile Thr Tyr Gly Glu Thr Gly Gly Asn Ser Pro Val Gln Glu Phe Thr
            35                  40                  45

Val Pro Gly Asn Thr Tyr Asn Thr Thr Ile Ser Gly Leu Lys Pro Gly
        50                  55                  60

Val Asp Tyr Thr Ile Thr Val Tyr Ala Val Thr Ser Arg Asp Asn Tyr
65                  70                  75                  80

Ser Tyr Leu Asn Pro Ile Ser Ile Asn Tyr Arg Thr Glu Ile Asp Lys
                85                  90                  95

Pro Ser Gln

<210> SEQ ID NO 22
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Val Ser Asp Val Pro Arg Asp Leu Glu Val Val Ala Ala Thr Pro Thr
1               5                   10                  15

Ser Leu Leu Ile Ser Trp Asp Tyr Pro Asn Ser Ala Ser Tyr Tyr Arg
                20                  25                  30

Ile Thr Tyr Gly Glu Thr Gly Gly Asn Ser Pro Val Gln Glu Phe Thr
            35                  40                  45

Val Pro Gly Asn Thr Tyr Asn Ala Thr Ile Ser Gly Leu Lys Pro Gly
        50                  55                  60

Val Asp Tyr Ile Ile Thr Val Tyr Ala Val Thr Ser Arg Asp Asn Tyr
65                  70                  75                  80

Ser Tyr Leu Asn Pro Ile Ser Ile Asn Tyr Arg Thr Glu Ile Asp Lys
                85                  90                  95

Pro Ser Gln

<210> SEQ ID NO 23
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Val Ser Asp Val Pro Arg Asp Leu Glu Val Val Ala Ala Thr Pro Thr
```

```
1               5                   10                  15
Ser Leu Leu Ile Ser Trp Asp Asp Tyr Thr Ser Ala Ser Tyr Tyr Arg
                20                  25                  30

Ile Thr Tyr Gly Glu Thr Gly Gly Asn Ser Pro Val Gln Glu Phe Thr
                35                  40                  45

Val Pro Gly Asn Thr Tyr Asn Ala Thr Val Ser Gly Leu Arg Pro Gly
            50                  55                  60

Val Asp Tyr Ile Ile Thr Val Tyr Ala Val Thr Tyr Arg Asp Asn Tyr
 65                 70                  75                  80

Ser Tyr Ser Asn Pro Ile Ser Ile Asn Tyr Arg Thr Glu Ile Asp Lys
                85                  90                  95

Pro Ser Gln
```

<210> SEQ ID NO 24
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

```
Val Ser Asp Val Pro Arg Asp Leu Glu Val Val Ala Ala Thr Pro Thr
 1               5                   10                  15

Ser Leu Leu Ile Ser Trp Asp Tyr Pro Asn Ser Ala Ser Tyr Tyr Arg
                20                  25                  30

Ile Thr Tyr Gly Glu Thr Gly Gly Asn Ser Pro Val Gln Glu Phe Thr
                35                  40                  45

Val Pro Gly Asn Thr Tyr Asn Ala Thr Ile Ser Gly Leu Lys Pro Gly
            50                  55                  60

Val Asp Tyr Ile Ile Thr Val Tyr Ala Val Thr Ser Arg Asp Asn Tyr
 65                 70                  75                  80

Ser Tyr Ser Asn Leu Ile Ser Ile Asn Tyr Arg Thr Glu Ile Asp Lys
                85                  90                  95

Pro Ser Gln
```

<210> SEQ ID NO 25
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

```
Val Ser Asp Val Pro Arg Asp Leu Glu Val Val Ala Ala Thr Pro Thr
 1               5                   10                  15

Ser Leu Leu Ile Ser Trp Asp Asn Ser Asn Tyr Ala Ser Tyr Tyr Arg
                20                  25                  30

Ile Thr Tyr Gly Glu Thr Gly Gly Asn Ser Pro Val Gln Glu Leu Thr
                35                  40                  45

Val Pro Gly Ser Thr Tyr Asn Ala Thr Ile Ser Gly Leu Lys Pro Gly
            50                  55                  60

Val Asp Tyr Ile Ile Thr Val Tyr Ala Val Thr Tyr Arg Asp Asn Tyr
 65                 70                  75                  80

Ser Tyr Ser Asn Leu Ile Ser Ile Asn Tyr Arg Ser Glu Ile Asp Lys
                85                  90                  95
```

Pro Ser Gln

<210> SEQ ID NO 26
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Val Ser Asp Val Pro Arg Ser Leu Glu Val Val Ala Ala Thr Pro Thr
1               5                   10                  15

Ser Leu Leu Ile Ser Trp Asp Tyr Pro Asn Ser Ala Ser Tyr Tyr Arg
            20                  25                  30

Ile Thr Tyr Gly Glu Thr Gly Gly Asn Ser Pro Val Gln Glu Phe Thr
        35                  40                  45

Val Pro Gly Asp Thr Tyr Asn Ala Thr Ile Ser Gly Leu Glu Pro Gly
    50                  55                  60

Val Asp Tyr Ile Ile Thr Val Tyr Ala Val Thr Tyr Arg Asp Asn Tyr
65                  70                  75                  80

Ser Tyr Ser Asn Ser Val Ser Ile Asn Tyr Arg Thr Glu Val Asp Lys
                85                  90                  95

Pro Ser Gln

<210> SEQ ID NO 27
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Val Ser Asp Val Pro Arg Asp Leu Glu Val Val Ala Ala Thr Pro Thr
1               5                   10                  15

Ser Leu Leu Ile Ser Trp Asp Tyr Pro Asn Ser Ala Ser Tyr Tyr Arg
            20                  25                  30

Ile Thr Tyr Ser Glu Thr Gly Gly Asn Ser Pro Val Gln Glu Phe Thr
        35                  40                  45

Val Pro Gly Asn Thr Tyr Asn Ala Thr Ile Ser Gly Leu Lys Pro Gly
    50                  55                  60

Val Asp Tyr Ile Ile Thr Val Tyr Ala Val Thr Tyr Arg Asp Asn Tyr
65                  70                  75                  80

Ser Tyr Ser Asn Leu Ile Ser Ile Asn Tyr Arg Thr Glu Ile Asp Lys
                85                  90                  95

Pro Ser Gln

<210> SEQ ID NO 28
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Val Ser Asp Val Pro Arg Asp Leu Glu Val Val Ala Ala Thr Pro Thr
1               5                   10                  15

Ser Leu Leu Ile Ser Trp Asp Asp Pro Asp Phe Ala Ser Tyr Tyr Arg

```
                20                  25                  30

Ile Thr Tyr Gly Glu Thr Gly Ser Ser Pro Val Gln Glu Phe Thr
            35                  40                  45

Val Pro Gly Asn Thr Tyr Ser Ala Thr Ile Ser Gly Leu Lys Pro Gly
 50                  55                  60

Arg Asp His Thr Ile Thr Val Tyr Ala Val Thr Tyr Arg Asp Asn Tyr
 65                  70                  75                  80

Ser Tyr Ser Asn Pro Ile Ser Ile Asn Tyr Arg Thr Glu Ile Asp Lys
                85                  90                  95

Pro Ser Gln

<210> SEQ ID NO 29
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Val Ser Asp Val Pro Arg Asp Leu Glu Val Val Ala Ala Thr Pro Thr
 1               5                  10                  15

Ser Leu Leu Ile Ser Trp Asp Tyr Pro Asn Ser Ala Ser Tyr Tyr Arg
                20                  25                  30

Ile Thr Tyr Gly Glu Thr Gly Gly Asn Ser Pro Val Gln Glu Phe Thr
            35                  40                  45

Val Pro Gly Ser Lys Ser Thr Ala Thr Ile Ser Gly Leu Lys Pro Gly
 50                  55                  60

Val Asp Tyr Thr Ile Thr Val Tyr Ala Val Thr Gly Arg Gly Asp Ser
 65                  70                  75                  80

Pro Ala Ser Ser Lys Pro Ile Ser Ile Asn Tyr Arg Thr Glu Ile Asp
                85                  90                  95

Lys Pro Ser Gln
            100

<210> SEQ ID NO 30
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Val Ser Asp Val Pro Arg Asp Leu Glu Val Val Ala Ala Thr Pro Thr
 1               5                  10                  15

Ser Leu Leu Ile Ser Trp Asp Ala Pro Ala Val Thr Val Arg Tyr Tyr
                20                  25                  30

Arg Ile Thr Tyr Gly Glu Thr Gly Gly Asn Ser Pro Val Gln Glu Phe
            35                  40                  45

Thr Val Pro Gly Asn Thr Tyr Asn Ala Thr Ile Ser Gly Leu Lys Pro
 50                  55                  60

Gly Val Asp Tyr Thr Ile Thr Val Tyr Ala Val Thr Gly Arg Gly Asp
 65                  70                  75                  80

Ser Pro Ala Ser Ser Lys Pro Ile Ser Ile Asn Tyr Arg Thr Glu Ile
                85                  90                  95

Asp Lys Pro Ser Gln
            100
```

<210> SEQ ID NO 31
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Tyr Arg Asp Asn
65                  70                  75                  80

Tyr Ser Tyr Ser Asn Pro Ile Ser Ile Asn Tyr Arg Thr Glu Ile Asp
                85                  90                  95

Lys Pro Ser Gln
            100

<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Thr Ser Arg Asp Asn Tyr Ser Trp Ser Asn
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Thr Ser Arg Asp Asn Tyr Ser Tyr Leu Asn
1               5                   10

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Asp Asp Tyr Thr Ser Ala Ser Tyr
1               5

<210> SEQ ID NO 35
<211> LENGTH: 10
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 35

Thr Ser Arg Asp Asn Tyr Ser Tyr Ser Asn
1               5                   10

<210> SEQ ID NO 36
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Asp Asn Ser Asn Tyr Ala Ser Tyr
1               5

<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Ser Thr Tyr Asn
1               5

<210> SEQ ID NO 38
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Asp Thr Tyr Asn
1               5

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Asp Asp Pro Asp Phe Ala Ser Tyr
1               5

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Asn Thr Tyr Ser
1               5
```

<210> SEQ ID NO 41
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (23)..(31)
<223> OTHER INFORMATION: This region may encompass "DAPAVTVRY" or
      "DYPNSASY" or "DDYTSASY" or "DNSNYASY" or "DDPDFASY" wherein some
      positions may be absent
<220> FEATURE:
<221> NAME/KEY: MOD_RES
<222> LOCATION: (52)..(56)
<223> OTHER INFORMATION: This region may encompass "GSKST" or "GNTYN" or
      "GSTYN" or "GDTYN" or "GNTYS"
<220> FEATURE:
<221> NAME/KEY: MOD_RES
<222> LOCATION: (76)..(86)
<223> OTHER INFORMATION: This region may encompass "TGRGDSPASSK" or
      "TYRDNYSYSN" or "TSRDNYSWSN" or "TSRDNYSYLN" or "TSRDNYSYSN"
      wherein some positions may be absent
<220> FEATURE:
<223> OTHER INFORMATION: See specification as filed for detailed
      description of substitutions and preferred embodiments

<400> SEQUENCE: 41

Val Ser Asp Val Pro Arg Asp Leu Glu Val Val Ala Ala Thr Pro Thr
1               5                   10                  15

Ser Leu Leu Ile Ser Trp Xaa Xaa Xaa Xaa Xaa Xaa Xaa Xaa Xaa Tyr
            20                  25                  30

Arg Ile Thr Tyr Gly Glu Thr Gly Gly Asn Ser Pro Val Gln Glu Phe
            35                  40                  45

Thr Val Pro Xaa Xaa Xaa Xaa Xaa Ala Thr Ile Ser Gly Leu Lys Pro
        50                  55                  60

Gly Val Asp Tyr Thr Ile Thr Val Tyr Ala Val Xaa Xaa Xaa Xaa Xaa
65                  70                  75                  80

Xaa Xaa Xaa Xaa Xaa Xaa Pro Ile Ser Ile Asn Tyr Arg Thr Glu Ile
                85                  90                  95

Asp Lys Pro Ser Gln
            100

<210> SEQ ID NO 42
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (23)..(31)
<223> OTHER INFORMATION: This region may encompass "DAPAVTVRY" or
      "DYPNSASY" or "DDYTSASY" or "DNSNYASY" or "DDPDFASY" wherein some
      positions may be absent
<220> FEATURE:
<221> NAME/KEY: MOD_RES
<222> LOCATION: (52)..(56)
<223> OTHER INFORMATION: This region may encompass "GSKST" or "GNTYN" or
      "GSTYN" or "GDTYN" or "GNTYS"
<220> FEATURE:
<221> NAME/KEY: MOD_RES
<222> LOCATION: (76)..(86)
<223> OTHER INFORMATION: This region may encompass "TGRGDSPASSK" or
      "TYRDNYSYSN" or "TSRDNYSWSN" or "TSRDNYSYLN" or "TSRDNYSYSN"
      wherein some positions may be absent
<220> FEATURE:

<223> OTHER INFORMATION: See specification as filed for detailed
      description of substitutions and preferred embodiments

<400> SEQUENCE: 42

Ser Ser Asp Ser Pro Arg Asn Leu Glu Val Thr Asn Ala Thr Pro Asn
1               5                   10                  15

Ser Leu Thr Ile Ser Trp Xaa Xaa Xaa Xaa Xaa Xaa Xaa Xaa Xaa Tyr
            20                  25                  30

Arg Ile Thr Tyr Gly Glu Thr Gly Gly Asn Ser Pro Ser Gln Glu Phe
            35                  40                  45

Thr Val Pro Xaa Xaa Xaa Xaa Xaa Ala Thr Ile Ser Gly Leu Lys Pro
        50                  55                  60

Gly Gln Asp Tyr Thr Ile Thr Val Tyr Ala Val Xaa Xaa Xaa Xaa Xaa
65                  70                  75                  80

Xaa Xaa Xaa Xaa Xaa Pro Ile Ser Ile Asn Tyr Arg Thr Glu Ile
                85                  90                  95

Asp Lys Pro Ser Gln
            100

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
tgtggatccc accatcacca t                                           21

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
ctgagacggt tgtcgattt c                                            21

<210> SEQ ID NO 45
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gtctgaaacc gtgccaggat tatatc                                      26

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
cgctgatggt cgcattataa                                             20

<210> SEQ ID NO 47
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Ser Ser Asp Ser Pro Arg Asn Leu Glu Val Thr Asn Ala Thr Pro Asn
1               5                   10                  15

Ser Leu Thr Ile Ser Trp Asp Asn Ser Asn Tyr Ala Ser Tyr Tyr Arg
                20                  25                  30

Ile Thr Tyr Gly Glu Thr Gly Gly Asn Ser Pro Ser Gln Glu Leu Thr
            35                  40                  45

Val Pro Gly Ser Thr Tyr Asn Ala Thr Ile Ser Gly Leu Lys Pro Cys
50                  55                  60

Gln Asp Tyr Ile Ile Thr Val Tyr Ala Val Thr Tyr Arg Asp Asn Tyr
65                  70                  75                  80

Ser Tyr Ser Asn Leu Ile Ser Ile Asn Tyr Arg Ser Glu Ile Asp Lys
                85                  90                  95

Pro Ser Gln

<210> SEQ ID NO 48
<211> LENGTH: 297
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48
tcctccgact ctccgcgtaa cctggaggtt accaacgcaa ctccgaactc tctgactatt      60
tcttgggaca attctaacta tgcttcgtat taccgtatca cctacggcga aaccggtggt     120
aactccccga gccaggaact cactgttccg ggaagtactt ataatgcgac catcagcggt     180
ctgaaaccgt gccaggatta tatcattacc gtgtacgctg taacctatcg tgacaattat     240
tcctattcaa atctaatcag catcaattat cgctccgaaa tcgacaaacc gtctcag        297

<210> SEQ ID NO 49
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Ser Ser Asp Ser Pro Arg Asn Leu Glu Val Thr Asn Ala Thr Pro Asn
1               5                   10                  15

Ser Leu Thr Ile Ser Trp Asp Asn Ser Asn Tyr Ala Ser Tyr Tyr Arg
                20                  25                  30

Ile Thr Tyr Gly Glu Thr Gly Gly Asn Ser Pro Ser Gln Glu Leu Thr
            35                  40                  45

Val Pro Gly Ser Thr Tyr Asn Ala Thr Ile Ser Gly Leu Lys Pro Gly
50                  55                  60

Gln Asp Tyr Ile Ile Thr Val Tyr Ala Val Thr Tyr Arg Asp Asn Tyr
65                  70                  75                  80

Ser Tyr Ser Asn Leu Ile Ser Ile Asn Tyr Arg Ser Glu Ile Asp Lys
                85                  90                  95

Pro Ser Gln Cys
        100

<210> SEQ ID NO 50
<211> LENGTH: 300
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
tcctccgact ctccgcgtaa cctggaggtt accaacgcaa ctccgaactc tctgactatt     60
tcttgggaca attctaacta tgcttcgtat taccgtatca cctacggcga aaccggtggt    120
aactccccga gccaggaact cactgttccg ggaagtactt ataatgcgac catcagcggt    180
ctgaaaccgg gccaggatta tatcattacc gtgtacgctg taacctatcg tgacaattat    240
tcctattcaa atctaatcag catcaattat cgctccgaaa tcgacaaacc gtctcagtgt    300

<210> SEQ ID NO 51
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Ser Ser Asp Ser Pro Arg Asn Leu Glu Val Thr Asn Ala Thr Pro Asn
1               5                   10                  15

Ser Leu Thr Ile Ser Trp Asp Ala Pro Ala Val Thr Val Arg Tyr Tyr
            20                  25                  30

Arg Ile Thr Tyr Gly Glu Thr Gly Gly Asn Ser Pro Ser Gln Glu Phe
        35                  40                  45

Thr Val Pro Gly Ser Lys Ser Thr Ala Thr Ile Ser Gly Leu Lys Pro
    50                  55                  60

Cys Gln Asp Tyr Thr Ile Thr Val Tyr Ala Val Thr Gly Arg Asp Gly
65                  70                  75                  80

Ser Pro Ala Ser Ser Lys Pro Ile Ser Ile Asn Tyr Arg Thr Glu Ile
                85                  90                  95

Asp Lys Pro Ser Gln
            100

<210> SEQ ID NO 52
<211> LENGTH: 303
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52
tcctccgact ctccgcgtaa cctggaggtt accaacgcaa ctccgaactc tctgactatt     60
tcttgggatg ctcctgctgt cacagtgaga tattaccgta tcacctacgg cgaaactggt    120
ggtaactccc cgagccagga attcactgtt ccggggagca agtctacagc gaccatcagc    180
ggtctgaaac cgtgccagga ttataccatt accgtgtacg ctgtaactgg ccgtgacgga    240
agccccgcaa gcagcaagcc aatcagcatc aattatcgca ccgaaatcga caaaccgtct    300
cag                                                                   303

<210> SEQ ID NO 53
<211> LENGTH: 497
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Met Gly Glu Gln Lys Leu Ile Ser Glu Glu Asp Leu Gly Gly Ser Gly
1               5                   10                  15

Gly Gly Ser Gly Gly Gly Ile Ser Leu Ile Ala Ala Leu Ala Val Asp
            20                  25                  30

Arg Val Ile Gly Met Glu Asn Ala Met Pro Trp Asn Leu Pro Ala Asp
        35                  40                  45

Leu Ala Trp Phe Lys Arg Asn Thr Leu Asn Lys Pro Val Ile Met Gly
    50                  55                  60

Arg His Thr Trp Glu Ser Ile Gly Arg Pro Leu Pro Gly Arg Lys Asn
65                  70                  75                  80

Ile Ile Leu Ser Ser Gln Pro Gly Thr Asp Asp Arg Val Thr Trp Val
                85                  90                  95

Lys Ser Val Asp Glu Ala Ile Ala Ala Gly Asp Val Pro Glu Ile
            100                 105                 110

Met Val Ile Gly Gly Gly Arg Val Tyr Glu Gln Phe Leu Pro Lys Ala
        115                 120                 125

Gln Lys Leu Tyr Leu Thr His Ile Asp Ala Glu Val Glu Gly Asp Thr
    130                 135                 140

His Phe Pro Asp Tyr Glu Pro Asp Asp Trp Glu Ser Val Phe Ser Glu
145                 150                 155                 160

Phe His Asp Ala Asp Ala Gln Asn Ser His Ser Tyr Ser Phe Glu Ile
                165                 170                 175

Leu Glu Arg Arg Gly Gly Ile Ser Leu Ile Ala Ala Leu Ala Val Asp
            180                 185                 190

Arg Val Ile Gly Met Glu Asn Ala Met Pro Trp Asn Leu Pro Ala Asp
        195                 200                 205

Leu Ala Trp Phe Lys Arg Asn Thr Leu Asn Lys Pro Val Ile Met Gly
    210                 215                 220

Arg His Thr Trp Glu Ser Ile Gly Arg Pro Leu Pro Gly Arg Lys Asn
225                 230                 235                 240

Ile Ile Leu Ser Ser Gln Pro Gly Thr Asp Asp Arg Val Thr Trp Val
                245                 250                 255

Lys Ser Val Asp Glu Ala Ile Ala Ala Gly Asp Val Pro Glu Ile
            260                 265                 270

Met Val Ile Gly Gly Gly Arg Val Tyr Glu Gln Phe Leu Pro Lys Ala
        275                 280                 285

Gln Lys Leu Tyr Leu Thr His Ile Asp Ala Glu Val Glu Gly Asp Thr
    290                 295                 300

His Phe Pro Asp Tyr Glu Pro Asp Asp Trp Glu Ser Val Phe Ser Glu
305                 310                 315                 320

Phe His Asp Ala Asp Ala Gln Asn Ser His Ser Tyr Ser Phe Glu Ile
                325                 330                 335

Leu Glu Arg Arg Gly Glu Leu Gly Gly Ser Gly Gly Gly Ser Gly
            340                 345                 350

Gly Gly Ser Gly Gly Gly Ser Gly Gly Gly Gly Ser Gly Gly

```
                355                 360                 365
Gly Gly Ser Gly Gly Gly Ser Gly Gly Gly Ser Gly Gly
        370                 375                 380

Gly Ser Gly Gly Ala Ser Ser Asp Ser Pro Arg Asn Leu Glu Val
385                 390                 395                 400

Thr Asn Ala Thr Pro Asn Ser Leu Thr Ile Ser Trp Asp Asn Ser Asn
                405                 410                 415

Tyr Ala Ser Tyr Tyr Arg Ile Tyr Gly Glu Thr Gly Gly Asn Ser
                420                 425                 430

Pro Ser Gln Glu Leu Thr Val Pro Gly Ser Thr Tyr Asn Ala Thr Ile
                435                 440                 445

Ser Gly Leu Lys Pro Gly Gln Asp Tyr Ile Ile Thr Val Tyr Ala Val
        450                 455                 460

Thr Tyr Arg Asp Asn Tyr Ser Tyr Ser Asn Leu Ile Ser Ile Asn Tyr
465                 470                 475                 480

Arg Ser Glu Ile Asp Lys Pro Ser Gln Gly Ser His His His His
                485                 490                 495

His
```

<210> SEQ ID NO 54
<211> LENGTH: 1504
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 54

```
ccatgggcga acaaaagctt atttctgaag aggacttggg cggttcaggt ggtggctcgg      60
gaggcggcat cagtctgatt gcggcgttag cggtagatcg cgttatcggc atggaaaacg     120
ccatgccgtg gaacctgcct gccgatctcg cctggtttaa acgcaacacc ttaaataaac     180
ccgtgattat gggccgccat acctgggaat caatcggtcg tccgttgcca ggacgcaaaa     240
atattatcct cagcagtcaa ccgggtacgg acgatcgcgt aacgtgggtg aagtcggtgg     300
atgaagccat cgcggcggct ggtgacgtac agaaatcat ggtgattggc ggcggtcgcg      360
tttatgaaca gttcttgcca aaagcgcaaa aactgtatct gacgcatatc gacgcagaag     420
tggaaggcga cacccatttc ccggattacg agccggatga ctgggaatcg gtattcagtg     480
aattccacga tgctgatgcg cagaactctc acagctatag ctttgagatt ctggagcggc     540
ggggcggcat tagccttatt gccgccttag cggttgatcg cgtgatcgga atggagaacg     600
caatgccctg gaatcttccg gcagaccttg cctggttcaa acgcaacact ttaaacaagc     660
ctgtcattat gggccgtcac acatgggagt caattggtcg tccctgcct gggcgcaaaa      720
atatcatctt gtcctcgcag cctgggacag atgatcgcgt tacatgggtg aagtccgtag     780
acgaagcgat tgccgctgcc ggcgatgtgc ccgagattat ggtaatcggg ggagggcgtg     840
tttacgaaca atttctgccc aaagctcaga attataccct gacgcacatc gacgcggagg     900
tcgaaggtga cacacacttt ccagattatg agcctgatga ttgggaatcc gttttctcag     960
aatttcatga cgcggatgct caaaactcgc actcgtactc ttttgaaatt ttagagcgcc    1020
gtggcgagct cggaggttcc ggcggggcg gaagcggagg tggaggctca ggggcggag     1080
ggtcgggcgg tggaggttcg ggggggaggcg ggagcggtgg cggtggttca ggaggagggg    1140
gttccggggg tggtggatcg ggcggtgcta gctcctccga ctctccgcgt aacctggagg    1200
```

```
ttaccaacgc aactccgaac tctctgacta tttcttggga caattctaac tatgcttcgt    1260
attaccgtat cacctacggc gaaaccggtg gtaactcccc gagccaggaa ctcactgttc    1320
cgggaagtac ttataatgcg accatcagcg gtctgaaacc gggccaggat tatatcatta    1380
ccgtgtacgc tgtaacctat cgtgacaatt attcctattc aaatctaatc agcatcaatt    1440
atcgctccga aatcgacaaa ccgtctcagg gatcccatca tcatcatcat cactagtaac    1500
tcga                                                                 1504
```

<210> SEQ ID NO 55
<211> LENGTH: 497
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 55

```
Met Gly Glu Gln Lys Leu Ile Ser Glu Glu Leu Gly Gly Ser Gly
1               5                   10                  15

Gly Gly Ser Gly Gly Gly Ile Ser Leu Ile Ala Ala Leu Ala Val Asp
            20                  25                  30

Arg Val Ile Gly Met Glu Asn Ala Met Pro Trp Asn Leu Pro Ala Asp
        35                  40                  45

Leu Ala Trp Phe Lys Arg Asn Thr Leu Asn Lys Pro Val Ile Met Gly
    50                  55                  60

Arg His Thr Trp Glu Ser Ile Gly Arg Pro Leu Pro Gly Arg Lys Asn
65                  70                  75                  80

Ile Ile Leu Ser Ser Gln Pro Gly Thr Asp Asp Arg Val Thr Trp Val
                85                  90                  95

Lys Ser Val Asp Glu Ala Ile Ala Ala Ala Gly Asp Val Pro Glu Ile
            100                 105                 110

Met Val Ile Gly Gly Gly Arg Val Tyr Glu Gln Phe Leu Pro Lys Ala
        115                 120                 125

Gln Lys Leu Tyr Leu Thr His Ile Asp Ala Glu Val Glu Gly Asp Thr
    130                 135                 140

His Phe Pro Asp Tyr Glu Pro Asp Asp Trp Glu Ser Val Phe Ser Glu
145                 150                 155                 160

Phe His Asp Ala Asp Ala Gln Asn Ser His Ser Tyr Ser Phe Glu Ile
                165                 170                 175

Leu Glu Arg Arg Gly Gly Ile Ser Leu Ile Ala Ala Leu Ala Val Asp
            180                 185                 190

Arg Val Ile Gly Met Glu Asn Ala Met Pro Trp Asn Leu Pro Ala Asp
        195                 200                 205

Leu Ala Trp Phe Lys Arg Asn Thr Leu Asn Lys Pro Val Ile Met Gly
    210                 215                 220

Arg His Thr Trp Glu Ser Ile Gly Arg Pro Leu Pro Gly Arg Lys Asn
225                 230                 235                 240

Ile Ile Leu Ser Ser Gln Pro Gly Thr Asp Asp Arg Val Thr Trp Val
                245                 250                 255

Lys Ser Val Asp Glu Ala Ile Ala Ala Ala Gly Asp Val Pro Glu Ile
            260                 265                 270

Met Val Ile Gly Gly Gly Arg Val Tyr Glu Gln Phe Leu Pro Lys Ala
        275                 280                 285

Gln Lys Leu Tyr Leu Thr His Ile Asp Ala Glu Val Glu Gly Asp Thr
    290                 295                 300
```

His Phe Pro Asp Tyr Glu Pro Asp Asp Trp Glu Ser Val Phe Ser Glu
305                 310                 315                 320

Phe His Asp Ala Asp Ala Gln Asn Ser His Ser Tyr Ser Phe Glu Ile
            325                 330                 335

Leu Glu Arg Arg Gly Glu Leu Gly Gly Ser Gly Gly Gly Gly Ser Gly
        340                 345                 350

Gly Gly Gly Ser Gly Gly Gly Gly Ser Gly Gly Gly Gly Ser Gly Gly
    355                 360                 365

Gly Gly Ser Gly Gly Gly Gly Ser Gly Gly Gly Gly Ser Gly Gly Gly
370                 375                 380

Gly Ser Gly Gly Ala Ser Ser Ser Asp Ser Pro Arg Asn Leu Glu Val
385                 390                 395                 400

Thr Asn Ala Thr Pro Asn Ser Leu Thr Ile Ser Trp Asp Asp Tyr Thr
            405                 410                 415

Ser Ala Ser Tyr Tyr Arg Ile Thr Tyr Gly Glu Thr Gly Gly Asn Ser
            420                 425                 430

Pro Ser Gln Glu Phe Thr Val Pro Gly Asn Thr Tyr Asn Ala Thr Val
        435                 440                 445

Ser Gly Leu Arg Pro Gly Gln Asp Tyr Ile Ile Thr Val Tyr Ala Val
    450                 455                 460

Thr Tyr Arg Asp Asn Tyr Ser Tyr Ser Asn Pro Ile Ser Ile Asn Tyr
465                 470                 475                 480

Arg Thr Glu Ile Asp Lys Pro Ser Gln Gly Ser His His His His His
            485                 490                 495

His

<210> SEQ ID NO 56
<211> LENGTH: 1505
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56
ccatgggcga acaaaagctt atttctgaag aggacttggg cggttcaggt ggtggctcgg      60
gaggcggcat cagtctgatt gcggcgttag cggtagatcg cgttatcggc atggaaaacg     120
ccatgccgtg gaacctgcct gccgatctcg cctggtttaa acgcaacacc ttaaataaac     180
ccgtgattat gggccgccat acctgggaat caatcggtcg tccgttgcca ggacgcaaaa     240
atattatcct cagcagtcaa ccgggtacgg acgatcgcgt aacgtgggtg aagtcggtgg     300
atgaagccat cgcggcggct ggtgacgtac cagaaatcat ggtgattggc ggcggtcgcg     360
tttatgaaca gttcttgcca aaagcgcaaa aactgtatct gacgcatatc gacgcagaag     420
tggaaggcga cacccatttc ccggattacg agccggatga ctgggaatcg gtattcagtg     480
aattccacga tgctgatgcg cagaactctc acagctatag ctttgagatt ctggagcggc     540
ggggcggcat tagccttatt gccgccttag cggttgatcg cgtgatcgga atggagaacg     600
caatgccctg gaatcttccg gcagaccttg cctggttcaa acgcaacact ttaaacaagc     660
ctgtcattat gggccgtcac acatgggagt caattggtcg tcccctgcct gggcgcaaaa     720
atatcatctt gtcctcgcag cctgggacag atgatcgcgt tacatgggtg aagtccgtag     780
acgaagcgat tgccgctgcc ggcgatgtgc ccgagattat ggtaatcggg ggagggcgtg     840
tttacgaaca atttctgccc aaagctcaga aattataccct gacgcacatc gacgcggagg     900

```
tcgaaggtga cacacacttt ccagattatg agcctgatga ttgggaatcc gttttctcag    960
aatttcatga cgcggatgct caaaactcgc actcgtactc ttttgaaatt ttagagcgcc   1020
gtggcgagct cggaggttcc ggcggggcg gaagcggagg tggaggctca ggggcggag   1080 ggtcgggcgg tggaggttcg gggggaggcg ggagcggtgg cggtggttca ggaggagggg   1140
gttccggggg tggtggatcg ggcggtgcta gctcctccga ctctccgcgt aacctggagg   1200
ttaccaacgc tactccgaac tctctgacta tctcttggga cgattatact tccgcttctt   1260
attaccgtat cacctacggc gaaactggtg gtaactcccc gagccaggaa ttcactgttc   1320
cgggaaatac ttataatgcg accgtcagcg gcctgagacc gggccaggat tatatcatta   1380
ccgtgtacgc tgtaacctat cgtgacaatt attcctattc aaacccaatc agcatcaatt   1440
atcgcaccga atcgacaaa ccgtctcagg gatcccatca tcatcatcat cactagtaac   1500
tcgag                                                               1505
```

<210> SEQ ID NO 57
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Met Gly Glu Gln Lys Leu Ile Ser Glu Glu Asp Leu Gly Gly Ser Gly
1               5                   10                  15

Gly Gly Ser Gly Gly Gly Ile Ser Leu Ile Ala Ala Leu Ala Val Asp
            20                  25                  30

Arg Val Ile Gly Met Glu Asn Ala Met Pro Trp Asn Leu Pro Ala Asp
        35                  40                  45

Leu Ala Trp Phe Lys Arg Asn Thr Leu Asn Lys Pro Val Ile Met Gly
    50                  55                  60

Arg His Thr Trp Glu Ser Ile Gly Arg Pro Leu Pro Gly Arg Lys Asn
65                  70                  75                  80

Ile Ile Leu Ser Ser Gln Pro Gly Thr Asp Asp Arg Val Thr Trp Val
                85                  90                  95

Lys Ser Val Asp Glu Ala Ile Ala Ala Gly Asp Val Pro Glu Ile
            100                 105                 110

Met Val Ile Gly Gly Gly Arg Val Tyr Glu Gln Phe Leu Pro Lys Ala
        115                 120                 125

Gln Lys Leu Tyr Leu Thr His Ile Asp Ala Glu Val Glu Gly Asp Thr
    130                 135                 140

His Phe Pro Asp Tyr Glu Pro Asp Asp Trp Glu Ser Val Phe Ser Glu
145                 150                 155                 160

Phe His Asp Ala Asp Ala Gln Asn Ser His Ser Tyr Ser Phe Glu Ile
                165                 170                 175

Leu Glu Arg Arg Gly Gly Ile Ser Leu Ile Ala Ala Leu Ala Val Asp
            180                 185                 190

Arg Val Ile Gly Met Glu Asn Ala Met Pro Trp Asn Leu Pro Ala Asp
        195                 200                 205

Leu Ala Trp Phe Lys Arg Asn Thr Leu Asn Lys Pro Val Ile Met Gly
    210                 215                 220

Arg His Thr Trp Glu Ser Ile Gly Arg Pro Leu Pro Gly Arg Lys Asn
225                 230                 235                 240

Ile Ile Leu Ser Ser Gln Pro Gly Thr Asp Asp Arg Val Thr Trp Val
            245                 250                 255

Lys Ser Val Asp Glu Ala Ile Ala Ala Ala Gly Asp Val Pro Glu Ile
        260                 265                 270

Met Val Ile Gly Gly Gly Arg Val Tyr Glu Gln Phe Leu Pro Lys Ala
            275                 280                 285

Gln Lys Leu Tyr Leu Thr His Ile Asp Ala Glu Val Glu Gly Asp Thr
        290                 295                 300

His Phe Pro Asp Tyr Glu Pro Asp Asp Trp Glu Ser Val Phe Ser Glu
305                 310                 315                 320

Phe His Asp Ala Asp Ala Gln Asn Ser His Ser Tyr Ser Phe Glu Ile
                325                 330                 335

Leu Glu Arg Arg Gly Glu Leu Gly Gly Ser Gly Gly Gly Ser Gly
            340                 345                 350

Gly Gly Gly Ser Gly Gly Gly Ser Gly Gly Gly Gly Ser Gly Gly
        355                 360                 365

Gly Gly Ser Gly Gly Gly Ser Gly Gly Gly Ser Gly Gly Gly
        370                 375                 380

Gly Ser Gly Gly Ala Ser Ser Ser Asp Ser Pro Arg Asn Leu Glu Val
385                 390                 395                 400

Thr Asn Ala Thr Pro Asn Ser Leu Thr Ile Ser Trp Asp Ala Pro Ala
            405                 410                 415

Val Thr Val Arg Tyr Tyr Arg Ile Thr Tyr Gly Glu Thr Gly Gly Asn
                420                 425                 430

Ser Pro Ser Gln Glu Phe Thr Val Pro Gly Ser Lys Ser Thr Ala Thr
            435                 440                 445

Ile Ser Gly Leu Lys Pro Gly Gln Asp Tyr Thr Ile Thr Val Tyr Ala
450                 455                 460

Val Thr Gly Arg Asp Gly Ser Pro Ala Ser Ser Lys Pro Ile Ser Ile
465                 470                 475                 480

Asn Tyr Arg Thr Glu Ile Asp Lys Pro Ser Gln Gly Ser His His His
            485                 490                 495

His His His

<210> SEQ ID NO 58
<211> LENGTH: 1511
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58
ccatgggcga acaaaagctt atttctgaag aggacttggg cggttcaggt ggtggctcgg    60
gaggcggcat cagtctgatt gcggcgttag cggtagatcg cgttatcggc atggaaaacg   120
ccatgccgtg gaacctgcct gccgatctcg cctggtttaa acgcaacacc ttaaataaac   180
ccgtgattat gggccgccat acctgggaat caatcggtcg tccgttgcca ggacgcaaaa   240
atattatcct cagcagtcaa ccgggtacgg acgatcgcgt aacgtgggtg aagtcggtgg   300
atgaagccat cgcggcggct ggtgacgtac agaaatcat ggtgattggc ggcggtcgcg   360
tttatgaaca gttcttgcca aaagcgcaaa aactgtatct gacgcatatc gacgcagaag   420
tggaaggcga cacccatttc ccggattacg agccggatga ctgggaatcg gtattcagtg   480
aattccacga tgctgatgcg cagaactctc acagctatag ctttgagatt ctggagcggc   540

```
ggggcggcat tagccttatt gccgccttag cggttgatcg cgtgatcgga atggagaacg    600
caatgccctg gaatcttccg gcagaccttg cctggttcaa acgcaacact ttaaacaagc    660
ctgtcattat gggccgtcac acatgggagt caattggtcg tccctgcct gggcgcaaaa    720 atatcatctt gtcctcgcag cctgggacag atgatcgcgt tacatgggtg aagtccgtag    780
acgaagcgat tgccgctgcc ggcgatgtgc ccgagattat ggtaatcggg ggagggcgtg    840
tttacgaaca atttctgccc aaagctcaga aattatacct gacgcacatc gacgcggagg    900
tcgaaggtga cacacacttt ccagattatg agcctgatga ttgggaatcc gttttctcag    960
aatttcatga cgcggatgct caaaactcgc actcgtactc ttttgaaatt ttagagcgcc   1020
gtggcgagct cggaggttcc ggcgggggcg gaagcggagg tggaggctca gggggcggag   1080
ggtcgggcgg tggaggttcg gggggaggcg ggagcggtgg cggtggttca ggaggagggg   1140
gttccggggg tggtggatcg ggcggtgcta gctcctccga ctctccgcgt aacctggagg   1200
ttaccaacgc aactccgaac tctctgacta tttcttggga tgctcctgct gtcacagtga   1260
gatattaccg tatcacctac ggcgaaactg gtggtaactc cccgagccag gaattcactg   1320
ttccggggag caagtctaca gcgaccatca gcggtctgaa accgggccag gattatacca   1380
ttaccgtgta cgctgtaact ggccgtgacg gaagccccgc aagcagcaag ccaatcagca   1440
tcaattatcg caccgaaatc gacaaaccgt ctcagggatc ccatcatcat catcatcact   1500
agtaactcga g                                                       1511
```

<210> SEQ ID NO 59
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Met Gly Glu Gln Lys Leu Ile Ser Glu Glu Asp Leu Gly Gly Ser Gly
1               5                   10                  15

Gly Gly Ser Gly Gly Gly Ile Ser Leu Ile Ala Ala Leu Ala Val Asp
            20                  25                  30

Arg Val Ile Gly Met Glu Asn Ala Met Pro Trp Asn Leu Pro Ala Asp
        35                  40                  45

Leu Ala Trp Phe Lys Arg Asn Thr Leu Asn Lys Pro Val Ile Met Gly
    50                  55                  60

Arg His Thr Trp Glu Ser Ile Gly Arg Pro Leu Pro Gly Arg Lys Asn
65                  70                  75                  80

Ile Ile Leu Ser Ser Gln Pro Gly Thr Asp Asp Arg Val Thr Trp Val
                85                  90                  95

Lys Ser Val Asp Glu Ala Ile Ala Ala Gly Asp Val Pro Glu Ile
            100                 105                 110

Met Val Ile Gly Gly Gly Arg Val Tyr Glu Gln Phe Leu Pro Lys Ala
        115                 120                 125

Gln Lys Leu Tyr Leu Thr His Ile Asp Ala Glu Val Glu Gly Asp Thr
    130                 135                 140

His Phe Pro Asp Tyr Glu Pro Asp Asp Trp Glu Ser Val Phe Ser Glu
145                 150                 155                 160

Phe His Asp Ala Asp Ala Gln Asn Ser His Ser Tyr Ser Phe Glu Ile
                165                 170                 175

Leu Glu Arg Arg Gly Gly Ile Ser Leu Ile Ala Ala Leu Ala Val Asp 180                 185                 190
Arg Val Ile Gly Met Glu Asn Ala Met Pro Trp Asn Leu Pro Ala Asp
                195                 200                 205

Leu Ala Trp Phe Lys Arg Asn Thr Leu Asn Lys Pro Val Ile Met Gly
            210                 215                 220

Arg His Thr Trp Glu Ser Ile Gly Arg Pro Leu Pro Gly Arg Lys Asn
225                 230                 235                 240

Ile Ile Leu Ser Ser Gln Pro Gly Thr Asp Asp Arg Val Thr Trp Val
                245                 250                 255

Lys Ser Val Asp Glu Ala Ile Ala Ala Ala Gly Asp Val Pro Glu Ile
            260                 265                 270

Met Val Ile Gly Gly Gly Arg Val Tyr Glu Gln Phe Leu Pro Lys Ala
        275                 280                 285

Gln Lys Leu Tyr Leu Thr His Ile Asp Ala Glu Val Glu Gly Asp Thr
        290                 295                 300

His Phe Pro Asp Tyr Glu Pro Asp Asp Trp Glu Ser Val Phe Ser Glu
305                 310                 315                 320

Phe His Asp Ala Asp Ala Gln Asn Ser His Ser Tyr Ser Phe Glu Ile
                325                 330                 335

Leu Glu Arg Arg Gly Glu Leu Gly Gly Gly Ser Gly Gly Gly Gly
            340                 345                 350

Ser Gly Gly Gly Gly Ser Ala Ser Ser Asp Ser Pro Arg Asn Leu
        355                 360                 365

Glu Val Thr Asn Ala Thr Pro Asn Ser Leu Thr Ile Ser Trp Asp Asn
        370                 375                 380

Ser Asn Tyr Ala Ser Tyr Tyr Arg Ile Thr Tyr Gly Glu Thr Gly Gly
385                 390                 395                 400

Asn Ser Pro Ser Gln Glu Leu Thr Val Pro Gly Ser Tyr Asn Ala
                405                 410                 415

Thr Ile Ser Gly Leu Lys Pro Gly Gln Asp Tyr Ile Ile Thr Val Tyr
            420                 425                 430

Ala Val Thr Tyr Arg Asp Asn Tyr Ser Tyr Ser Asn Leu Ile Ser Ile
        435                 440                 445

Asn Tyr Arg Ser Glu Ile Asp Lys Pro Ser Gln Gly Ser His His His
    450                 455                 460

His His His
465

<210> SEQ ID NO 60
<211> LENGTH: 470
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Met Ala Glu Ala Gly Ile Thr Gly Thr Trp Tyr Asn Gln Ser Gly Ser
1               5                   10                  15

Thr Phe Thr Val Thr Ala Gly Ala Asp Gly Asn Leu Thr Gly Gln Tyr
            20                  25                  30

Glu Asn Arg Ala Gln Gly Thr Gly Cys Gln Asn Ser Pro Tyr Thr Leu
        35                  40                  45

Thr Gly Arg Tyr Asn Gly Thr Lys Leu Glu Trp Arg Val Glu Trp Asn
    50                  55                  60

```
Asn Ser Thr Glu Asn Cys His Ser Arg Thr Glu Trp Arg Gly Gln Tyr
 65                  70                  75                  80

Gln Gly Gly Ala Glu Ala Arg Ile Asn Thr Gln Trp Asn Leu Thr Tyr
             85                  90                  95

Glu Gly Gly Ser Gly Pro Ala Thr Glu Gln Gly Gln Asp Thr Phe Thr
            100                 105                 110

Lys Val Lys Glu Leu Gly Gly Ser Gly Gly Gly Ser Gly Gly Gly Ser
        115                 120                 125

Gly Gly Met Ile Ser Leu Ile Ala Ala Leu Ala Val Asp Arg Val Ile
    130                 135                 140

Gly Met Glu Asn Ala Met Pro Trp Asn Leu Pro Ala Asp Leu Ala Trp
145                 150                 155                 160

Phe Lys Arg Asn Thr Leu Asn Lys Pro Val Ile Met Gly Arg His Thr
                165                 170                 175

Trp Glu Ser Ile Gly Arg Pro Leu Pro Gly Arg Lys Asn Ile Ile Leu
            180                 185                 190

Ser Ser Gln Pro Gly Thr Asp Asp Arg Val Thr Trp Val Lys Ser Val
        195                 200                 205

Asp Glu Ala Ile Ala Ala Gly Asp Val Pro Glu Ile Met Val Ile
    210                 215                 220

Gly Gly Gly Arg Val Tyr Glu Gln Phe Leu Pro Lys Ala Gln Lys Leu
225                 230                 235                 240

Tyr Leu Thr His Ile Asp Ala Glu Val Glu Gly Asp Thr His Phe Pro
                245                 250                 255

Asp Tyr Glu Pro Asp Asp Trp Glu Ser Val Phe Ser Glu Phe His Asp
            260                 265                 270

Ala Asp Ala Gln Asn Ser His Ser Tyr Ser Phe Glu Ile Leu Glu Arg
        275                 280                 285

Arg Gly Met Ile Ser Leu Ile Ala Ala Leu Ala Val Asp Arg Val Ile
    290                 295                 300

Gly Met Glu Asn Ala Met Pro Trp Asn Leu Pro Ala Asp Leu Ala Trp
305                 310                 315                 320

Phe Lys Arg Asn Thr Leu Asn Lys Pro Val Ile Met Gly Arg His Thr
                325                 330                 335

Trp Glu Ser Ile Gly Arg Pro Leu Pro Gly Arg Lys Asn Ile Ile Leu
            340                 345                 350

Ser Ser Gln Pro Gly Thr Asp Asp Arg Val Thr Trp Val Lys Ser Val
        355                 360                 365

Asp Glu Ala Ile Ala Ala Gly Asp Val Pro Glu Ile Met Val Ile
    370                 375                 380

Gly Gly Gly Arg Val Tyr Glu Gln Phe Leu Pro Lys Ala Gln Lys Leu
385                 390                 395                 400

Tyr Leu Thr His Ile Asp Ala Glu Val Glu Gly Asp Thr His Phe Pro
                405                 410                 415

Asp Tyr Glu Pro Asp Asp Trp Glu Ser Val Phe Ser Glu Phe His Asp
            420                 425                 430

Ala Asp Ala Gln Asn Ser His Ser Tyr Ser Phe Glu Ile Leu Glu Arg
        435                 440                 445

Arg Gly Gly Ser Gly Gly Gly Ser Gly Gly Gly Ser Gly Gly Asp Tyr
    450                 455                 460

Lys Asp Asp Asp Lys
465                 470
```

```
<210> SEQ ID NO 61
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Ser Ser Asp Ser Pro Arg Asn Leu Glu Val Thr Asn Ala Thr Pro Asn
1               5                   10                  15

Ser Leu Thr Ile Ser Trp Asp Asn Ser Asn Tyr Ala Ser Tyr Tyr Arg
            20                  25                  30

Ile Thr Tyr Gly Glu Thr Gly Gly Asn Ser Pro Ser Gln Glu Leu Thr
        35                  40                  45

Val Pro Gly Ser Thr Tyr Asn Ala Thr Ile Ser Cys Leu Lys Pro Gly
    50                  55                  60

Gln Asp Tyr Ile Ile Thr Val Tyr Ala Val Thr Tyr Arg Asp Asn Tyr
65                  70                  75                  80

Ser Tyr Ser Asn Leu Ile Ser Ile Asn Tyr Arg Ser Glu Ile Asp Lys
                85                  90                  95

Pro Ser Gln

<210> SEQ ID NO 62
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Ser Ser Asp Ser Pro Arg Asn Leu Glu Val Thr Asn Ala Thr Pro Asn
1               5                   10                  15

Ser Leu Thr Ile Ser Trp Asp Asn Ser Asn Tyr Ala Ser Tyr Tyr Arg
            20                  25                  30

Ile Thr Tyr Gly Glu Thr Gly Gly Asn Ser Pro Ser Gln Glu Leu Thr
        35                  40                  45

Val Pro Gly Ser Thr Tyr Asn Ala Thr Ile Ser Gly Leu Cys Pro Gly
    50                  55                  60

Gln Asp Tyr Ile Ile Thr Val Tyr Ala Val Thr Tyr Arg Asp Asn Tyr
65                  70                  75                  80

Ser Tyr Ser Asn Leu Ile Ser Ile Asn Tyr Arg Ser Glu Ile Asp Lys
                85                  90                  95

Pro Ser Gln

<210> SEQ ID NO 63
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 63

Gly Gly Gly Gly Ser
1               5
```

```
<210> SEQ ID NO 64
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 64

Glu Ala Ala Ala Lys
1               5

<210> SEQ ID NO 65
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 65

His His His His His His
1               5

<210> SEQ ID NO 66
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Leu Thr Val Pro Gly Ser
1               5

<210> SEQ ID NO 67
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gly Leu Lys Pro Gly
1               5

<210> SEQ ID NO 68
<211> LENGTH: 75
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Ser Pro Arg Asn Leu Glu Val Thr Asn Ala Thr Pro Asn Ser Leu Thr
1               5                   10                  15

Ile Ser Trp Asp Asn Ser Asn Tyr Ala Ser Tyr Arg Ile Thr Tyr
                20                  25                  30

Gly Glu Thr Gly Gly Asn Ser Pro Ser Gln Glu Leu Thr Val Pro Gly
            35                  40                  45

Ser Thr Tyr Asn Ala Thr Ile Ser Gly Leu Lys Pro Gly Gln Asp Tyr
```

```
                  50                  55                  60

Ile Ile Thr Val Tyr Ala Val Thr Tyr Arg Asp
 65                  70                  75

<210> SEQ ID NO 69
<211> LENGTH: 78
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Ala Pro Lys Asn Leu Val Val Ser Glu Val Thr Glu Asp Ser Ala Arg
 1               5                  10                  15

Leu Ser Trp Asp Asp Pro Trp Ala Phe Tyr Glu Ser Phe Leu Ile Gln
                20                  25                  30

Tyr Gln Glu Ser Glu Lys Val Gly Glu Ala Ile Val Leu Thr Val Pro
             35                  40                  45

Gly Ser Glu Arg Ser Tyr Asp Leu Thr Gly Leu Lys Pro Gly Thr Glu
         50                  55                  60

Tyr Thr Val Ser Ile Tyr Gly Val His Asn Val Tyr Lys Asp
 65                  70                  75

<210> SEQ ID NO 70
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Gly Gly Gly Gly Ser Gly Gly Gly Gly Ser Gly Gly Gly Gly Ser Gly
 1               5                  10                  15

Gly Gly Gly Ser Gly Gly Gly Gly Ser Gly Gly Gly Gly Ser Gly Gly
                20                  25                  30

Gly Gly Ser Gly Gly Gly Gly Ser Gly Gly Gly Gly Ser
             35                  40                  45
```

EPCAM TARGETED POLYPEPTIDES, CONJUGATES THEREOF, AND METHODS OF USE THEREOF

RELATED APPLICATION

This application claims the benefit of priority of U.S. Provisional Application Ser. No. 62/458,432 filed on Feb. 13, 2017, which application is incorporated by reference herein.

SEQUENCE LISTING

The instant application contains a Sequence Listing which has been submitted electronically in ASCII format and is hereby incorporated by reference in its entirety. Said ASCII copy, created on Feb. 28, 2018, is named 09531_432US1_SL.txt and is 70,637 bytes in size.

GOVERNMENT FUNDING

This invention was made with government support under T32 GM008244, R21 EB019518, R21 CA185627 and F30 CA210345 awarded by the National Institutes of Health. The government has certain rights in the invention.

BACKGROUND OF THE INVENTION

Epithelial cell adhesion molecule (EpCAM) is a transmembrane glycoprotein that mediates $Ca^{2+}$-independent homotypic cell-cell adhesion in epithelia and is involved in cell signaling, migration, proliferation, and differentiation. EpCAM is an attractive cancer target due to its overexpression in many different carcinomas including those of the breast, pancreas, esophagus, colon, and prostate (Went, et al., *Hum. Pathol.* 2004, 35 (1), 122-128). Many ligands have been evolved for EpCAM binding including, antibodies and their fragments, shark vNARs, DARPins, and small cyclic peptides (Martin-Killias, et al., *Clin. Cancer Res.* 2011, 17 (1), 100-110; Stefan, et al., *J. Mol. Biol.* 2011, 413 (4), 826-843; Zielonka, et al., *J. Biotechnol.* 2014, 191, 236-245; Eder, et al., *Eur. J. Nucl. Med. Mol. Imaging* 2010, 37 (7), 1397-1407; Iwasaki, et al., *J. Mol. Evol.* 2015, 81 (5-6), 210-217). However, many of these ligands have low affinity, insufficient specificity, target different epitopes, are too large in size and/or present production and downstream handling difficulties.

Accordingly, new compositions and methods are needed to treat and monitor cancer progression. In particular, new compositions and methods are needed for targeting EpCAM.

SUMMARY OF THE INVENTION

Thus, certain embodiments of the invention provide a polypeptide comprising an amino acid sequence having between about 65% to about 99% sequence identity to SEQ ID NO: 1 or SEQ ID NO:5, wherein the polypeptide comprises one or more variations that increase its binding affinity to epithelial cell adhesion molecule (EpCAM).

Certain embodiments of the invention provide a polypeptide comprising an amino acid sequence having at least about 85% sequence identity to a sequence selected from the group consisting of SEQ ID NO:6, SEQ ID NO:7, SEQ ID NO:8, SEQ ID NO:9, SEQ ID NO: 10, SEQ ID NO: 11, SEQ ID NO: 12, SEQ ID NO: 13, SEQ ID NO: 14, SEQ ID NO: 15, SEQ ID NO: 19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:47, SEQ ID NO:49, SEQ ID NO:61, and SEQ ID NO:62, wherein the polypeptide is capable of binding to epithelial cell adhesion molecule (EpCAM).

Certain embodiments of the invention provide a nucleic acid encoding a polypeptide described herein.

Certain embodiments of the invention provide an expression cassette comprising a nucleic acid sequence as described herein and a promoter operably linked to the nucleic acid.

Certain embodiments of the invention provide a vector comprising an expression cassette described herein.

Certain embodiments of the invention provide a conjugate of formula (I):

$$P\text{-}(L\text{-}A)_n \qquad (I)$$

wherein:

P is a polypeptide as described herein that binds to epithelial cell adhesion molecule (EpCAM);

each L is independently a direct bond or a linking group;

each A is independently a detectable agent or a biologically active agent; and n is 1 to 5.

Certain embodiments of the invention provide a chemically self-assembled nanoring (CSAN) comprising a plurality of conjugates as described herein and a plurality of BisMTX compounds.

Certain embodiments of the invention provide a BisMTX compound described herein.

Certain embodiments of the invention provide a CSAN as described herein.

Certain embodiments of the invention provide a CSAN operably linked to a peptide of the invention Certain embodiments of the invention provide a pharmaceutical composition comprising a conjugate (e.g., conjugate of formula (I) or CSAN conjugated to a peptide of the invention) described herein and a pharmaceutically acceptable excipient.

Certain embodiments of the invention provide a method for treating or preventing cancer in an animal (e.g., a human) comprising administering a therapeutically effective amount of a conjugate (e.g., conjugate of formula (I) or CSAN conjugated to a peptide of the invention) described herein to the animal.

Certain embodiments of the invention provide a conjugate (e.g., conjugate of formula (I) or CSAN conjugated to a peptide of the invention) for use in medical therapy.

Certain embodiments of the invention provide a conjugate (e.g., conjugate of formula (I) or CSAN conjugated to a peptide of the invention) or the prophylactic or therapeutic treatment of cancer.

Certain embodiments of the invention provide the use of a conjugate described herein or a CSAN described herein to prepare a medicament for treating cancer in an animal (e.g., a human).

Certain embodiments of the invention provide a method of detecting an EpCAM molecule, comprising contacting a cell with a conjugate described herein described herein.

Certain embodiments of the invention provide a method of detecting EpCAM positive cells in a biological sample obtained from an animal, comprising detecting whether EpCAM positive cells are present in the sample by contacting the sample with a conjugate described herein and detecting a signal from the detectable agent.

Certain embodiments of the invention provide a method of detecting cancer cells in a biological sample obtained from an animal, comprising contacting the sample with a conjugate described herein and detecting a signal from the detectable agent, wherein a signal that is greater than a signal from a non-cancerous control sample indicates the presence of cancer cells in the biological sample.

Certain embodiments of the invention provide a method of diagnosing cancer in an animal (e.g., a human patient), comprising 1) obtaining a biological sample from the animal; 2) detecting whether cells within the sample overexpress EpCAM as compared to cells from a control sample by contacting the sample with a conjugate described herein and quantifying EpCAM expression; and 3) diagnosing the animal with cancer when cells that overexpress EpCAM are detected in the sample.

Certain embodiments of the invention provide a method of detecting cancer in an animal (e.g., a human patient), comprising administering a conjugate of described herein to the animal, wherein the conjugate binds to an EpCAM molecule; and detecting a signal from the detectable agent, wherein a signal greater than a signal from a control animal without cancer indicates the animal has cancer.

Certain embodiments of the invention provide a method for determining the effectiveness of a cancer therapy in an animal (e.g., a human patient), comprising
1) administering a conjugate described herein to the animal and measuring a first signal from the detectable agent;
2) administering a cancer therapy;
3) administering a conjugate described herein to the animal and measuring a second signal from the detectable agent; and
4) comparing the first signal with the second signal, wherein the cancer therapy is effective if the second signal is less than the first signal.

Certain embodiments of the invention provide a kit comprising:
1) a conjugate described herein;
2) instructions for loading a radionuclide into the conjugate to generate a radiolabeled conjugate; and
3) instructions for administering the radiolabeled conjugate to an animal.

Certain embodiments of the invention provide a method of using a polypeptide, conjugate or CSAN described herein.

The invention also provides processes and intermediates disclosed herein that are useful for preparing compounds, peptides and CSANs described herein.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIGS. 1A-D. Characterization of EpCAM-binding fibronectin populations and individual clones. Polyclonal populations of soluble EpCAM-binding fibronectin domains were assessed for relative affinity against EpCAM-expressing MCF-7 cells at 10 nM by flow cytometry analysis (FIG. 1A). The percentage of events appearing above the $95^{th}$ percentile and 2-fold above the $95^{th}$ percentile of the negative control were quantified as mean±range of 2 trials. (FIG. 1B). Individual fibronectin clones were titrated against MCF-7 cells to determine their affinities (FIG. 1C). Affinities are presented as mean±standard error of 2-5 titrations. The same fibronectin clones were assessed for binding against EpCAM-negative U87 cells at 100 nM by flow cytometry analysis to determine specificity (FIG. 1D). Median fluorescence intensities are presented as mean±standard error of 2-5 trials. All samples include U87 (EpCAM-negative) data; most U87 bars are not visible because of their near-zero fluorescence after background correction.

FIG. 2. Sequences for EpCAM-binding fibronectin domains. Sequences of EpCAM-binding fibronectin domains were compared by sequence alignment. Residues that match consensus are denoted by a •. Engineered loop residues are shown in bold. The P87L/S mutation is shown in italics. Figure discloses SEQ ID NOS 6, 6-7, 6, and 8-15, respectively, in order of appearance.

(FIG. 6A) Clone 3.2.20 was titrated twice, and the $K_D$ value is shown as the mean±standard deviation of the two independent trials. (FIG. 6B) All other clones were titrated only once, and are portrayed as estimates without error. Estimated $K_D$ values ranged from 130 nM to 190 nM. Notably, no clones possessed measurable affinity for the irrelevant soluble human CD3 ectodomain.

FIG. 7. BLAST Alignment of Fn3HP Clone and Centyrin® Scaffold (Janssen R&D). BLAST alignment of the anti-EpCAM Fn 3.4.5 clone with the Centyrin® platform identified two homologous regions. Figure discloses SEQ ID NOS 68-69, respectively, in order of appearance.

FIG. 8. Fibronectin Structure Highlighting Binding and Cysteine-Amenable Regions. The fibronectin scaffold consists of seven anti-parallel β-sheets connected by flexible loop regions. Three of these loop regions—termed the BC, DE, and FG loops—comprise the suspected binding paratope (depicted in red). The EF loop (depicted in blue) houses the homologous residues identified in the BLAST alignment.

FIG. 9. Expression for Fn 3.4.5 G65C and CtermC colonies.

FIG. 17. Analysis of NODAGA-Fn-NT and NODAGA-Fn-C5 protein structure using circular dichroism.

FIG. 22. Schematic of 1DD-Fn-v4. Figure discloses "$(G_4S)_9$" as SEQ ID NO: 70.

FIG. 24. Titration of 1DD-Fn-v4 against EpCAM+ MCF-7 cells.

FIGS. 29A-C. Cell Surface Engineering with Chemically Self-Assembled Nanorings (CSANs). (A) CSANs are comprised of targeted-$DHFR^2$ fusion proteins that are spontaneously oligomerized by the chemical dimerizer, bisMTX; they can be pharmacologically disassembled by the FDA-approved antibiotic trimethoprim. (B) DSPE-PEG$_{2000}$-DBCO moieties spontaneously insert into cell membranes, driven by negative enthalpy and stabilized by the hydrophobic effect.[18] EpCAM-targeted Fn3 CSANs oligomerized with an azide-bisMTX dimerizer are then installed on the cell surface through a copper-free, strain-promoted alkyne/azide cycloaddition. The CSAN-functionalized cells can then form targeted interactions with EpCAM+ cells, and these interactions can be reversed with trimethoprim. (C) Similarly, cells modified with DSPE-PEG$_{2000}$-biotin moieties can be functionalized with bispecific mSA/Fn3 CSANs, enabling recognition of EpCAM+ target cells. Trimethoprim-induced disassembly of the CSAN reverses the intercellular interactions.

FIGS. 30A-H. Phospholipid Conjugates Hydrophobically Insert into Cell Membranes. Cells were modified with increasing concentrations of either DSPE-PEG$_{2000}$-biotin or DSPE-PEG$_{2000}$-DBCO through one of two methods: (1) resuspension in phospholipid-containing buffer (ex vitro), or (2) active culture in phospholipid-containing media (in vitro). Cells were subsequently analyzed by flow cytometry using streptavidin- or azide-conjugated Alexa Fluor 488 to assess the presence of biotin and DBCO moieties, respectively, on the cell surface. Both adherent MCF-7 cells and suspensive Raji cells can be successfully modified with DSPE-PEG$_{2000}$-biotin or DSPE-PEG$_{2000}$-DBCO through both the ex vitro and in vitro approaches. While insertion experiments were performed in triplicate, a representative trial of each condition is shown here. A quantitative analysis of the triplicate data is presented in FIG. 37A-B.

FIGS. 31A-D. Cryo-EM Characterization of CSAN Species. The formation of (A) mSA CSANs, (B) Fn3 CSANs, and (C) bispecific mSA/Fn3 CSANs was demonstrated by cryo-EM. The values in parentheses represent the mean diameter±standard deviation of n=29, 40, and 39 nanorings, respectively. (D) The size distribution of mSA, Fn3, and mSA/Fn3 CSANs as assessed by cryo-EM.

FIGS. 32A-E. CSANs are Readily Installed on Phospholipid-Modified Cells. For all panels, cells were labeled with CSANs through one of several methods and then analyzed by flow cytometry with staining for surface-bound nanorings via either an anti-FLAG phycoerythrin or anti-MYC Alexa Fluor 647 conjugate. The non-specific binding of the antibody-fluorophore conjugate is shown in grey, while the specific detection of the indicated CSAN is shown in color. (A) mSA CSANs bind to MCF-7 cells modified with DSPE-PEG$_{2000}$-biotin. (B) Fn3 CSANs formed with azide-bisMTX are conjugated to Raji cells modified with DSPE-PEG$_{2000}$-DBCO. (C) Fn3 CSANs bind to unmodified, EpCAM+ MCF-7 cells. (D) Bispecific mSA/Fn3 CSANs bind to Raji cells modified with DSPE-PEG$_{2000}$-biotin. (E) Bispecific mSA/Fn3 CSANs bind to unmodified, EpCAM+ MCF-7 cells. All experiments were performed in triplicate, with a representative histogram shown for each scenario.

FIG. 33A-D. Membrane Stability and Controlled Dissociation of Phospholipid-Anchored CSANs. (A) Biotin-modified Raji cells were labeled with reduced-avidity mSA CSANs and analyzed by flow cytometry every 24 h, staining for either the CSANs (black) or, in the case of the lipid-only control (grey), for biotin. For this analysis, the MFI values are corrected for the number of cell divisions (as determined by CellTrace Violet labeling) and scaled relative to the MFI values obtained at t=0 h. (B) Biotin-modified Raji cells were labeled with mSA/Fn3 CSANs and then resuspended in culture media with or without 2 μM trimethoprim for 1-2 h at 37° C. Cells were then analyzed by flow cytometry to detect the surface-bound CSANs. (C) Biotin-modified Raji cells labeled with reduced-avidity mSA CSANs were pooled with CTV-labeled Raji cells at a 7:3 ratio and co-cultured for 72 h. Cells were analyzed by flow cytometry every 24 h to ascertain whether the lipid-anchored CSANs had migrated onto the membranes of the CTV+ Raji cells. (D) Raji cells modified with only DSPE-PEG$_{2000}$-biotin (no CSANs) were pooled with CTV-labeled Raji cells at a 7:3 ratio and co-cultured for 72 h. Cells were analyzed by flow cytometry every 24 h to ascertain whether the phospholipid conjugates had migrated onto the membranes of the CTV+ Raji cells. For all panels, data is presented as the mean±standard deviation of at least three trials.

FIGS. 34A-F. CSANs Direct Reversible Cell-Cell Interactions. For the fluorescence microscopy experiment (top row), Raji cells were sequentially labeled with CFSE, DSPE-PEG$_{2000}$-biotin ex vitro, and with or without mSA/Fn3 CSANs; they were then incubated with a monolayer of EpCAM+ MCF-7 cells. (A) In the absence of CSANs, the phospholipid-modified Raji cells are unable to interact with the MCF-7 cells. (B) When functionalized with the mSA/Fn3 CSANs, the EpCAM-targeted Raji cells adhere to the MCF-7 cell monolayer. (C) The EpCAM-targeted Raji cells can be dissociated from the MCF-7 cell monolayer by disassembling the CSAN with trimethoprim (TMP). Scale bars in (a-c) represent 100 μm. For the flow cytometry experiment (bottom row), the target MCF-7 cells were labeled with CFSE while the Raji cells were labeled with CTV. Raji cells were again modified with DSPE-PEG$_{2000}$-biotin ex vitro and with or without mSA/Fn3 CSANs. (D) In the absence of CSANs, the phospholipid-modified Raji cells are unable to interact with the MCF-7 cells. (E) When functionalized with the mSA/Fn3 CSANs, the EpCAM-targeted Raji cells formed stable clusters with the MCF-7 cells. (F) The Raji/MCF-7 cell clusters were readily dissociated with trimethoprim. Data are representative of replicate (n=3) experiments.

FIG. 35A-D. Bioorthogonal CSANs Enable Formation of Multicellular Interactions. For this experiment, three populations of cells were used: (1) EpCAM+ MCF-7 cells adhered to glass coverslips; (2) CFSE-labeled Raji cells sequentially modified with DSPE-PEG$_{2000}$-biotin and mSA/Fn3 CSANs; and (3) a second population of Raji cells labeled with CellTrace Far Red, DSPE-PEG$_{2000}$-DBCO, and mSA CSANs oligomerized with azide-bisMTX, granting them the ability to target unoccupied biotin moieties on the CFSE-labeled Raji cells. (A) In the absence of CSANs, neither Raji cell population is able to adhere to the MCF-7 cell monolayer. (B) When functionalized with the CSANs, the two Raji cell populations are able to interact with each other and the MCF-7 cell monolayer. (C) The cell-cell interactions are largely reversed when the CSAN scaffold is dissassembled with trimethoprim. (D) As the Far Red-labeled Raji cells only have the capability of targeting biotin, they are unable to adhere to the MCF-7 cell monolayer in the absence of the CFSE-labeled Raji cells that were modified with DSPE-PEG$_{2000}$-biotin. Scale bars represent 100 μm.

FIG. 36A-B. Cell Viability is Not Affected by the Hydrophobic Insertion of Phospholipid Conjugates. MCF-7 and Raji cells were modified with increasing concentrations of DSPE-PEG$_{2000}$-biotin or DSPE-PEG$_{2000}$-DBCO through either the ex vitro (buffer) or in vitro (culture) methods, as described in the methods. Following the phospholipid incubation, cells were pelleted (500 g, 5 min, 4° C.) and washed once in 1 mL PBS. Cell viability was determined via trypan blue exclusion using an automated cell counter. For data analysis, the viability of cells incubated in only PBS (no phospholipids) was normalized to 100%, with all other measurements scaled to this reference. Data is presented as the mean±standard deviation of three trials.

FIGS. 37A-B. Membrane Insertion of Phospholipid Conjugates. MCF-7 and Raji cells were modified with increasing concentrations of DSPE-PEG$_{2000}$-biotin or DSPE-PEG$_{2000}$-DBCO through either the ex vitro (buffer) or in vitro (culture) methods, as described in the methods. Cells were subsequently analyzed by flow cytometry using streptavidin- or azide-conjugated AlexaFluor 488 to assess the presence of biotin and DBCO moieties, respectively, on the cell surface. As shown, both (A) adherent MCF-7 cells and (B) suspensive Raji cells can be successfully modified with DSPE-PEG$_{2000}$-biotin or DSPE-PEG$_{2000}$-DBCO through both the ex vitro and in vitro approaches. In an effort to quantitate the results presented in FIGS. 30A-H and more clearly demonstrate the optimal labeling concentration for each scenario, the mean fluorescence intensity (MFI) within each experimental series is scaled such that the maximum labeling obtained under the specified conditions is presented as a labeling extent of 1.0. For example, Raji cells are optimally labeled with DSPE-PEG$_{2000}$-biotin ex vitro at a lipid concentration of 10 μM. Data is presented as the mean±standard deviation of at least three trials.

FIGS. 38A-B. Elevated Temperature Promotes the DBCO/Azide Ligation on the Cell Surface. To explore the role of temperature on the efficiency of the copper-free ligation between membrane-tethered DBCO species and free azide groups, Raji cells modified with 10 μM DSPE-PEG$_{2000}$-DBCO were resuspended in PBS containing various concentrations of azide/Fn3 CSANs (0-500 nM) and incubated at either 4° C. or 37° C. for 3 h. The cells were then pelleted (500 g, 5 min, 4° C.), washed once in 1 mL PBS, and labeled with 50 μL anti-MYC (clone 9E10) Alexa Fluor 647 conjugate (5 μg/mL in PBS) to probe for surface-bound Fn3 CSANs. After incubating at 4° C. for ≥30 min in the dark, cells were again pelleted and washed thrice with 1 mL cold PBSA before the fluorescence was analyzed on a BD LSR II flow cytometer.

FIGS. 39A-D. SEC Demonstrates Successful Oligomerization of DHFR$^2$ Monomers into CSANs. The ability of monomeric DHFR$^2$ fusion proteins to oligomerize into multimeric CSANs in the presence of a dimerizer (either bisMTX or azide-bisMTX) was assessed by size exclusion chromatography. DHFR$^2$-Fn3 subunits oligomerize into EpCAM-targeted Fn3 CSANs in the presence of either (A) bisMTX, or (B) azide-bisMTX, demonstrating that both dimerizers effectively oligomerize the subunits. (C) mSA-DHFR$^2$ subunits ologomerize into mSA CSANs in the presence of bisMTX. (D) DHFR$^2$-Fn3 subunits and mSA-DHFR$^2$ subunits can be co-assembled into bispecific mSA/Fn3 CSANs in the presence of bisMTX. Peaks with a retention time of ~38 minutes represent residual buffer from protein purification which, upon mixing with the PBS running buffer, generates a detectable solvent peak on the instrument.

FIGS. 40A-B. Affinity and Selectivity of EpCAM-Targeted CSANs. The anti-EpCAM affinity and selectivity of monospecific Fn3 and bispecific mSA/Fn3 CSANs was assessed by flow cytometry, as described in the methods. (A) The Fn3 CSANs (black diamonds and solid black line) and mSA/Fn3 CSANs (grey circles and dashed grey line) bind to EpCAM+ MCF-7 cells with apparent K$_d$ values of 21±6 nM and 24±6 nM, respectively. (B) Neither species exhibits significant binding to EpCAM-U87 cells (white bars; p>0.05 for U87 MFI compared to control) at 500 nM.

FIGS. 41A-B. (A) $^1$H NMR Spectrum of Azide-BisMTX. Spectrum was collected on a Bruker Ascend 500 NMR in DMSO-d$^6$. (B) HPLC Analysis of Azide-BisMTX. Chromatogram was collected on a Thermo Fisher Ultimate 3000 HPLC equipped with a C18 column (Higgins Analytical) in 40% acetonitrile/60% water (with 0.1% TFA).

FIG. 42. DLS Analysis of the Hydrodynamic Diameter of CSAN Species. For analysis, 60 μL of CSANs in PBS was loaded into a cuvette and analyzed on a Punk DLS unit (Unchained Labs). Hydrodynamic diameter values represent the mean±standard deviation of at least three measurements.

FIGS. 43A-B. Optimizing the CSAN Labeling Concentration for Biotin-Modified Raji Cells. (A) The presence of both mSA-DHFR$^2$ and DHFR$^2$-Fn3 subunits in the CSAN was confirmed via flow cytometry by probing for both the FLAG and MYC epitope tags present on the respective fusion proteins. Briefly, Raji cells were modified with 10 μM DSPE-PEG$_{2000}$-biotin ex vitro and labeled with 100 nM mSA/Fn3 CSANs. Cells were then labeled with anti-FLAG PE and anti-MYC (clone 9E10) Alexa Fluor 647 conjugates and analyzed by flow cytometry. As Raji cells do not express EpCAM, the MYC epitope tag would only be present if the DHFR$^2$-Fn3 subunits were incorporated in the bispecific CSAN (and thereby tethered to the cell surface through the biotin/mSA interaction). (B) Raji cells were modified with 10 μM DSPE-PEG$_{2000}$-biotin ex vitro, labeled with various concentrations of mSA/Fn3 CSANs, labeled with anti-FLAG PE and anti-MYC (clone 9E10) Alexa Fluor 647 conjugates, and analyzed by flow cytometry, as described in the methods. Fluorescent signal reached a maximum value at 100 nM of mSA/Fn3 CSANs, with higher concentrations providing the same (or a diminished) signal. This indicates that biotin-modified Raji cell surfaces are saturated with CSANs when labeled with 100 nM of ligand.

FIG. 44. Plasma Stability of Phospholipid-Anchored CSANs. The stability of phospholipid-anchored CSANs in plasma was directly compared to that of media. Raji cells (2.0×10$^6$) were modified with 10 μM DSPE-PEG$_{2000}$-biotin in vitro and labeled with 100 nM "reduced-avidity" mSA CSANs, as described in the methods. The cells were then divided into two aliquots of 1.0×10$^6$ cells each; one aliquot was resuspended in 800 μL RPMI while the other was resuspended in 800 μL mouse plasma. The cells were incubated at 37° C., 5% CO$_2$ for 24 h, labeled with anti-FLAG PE conjugate (1 μg/mL in PBS) to detect cell surface CSANs, and analyzed on an LSR II flow cytometer. The MFI of the cells incubated in RPMI was normalized to 1.0 (as the CSANs were shown to be highly stable under these conditions (FIG. 34A) with the MFI of the cells incubated in mouse plasma scaled accordingly. Compared to 100±1% stability in media, the CSANs exhibited 54±1% stability over 24 h (p<0.001). Data is presented as the mean±standard deviation of three trials.

DETAILED DESCRIPTION

Polypeptides of the Invention

Figure 1A:
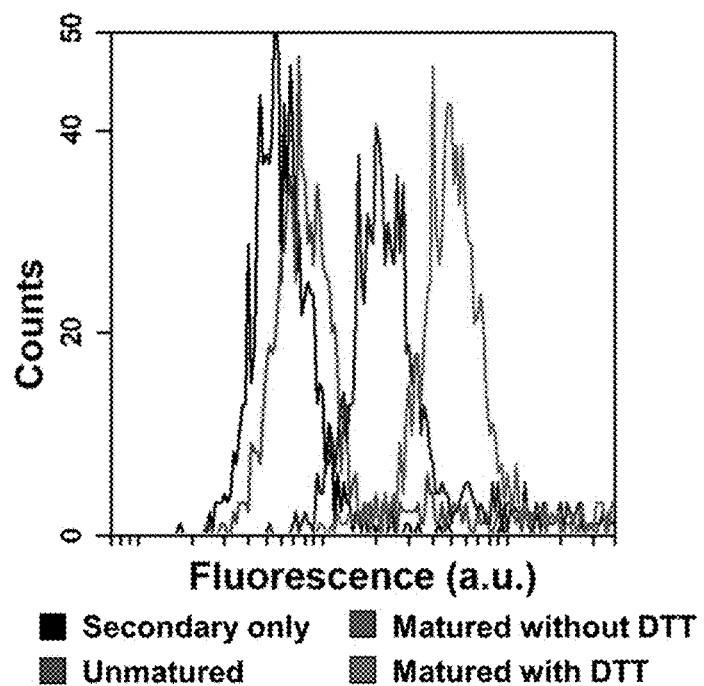

As described herein, fibronectin domains (e.g., ~10 kDa molecular weight) were engineered for strong, selective binding to the epithelial cell adhesion molecule (EpCAM), which is upregulated in numerous cancers and may be used as an oncology target. Certain polypeptides that were identified are shown in Table 1 below. As described herein, these polypeptides can be modified (e.g., mutated, conjugated both site-specifically and non-specifically, and/or fused to other proteins) to suit the needs of numerous downstream applications without significantly affecting their, e.g., production, structure, binding affinity, and/or target selectivity. For example, these polypeptides can be used for molecular imaging (PET, ultrasound, etc.), molecularly targeted therapies, ex vivo diagnostics, and biotechnological applications. As these polypeptides recognize an epitope on EpCAM that enables the activation of T cells, they may also be useful as targeting ligands for T cell directing immunotherapies. As described herein, these polypeptides may also be incorporated in CSANs.

TABLE 1

| | |
|---|---|
| Wildtype⁺ | VSDVPRDLEVVAATPTSLLISW<u>DAPAVTVRY</u>YRITYGETGGNSPVQEFTVP<u>GSKST</u>AT ISGLKPGVDYTITVYAV<u>TGRGDSPASSK</u>PISINYRTEIDKPSQ (SEQ ID NO: 1) |
| WT Loop Region 1 | DAPAVTVRY (SEQ ID NO: 2) |
| WT Loop Region 2 | GSKST (SEQ ID NO: 3) |
| WT Loop Region 3 | TGRGDSPASSK (SEQ ID NO: 4) |
| Hydrophilic Scaffold with WT Loops | SSDSPRNLEVTNATPNSLTISW<u>DAPAVTVRY</u>YRITYGETGGNSPSQEFTVP<u>GSKSTA</u><br>^  ^  ^  ^^^    ^  ^                           ^<br>TISGLKPGQDYTITVYAV<u>TGRGDSPASSK</u>PISINYRTEIDKPSQ (SEQ ID NO: 5)<br>                ^ |
| Consensus Sequence | SSDSPRNLEVTNATPNSLTISW<u>DYPNSASY</u>YRITYGETGGNSPSQEFTVP<u>GNTYN</u>AT ISGLKPGQDYIITVYAV<u>TYRDNYSYSN</u>PISINYRTEIDKPSQ (SEQ ID NO: 6) |
| A5 | SSDSPRNLEVTNATPNSLTISW<u>DYPNSASY</u>YRITYGETGGNSPSQEFTVP<u>GNTYN</u>AT ISGLRPDQDYIITVYAV<u>TSRDNYSWSN</u>PISINYRTEIDKPSQ (SEQ ID NO: 7)<br>    * *              *        * |
| B1 | SSDSPRNLEVTNATPNSLTISW<u>DYPNSASY</u>YRITYGETGGNSPSQEFTVP<u>GNTYN</u>AT ISGLKPGQDYIITVYAV<u>TYRDNYSYSN</u>PISINYRTEIDKPSQ (SEQ ID NO: 6) |
| B17 | SSDSPRNLEVTNATPNSLTISW<u>DYPNSASY</u>YRITYGETGGNSPSQEFTVP<u>GNTYN</u>TT<br>                                                      *<br>ISGLKPGQDYTITVYAV<u>TSRDNYSYLN</u>PISINYRTEIDKPSQ (SEQ ID NO: 8)<br>        *        *        * |
| B20 | SSDSPRNLEVTNATPNSLTISW<u>DYPNSASY</u>YRITYGETGGNSPSQEFTVP<u>GNTYN</u>AT ISGLKPGQDYIITVYAV<u>TSRDNYSYLN</u>PISINYRTEIDKPSQ (SEQ ID NO: 9)<br>      *      * |

TABLE 1-continued

| | |
|---|---|
| B22 | SSDSPRNLEVTNATPNSLTISW*DDYTSASY*YRITYGETGGNSPSQEFTVP*GNTYN*AT<br>                                              \*\*\*<br>VSGLRPGQDYIITVYAV*TYRDNYSYSN*PISINYRTEIDKPSQ (SEQ ID NO: 10)<br>\*  \* |
| C3 | SSDSPRNLEVTNATPNSLTISW*DYPNSASY*YRITYGETGGNSPSQEFTVP*GNTYN*AT<br>ISGLKPGQDYIITVYAV*TSRDNYSYSN*LISINYRTEIDKPSQ (SEQ ID NO: 11)<br>                \*        \* |
| C5 | SSDSPRNLEVTNATPNSLTISW*DNSNYASY*YRITYGETGGNSPSQELTVP*GSTYN*AT<br>                      \*\* \*                \*    \*<br>ISGLKPGQDYIITVYAV*TYRDNYSYSN*LISINYRSEIDKPSQ (SEQ ID NO: 12)<br>                \*        \* |
| Fn_C5_G65C | SSDSPRNLEVTNATPNSLTISW*DNSNYASY*YRITYGETGGNSPSQELTVP*GSTYN*AT<br>                      \*\* \*                \*    \*<br>ISGLKPCQDYIITVYAV*TYRDNYSYSN*LISINYRSEIDKPSQ (SEQ ID NO: 47)<br>\*                \*      \*      \* |
| Fn_C5_CtermC | SSDSPRNLEVTNATPNSLTISW*DNSNYASY*YRITYGETGGNSPSQELTVP*GSTYN*AT<br>                      \*\* \*                \*    \*<br>ISGLKPGQDYIITVYAV*TYRDNYSYSN*LISINYRSEIDKPSQC (SEQ ID NO: 49)<br>                \*      \*        \* |
| Fn_C5_G61C | SSDSPRNLEVTNATPNSLTISW*DNSNYASY*YRITYGETGGNSPSQELTVP*GSTYN*AT<br>                      \*\* \*                \*    \*<br>ISCLKPGQDYIITVYAV*TYRDNYSYSN*LISINYRSEIDKPSQ (SEQ ID NO: 61)<br>  \*                \*      \*      \* |
| Fn_C5_K63C | SSDSPRNLEVTNATPNSLTISW*DNSNYASY*YRITYGETGGNSPSQELTVP*GSTYN*AT<br>                      \*\* \*                \*    \*<br>ISGLCPGQDYIITVYAV*TYRDNYSYSN*LISINYRSEIDKPSQ (SEQ ID NO: 62)<br>                \*      \*      \* |
| C6 | SSDSPRSLEVTNATPNSLTISW*DYPNSASY*YRITYGETGGNSPSQEFTVP*GDTYN*AT<br>      \*                                                  \*<br>ISGLEPGQDYIITVYAV*TYRDNYSYSN*SVSINYRTEVDKPSQ (SEQ ID NO: 13)<br>    \*                \*          \*\*        \* |
| C8 | SSDSPRNLEVTNATPNSLTISW*DYPNSASY*YRITYSETGGNSPSQEFTVP*GNTYN*AT<br>                                    \*<br>ISGLKPGQDYIITVYAV*TYRDNYSYSN*LISINYRTEIDKPSQ (SEQ ID NO: 14)<br>                \* |
| C10 | SSDSPRNLEVTNATPNSLTISW*DDPDFASY*YRITYGETGGSSPSQEFTVP*GNTYS*AT<br>                      \* \*\*            \*                  \*<br>ISGLKPGRDHTITVYAV*TYRDNYSYSN*PISINYRTEIDKPSQ (SEQ ID NO: 15)<br>         \* \*\* |
| Consensus Loop Region 1 | DYPNSASY (SEQ ID NO: 16) |
| Consensus Loop Region 2 | GNTYN (SEQ ID NO: 17) |
| Consensus Loop Region 3 | TYRDNYSYSN (SEQ ID NO: 18) |
| A5' | VSDVPRDLEVVAATPTSLLISW*DYPNSASY*YRITYGETGGNSPVQEFTVP*GNTYN*ATI<br>SGLRPDVDYIITVYAV*TSRDNYSWSN*PISINYRTEIDKPSQ (SEQ ID NO: 19)<br>   ^  ^  ^          \*        \* |
| B1' | VSDVPRDLEVVAATPTSLLISW*DYPNSAS*YYRITYGETGGNSPVQEFTVP*GNTYN*ATI<br>SGLKPGVDYIITVYAV*TYRDNYSYSN*PISINYRTEIDKPSQ (SEQ ID NO: 20) |
| B17' | VSDVPRDLEVVAATPTSLLISW*DYPNSASY*YRITYGETGGNSPVQEFTVP*GNTYN*TTI<br>SGLKPGVDYTITVYAV*TSRDNYSYLN*PISINYRTEIDKPSQ (SEQ ID NO: 21)<br>                \*        \* |
| B20' | VSDVPRDLEVVAATPTSLLISW*DYPNSASY*YRITYGETGGNSPVQEFTVP*GNTYN*ATI<br>SGLKPGVDYIITVYAV*TSRDNYSYLN*PISINYRTEIDKPSQ (SEQ ID NO: 22)<br>  ^      \*      \* |

TABLE 1-continued

```
B22'          VSDVPRDLEVVAATPTSLLISWDDYTSASYYRITYGETGGNSPVQEFTVPGNTYNATV
                                   ***                              ^
              SGLRPGVDYIITVYAVTYRDNYSYSNPISINYRTEIDKPSQ (SEQ ID NO: 23)

C3'           VSDVPRDLEVVAATPTSLLISWDYPNSASYYRITYGETGGNSPVQEFTVPGNTYNATI
              SGLKPGVDYIITVYAVTSRDNYSYSNLISINYRTEIDKPSQ (SEQ ID NO: 24)
                              ^        *         ^

C5'           VSDVPRDLEVVAATPTSLLISWDNSNYASYYRITYGETGGNSPVQELTVPGSTYNATI
                                   ** *                           ^   *
              SGLKPGVDYIITVYAVTYRDNYSYSNLISINYRSEIDKPSQ (SEQ ID NO: 25)

C6'           VSDVPRSLEVVAATPTSLLISWDYPNSASYYRITYGETGGNSPVQEFTVPGDTYNATI
                     ^                                            *
              SGLEPGVDYIITVYAVTYRDNYSYSNSVSINYRTEVDKPSQ (SEQ ID NO: 26)

C8'           VSDVPRDLEVVAATPTSLLISWDYPNSASYYRITYSETGGNSPVQEFTVPGNTYNATI

SGLKPGVDYIITVYAVTYRDNYSYSNLISINYRTEIDKPSQ (SEQ ID NO: 27)

C10'          VSDVPRDLEVVAATPTSLLISWDDPDFASYYRITYGETGGSSPVQEFTVPGNTYSATI
                                   * **                           *
              SGLKPGRDHTITVYAVTYRDNYSYSNPISINYRTEIDKPSQ (SEQ ID NO: 28)

WT Scaffold   VSDVPRDLEVVAATPTSLLISWDYPNSASYYRITYGETGGNSPVQEFTVPGSKSTATI
with          SGLKPGVDYTITVYAVTGRGDSPASSKPISINYRTEIDKPSQ (SEQ ID NO: 29)
Consensus
Loop Region
1

WT Scaffold   VSDVPRDLEVVAATPTSLLISWDAPAVTVRYYRITYGETGGNSPVQEFTVPGNTYNAT
with          ISGLKPGVDYTITVYAVTGRGDSPASSKPISINYRTEIDKPSQ (SEQ ID NO: 30)
Consensus
Loop Region
2

WT Scaffold   VSDVPRDLEVVAATPTSLLISWDAPAVTVRYYRITYGETGGNSPVQEFTVPGSKSTAT
with          ISGLKPGVDYTITVYAVTYRDNYSYSNPISINYRTEIDKPSQ (SEQ ID NO: 31)
Consensus
Loop Region
3
```

⁺The wildtype sequence is from the human tenth type III fibronectin domain (¹⁰Fn3). Wildtype loop regions are underlined and engineered loop regions are in italics and underlined.
The * symbol indicates a variant amino acid residue as compared to the consensus sequence SEQ ID NO: 6.
The ^ symbol indicates a variant amino acid residue as compared to the wildtype sequence SEQ ID NO: 1. Polypeptides A5'-C10' comprise 1) a WT scaffold; and 2) the consensus engineered loop regions, wherein the variations from its corresponding peptide are inserted into these scaffold and loop regions (e.g., variations from A5 are shown in A5'). Therefore, changes to the scaffold of A5'-C10' are shown as compared to the scaffold of SEQ ID NO: 1 (^) and changes to the loop regions of these polypeptides are shown as compared to the loop regions of SEQ ID NO: 6 (*).

The wildtype sequence of the human tenth type III fibronectin domain ($^{10}$Fn3) is shown in Table 1 as SEQ ID NO: 1. The $^{10}$Fn3 protein comprises seven beta-strand domain sequences designated A through G and six loop regions (AB loop, BC loop, CD loop, DE loop, EF loop, and FG loop) which connect the seven beta-strand domain sequences. The beta strands positioned closest to the N- and C-termini may adopt a beta-like conformation in solution. In SEQ ID NO: 1, the BC loop corresponds to residues 23-31 (i.e., Loop Region 1), the DE loop corresponds to residues 52-56 (i.e., Loop Region 2) and the FG loop corresponds to residues 76-86 (i.e., Loop Region 3). As described herein, the residues that are not part of the BC, DE or FG loops comprise the scaffold portion of the polypeptide (i.e., residues 1-22, 32-51, 57-75 and 87-101 in SEQ ID NO:1; see also, SEQ ID NO:41 and SEQ ID NO:42). In Hackel et al., *Protein Eng Des Sel.*, 25(10):639-47 (2012) the scaffold portion of the wildtype $^{10}$Fn3 sequence was evolved to be more hydrophilic. This more hydrophilic sequence is included in Table 1 and is shown as SEQ ID NO:5 (variations relative to the WT sequence are shown with a ^; loop regions are underlined and occur at the same location as the WT). This hydrophilic sequence was then used as the basis for a library (Woldring et al., *PLoS One*, 10(9):e0138956 (2015)) that was subsequently used to develop the polypeptides of the invention (see, Example 1). A consensus sequence (i.e., most frequent residue at each position) was calculated from the polypeptides identified in Example 1 and is shown as SEQ ID NO:6.

Accordingly, certain embodiments of the invention provide a polypeptide comprising an amino acid sequence having between about 65% to about 99% sequence identity to SEQ ID NO:1 or SEQ ID NO:5, wherein the polypeptide comprises one or more variations that increase its binding affinity to epithelial cell adhesion molecule (EpCAM) (e.g., as compared to the binding affinity of SEQ ID NO: 1 polypeptide or as compared to the binding affinity of SEQ ID NO:5 polypeptide). As used herein, the term "variation" refers to an amino acid substitution, insertion and/or deletion. Assays for measuring the binding affinity between two molecules are known in the art. For example, binding affinity may be measured using an assay described in Example 1.

In certain embodiments, the polypeptide comprises an amino acid sequence having between about 65% to about 99% sequence identity to SEQ ID NO:1. In certain embodiments, the polypeptide comprises an amino acid sequence having between about 65% to about 99% sequence identity to SEQ ID NO:5.

In certain embodiments, the polypeptide comprises at least one loop region selected from the group consisting of: DAPAVTVRY (SEQ ID NO:2); GSKST (SEQ ID NO:3); TGRGDSPASSK (SEQ ID NO:4); DYPNSASY (SEQ ID NO:16); GNTYN (SEQ ID NO:17); TYRDNYSYSN (SEQ ID NO:18); TSRDNYSWSN (SEQ ID NO:32); TSRDNYSYLN (SEQ ID NO:33); DDYTSASY (SEQ ID NO:34); TSRDNYSYSN (SEQ ID NO:35); DNSNYASY (SEQ ID NO:36); GSTYN (SEQ ID NO:37); GDTYN (SEQ ID NO:38); DDPDFASY (SEQ ID NO:39); and GNTYS (SEQ ID NO:40).

In certain embodiments, the polypeptide comprises one or more variations located within a loop region (e.g., as compared to a loop region of SEQ ID NO: 1 or SEQ ID NO:5). In certain embodiments, the polypeptide comprises two or more variations located within a loop region. In certain embodiments, the polypeptide comprises three or more variations located within a loop region. In certain embodiments, a single loop region comprises one variation (e.g., Loop Region 1 comprises one variation as compared to SEQ ID NO:1 or SEQ ID NO:5). In certain embodiments, a single loop region comprises two variations (e.g., Loop Region 1 comprises two variations as compared to SEQ ID NO: 1 or SEQ ID NO:5). In certain embodiments, a single loop region comprises three variations (e.g., Loop Region 1 comprises three variations as compared to SEQ ID NO: 1 or SEQ ID NO:5). In certain embodiments, the loop region comprising the variation(s) is Loop Region 1 (as compared to SEQ ID NO:2). In certain embodiments, the loop region comprising the variation(s) is Loop Region 2 (as compared to SEQ ID NO:3). In certain embodiments, the loop region comprising the variation is Loop Region 3 (as compared to SEQ ID NO:4).

In certain embodiments, the polypeptide comprises at least one loop region selected from the group consisting of: DYPNSASY (SEQ ID NO:16); GNTYN (SEQ ID NO:17); TYRDNYSYSN (SEQ ID NO:18); TSRDNYSWSN (SEQ ID NO:32); TSRDNYSYLN (SEQ ID NO:33); DDYTSASY (SEQ ID NO:34); TSRDNYSYSN (SEQ ID NO:35); DNSNYASY (SEQ ID NO:36); GSTYN (SEQ ID NO:37); GDTYN (SEQ ID NO:38); DDPDFASY (SEQ ID NO:39); and GNTYS (SEQ ID NO:40).

In certain embodiments, the polypeptide comprises one or more variations that are not located within a loop region (e.g., as compared to SEQ ID NO: 1 or SEQ ID NO:5). In certain embodiments, the polypeptide comprises two or more variations that are not located within a loop region. In certain embodiments, the polypeptide comprises between one and five variations that are not located within a loop region. In certain embodiments, the polypeptide comprises one variation that is not located within a loop region. In certain embodiments, the polypeptide comprises two variations that are not located within a loop region. In certain embodiments, the polypeptide comprises three variations that are not located within a loop region. In certain embodiments, the polypeptide comprises four variations that are not located within a loop region. In certain embodiments, the polypeptide comprises five variations that are not located within a loop region.

In certain embodiments, the one or more variations that are not located within a loop region are located near a loop region. For example, in certain embodiments, the one or more variations are located within 3 amino acids of the N' or C' terminus of a loop region. In certain embodiments, the one or more variations are located within 2 amino acids of the N' or C' terminus of a loop region. In certain embodiments, the one or more variations are located within 1 amino acid of the N' or C' terminus of a loop region. In certain embodiments, the one or more variations are located within 2 amino acids of the C' terminus of Loop Region 3 (e.g., Loop Region 3 has the sequence of SEQ ID NO:4). In certain embodiments, the variation is located within 1 amino acid of the C' terminus of Loop Region 3 (e.g., Loop Region 3 has the sequence of SEQ ID NO:4).

As used herein, P87 refers the amino acid residue at position 87 in the WT sequence (SEQ ID NO:1) or hydrophilic sequence (SEQ ID NO:5) (see, FIG. 2). This residue corresponds to P85 within the consensus sequence (SEQ ID NO:6). Other equivalent residues are present in other fibronectin domain sequences (e.g., other isoforms or variants). While this amino acid residue is described based on its position in SEQ ID NO: 1/5, one skilled in the art may readily determine equivalent residues in other fibronectin domain sequences using known techniques and algorithms (e.g., BLAST or ALIGN). Accordingly, in certain embodiments, the polypeptide comprises a variation at residue P87, or at a residue corresponding to, or alignable with, residue P87 (i.e., as compared to SEQ ID NO:1 or SEQ ID NO:5). In certain embodiments, the variation is P87S or P87L.

As described herein, a polypeptide of the invention may be altered to include a cysteine variation, which may be used to, e.g., conjugate the polypeptide to another molecule (see, e.g., the Examples). Accordingly, certain embodiments of the invention provide a polypeptide described herein comprising a cysteine variation. In certain embodiments, the cysteine variation is located in a non-paratopic region of the fibronectin domain.

As used herein, G61, K63 and G65 refer the amino acid residues at position 61, 63 and 65, respectively, in the WT sequence (SEQ ID NO:1). These residues correspond to G60, K62 and G64 within the consensus sequence (SEQ ID NO:6). Other equivalent residues are present in other fibronectin domain sequences (e.g., other isoforms or variants). While this amino acid residue is described based on its position in SEQ ID NO: 1, one skilled in the art may readily determine equivalent residues in other fibronectin domain sequences using known techniques and algorithms (e.g., BLAST or ALIGN). Accordingly, in certain embodiments, the polypeptide comprises a cysteine variation at residue G61, K63 and/or G65, or at a residue corresponding to, or alignable with, these residues (i.e., as compared to SEQ ID NO: 1) (see, e.g., SEQ ID NOs:47, 61 and 62). In certain embodiments, a cysteine residue is added to the C-terminus of the fibronectin domain (see, e.g., SEQ ID NO:49).

In certain embodiments, the polypeptide comprises an amino acid sequence having between about 65% to about 99%, about 70% to about 99%, about 71% to about 99%, about 72% to about 99%, about 73% to about 99%, about 74% to about 99%, about 75% to about 99%, about 76% to about 99%, about 77% to about 99%, about 78% to about 99%, about 79% to about 99%, about 80% to about 99%, about 81% to about 99%, about 82% to about 83% to about 99%, about 84% to about 99%, about 85% to about 99%, about 86% to about 99%, about 87% to about 99%, about 88% to about 99%, about 89% to about 99%, about 90% to about 99%, about 91% to about 99%, about 92% to about 99%, about 93% to about 99%, about 94% to about 99%, about 95% to about 99%, about 96% to about 99%, about 97% to about 99% or about 98% to about 99% sequence identity to SEQ ID NO: 1 or SEQ ID NO:5. In certain embodiments, the polypeptide comprises an amino acid sequence having about 90%, 91%, 92%, 93%, 94%, 95%, 96%, 97%, 98% or 99% sequence identity to SEQ ID NO:1 or SEQ ID NO:5.

In certain embodiments, the polypeptide consists of an amino acid sequence having between about 65% to about 99%, about 70% to about 99%, about 71% to about 99%, about 72% to about 99%, about 73% to about 99%, about 74% to about 99%, about 75% to about 99%, about 76% to about 99%, about 77% to about 99%, about 78% to about 99%, about 79% to about 99%, about 80% to about 99%, about 81% to about 99%, about 82% to about 99%, about 83% to about 99%, about 84% to about 99%, about 85% to about 99%, about 86% to about 99%, about 87% to about 99%, about 88% to about 99%, about 89% to about 99%, about 90% to about 99%, about 91% to about 99%, about 92% to about 99%, about 93% to about 99%, about 94% to about 99%, about 95% to about 99%, about 96% to about 99%, about 97% to about 99% or about 98% to about 99% sequence identity to SEQ ID NO: 1 or SEQ ID NO:5. In certain embodiments, the polypeptide consists of an amino acid sequence having about 90%, 91%, 92%, 93%, 94%, 95%, 96%, 97%, 98% or 99% sequence identity to SEQ ID NO:1 or SEQ ID NO:5.

In certain embodiments, the polypeptide comprises an amino acid sequence having between about 65% to about 99% sequence identity to:

```
                                        (SEQ ID NO: 41)
1) VSDVPRDLEVVAATPTSLLISWX1YRITYGETGGNSPVQEFTVPX2A

TISGLKPGVDYTITVYAVX3PISINYRTEIDKPSQ;
or
                                        (SEQ ID NO: 42)
2) SSDSPRNLEVTNATPNSLTISWX1YRITYGETGGNSPSQEFTVPX2A

TISGLKPGQDYTITVYAVX3PISINYRTEIDKPSQ;
wherein X1 is selected from (SEQ ID NO: 2)
DAPAVTVRY;

(SEQ ID NO: 16)
DYPNSASY;

(SEQ ID NO: 34)
DDYTSASY;

(SEQ ID NO: 36)
DNSNYASY;
and (SEQ ID NO: 39)
DDPDFASY;
``` wherein $X_2$ is selected from GSKST (SEQ ID NO:3); GNTYN (SEQ ID NO: 17); GSTYN (SEQ ID NO:37); GDTYN (SEQ ID NO:38); and GNTYS (SEQ ID NO:40); and wherein $X_3$ is selected from TGRGDSPASSK (SEQ ID NO:4); TYRDNYSYSN (SEQ ID NO: 18); TSRDNYSWSN (SEQ ID NO:32); TSRDNYSYLN (SEQ ID NO:33); and TSRDNYSYSN (SEQ ID NO:35).

In certain embodiments, $X_1$ is not SEQ ID NO:2, when $X_2$ is SEQ ID NO:3 and $X_3$ is SEQ ID NO:4; $X_2$ is not SEQ ID NO:3, when $X_1$ is SEQ ID NO:2 and $X_3$ is SEQ ID NO:4; and $X_3$ is not SEQ ID NO:4, when $X_2$ is SEQ ID NO:3 and $X_1$ is SEQ ID NO:2.

In certain embodiments, the polypeptide comprises an amino acid sequence having between about 65% to about 99%, about 70% to about 99%, about 71% to about 99%, about 72% to about 99%, about 73% to about 99%, about 74% to about 99%, about 75% to about 99%, about 76% to about 99%, about 77% to about 99%, about 78% to about 99%, about 79% to about 99%, about 80% to about 99%, about 81% to about 99%, about 82% to about 99%, about 83% to about 99%, about 84% to about 99%, about 85% to about 99%, about 86% to about 99%, about 87% to about 99%, about 88% to about 99%, about 89% to about 99%, about 90% to about 99%, about 91% to about 99%, about 92% to about 99%, about 93% to about 99%, about 94% to about 99%, about 95% to about 99%, about 96% to about 99%, about 97% to about 99% or about 98% to about 99% sequence identity to SEQ ID NO:41 or SEQ ID NO:42. In certain embodiments, the polypeptide comprises an amino acid sequence having about 90%, 91%, 92%, 93%, 94%, 95%, 96%, 97%, 98% or 99% sequence identity to SEQ ID NO:41 or SEQ ID NO:42.

In certain embodiments, the polypeptide consists of an amino acid sequence having between about 65% to about 99%, about 70% to about 99%, about 71% to about 99%, about 72% to about 99%, about 73% to about 99%, about 74% to about 99%, about 75% to about 99%, about 76% to about 99%, about 77% to about 99%, about 78% to about 99%, about 79% to about 99%, about 80% to about 99%, about 81% to about 99%, about 82% to about 99%, about 83% to about 99%, about 84% to about 99%, about 85% to about 99%, about 86% to about 99%, about 87% to about 99%, about 88% to about 99%, about 89% to about 99%, about 90% to about 99%, about 91% to about 99%, about 92% to about 99%, about 93% to about 99%, about 94% to about 99%, about 95% to about 99%, about 96% to about 99%, about 97% to about 99% or about 98% to about 99% sequence identity to SEQ ID NO:41 or SEQ ID NO:42. In certain embodiments, the polypeptide consists of an amino acid sequence having about 90%, 91%, 92%, 93%, 94%, 95%, 96%, 97%, 98% or 99% sequence identity to SEQ ID NO:41 or SEQ ID NO:42.

Certain embodiments of the invention provide a polypeptide comprising an amino acid sequence having at least about 85% sequence identity to a sequence selected from the group consisting of SEQ ID NO:6, SEQ ID NO:7, SEQ ID NO:8, SEQ ID NO:9, SEQ ID NO: 10, SEQ ID NO:11, SEQ ID NO:12, SEQ ID NO:13, SEQ ID NO:14, SEQ ID NO:15, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, and SEQ ID NO:31, SEQ ID NO:47, SEQ ID NO:49, SEQ ID NO:61, and SEQ ID NO:62, wherein the polypeptide is capable of binding to epithelial cell adhesion molecule (EpCAM). In certain embodiments, the polypeptide comprises an amino acid sequence having at least about 86%, 87%, 88%, 89%, 90%, 91%, 92%, 93%, 94%, 95%, 96%, 97%, 98%, 99% or 100% sequence identity a sequence selected from the group consisting of SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:47, SEQ ID NO:49, SEQ ID NO:61, and SEQ ID NO:62. In certain embodiments, the polypeptide consists of an amino acid sequence having at least about 86%, 87%, 88%, 89%, 90%, 91%, 92%, 93%, 94%, 95%, 96%, 97%, 98%, 99% or 100% sequence identity a sequence selected from the group consisting of SEQ ID NO:6, SEQ ID NO:7, SEQ ID NO:8, SEQ ID NO:9, SEQ ID NO:10, SEQ ID NO: 11, SEQ ID NO:12, SEQ ID NO:13, SEQ ID NO:14, SEQ ID NO:15, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, and SEQ ID NO:31, SEQ ID NO:47, SEQ ID NO:49, SEQ ID NO:61, and SEQ ID NO:62.

In certain embodiments, the polypeptide comprises an amino acid sequence having at least about 90% sequence identity to SEQ ID NO:6. In certain embodiments, the polypeptide comprises an amino acid sequence having at least about 95% sequence identity to SEQ ID NO:6. In certain embodiments, the polypeptide comprises an amino acid sequence having at least about 96% sequence identity to SEQ ID NO:6. In certain embodiments, the polypeptide comprises an amino acid sequence having at least about 97% sequence identity to SEQ ID NO:6. In certain embodiments, the polypeptide comprises an amino acid sequence having at least about 98% sequence identity to SEQ ID NO:6. In certain embodiments, the polypeptide comprises an amino acid sequence having at least about 99% sequence identity to SEQ ID NO:6. In certain embodiments, the polypeptide comprises SEQ ID NO:6. In certain embodiments, the polypeptide consists of SEQ ID NO:6.

In certain embodiments, the polypeptide comprises an amino acid sequence having at least about 90% sequence identity to SEQ ID NO: 10. In certain embodiments, the polypeptide comprises an amino acid sequence having at least about 95% sequence identity to SEQ ID NO: 10. In certain embodiments, the polypeptide comprises an amino acid sequence having at least about 96% sequence identity to SEQ ID NO: 10. In certain embodiments, the polypeptide comprises an amino acid sequence having at least about 97% sequence identity to SEQ ID NO: 10. In certain embodiments, the polypeptide comprises an amino acid sequence having at least about 98% sequence identity to SEQ ID NO: 10. In certain embodiments, the polypeptide comprises an amino acid sequence having at least about 99% sequence identity to SEQ ID NO: 10. In certain embodiments, the polypeptide comprises SEQ ID NO: 10. In certain embodiments, the polypeptide consists of SEQ ID NO: 10.

In certain embodiments, the polypeptide comprises an amino acid sequence having at least about 90% sequence identity to SEQ ID NO: 11. In certain embodiments, the polypeptide comprises an amino acid sequence having at least about 95% sequence identity to SEQ ID NO: 11. In certain embodiments, the polypeptide comprises an amino acid sequence having at least about 96% sequence identity to SEQ ID NO: 11. In certain embodiments, the polypeptide comprises an amino acid sequence having at least about 97% sequence identity to SEQ ID NO: 11. In certain embodiments, the polypeptide comprises an amino acid sequence having at least about 98% sequence identity to SEQ ID NO: 11. In certain embodiments, the polypeptide comprises an amino acid sequence having at least about 99% sequence identity to SEQ ID NO: 11. In certain embodiments, the polypeptide comprises SEQ ID NO: 11. In certain embodiments, the polypeptide consists of SEQ ID NO: 11.

In certain embodiments, the polypeptide comprises an amino acid sequence having at least about 90% sequence identity to SEQ ID NO: 12. In certain embodiments, the polypeptide comprises an amino acid sequence having at least about 95% sequence identity to SEQ ID NO: 12. In certain embodiments, the polypeptide comprises an amino acid sequence having at least about 96% sequence identity to SEQ ID NO: 12. In certain embodiments, the polypeptide comprises an amino acid sequence having at least about 97% sequence identity to SEQ ID NO: 12. In certain embodiments, the polypeptide comprises an amino acid sequence having at least about 98% sequence identity to SEQ ID NO: 12. In certain embodiments, the polypeptide comprises an amino acid sequence having at least about 99% sequence identity to SEQ ID NO:12. In certain embodiments, the polypeptide comprises SEQ ID NO:12. In certain embodiments, the polypeptide consists of SEQ ID NO: 12.

In certain embodiments, the polypeptide comprises an amino acid sequence having at least about 90% sequence identity to SEQ ID NO: 13. In certain embodiments, the polypeptide comprises an amino acid sequence having at least about 95% sequence identity to SEQ ID NO:13. In certain embodiments, the polypeptide comprises an amino acid sequence having at least about 96% sequence identity to SEQ ID NO: 13. In certain embodiments, the polypeptide comprises an amino acid sequence having at least about 97% sequence identity to SEQ ID NO:13. In certain embodiments, the polypeptide comprises an amino acid sequence having at least about 98% sequence identity to SEQ ID NO:13. In certain embodiments, the polypeptide comprises an amino acid sequence having at least about 99% sequence identity to SEQ ID NO:13. In certain embodiments, the polypeptide comprises SEQ ID NO:13. In certain embodiments, the polypeptide consists of SEQ ID NO: 13.

In certain embodiments, the polypeptide comprises an amino acid sequence having at least about 90% sequence identity to SEQ ID NO: 14. In certain embodiments, the polypeptide comprises an amino acid sequence having at least about 95% sequence identity to SEQ ID NO: 14. In certain embodiments, the polypeptide comprises an amino acid sequence having at least about 96% sequence identity to SEQ ID NO: 14. In certain embodiments, the polypeptide comprises an amino acid sequence having at least about 97% sequence identity to SEQ ID NO: 14. In certain embodiments, the polypeptide comprises an amino acid sequence having at least about 98% sequence identity to SEQ ID NO: 14. In certain embodiments, the polypeptide comprises an amino acid sequence having at least about 99% sequence identity to SEQ ID NO: 14. In certain embodiments, the polypeptide comprises SEQ ID NO: 10. In certain embodiments, the polypeptide consists of SEQ ID NO: 14.

In certain embodiments, the polypeptide comprises an amino acid sequence having at least about 90% sequence identity to SEQ ID NO: 15. In certain embodiments, the polypeptide comprises an amino acid sequence having at least about 95% sequence identity to SEQ ID NO:15. In certain embodiments, the polypeptide comprises an amino acid sequence having at least about 96% sequence identity to SEQ ID NO: 15. In certain embodiments, the polypeptide comprises an amino acid sequence having at least about 97% sequence identity to SEQ ID NO:15. In certain embodiments, the polypeptide comprises an amino acid sequence having at least about 98% sequence identity to SEQ ID NO:15. In certain embodiments, the polypeptide comprises an amino acid sequence having at least about 99% sequence identity to SEQ ID NO:15. In certain embodiments, the polypeptide comprises SEQ ID NO:15. In certain embodiments, the polypeptide consists of SEQ ID NO: 15.

In certain embodiments, the polypeptide comprises an amino acid sequence having at least about 90% sequence identity to SEQ ID NO:47. In certain embodiments, the polypeptide comprises an amino acid sequence having at least about 95% sequence identity to SEQ ID NO:47. In certain embodiments, the polypeptide comprises an amino acid sequence having at least about 96% sequence identity to SEQ ID NO:47. In certain embodiments, the polypeptide comprises an amino acid sequence having at least about 97% sequence identity to SEQ ID NO:47. In certain embodiments, the polypeptide comprises an amino acid sequence having at least about 98% sequence identity to SEQ ID NO:47. In certain embodiments, the polypeptide comprises an amino acid sequence having at least about 99% sequence identity to SEQ ID NO:47. In certain embodiments, the polypeptide comprises SEQ ID NO:47. In certain embodiments, the polypeptide consists of SEQ ID NO:47.

In certain embodiments, the polypeptide comprises an amino acid sequence having at least about 90% sequence identity to SEQ ID NO:49. In certain embodiments, the polypeptide comprises an amino acid sequence having at least about 95% sequence identity to SEQ ID NO:49. In certain embodiments, the polypeptide comprises an amino acid sequence having at least about 96% sequence identity to SEQ ID NO:49. In certain embodiments, the polypeptide comprises an amino acid sequence having at least about 97% sequence identity to SEQ ID NO:49. In certain embodiments, the polypeptide comprises an amino acid sequence having at least about 98% sequence identity to SEQ ID NO:49. In certain embodiments, the polypeptide comprises an amino acid sequence having at least about 99% sequence identity to SEQ ID NO:49. In certain embodiments, the polypeptide comprises SEQ ID NO:49. In certain embodiments, the polypeptide consists of SEQ ID NO:49.

In certain embodiments, the polypeptide comprises an amino acid sequence having at least about 90% sequence identity to SEQ ID NO:61. In certain embodiments, the polypeptide comprises an amino acid sequence having at least about 95% sequence identity to SEQ ID NO:61. In certain embodiments, the polypeptide comprises an amino acid sequence having at least about 96% sequence identity to SEQ ID NO:61. In certain embodiments, the polypeptide comprises an amino acid sequence having at least about 97% sequence identity to SEQ ID NO:61. In certain embodiments, the polypeptide comprises an amino acid sequence having at least about 98% sequence identity to SEQ ID NO:61. In certain embodiments, the polypeptide comprises an amino acid sequence having at least about 99% sequence identity to SEQ ID NO:61. In certain embodiments, the polypeptide comprises SEQ ID NO:61. In certain embodiments, the polypeptide consists of SEQ ID NO:61.

In certain embodiments, the polypeptide comprises an amino acid sequence having at least about 90% sequence identity to SEQ ID NO:62. In certain embodiments, the polypeptide comprises an amino acid sequence having at least about 95% sequence identity to SEQ ID NO:62. In certain embodiments, the polypeptide comprises an amino acid sequence having at least about 96% sequence identity to SEQ ID NO:62. In certain embodiments, the polypeptide comprises an amino acid sequence having at least about 97% sequence identity to SEQ ID NO:62. In certain embodiments, the polypeptide comprises an amino acid sequence having at least about 98% sequence identity to SEQ ID NO:62. In certain embodiments, the polypeptide comprises an amino acid sequence having at least about 99% sequence identity to SEQ ID NO:62. In certain embodiments, the polypeptide comprises SEQ ID NO:62. In certain embodiments, the polypeptide consists of SEQ ID NO:62.

In certain embodiments, a polypeptide of the invention comprises at least three loop regions (e.g., when the polypeptide is folded at physiological conditions).

In certain embodiments, a polypeptide as described herein has an EpCAM $K_d$ of about 10 µM to about 100 pM. In certain embodiments, a polypeptide as described herein has an EpCAM $K_d$ of about 9 µM to about 100 pM. In certain embodiments, a polypeptide as described herein has an EpCAM $K_d$ of about 8 µM to about 100 pM. In certain embodiments, a polypeptide as described herein has an EpCAM $K_d$ of about 7 µM to about 100 pM. In certain embodiments, a polypeptide as described herein has an EpCAM $K_d$ of about 6 µM to about 100 pM. In certain embodiments, a polypeptide as described herein has an EpCAM $K_d$ of about 5 µM to about 100 pM. In certain embodiments, a polypeptide as described herein has an EpCAM $K_d$ of about 4 µM to about 100 pM. In certain embodiments, a polypeptide as described herein has an EpCAM $K_d$ of about 3 µM to about 100 pM. In certain embodiments, a polypeptide as described herein has an EpCAM $K_d$ of about 2 µM to about 100 pM. In certain embodiments, a polypeptide as described herein has an EpCAM $K_d$ of about 1 µM to about 100 pM. In certain embodiments, the polypeptide has an EpCAM $K_d$ of about 800 nM to about 100 pM. In certain embodiments, the polypeptide has an EpCAM $K_d$ of about 500 nM to about 100 pM. In certain embodiments, the polypeptide has an EpCAM $K_d$ of about 100 nM to about 100 pM. In certain embodiments, the polypeptide has an EpCAM $K_d$ of about 100 nM to about 500 pM. In certain embodiments, the polypeptide has an EpCAM $K_d$ of about 100 nM to about 800 pM. In certain embodiments, the polypeptide has an EpCAM $K_d$ of about 50 nM to about 1 nM. In certain embodiments, the polypeptide has an EpCAM $K_d$ of about 25 nM to about 1 nM.

In certain embodiments, the polypeptide further comprises a tag operably linked to the amino acid sequence having between about 65% to about 99% sequence identity to SEQ ID NO:1 or SEQ ID NO:5. Tags are known in the art and include but are not limited to, e.g., FLAG tags, MYC tags, HIS tags, etc. In certain embodiments, the tag is operably linked to the amino acid sequence at the N-terminus. In certain embodiments, the tag is operably linked to the amino acid sequence at the C-terminus.

As described herein, a polypeptide of the invention may be operably linked to a bivalent dihydrofolate reductase (DHFR$^2$) fusion protein. Such polypeptides may be incorporated into a CSAN. Thus, certain embodiments of the invention provide a fusion protein comprising a first dihydrofolate reductase (DHFR) peptide, a second DHFR peptide, a linker peptide, a polypeptide of the invention, and optionally, at least one peptide encoding a tag, wherein the first DHFR peptide is operably linked to the second DHFR peptide, and wherein the linker peptide operably links the second DHFR peptide to the polypeptide of the invention. In certain embodiments, the tag is operably linked to the first DHFR peptide.

Certain embodiments of the invention provide a polypeptide as described herein.

Certain embodiments of the invention provide a compound comprising a polypeptide as described herein.

Certain embodiments of the invention provide a nucleic acid encoding a polypeptide described herein. In certain embodiments, the nucleic acid further comprises a promoter.

Certain embodiments of the invention provide an expression cassette comprising a nucleic acid sequence described herein and a promoter operably linked to the nucleic acid.

In certain embodiments, the promoter is a regulatable promoter. In certain embodiments, the promoter is a constitutive promoter.

In certain embodiments, the expression cassette further comprises an expression control sequence (e.g., an enhancer) operably linked to the nucleic acid sequence. Expression control sequences and techniques for operably linking sequences together are well known in the art.

Certain embodiments of the invention provide a vector comprising an expression cassette described herein.

Certain embodiments of the invention provide a cell comprising a polypeptide described herein, a nucleic acid described herein, an expression cassette described herein or a vector described herein.

Certain embodiments of the invention provide a cell comprising a conjugate or a CSAN described herein.

Certain embodiments of the invention provide methods as described herein for identifying polypeptides that bind to EpCAM (e.g., with high affinity and specificity).

Conjugates

Described herein are fibronectin domain polypeptides that have been modified to bind to EpCAM. In certain embodiments, these polypeptides may be included in a conjugate that comprises a detectable agent or a biologically active agent. For example, in certain embodiments, the conjugate may comprise a chelator that can be labeled with a radionuclide for diagnostic imaging (e.g., PET imaging) or radiation therapy for the treatment of cancer. In certain embodiments, these polypeptides may also be included in conjugates that comprise a fluorescent molecular functional group that can be used for assays designed to identify and quantify the concentration of EpCAM on cell surfaces. In other embodiments, the polypeptides may be included in conjugates that comprise a biologically active agent, wherein such conjugates may be used for molecularly targeted therapies.

Thus, certain embodiments of the invention provide a polypeptide described herein operably linked to an agent described herein (e.g., a detectable agent or a biologically active agent). As discussed herein, the linker group is not critical, provided it does not disrupt the functionality of the polypeptide or agent. In certain embodiments, the polypeptide and agent may be linked using a method described herein. For example, certain polypeptides described herein have been modified to comprise a cysteine, and therefore, sulfhydryl/maleimide chemistry may be used to link the two components. In other embodiments, the agent may be linked to the polypeptide non-specifically, for example, using activated esters to react with the primary amines located on the polypeptide's N-terminus and lysine side chains (e.g., a polypeptide of the invention could be non-specifically biotinylated using an NHS-biotin, such as EZ-Link Sulfo-NHS-Biotin).

Certain embodiments of the invention provide a process comprising linking a polypeptide as described herein to a detectable agent or a biologically active agent either directly or indirectly through a linker group.

Certain embodiments of the invention provide a conjugate of formula (I):

$$P\text{-}(L\text{-}A)_n \quad (I)$$

wherein:

P is a polypeptide described herein that binds to epithelial cell adhesion molecule (EpCAM);

each L is independently a direct bond or a linking group;

each A is independently a detectable agent or a biologically active agent; and n is 1 to 5.

In certain embodiments, n is 1, 2, 3, 4 or 5. In certain embodiments, n is 1. In certain embodiments, n is 2. In certain embodiments, when n is greater than 1, -(L-A) is independently selected, and therefore, may be the same or different (e.g., one A may be a radiolabeled chelating group and another A may be a fluorescent group).

The invention also provides processes and intermediates disclosed herein that are useful for preparing conjugates of formula I.

In certain embodiments, a conjugate of formula (I) has an EpCAM $K_d$ of about 10 μM to about 100 pM. In certain embodiments, a conjugate of formula (I) has an EpCAM $K_d$ of about 1,000 nM to about 100 pM. In certain embodiments, a conjugate of formula (I) has an EpCAM $K_d$ of about 100 nM to about 100 pM.

A polypeptide can be linked to the remainder of a conjugate of formula I at its carboxy terminus, amino terminus, or through any other convenient point of attachment (e.g., attached to an amino acid located within the internal portion of the polypeptide), such as, for example, through the sulfur of a cysteine or through a free amine of an amino acid. Specifically, L may be covalently attached to the polypeptide at any synthetically feasible position. Ideally, L is covalently attached to the polypeptide at a position that does not interfere with or destroy its EpCAM binding capabilities and does not interfere with or destroy the functionality of the detectable agent or biologically active agent. In certain embodiments, L is covalently attached through an amine group of an amino acid (e.g., generating an amide). In certain embodiments, L is covalently attached through an alcohol group of an amino acid (e.g., generating an ester). In certain embodiments, L is covalently attached through an amine group located at the N-terminus of the polypeptide. In certain embodiments, L is covalently attached to an amine group of a lysine located within the internal portion of the amino acid sequence.

Conjugates of formula (I) may be synthesized using methods known in the art or using methods described herein (e.g., the Examples). For example, the polypeptides described herein may be produced in bacteria or generated using solid phase synthesis and subsequently characterized using, e.g., HPLC, LCMS or Mass Spec. A detectable agent or biologically active agent (A), such as chelators or fluorophores, may be conjugated to the polypeptides as described herein via a linking group (L), and subsequently characterized using, e.g., HPLC, LCMS or Mass Spec. The conjugate may then be purified using, e.g., HPLC or SEC.

Certain embodiments of the invention provide a conjugate as described herein.

A: Detectable Agents and/or Biologically Active Agents

As described herein, conjugates of formula (I) comprise one or more detectable agents or biologically active agents.

Detectable Agents

In certain embodiments of the invention at least one A is a detectable agent. Detectable agents include, but are not limited to, fluorescent groups and chelating groups, which may be labeled with radionuclides. When more than one detectable group is attached to the polypeptide, the detectable groups and linking groups are independently selected, and therefore, may be the same or may be different. For example, in certain embodiments, a chelating group, which may be labeled with a radionuclide, and a fluorescent group may be linked to a polypeptide via individual linking groups (L).

In certain embodiments, the detectable agent (A) comprises a chelating group, which may be labeled with a radionuclide. Thus, depending on the type of radionuclide selected, the conjugates may be used for, e.g., diagnostic imaging (e.g., PET imaging, ultrasound) or radiation therapy for the treatment of cancer. Further, when the detectable agent comprises a diagnostic radionuclide, the conjugates may be used to monitor therapy response.

In certain other embodiments, the detectable agent comprises a fluorescent group, and the resulting conjugates may be used, e.g., for assays designed to identify and quantify the concentration of EpCAM on cell surfaces.

Chelating Groups and Radionuclides

In certain embodiments of the invention, the detectable agent comprises a chelating group. As used herein, a "chelating group" is a group that can include a detectable group, e.g., a radionuclide (e.g., a metallic radioisotope). Any suitable chelating group can be employed. Suitable chelating groups are disclosed, e.g., in Rockey et al., Bioorganic & Medicinal Chemistry 19 (2011) 4080-4090; Poster Sessions, Proceedings of the 46th Annual Meeting, J. Nuc. Med., p. 316, No. 1386; Scientific Papers, Proceedings of the 46th Annual Meeting, J. Nuc. Med., p. 123, No. 499; Scientific Papers, Proceedings of the 46th Annual Meeting, J. Nuc. Med., p. 102, No. 413; Scientific Papers, Proceedings of the 46th Annual Meeting, J. Nuc. Med., p. 102, No. 414; Scientific Papers, Proceedings of the 46th Annual Meeting, J. Nuc. Med., p. 103, No. 415; Poster Sessions, Proceedings of the 46th Annual Meeting, J. Nuc. Med., p. 318, No. 1396; Poster Sessions, Proceedings of the 46th Annual Meeting, J. Nuc. Med., p. 319, No. 1398; M. Moi et al., J. Amer. Chem., Soc., 49, 2639 (1989); S. V. Deshpande et al., J. Nucl. Med., 31, 473 (1990); G. Kuser et al., Bioconj. Chem., 1, 345 (1990); C. J. Broan et al., J. C. S. Chem. Comm., 23, 1739 (1990); C. J. Anderson et al., J. Nucl. Med. 36, 850 (1995); U.S. Pat. Nos. 5,739,313; and 6,004,533. Additionally, examples of certain chelating groups include, but are not limited to: p-SCN-Bn-TCMC, p-NO2-Bn-Cyclen, p-NO2-Bn-DOTA, p-NH2-Bn-DOTA, p-NH2-Bn-DOTA-tetra(t-Bu-ester), p-SCN-Bn-DOTA, DOTA-tris (t-Bu ester), DOTA-mono-NHS-tris(t-Bu ester), Maleimido-mono-amide-DOTA-tris (t-Bu ester), Maleimido-mono-amide-DOTA, Fmoc-L-Lys-mono-amide-DOTA-tris(t-Bu ester), 2-Aminoethyl-mono-amide-DOTA-tris(t-Bu ester), Azido-mono-amide-DOTA-tris(t-butyl ester), DOTA-NHS-ester, Azido-mono-amide-DOTA, p-NH2-Bn-DTPA, p-NH2-Bn-DTPA-penta (t-Bu ester), p-SCN-Bn-DTPA, p-NH2-CHX-A"-DTPA, CHX-A"-DTPA, DTPA-tetra (t-Bu ester), Maleimido-mono-amide-DTPA, p-NH2-Bn-PCTA, p-SCN-Bn-PCTA, p-NH2-Bn-oxo-DO3A, p-SCN-Bn-oxo-DO3A, p-NH2-Bn-NOTA, p-SCN-Bn-NOTA, NOTA-bis(t-Bu ester), Maleimido-mono-amide-NOTA, Deferoxamine-p-SCN, Deferoxamine-maleimide, DOTA-Biotin-Sarcosine, DO3A-Serotonin, Samplet Pack-Bifunctionals, Cyclen, Cyclam, DO2A, DO3A, DOTA, DOTA-NHS, DOTP, DOTMA, TETA, DOTAM, DiAmSar, CB-Cyclam, CB-TE2A, NOTA, TACN, Tm-DOTA, Gd-DOTA, Tm[DOTP]5-, Tm-DOTMA, Eu-DOTA-4AmC, Tm-p-SCN-Bn-DOTA, Gd-p-SCN-Bn-DOTA, Ho-p-SCN-Bn-DOTA, Tm-Maleimido-DOTA, Ho-Maleimido-DOTA, Bis-CBZ-Cyclen, TrisBOC-Cyclen, NO2A-(t-Bu ester), DO2A-t-Bu-ester, DO3A-t-Bu-ester and NODAGA (e.g., maleimide-NODAGA).

In certain embodiments, the detectable agent comprises a chelating group selected from:

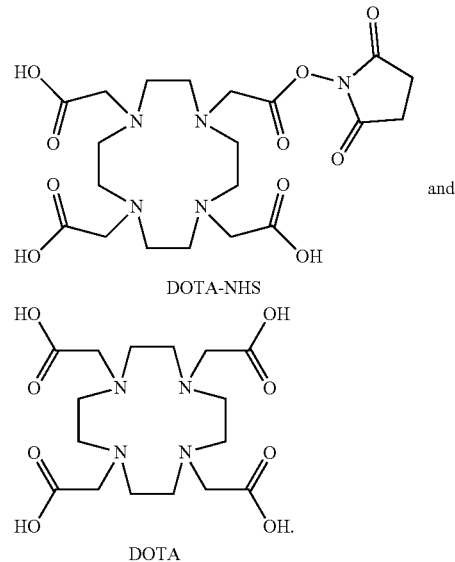

DOTA-NHS and

DOTA

In certain embodiments, the detectable agent comprises DOTA.

In certain embodiments, the detectable agent comprises NODAGA. In certain embodiments, the detectable agent comprises maleimide-NODAGA.

Conjugates of the invention, e.g., radiolabeled conjugates of formula I, are useful for imaging cells and tissues that include EpCAM, as well as for therapy. Accordingly, in certain embodiments, the invention also provides conjugates of formula I, wherein A comprises a chelating group that includes one or more detectable radionuclides (e.g., one or more metallic radionuclides, e.g., emits a signal). Methods for making such detectable agents are known to the art worker. Such conjugates can be useful to image tissues expressing EpCAM in vivo, ex vivo or in vitro or for therapeutic purposes.

As used herein, a "detectable radionuclide" is any suitable radionuclide (i.e., a radioisotope) useful in an imaging procedure, e.g., a diagnostic procedure, in vivo, ex vivo or in vitro, or for, e.g., therapy, e.g., cancer therapy. Suitable detectable radionuclides include metallic radionuclides (i.e., metallic radioisotopes) and non-metal nuclides.

Suitable metallic radionuclides (i.e., metallic radioisotopes or metallic paramagnetic ions) include Antimony-124, Antimony-125, Arsenic-74, Barium-103, Barium-140, Beryllium-7, Bismuth-206, Bismuth-207, Cadmium-109, Cadmium-115m, Calcium-45, Cerium-139, Cerium-141, Cerium-144, Cesium-137, Chromium-51, Cobalt-55, Cobalt-56, Cobalt-57, Cobalt-58, Cobalt-60, Cobalt-64, Copper-64, Copper-67, Erbium-169, Europium-152, Gallium-64, Gallium-68, Gadolinium-153, Gadolinium-157 Gold-195, Gold-199, Hafnium-175, Hafnium-175-181, Holmium-166, Indium-110, Indium-111, Iridium-192, Iron-55, Iron-59, Krypton-85, Lead-210, Manganese-54, Mercury-197, Mercury-203, Molybdenum-99, Neodymium-147, Neptunium-237, Nickel-63, Niobium-95, Osmium-185+ 191, Palladium-103, Platinum-195m, Praseodymium-143, Promethium-147, Protactinium-233, Radium-226, Rhenium-186, Rhenium-188, Rubidium-86, Ruthenium-103, Ruthenium-106, Scandium-44, Scandium-46, Selenium-75, Silver-110m, Silver-111, Sodium-22, Strontium-85, Strontium-89, Strontium-90, Sulfur-35, Tantalum-182, Technetium-99m, Tellurium-125, Tellurium-132, Thallium-204, Thorium-228, Thorium-232, Thallium-170, Tin-113, Tin-114, Tin-117m, Titanium-44, Tungsten-185, Vanadium-48, Vanadium-49, Ytterbium-169, Yttrium-86, Yttrium-88, Yttrium-90, Yttrium-91, Zinc-65, and Zirconium-95.

Suitable non-metal nuclides include, e.g., Fluorine-18.

In certain embodiments, at least one A comprises a chelating group (e.g., NODAGA, DOTA or DOTA-NHS) that includes one or more detectable radionuclides, wherein the detectable radionuclide is Copper-64. In certain embodiments, such a detectable group is attached to a polypeptide described herein using methods known in the art (see, e.g., Hackel et al., Protein Engineering, Design & Selection, pages 1-9, 2012 (doi:10.1093/protein/gzs036); Hackel et al., Radiology, 263(1): 179-188 (2012); Natarajan et al., Clinical Cancer Res, 19(24): 6820-6829 (2013)).

In some embodiments of the invention, the chelating group can include more than one metallic radioisotope. In some embodiments, the detectable chelating group can include 2 to about 10, 2 to about 8, 2 to about 6, or 2 to about 4 metallic radioisotopes.

Fluorescent Groups

In certain embodiments, the detectable agent comprises a fluorescent group, which may also be called a "fluorescent tag" or a "fluorophore". Thus, the resulting conjugates may be used, e.g., for assays designed to identify and quantify the concentration of EpCAM on cell surfaces.

A fluorophore is a molecule that absorbs light (i.e., excites) at a characteristic wavelength and emits light (i.e. fluoresces and emits a signal) at a second lower-energy wavelength. The detectable agent may include, but is not limited to, one or more of the following fluorescent groups: fluorescein, tetrachlorofluorescein, hexachlorofluorescein, tetramethylrhodamine, rhodamine, cyanine-derivative dyes, Texas Red, Bodipy, and Alexa dyes. Examples of certain fluorophores are listed at www.researchservices.umn.edu/sites/researchservices.umn.edu/files/configuration-lsr-fortessa-h0081.pdf, which is incorporated by reference herein, which includes, e.g., FITC, GFP, 488 B, Brilliant Blue 515, CFSE, 7-AAD, PerCP, PerCP-Cy5-5, 488 A, PerCP-eFluor 710, SSC, APC-Cy7, APC-H7, 640A, APC-Alexa Fluor 750, APC-eFluor 780, Alexa Fluor 647, APC, 640 C, Sytox Red, Alexa Fluor 700, 640 B, Qdot 705, 405 B, Brilliant Violet 711, Qdot 605, 405 D, Brilliant Violet 605, eFluor 605, Pacific Blue, 405 F, Brilliant Violet 421, DyeCycle Violet, eFluor 450, Horizon v450, Qdot 800, 405 A, Brilliant Violet 786, Qdot 655, 405 C, Brilliant Violet 650, eFluor 650, Pacific Orange, 405 E, Brilliant Violet 510, Horizon v500, L/D Fixable Aqua, PE-Cy7, 561 A, DsRed, PE, 561 C, Cy3, tdTomato, PE-CF594, PE-Texas Red, PI, 561 B, mCherry, PE-Alexa Fluor, 355 B, Brilliant Ultraviolet 737, Alexa Fluor 350, 355 D, Brilliant Ultraviolet 395, 355 A, Brilliant Ultraviolet 805, 355 C and Brilliant Ultraviolet 496. Characteristic absorption and emission wavelengths for each of these are well known to those of skill in the art.

In certain embodiments, the fluorophore is one or more of the fluorophores listed in Table 2.

TABLE 2

| Probe | Excitation (nm) | Emission (nm) |
| --- | --- | --- |
| Hydroxycoumarin | 325 | 386 |
| Alexa fluor | 325 | 442 |
| Aminocoumarin | 350 | 445 |
| Methoxycoumarin | 360 | 410 |
| Cascade Blue | (375); 401 | 423 |
| Pacific Blue | 403 | 455 |
| Pacific Orange | 403 | 551 |
| Lucifer yellow | 425 | 528 |
| Alexa fluor 430 | 430 | 545 |
| NBD | 466 | 539 |
| R-Phycoerythrin (PE) | 480; 565 | 578 |
| PE-Cy5 conjugates | 480; 565; 650 | 670 |
| RE-Cy7 conjugates | 480; 565; 743 | 767 |
| Red 613 | 480; 565 | 613 |
| PerCP | 490 | 675 |
| Cy2 | 490 | 510 |
| TruRed | 490, 675 | 695 |
| FluorX | 494 | 520 |
| Fluorescein | 495 | 519 |
| FAM | 495 | 515 |
| BODIPY-FL | 503 | 512 |
| TET | 526 | 540 |
| Alexa fluor 532 | 530 | 555 |
| HEX | 535 | 555 |
| TRITC | 547 | 572 |
| Cy3 | 550 | 570 |
| TMR | 555 | 575 |
| Alexa fluor 546 | 556 | 573 |
| Alexa fluor 555 | 556 | 573 |
| Tamara | 565 | 580 |
| X-Rhodamine | 570 | 576 |
| Lissamine Rhodamine B | 570 | 590 |
| ROX | 575 | 605 |
| Alexa fluor 568 | 578 | 603 |
| Cy3.5 581 | 581 | 596 |
| Texas Red | 589 | 615 |
| Alexa fluor 594 | 590 | 617 |
| Alexa fluor 633 | 621 | 639 |
| LC red 640 | 625 | 640 |
| Allophycocyanin (APC) | 650 | 660 |
| Alexa fluor 633 | 650 | 688 |
| APC-Cy7 conjugates | 650; 755 | 767 |
| Cy5 | 650 | 670 |
| Alexa fluor 660 | 663 | 690 |
| Cy5.5 | 675 | 694 |
| LC red 705 | 680 | 710 |
| Alexa fluor 680 | 679 | 702 |
| Cy7 | 743 | 770 |
| IRDye 800 CW | 774 | 789 |
| Alexa Fluor 488 | 490 | 525 |
| Alexa Fluor 647 | 650 | 665 |
| Brilliant Violet 421 | 405 | 421 |

In certain in vivo embodiments, the fluorophore emits in the near infrared range, such as in the 650-900 nm range. (Weissleder et al., "Shedding light onto live molecular targets, *Nature Medicine,* 9:123-128 (2003)).

Biologically Active Agents

In certain embodiments of the invention at least one A is a biologically active agent. The biologically active agent may have activity when it is linked to the polypeptide or may become active when the linking group is hydrolyzed and the biologically active agent is released from the remainder of the conjugate.

In certain embodiments of the invention, at least one A is biotin or comprises biotin. Biotin moieties may be used to further link a polypeptide of the invention to a streptavidin-functionalized molecule (e.g., a CSAN, detectable agent or biologically active agent).

In certain embodiments, the biologically active agent is a pharmaceutically active agent.

In certain embodiments, the biologically active agent is a chemotherapeutic agent. In certain embodiments, the biologically active agent is a chemotherapeutic agent belonging to the class of chalicheamicins. In certain embodiments, the biologically active agent is a chemotherapeutic agent belonging to the class of auristatins (including but not limited to monomethyl auristatin E [MMAE], monomethyl auristatin F [MMAF], etc.). In certain embodiments, the biologically active agent is a chemotherapeutic agent belonging to the class of maytansinoids (including but not limited to emtansine, also called DM1).

In certain embodiments, the biologically active agent is a peptide.

In certain embodiments, the biologically active agent is an antibody.

In certain embodiments, the biologically active agent is an immunotherapeutic agent.

In certain embodiments, the biologically active agent is a fusion protein consisting of other functional or non-functional protein and peptide domains.

In certain embodiments, the biologically active agent is a fusion protein capable of assembling, either spontaneously or upon induction (e.g., via addition of a chemical dimerizer, a protein dimerizer, a chemical substrate, a protein substrate, an enzyme, etc.), into a supramolecular structure. In certain embodiments, the biologically active agent is a polypeptide comprising a first dihydrofolate reductase (DHFR) peptide, a second DHFR peptide; and optionally, a tag peptide. Thus, in certain embodiments, P is a polypeptide as described herein that binds to epithelial cell adhesion molecule (Ep-CAM); L is a peptide linking group; A is a polypeptide comprising a first dihydrofolate reductase (DHFR) peptide, a second DHFR peptide; and optionally, a tag peptide; and n is 1. In certain embodiments, a conjugate of the invention is selected from the group consisting of SEQ ID NO: 53, SEQ ID NO: 55 and SEQ ID NO: 59.

In certain embodiments, the biologically active agent is a chemically self-assembled nanoring (CSAN) that is formed upon the addition of a chemical dimerizer (e.g., bis-methotrexate), wherein the nanoring is comprised of multiple fusion proteins, each consisting of two subunits of dihydrofolate reductase (DHFR) joined by a peptide linker of variable length (e.g., 1-13 amino acids) and further conjugated to other proteins (e.g., to a polypeptide described herein through L) and peptides (Carlson, J. C. T., et al. *J. Am. Chem. Soc.* 2006, 128, 7630-7638; Fegan, A., et al. *Mol. Pharmaceutics.* 2012, 9, 3218-3227; Li, Q., et al., *J. Am. Chem. Soc.* 2010, 132, 17247-17257; Shah, R, et al., *Mol. Pharmaceutics.* 2016, 13 (7), 2193-2203; Gangar, A., et al., *J. Am. Chem. Soc.* 2012, 134, 2895-2897; Shen, J., et al., *J. Am. Chem. Soc.* 2015, 137, 10108-10111; Qing, L., et al., *Angew. Chem. Int. Ed.* 2008, 47, 10179-10182; Gangar, A., et al., *Mol. Pharmaceutics.* 2013, 10, 3514-3518; Gabrielse, K., et al., *Angew. Chem. Int. Ed.* 2014, 53, 5112-5116).

In certain embodiments, a polypeptide of the invention is operably linked to a self-assembling hydrogel. In certain embodiments, a polypeptide of the invention (e.g., comprising a cysteine) is operably linked to a maleimide functionalized hydrogel matrix.

Linking Group L

In certain embodiments of the invention L is a linking group that joins the detectable agent or biologically active agent (A) to a polypeptide that binds to an EpCAM (P). The nature of the linking group L is not critical provided the resulting conjugates retain the useful biological properties described herein (e.g., the polypeptide retains its EpCAM binding capabilities and the detectable or biologically active agent retains its functionality).

In one embodiment of the invention the linking group has a molecular weight of from about 20 daltons to about 20,000 daltons.

In one embodiment of the invention the linking group has a molecular weight of from about 20 daltons to about 5,000 daltons.

In one embodiment of the invention the linking group has a molecular weight of from about 20 daltons to about 1,000 daltons.

In one embodiment of the invention the linking group has a molecular weight of from about 20 daltons to about 200 daltons.

In another embodiment of the invention the linking group has a length of about 5 angstroms to about 60 angstroms.

In another embodiment of the invention the linking group separates the polypeptide from the remainder of the conjugate of formula I by about 5 angstroms to about 40 angstroms, inclusive, in length.

In another embodiment of the invention the linking group is a divalent, branched or unbranched, saturated or unsaturated, hydrocarbon chain, having from 1 to 25 carbon atoms, wherein one or more (e.g. 1, 2, 3, or 4) of the carbon atoms is optionally replaced by (—O—) or a divalent ring of formula:

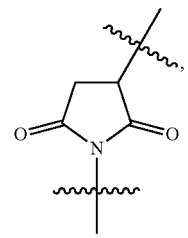 [SMILES: *C1CC(=O)N(*)C1=O]

and wherein the chain or ring is optionally substituted on carbon with one or more (e.g. 1, 2, 3, or 4) substituents selected from $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo (═O), carboxy, aryl, aryloxy, heteroaryl, and heteroaryloxy.

In another embodiment of the invention the linking group is a divalent, branched or unbranched, saturated or unsaturated, hydrocarbon chain, having from 2 to 25 carbon atoms, wherein one or more (e.g. 1, 2, 3, or 4) of the carbon atoms is optionally replaced by (—O—), and wherein the chain is optionally substituted on carbon with one or more (e.g. 1, 2, 3, or 4) substituents selected from $(C_1-C_6)$alkoxy, $(C_3-C_6)$cycloalkyl, $(C_1-C_6)$alkanoyl, $(C_1-C_6)$alkanoyloxy, $(C_1-C_6)$ alkoxycarbonyl, (C₁-C₆)alkylthio, azido, cyano, nitro, halo, hydroxy, oxo (═O), carboxy, aryl, aryloxy, heteroaryl, and heteroaryloxy.

In another embodiment of the invention the linking group is a divalent, branched or unbranched, saturated or unsaturated, hydrocarbon chain, having from 2 to 10 carbon atoms, wherein one or more (e.g. 1, 2, 3, or 4) of the carbon atoms is optionally replaced by (—O—), and wherein the chain is optionally substituted on carbon with one or more (e.g. 1, 2, 3, or 4) substituents selected from (C₁-C₆)alkoxy, (C₃-C₆)cycloalkyl, (C₁-C₆)alkanoyl, (C₁-C₆)alkanoyloxy, (C₁-C₆)alkoxycarbonyl, (C₁-C₆)alkylthio, azido, cyano, nitro, halo, hydroxy, oxo (═O), carboxy, aryl, aryloxy, heteroaryl, and heteroaryloxy.

In another embodiment of the invention the linking group is a divalent, branched or unbranched, saturated or unsaturated, hydrocarbon chain, having from 2 to 25 carbon atoms, wherein the chain is optionally substituted on carbon with one or more (e.g. 1, 2, 3, or 4) substituents selected from (C₁-C₆)alkoxy, (C₃-C₆)cycloalkyl, (C₁-C₆)alkanoyl, (C₁-C₆)alkanoyloxy, (C₁-C₆)alkoxycarbonyl, (C₁-C₆)alkylthio, azido, cyano, nitro, halo, hydroxy, oxo (═O), carboxy, aryl, aryloxy, heteroaryl, and heteroaryloxy.

In another embodiment of the invention the linking group is a divalent, branched or unbranched, saturated or unsaturated, hydrocarbon chain, having from 2 to 10 carbon atoms, wherein the chain is optionally substituted on carbon with one or more (e.g. 1, 2, 3, or 4) substituents selected from (C₁-C₆)alkoxy, (C₃-C₆)cycloalkyl, (C₁-C₆)alkanoyl, (C₁-C₆)alkanoyloxy, (C₁-C₆)alkoxycarbonyl, (C₁-C₆)alkylthio, azido, cyano, nitro, halo, hydroxy, oxo (═O), carboxy, aryl, aryloxy, heteroaryl, and heteroaryloxy.

In another embodiment of the invention the linking group is a divalent, branched or unbranched, saturated or unsaturated, hydrocarbon chain, having from 2 to 10 carbon atoms.

In another embodiment of the invention the linking group is a divalent, branched or unbranched, saturated hydrocarbon chain, having from 2 to 10 carbon atoms.

In another embodiment of the invention the linking group is a divalent, unbranched, saturated hydrocarbon chain, having from 2 to 10 carbon atoms.

In another embodiment of the invention the linking group is a divalent, unbranched, saturated hydrocarbon chain, having from 2 to 6 carbon atoms.

In another embodiment of the invention the linking group is a divalent, unbranched, saturated hydrocarbon chain, having from 2 to 4 carbon atoms.

In another embodiment of the invention the linking group comprises a polyethyleneoxy chain. In another embodiment of the invention the polyethyleneoxy chain comprises 2, 3, 4, 5, 6, 7, 8, 9, or 10 repeating ethyleneoxy units.

In another embodiment of the invention the linking group is —C(═O)—.

In another embodiment of the invention the linking group is a divalent radical formed from a protein.

In another embodiment of the invention the linking group is a divalent radical formed from a polypeptide.

In another embodiment of the invention the linking group is a divalent radical formed from an amino acid.

In another embodiment of the invention the carboxylic acid of the detectable agent or biologically active agent is reacted with an amine of the polypeptide to form an amide bond.

In certain embodiments of the invention, L comprises a peptide. In certain embodiments of the invention, L is a peptide. For example, in certain embodiments, the peptide is about 1 to about 50 amino acids in length, or about 1 to about 30 amino acids in length, or about 1 to about 20 amino acids in length or about 1 to about 15 amino acids in length. In certain embodiments, the peptide is a recombinant peptide. In certain embodiments, the L comprises a peptide comprising a (G₄S)x amino acid sequence, wherein x is 1 or more (SEQ ID NO: 63). In certain embodiments, the L comprises a peptide comprising a (EAAAK)x amino acid sequence, wherein x is 1 or more (SEQ ID NO: 64).

In certain embodiments of the invention, L is a direct bond. In certain embodiments, L is a direct bond and "P" is bonded to "A" through an amide bond.

In certain embodiments, "P" is linked to "A" using sulfhydryl/maleimide chemistry.

Thus, in one embodiment, L comprises a divalent ring of formula:

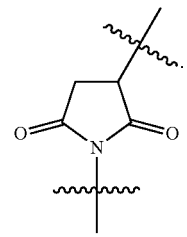 [SMILES: *C1CC(=O)N(*)C1=O]

In another embodiment, L is a divalent ring of formula:

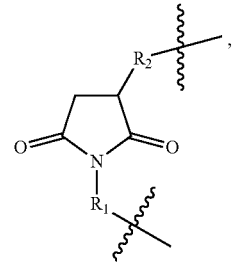

wherein R₁ and R₂ are each independently direct bond or a divalent, branched or unbranched, saturated or unsaturated, hydrocarbon chain, having from 1 to 25 carbon atoms, wherein one or more (e.g. 1, 2, 3, or 4) of the carbon atoms is optionally replaced by (—O—) and wherein the chain is optionally substituted on carbon with one or more (e.g. 1, 2, 3, or 4) substituents selected from (C₁-C₆)alkoxy, (C₃-C₆)cycloalkyl, (C₁-C₆)alkanoyl, (C₁-C₆)alkanoyloxy, (C₁-C₆)alkoxycarbonyl, (C₁-C₆)alkylthio, azido, cyano, nitro, halo, hydroxy, oxo (═O), carboxy, aryl, aryloxy, heteroaryl, and heteroaryloxy.

In another embodiment, a conjugate as described herein has the following formula:

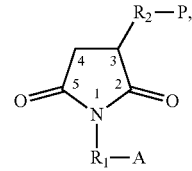

wherein "A" is a detectable agent or biologically active agent;

$R_1$ and $R_2$ are each independently a direct bond or a divalent, branched or unbranched, saturated or unsaturated, hydrocarbon chain, having from 1 to 25 carbon atoms, wherein one or more (e.g. 1, 2, 3, or 4) of the carbon atoms is optionally replaced by (—O—) and wherein the chain is optionally substituted on carbon with one or more (e.g. 1, 2, 3, or 4) substituents selected from ($C_1$-$C_6$)alkoxy, ($C_3$-$C_6$)cycloalkyl, ($C_1$-$C_6$)alkanoyl, ($C_1$-$C_6$)alkanoyloxy, ($C_1$-$C_6$)alkoxycarbonyl, ($C_1$-$C_6$)alkylthio, azido, cyano, nitro, halo, hydroxy, oxo (=O), carboxy, aryl, aryloxy, heteroaryl, and heteroaryloxy.

In another embodiment, a conjugate as described herein has the following formula:

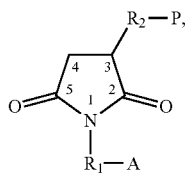

wherein "A" is a detectable agent or biologically active agent;

$R_1$ is a direct bond or a divalent, branched or unbranched, saturated or unsaturated, hydrocarbon chain, having from 1 to 25 carbon atoms, wherein one or more (e.g. 1, 2, 3, or 4) of the carbon atoms is optionally replaced by (—O—) and wherein the chain is optionally substituted on carbon with one or more (e.g. 1, 2, 3, or 4) substituents selected from ($C_1$-$C_6$)alkoxy, ($C_3$-$C_6$)cycloalkyl, ($C_1$-$C_6$)alkanoyl, ($C_1$-$C_6$)alkanoyloxy, ($C_1$-$C_6$)alkoxycarbonyl, ($C_1$-$C_6$)alkylthio, azido, cyano, nitro, halo, hydroxy, oxo (=O), carboxy, aryl, aryloxy, heteroaryl, and heteroaryloxy;

$R_2$ is a direct bond; and

"P" is a polypeptide described herein which is linked to position 3 of the ring through a sulfur atom (e.g, of a cysteine residue).

In certain embodiments of the invention, L comprises polyethylene glycol (PEG).

In certain embodiments of the invention, L may comprise biotin. In certain embodiments of the invention, L may comprise a binding pair, such as biotin and avidin/streptavidin.

Certain Chemically Self-Assembled Nanorings (CSANs) Embodiments

As described herein, a conjugate of the invention may be incorporated into a chemically self-assembled nanoring (CSAN) and used for diagnostic or therapeutic purposes. A CSAN may be formed when conjugates of the invention are contacted with a chemical dimerizer (e.g., bis-methotrexate). As described herein, the nanoring is comprised of multiple fusion proteins, each consisting of two subunits of dihydrofolate reductase (DHFR) joined by a peptide linker of variable length (e.g., 1-13 amino acids) and further conjugated to other proteins (e.g., to a polypeptide described herein through L) and peptides (see, e.g., Carlson, J. C. T., et al. *J. Am. Chem. Soc.* 2006, 128, 7630-7638; Fegan, A., et al. *Mol. Pharmaceutics.* 2012, 9, 3218-3227; Li, Q., et al., *J. Am. Chem. Soc.* 2010, 132, 17247-17257; Shah, R, et al., *Mol. Pharmaceutics.* 2016, 13 (7), 2193-2203; Gangar, A., et al., *J. Am. Chem. Soc.* 2012, 134, 2895-2897; Shen, J., et al., *J. Am. Chem. Soc.* 2015, 137, 10108-10111; Qing, L., et al., *Angew. Chem. Int. Ed.* 2008, 47, 10179-10182; Gangar, A., et al., *Mol. Pharmaceutics.* 2013, 10, 3514-3518; Gabrielse, K., et al., *Angew. Chem. Int. Ed.* 2014, 53, 5112-5116. These documents are incorporated by reference in their entirety for all purposes).

Thus, certain embodiments of the invention provide a chemically self-assembled nanoring (CSAN) comprising a plurality of conjugates of formula I, wherein P is a polypeptide as described herein that binds to epithelial cell adhesion molecule (EpCAM), L is a direct bond or a linking group described herein, and A is biotin; a plurality of bis-methotrexate (bisMTX) compounds; and a plurality of fusion proteins, wherein each fusion protein comprises a first DHFR subunit operably linked to a second DHFR subunit and a streptavidin domain operably linked to either the first or second DHFR subunit.

Certain embodiments of the invention also provide a chemically self-assembled nanoring (CSAN) comprising a plurality of conjugates as described herein and a plurality of bis-methotrexate (bisMTX) compounds. In certain embodiments, the conjugates are conjugates of formula I, wherein P is a polypeptide as described herein that binds to epithelial cell adhesion molecule (EpCAM); L is a peptide linking group; A is a polypeptide comprising a first dihydrofolate reductase (DHFR) peptide, a second DHFR peptide; and optionally, a tag peptide; and n is 1. In certain embodiments, the conjugate is SEQ ID NO: 53, SEQ ID NO: 55 or SEQ ID NO: 59.

The plurality of conjugates of the invention may consist of a single type of conjugate or may be a mixture of different types of conjugates (e.g., 2, 3, 4, 5 or more types of conjugates).

Certain bisMTX compounds are known in the art. In certain embodiments, the bixMTX compound is a bixMTX compound described in, e.g., Carlson, J. C. T., et al. *J. Am. Chem. Soc.* 2006, 128, 7630-7638; Fegan, A., et al. *Mol. Pharmaceutics.* 2012, 9, 3218-3227; Li, Q., et al., *J. Am. Chem. Soc.* 2010, 132, 17247-17257; Shah, R, et al., *Mol. Pharmaceutics.* 2016, 13 (7), 2193-2203; Gangar, A., et al., *J. Am. Chem. Soc.* 2012, 134, 2895-2897; Shen, J., et al., *J. Am. Chem. Soc.* 2015, 137, 10108-10111; Qing, L., et al., *Angew. Chem. Int. Ed.* 2008, 47, 10179-10182; Gangar, A., et al., *Mol. Pharmaceutics.* 2013, 10, 3514-3518; Gabrielse, K., et al., *Angew. Chem. Int. Ed.* 2014, 53, 5112-5116; US Patent publication US2015-0343082, US Patent publication US2015-0017189, U.S. Pat. No. 8,236,925 or 8,580,921 (these documents are incorporated by reference herein for all purposes).

The plurality of bisMTX compounds may consist of a single type of bisMTX or may be a mixture of different types of compounds (e.g., 2, 3, 4, 5 or more types of compounds).

In certain embodiments, the bisMTX compound is modified to comprise a bioorthogonal ligation handle, such as an azide group. In certain embodiments, the bisMTX compound is azide-bisMTX:

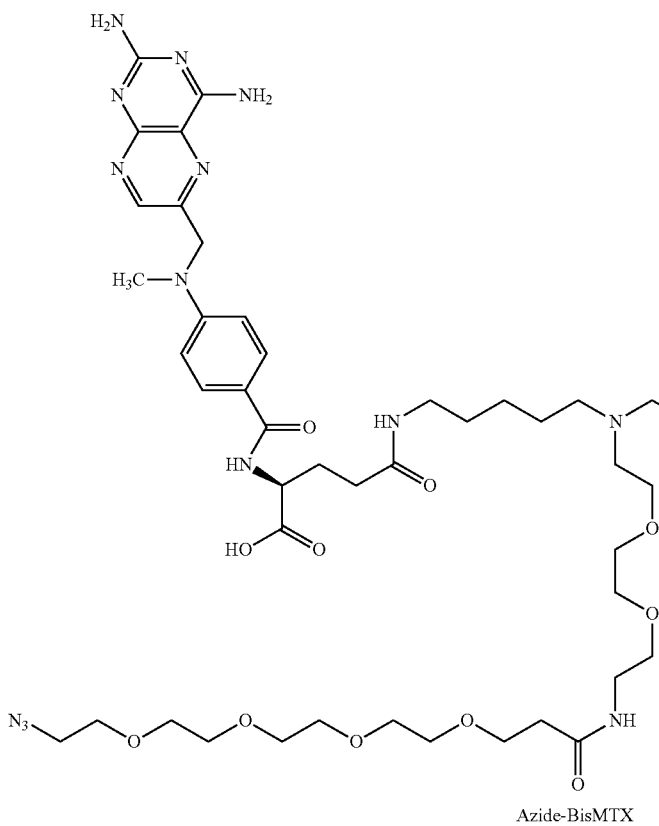

Azide-BisMTX

Certain embodiments of the invention provide an azide-bisMTX compound as described herein.

CSANs comprising a plurality of azide-bisMTX compounds could be linked to other molecules, such as DBCO through a copper-free, strain-promoted alkyne/azide cycloaddition (SPAAC) involving the DBCO/azide groups. In certain embodiments, a CSAN comprising such azide-bisMTX compounds could be bound to a DBCO functionalized phospholipid (e.g., 1,2-di stearoyl-sn-glycero-3-phosphoethanolamine-N-{dibenzocyclooctyl(polyethylene glycol)-2000} (DSPE-PEG$_{2000}$-DBCO)). In certain embodiments, the phospholipid is incorporated into a cell membrane (e.g., an immune cell, such as a T cell). Thus, certain embodiments of the invention provide a CSAN linked to a target cell via a linkage between an azide-bisMTX compound and a DBCO functionalized phospholipid, wherein the phospholipid is incorporated into the target cell membrane. In certain embodiments, the target cell is an immune cell, such as a T cell.

In certain embodiments, the CSAN may be multi-functional and may comprise one or more types of functionalized-DHFR$^2$ polypeptides, in addition to a conjugate of the invention. For example, in certain embodiments the CSAN further comprises a plurality of streptavidin-DHFR$^2$ polypeptides, wherein the streptavidin-DHFR$^2$ polypeptide comprises streptavidin domain peptide operably linked to a first dihydrofolate reductase (DHFR) peptide and a second DHFR peptide operably linked to a the first DHFR peptide. In such embodiments, the CSAN would be capable of binding to a biotin functionalized molecule or cell (e.g., an immune cell, such as a T cell). Thus, certain embodiments of the invention provide a CSAN linked to a target cell via a linkage between a streptavidin-DHFR$^2$ polypeptide and a biotin functionalized phospholipid, wherein the phospholipid is incorporated into the target cell membrane. In certain embodiments, the target cell is an immune cell, such as a T cell. In certain embodiments, the biotin functionalized phospholipid is 1,2-distearoyl-sn-glycero-3-phosphoethanolamine-N-{biotinyl(polyethylene glycol)-2000} (DSPE-PEG$_{2000}$-biotin).

Thus, certain embodiments of the invention provide a CSAN described herein operably linked to an immune cell (e.g., a T cell). Such CSANs linked to immune cells may be used, e.g., in immunotherapies for the treatment of cancer.

Methods of Treatment

Certain embodiments of the invention provide a pharmaceutical composition comprising a conjugate of formula I and a pharmaceutically acceptable excipient.

Certain embodiments of the invention provide a method for treating or preventing cancer in an animal (e.g., a human) comprising administering a therapeutically effective amount of a conjugate (e.g., comprising a therapeutic radionuclide and/or a biologically active agent) of formula I to the animal.

Certain embodiments of the invention provide a pharmaceutical composition comprising a CSAN described herein and a pharmaceutically acceptable excipient.

Certain embodiments of the invention provide a method for treating or preventing cancer in an animal (e.g., a human) comprising administering a therapeutically effective amount of a CSAN described herein to the animal.

The terms "treat" and "treatment" refer to both therapeutic treatment and prophylactic or preventative measures, wherein the object is to prevent or slow down (lessen) an undesired physiological change or disorder, such as the growth, development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "therapeutically effective amount" means an amount of a conjugate (e.g., conjugate of formula (I) or CSAN conjugated to a peptide of the invention) of the present invention that (i) treats the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the conjugate may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, head and neck cancer, and melanoma.

The invention also provides a conjugate of formula I for use in medical therapy.

The invention also provides a conjugate of formula I for the prophylactic or therapeutic treatment of cancer.

The invention also provides the use of a conjugate of formula (I) to prepare a medicament for treating cancer in an animal (e.g. a mammal such as a human).

In certain embodiments, the cancer is a carcinoma. In certain embodiments, the cancer is breast, pancreas, esophagus, colon, hepatic, or prostate cancer.

Diagnostic Methods

Certain embodiments of the invention provide a method of detecting an EpCAM molecule, comprising contacting a cell with a conjugate of formula (I). In certain embodiments, the detectable agent comprises a chelating group labeled with a radionuclide. In certain embodiments, the detectable agent comprises a fluorescent group. In certain embodiments, the method further comprises quantifying the concentration of EpCAM on the surface of the cell by measuring a signal from the detectable agent (e.g., a fluorescent signal or a radioactive signal).

Cancer cells/tissues have been shown to overexpress EpCAM (i.e., express more than the physiologically "normal" level of EpCAM. Accordingly, in certain embodiments, the invention relates to methods of using the conjugates for in vitro, in situ, ex vivo and in vivo diagnosis of cancer, as well as for determining the effectiveness of a cancer treatment.

Certain embodiments of the invention provide a method of detecting EpCAM positive cells in a biological sample obtained from an animal, comprising detecting whether EpCAM positive cells are present in the sample by contacting the sample with a conjugate of formula (I) and detecting a signal from the detectable agent (e.g., a radioactive signal or fluorescent signal). For example, detecting a signal greater than a signal detected from a control sample (e.g., a sample that does not comprise EpCAM positive cells) indicates the presence of EpCAM positive cells in the biological sample.

In certain embodiments, the signal detected from the biological sample is 1-100% greater than the signal detected from the control sample. In certain embodiments, the signal detected from the biological sample is 10%, 20%, 30%, 40%, 50%, 60%, 70%, 80%, or 90% greater than the signal detected from the control sample.

Certain embodiments of the invention provide a method of detecting cancer cells in a biological sample obtained from an animal, comprising detecting whether cancer cells are present in the sample by contacting the sample with a conjugate of formula (I) and detecting a signal from the detectable agent (e.g., a radioactive signal or fluorescent signal). For example, detecting a signal greater than a signal detected from a control sample (e.g., a sample that does not comprise cancer cells) indicates the presence of cancer cells in the biological sample. In certain embodiments, the signal detected from the biological sample is 1-100% greater than the signal detected from the control sample. In certain embodiments, the signal detected from the biological sample is 10%, 20%, 30%, 40%, 50%, 60%, 70%, 80%, or 90% greater than the signal detected from the control sample.

Certain embodiments of the invention provide a method of diagnosing cancer in an animal (e.g., a human patient), comprising 1) obtaining a biological sample from the animal; 2) detecting whether cells within the sample overexpress EpCAM as compared to cells from a control sample by contacting the sample with a conjugate of Formula (I) and quantifying EpCAM expression (e.g., by detecting a signal from the detectable agent, such as a radioactive signal or fluorescent signal, and quantifying the signal); and 3) diagnosing the animal with cancer when overexpression of EpCAM in the sample is detected.

Certain embodiments of the invention provide an in vivo method of detecting cancer in an animal (e.g., a human patient), comprising administering a conjugate of formula (I) to the animal, wherein the conjugate binds to an EpCAM molecule; and detecting a signal (e.g., a radioactive signal or fluorescent signal emitting in the near infrared range) from the detectable agent. For example, detecting a signal greater than a signal detected from a control animal without cancer indicates the animal has cancer. In certain embodiments, the signal from the animal is 1-100% greater than the signal from the control animal. In certain embodiments, the signal from the animal is 10%, 20%, 30%, 40%, 50%, 60%, 70%, 80%, or 90% greater than the signal from the control animal. In certain embodiments of the invention, the signal from the detectable agent is measured using PET imaging or by ultrasound.

Certain embodiments of the invention provide an in vivo method of detecting cancer in an animal (e.g., a human patient), comprising 1) detecting whether cells that overexpress EpCAM are present in the animal (i.e., as compared to cells in a control animal) by administering a conjugate of Formula (I) to the animal and quantifying EpCAM expression (e.g., by detecting a signal from the detectable agent, such as a radioactive signal or fluorescent signal, and quantifying the signal); and 2) diagnosing the animal with cancer when overexpression of EpCAM in the sample is detected. In certain embodiments of the invention, the signal from the detectable agent is detected using PET imaging or by ultrasound.

Certain embodiments of the invention provide a method for determining the effectiveness of a cancer therapy in an animal (e.g., a human patient), comprising
1) administering a conjugate of formula (I) to the animal and measuring a first signal (e.g., a radioactive signal or fluorescent signal emitting in the near infrared range) from the detectable agent;
2) administering a cancer therapy;
3) administering a conjugate of formula (I) to the animal and measuring a second signal (e.g., a radioactive signal or fluorescent signal emitting in the near infrared range) from the detectable agent; and
4) comparing the first signal with the second signal, wherein the cancer therapy is effective if the second signal is less than the first signal.

In certain embodiments, the second signal is 1-100% less than the first signal. In certain embodiments, the first signal is 10%, 20%, 30%, 40%, 50%, 60%, 70%, 80%, or 90% less than the first signal. In certain embodiments of the invention, the signal from the detectable agent is measured using PET imaging or by ultrasound.

In certain embodiments, a CSAN as described herein may also be used in a diagnostic method described herein.

Administration

The polypeptides and conjugates (e.g., conjugates of formula I and CSANs conjugated to a peptide of the invention) described herein can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present polypeptides and conjugates may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the polypeptides and conjugates may be combined with one or more excipients and used in the form of ingestible tablets, buccal tablets, troches, capsules, elixirs, suspensions, syrups, wafers, and the like. Such compositions and preparations should contain at least 0.1% of polypeptides or conjugates. The percentage of the compositions and preparations may, of course, be varied and may conveniently be between about 2 to about 60% of the weight of a given unit dosage form. The amount of the polypeptides or conjugates in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the polypeptides or conjugates, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the polypeptides or conjugates may be incorporated into sustained-release preparations and devices.

The polypeptides or conjugates may also be administered intravenously or intraperitoneally by infusion or injection. Solutions of the polypeptides or conjugates can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

In certain embodiments, a conjugate (e.g., conjugate of formula (I) or CSAN conjugated to a peptide of the invention), wherein the detectable group comprises a chelating group labeled with a radionuclide, is formulated for administration by infusion.

The pharmaceutical dosage forms suitable for injection or infusion can include sterile aqueous solutions or dispersions or sterile powders comprising the polypeptides or conjugates which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the polypeptides or conjugates in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the polypeptides or conjugates plus any additional desired ingredient present in the previously sterile-filtered solutions.

For topical administration, the present polypeptides or conjugates may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present polypeptides or conjugates can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the polypeptides or conjugates (e.g., conjugates of formula I or CSANs) to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the polypeptides and conjugates (e.g., conjugates of formula I or CSANs) can be determined by comparing their in vitro activity, and in vivo activity in animal models. Methods for the extrapolation of effective dosages in mice, and other animals, to humans are known to the art; for example, see U.S. Pat. No. 4,938,949.

The amount of the polypeptides or conjugates, required for use in treatment will vary with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

Polypeptides or conjugates of the invention can also be administered in combination with other therapeutic agents, for example, other agents that are useful for the treating cancer. Examples of such agents include chemotherapeutic agents. Accordingly, one embodiment the invention also provides a composition comprising a conjugate (e.g., conjugate of formula I or CSAN), at least one other therapeutic agent, and a pharmaceutically acceptable diluent or carrier.

Kits

Certain embodiments of the invention provide a kit comprising:
1) a conjugate of formula (I); and
2) instructions for administering the conjugate to an animal.

Certain embodiments of the invention provide a kit comprising:
1) a conjugate of formula (I);
2) instructions for loading a radionuclide into the conjugate to generate a radiolabeled conjugate; and
3) instructions for administering the radiolabeled conjugate to an animal.

Certain embodiments of the invention provide a kit comprising:
1) a conjugate of formula (I);
2) a radionuclide;
3) instructions for loading the radionuclide into the conjugate to generate a radiolabeled conjugate; and
4) instructions for administering the radiolabeled conjugate to an animal.

Certain embodiments of the invention provide a kit comprising:
1) a CSAN described herein; and
2) instructions for administering the CSAN to an animal.

The invention also provides a kit comprising a conjugate of formula I or a CSAN, at least one other therapeutic agent, packaging material, and instructions for administering the conjugate of formula I or CSAN and the other therapeutic agent or agents to an animal to treat cancer.

Certain Definitions

As used herein, the following definitions are used, unless otherwise described: halo is fluoro, chloro, bromo, or iodo. Alkyl, alkoxy, alkenyl, alkynyl, etc. denote both straight and branched groups; but reference to an individual radical such as propyl embraces only the straight chain radical, a branched chain isomer such as isopropyl being specifically referred to. Aryl denotes a phenyl radical or an ortho-fused bicyclic carbocyclic radical having about nine to ten ring atoms in which at least one ring is aromatic. Heteroaryl encompasses a radical of a monocyclic aromatic ring containing five or six ring atoms consisting of carbon and one to four heteroatoms each selected from the group consisting of non-peroxide oxygen, sulfur, and N(L) wherein L is absent or is H, O, $(C_1-C_4)$alkyl, phenyl or benzyl, as well as a radical of an ortho-fused bicyclic heterocycle of about eight to ten ring atoms comprising one to four heteroatoms each selected from the group consisting of non-peroxide oxygen, sulfur, and N(L).

Specific values listed below for radicals, substituents, and ranges, are for illustration only; they do not exclude other defined values or other values within defined ranges for the radicals and substituents.

Specifically, $(C_1-C_6)$alkyl can be methyl, ethyl, propyl, isopropyl, butyl, iso-butyl, sec-butyl, pentyl, 3-pentyl, or hexyl; $(C_3-C_6)$cycloalkyl can be cyclopropyl, cyclobutyl, cyclopentyl, or cyclohexyl; $(C_3-C_6)$cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_2-C_6)$alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl; $(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_1-C_6)$alkanoyl can be acetyl, propanoyl or butanoyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; ($C_2$-$C_6$)alkanoyloxy can be acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazolyl, isothiazolyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

The term "nucleic acid" refers to deoxyribonucleotides or ribonucleotides and polymers thereof in either single- or double-stranded form, composed of monomers (nucleotides) containing a sugar, phosphate and a base which is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al. (1991) Nucl. Acids Res., 19:508; Ohtsuka et al. (1985) JBC, 260:2605; Rossolini et al. (1994) Mol. Cell. Probes, 8:91. A "nucleic acid fragment" is a fraction of a given nucleic acid molecule. Deoxyribonucleic acid (DNA) in the majority of organisms is the genetic material while ribonucleic acid (RNA) is involved in the transfer of information contained within DNA into proteins. The term "nucleotide sequence" refers to a polymer of DNA or RNA that can be single- or double-stranded, optionally containing synthetic, non-natural or altered nucleotide bases capable of incorporation into DNA or RNA polymers. The terms "nucleic acid," "nucleic acid molecule," "nucleic acid fragment," "nucleic acid sequence or segment," or "polynucleotide" may also be used interchangeably with gene, cDNA, DNA and RNA encoded by a gene.

By "portion" or "fragment," as it relates to a nucleic acid molecule, sequence or segment of the invention, when it is linked to other sequences for expression, is meant a sequence having at least 80 nucleotides, more preferably at least 150 nucleotides, and still more preferably at least 400 nucleotides. If not employed for expressing, a "portion" or "fragment" means at least 9, preferably 12, more preferably 15, even more preferably at least 20, consecutive nucleotides, e.g., probes and primers (oligonucleotides), corresponding to the nucleotide sequence of the nucleic acid molecules of the invention.

The term "amino acid," comprises the residues of the natural amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenyl-alanine, phenylglycine, propargylglycine, sarcosine, and tert-butylglycine). The term also comprises natural and unnatural amino acids bearing a conventional amino protecting group (e.g. acetyl or benzyloxycarbonyl), as well as natural and unnatural amino acids protected at the carboxy terminus (e.g. as a ($C_1$-$C_6$) alkyl, phenyl or benzyl ester or amide; or as an α-methylbenzyl amide). Other suitable amino and carboxy protecting groups are known to those skilled in the art (See for example, T. W. Greene, *Protecting Groups In Organic Synthesis*; Wiley: New York, 1981, and references cited therein). An amino acid can be linked to the remainder of a conjugate of formula I through the carboxy terminus, the amino terminus, or through any other convenient point of attachment, such as, for example, through the sulfur of a cysteine.

The terms "protein," "peptide" and "polypeptide" are used interchangeably herein. Polypeptide sequences specifically recited herein are written with the amino terminus on the left and the carboxy terminus on the right.

The invention encompasses isolated or substantially purified nucleic acid or protein compositions. In the context of the present invention, an "isolated" or "purified" DNA molecule or an "isolated" or "purified" polypeptide is a DNA molecule or polypeptide that exists apart from its native environment and is therefore not a product of nature. An isolated DNA molecule or polypeptide may exist in a purified form or may exist in a non-native environment such as, for example, a transgenic host cell. For example, an "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein or polypeptide having less than about 30%, 20%, 10%, 5%, (by dry weight) of contaminating protein. When the protein of the invention, or biologically active portion thereof, is recombinantly produced, preferably culture medium represents less than about 30%, 20%, 10%, or 5% (by dry weight) of chemical precursors or non-protein-of-interest chemicals. Fragments and variants of the disclosed nucleotide sequences and proteins or partial-length proteins encoded thereby are also encompassed by the present invention. By "fragment" or "portion" is meant a full length or less than full length of the nucleotide sequence encoding, or the amino acid sequence of, a polypeptide or protein.

"Naturally occurring" is used to describe an object that can be found in nature as distinct from being artificially produced. For example, a protein or nucleotide sequence present in an organism (including a virus), which can be isolated from a source in nature and which has not been intentionally modified by man in the laboratory, is naturally occurring.

"Wild-type" refers to the normal gene, or organism found in nature without any known mutation.

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis that encode the native protein, as well as those that encode a polypeptide having amino acid substitutions. Generally, nucleotide sequence variants of the invention will have at least 40, 50, 60, to 70%, e.g., preferably 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) nucleotide sequence.

"Conservatively modified variations" of a particular nucleic acid sequence refers to those nucleic acid sequences that encode identical or essentially identical amino acid sequences, or where the nucleic acid sequence does not encode an amino acid sequence, to essentially identical sequences. Because of the degeneracy of the genetic code, a large number of functionally identical nucleic acids encode any given polypeptide. For instance the codons CGT, CGC, CGA, CGG, AGA, and AGG all encode the amino acid arginine. Thus, at every position where an arginine is specified by a codon, the codon can be altered to any of the corresponding codons described without altering the encoded protein. Such nucleic acid variations are "silent variations" which are one species of "conservatively modified variations." Every nucleic acid sequence described herein which encodes a polypeptide also describes every possible silent variation, except where otherwise noted. One of skill will recognize that each codon in a nucleic acid (except ATG, which is ordinarily the only codon for methionine) can be modified to yield a functionally identical molecule by standard techniques. Accordingly, each "silent variation" of a nucleic acid which encodes a polypeptide is implicit in each described sequence.

"Recombinant DNA molecule" is a combination of DNA sequences that are joined together using recombinant DNA technology and procedures used to join together DNA sequences as described, for example, in Sambrook and Russell, Molecular Cloning: A Laboratory Manual, Cold Spring Harbor, N.Y.: Cold Spring Harbor Laboratory Press ($3^{rd}$ edition, 2001).

The terms "heterologous DNA sequence," "exogenous DNA segment" or "heterologous nucleic acid," each refer to a sequence that originates from a source foreign to the particular host cell or, if from the same source, is modified from its original form. Thus, a heterologous gene in a host cell includes a gene that is endogenous to the particular host cell but has been modified. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides.

A "homologous" DNA sequence is a DNA sequence that is naturally associated with a host cell into which it is introduced.

The term "gene" is used broadly to refer to any segment of nucleic acid associated with a biological function. Genes include coding sequences and/or the regulatory sequences required for their expression. For example, gene refers to a nucleic acid fragment that expresses mRNA, functional RNA, or a specific protein, including its regulatory sequences. Genes also include nonexpressed DNA segments that, for example, form recognition sequences for other proteins. Genes can be obtained from a variety of sources, including cloning from a source of interest or synthesizing from known or predicted sequence information, and may include sequences designed to have desired parameters. In addition, a "gene" or a "recombinant gene" refers to a nucleic acid molecule comprising an open reading frame and including at least one exon and (optionally) an intron sequence. The term "intron" refers to a DNA sequence present in a given gene which is not translated into protein and is generally found between exons.

A "vector" is defined to include, inter alia, any viral vector, plasmid, cosmid, phage or binary vector in double or single stranded linear or circular form which may or may not be self-transmissible or mobilizable, and which can transform prokaryotic or eukaryotic host either by integration into the cellular genome or exist extrachromosomally (e.g., autonomous replicating plasmid with an origin of replication).

"Cloning vectors" typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance or ampicillin resistance.

"Expression cassette" as used herein means a DNA sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. The expression of the nucleotide sequence in the expression cassette may be under the control of a constitutive promoter or of an inducible promoter that initiates transcription only when the host cell is exposed to some particular external stimulus. In the case of a multicellular organism, the promoter can also be specific to a particular tissue or organ or stage of development.

Such expression cassettes will comprise the transcriptional initiation region of the invention linked to a nucleotide sequence of interest. Such an expression cassette is provided with a plurality of restriction sites for insertion of the gene of interest to be under the transcriptional regulation of the regulatory regions. The expression cassette may additionally contain selectable marker genes.

The term "RNA transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA" (mRNA) refers to the RNA that is without introns and that can be translated into protein by the cell. "cDNA" refers to a single- or a double-stranded DNA that is complementary to and derived from mRNA.

"Regulatory sequences" and "suitable regulatory sequences" each refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences that may be a combination of synthetic and natural sequences. As is noted above, the term "suitable regulatory sequences" is not limited to promoters. However, some suitable regulatory sequences useful in the present invention will include, but are not limited to constitutive promoters, tissue-specific promoters, development-specific promoters, inducible promoters and viral promoters.

"5' non-coding sequence" refers to a nucleotide sequence located 5' (upstream) to the coding sequence. It is present in the fully processed mRNA upstream of the initiation codon and may affect processing of the primary transcript to mRNA, mRNA stability or translation efficiency (Turner et al. (1995) Mol. Biotech. 3:225).

"3' non-coding sequence" refers to nucleotide sequences located 3' (downstream) to a coding sequence and include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor.

The term "translation leader sequence" refers to that DNA sequence portion of a gene between the promoter and coding sequence that is transcribed into RNA and is present in the fully processed mRNA upstream (5') of the translation start codon. The translation leader sequence may affect processing of the primary transcript to mRNA, mRNA stability or translation efficiency.

The term "mature" protein refers to a post-translationally processed polypeptide without its signal peptide. "Precursor" protein refers to the primary product of translation of an mRNA. "Signal peptide" refers to the amino terminal extension of a polypeptide, which is translated in conjunction with the polypeptide forming a precursor peptide and which is required for its entrance into the secretory pathway. The term "signal sequence" refers to a nucleotide sequence that encodes the signal peptide.

"Promoter" refers to a nucleotide sequence, usually upstream (5') to its coding sequence, which controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue specificity of a promoter. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions.

The "initiation site" is the position surrounding the first nucleotide that is part of the transcribed sequence, which is also defined as position+1. With respect to this site all other sequences of the gene and its controlling regions are numbered. Downstream sequences (i.e. further protein encoding sequences in the 3' direction) are denominated positive, while upstream sequences (mostly of the controlling regions in the 5' direction) are denominated negative.

Promoter elements, particularly a TATA element, that are inactive or that have greatly reduced promoter activity in the absence of upstream activation are referred to as "minimal or core promoters." In the presence of a suitable transcription factor, the minimal promoter functions to permit transcription. A "minimal or core promoter" thus consists only of all basal elements needed for transcription initiation, e.g., a TATA box and/or an initiator.

"Constitutive expression" refers to expression using a constitutive or regulated promoter. "Conditional" and "regulated expression" refer to expression controlled by a regulated promoter.

"Operably-linked" refers to the association of nucleic acid sequences on single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation. "Operably-linked" also refers to the association two chemical moieties so that the function of one is affected by the other, e.g., an arrangement of elements wherein the components so described are configured so as to perform their usual function.

"Expression" refers to the transcription and/or translation in a cell of an endogenous gene, transgene, as well as the transcription and stable accumulation of sense (mRNA) or functional RNA. In the case of antisense constructs, expression may refer to the transcription of the antisense DNA only. Expression may also refer to the production of protein.

"Transcription stop fragment" refers to nucleotide sequences that contain one or more regulatory signals, such as polyadenylation signal sequences, capable of terminating transcription. Examples of transcription stop fragments are known to the art.

"Translation stop fragment" refers to nucleotide sequences that contain one or more regulatory signals, such as one or more termination codons in all three frames, capable of terminating translation. Insertion of a translation stop fragment adjacent to or near the initiation codon at the 5' end of the coding sequence will result in no translation or improper translation. Excision of the translation stop fragment by site-specific recombination will leave a site-specific sequence in the coding sequence that does not interfere with proper translation using the initiation codon.

"Homology" refers to the percent identity between two polynucleotides or two polypeptide sequences. Two DNA or polypeptide sequences are "homologous" to each other when the sequences exhibit at least about 75% to 85% (including 75%, 76%, 77%, 78%, 79%, 80%, 81%, 82%, 83%, 84%, and 85%), at least about 90%, or at least about 95% to 99% (including 95%, 96%, 97%, 98%, 99%) contiguous sequence identity over a defined length of the sequences.

The following terms are used to describe the sequence relationships between two or more sequences (e.g., nucleic acids, polynucleotides or polypeptides): (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full length cDNA, gene sequence or peptide sequence, or the complete cDNA, gene sequence or peptide sequence.

(b) As used herein, "comparison window" makes reference to a contiguous and specified segment of a sequence, wherein the sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the sequence a gap penalty is typically introduced and is subtracted from the number of matches.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988) CABIOS, 4:11; the local homology algorithm of Smith et al. (1981) Adv. Appl. Math. 2:482; the homology alignment algorithm of Needleman and Wunsch, (1970) JMB, 48:443; the search-for-similarity-method of Pearson and Lipman, (1988) Proc. Natl. Acad. Sci. USA, 85:2444; the algorithm of Karlin and Altschul, (1990) Proc. Natl. Acad. Sci. USA, 87:2264, modified as in Karlin and Altschul, (1993) Proc. Natl. Acad. Sci. USA, 90:5873.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) Gene 73:237; Higgins et al. (1989) CABIOS 5:151; Corpet et al. (1988) Nucl. Acids Res. 16:10881; Huang et al. (1992) CABIOS 8:155; and Pearson et al. (1994) Meth. Mol. Biol. 24:307. The ALIGN program is based on the algorithm of Myers and Miller, supra. The BLAST programs of Altschul et al. (1990) JMB, 215:403; Nucl. Acids Res., 25:3389 (1990), are based on the algorithm of Karlin and Altschul supra.

Software for performing BLAST analyses is publicly available through the National Center for Biotechnology Information (available on the world wide web at ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized as described in Altschul et al. (1997) Nucleic Acids Res. 25:3389. Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g., BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=-4, and a comparison of both strands. For amino acid sequences, the BLASTP program uses as defaults a wordlength (W) of 3, an expectation (E) of 10, and the BLOSUM62 scoring matrix. See the world wide web at ncbi.nlm.nih.gov. Alignment may also be performed manually by visual inspection.

For purposes of the present invention, comparison of sequences for determination of percent sequence identity to another sequence may be made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of sequences means that a polynucleotide comprises a sequence that has at least 70%, 71%, 72%, 73%, 74%, 75%, 76%, 77%, 78%, or 79%, at least 80%, 81%, 82%, 83%, 84%, 85%, 86%, 87%, 88%, or 89%, at least 90%, 91%, 92%, 93%, or 94%, and at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, at least 80%, 90%, at least 95%.

Another indication that nucleotide sequences are substantially identical is if two molecules hybridize to each other under stringent conditions (see below). Generally, stringent conditions are selected to be about 5° C. lower than the thermal melting point (Tm) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70%, 71%, 72%, 73%, 74%, 75%, 76%, 77%, 78%, or 79%, 80%, 81%, 82%, 83%, 84%, 85%, 86%, 87%, 88%, or 89%, at least 90%, 91%, 92%, 93%, or 94%, or 95%, 96%, 97%, 98% or 99%, sequence identity to the reference sequence over a specified comparison window. Optimal alignment is conducted using the homology alignment algorithm of Needleman and Wunsch, J. Mol. Biol. 48:443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The thermal melting point (Tm) is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl (1984) Anal. Biochem. 138:267; $T_m$ 81.5° C.+16.6 (log M)+0.41 (% GC) −0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired temperature, those of ordinary skill will understand that variations in the stringency of hybridization and/or wash solutions are inherently described. If the desired degree of mismatching results in a temperature of less than 45° C. (aqueous solution) or 32° C. (formamide solution), it is preferred to increase the SSC concentration so that a higher temperature can be used. An extensive guide to the hybridization of nucleic acids is found in Tijssen, Laboratory Techniques in Biochemistry and Molecular Biology Hybridization with Nucleic Acid Probes, part I chapter 2 "Overview of principles of hybridization and the strategy of nucleic acid probe assays" Elsevier, New York (1993). Generally, highly stringent hybridization and wash conditions are selected to be about 5° C. lower than the $T_m$ for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

By "variant" polypeptide is intended a polypeptide derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may results form, for example, genetic polymorphism or from human manipulation. Methods for such manipulations are generally known in the art.

Thus, the polypeptides of the invention may be altered in various ways including amino acid substitutions, deletions, truncations, and insertions. Methods for such manipulations are generally known in the art. For example, amino acid sequence variants of the polypeptides can be prepared by mutations in the DNA. Methods for mutagenesis and nucleotide sequence alterations are well known in the art. See, for example, Kunkel (1985) Proc. Natl. Acad. Sci. USA 82:488; Kunkel et al. (1987) Meth. Enzymol. 154:367; U.S. Pat. No. 4,873,192; Walker and Gaastra (1983) Techniques in Mol. Biol. (MacMillan Publishing Co., and the references cited therein. Guidance as to appropriate amino acid substitutions that do not affect biological activity of the protein of interest may be found in the model of Dayhoff et al., Atlas of Protein Sequence and Structure (Natl. Biomed. Res. Found. 1978). Conservative substitutions, such as exchanging one amino acid with another having similar properties, are preferred.

Thus, the genes and nucleotide sequences of the invention include both the naturally occurring sequences as well as mutant forms. Likewise, the polypeptides of the invention encompass naturally occurring proteins as well as variations and modified forms thereof. Such variants will continue to possess the desired activity. In certain embodiments, the deletions, insertions, and substitutions of the polypeptide sequence encompassed herein may not produce radical changes in the characteristics of the polypeptide. However, when it is difficult to predict the exact effect of the substitution, deletion, or insertion in advance of doing so, one skilled in the art will appreciate that the effect will be evaluated by routine screening assays.

Individual substitutions deletions or additions that alter, add or delete a single amino acid or a small percentage of amino acids (typically less than 5%, more typically less than 1%) in an encoded sequence are "conservatively modified variations," where the alterations result in the substitution of an amino acid with a chemically similar amino acid. Conservative substitution tables providing functionally similar amino acids are well known in the art. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (Q). In addition, individual substitutions, deletions or additions which alter, add or delete a single amino acid or a small percentage of amino acids in an encoded sequence are also "conservatively modified variations."

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms".

"Transformed," "transgenic," "transduced" and "recombinant" refer to a host cell or organism into which a heterologous nucleic acid molecule has been introduced. The nucleic acid molecule can be stably integrated into the genome generally known in the art and are disclosed in Sambrook and Russell, supra. See also Innis et al., PCR Protocols, Academic Press (1995); and Gelfand, PCR Strategies, Academic Press (1995); and Innis and Gelfand, PCR Methods Manual, Academic Press (1999). Known methods of PCR include, but are not limited to, methods using paired primers, nested primers, single specific primers, degenerate primers, gene-specific primers, vector-specific primers, partially mismatched primers, and the like. For example, "transformed," "transformant," and "transgenic" cells have been through the transformation process and contain a foreign gene integrated into their chromosome. The term "untransformed" refers to normal cells that have not been through the transformation process.

"Genetically altered cells" denotes cells which have been modified by the introduction of recombinant or heterologous nucleic acids (e.g., one or more DNA constructs or their RNA counterparts) and further includes the progeny of such cells which retain part or all of such genetic modification.

As used herein, the term "derived" or "directed to" with respect to a nucleotide molecule means that the molecule has complementary sequence identity to a particular molecule of interest.

The invention will now be illustrated by the following non-limiting Examples.

Example 1. Titratable Avidity Reduction Enhances Affinity Discrimination in Mammalian Cellular Selections of Yeast-Displayed Ligands Yeast surface display selections against mammalian cell monolayers have proven effective in isolating proteins with novel binding activity. Recent advances in this technique allow for recovery of clones with even micromolar binding affinity. However, no efficient method has been shown for affinity based selection in this context. This study demonstrates the effectiveness of titratable avidity reduction using dithiothreitol (DTT) to achieve this goal. Specifically, affinity maturation of an EpCAM-binding fibronectin population was performed, yielding an enriched pool of ligands with significantly stronger affinity than an analogous pool sorted by standard cellular selection methods. Collectively, this study offers a facile approach for affinity selection of yeast displayed ligands against full length cellular targets and demonstrates the effectiveness of this method by generating EpCAM-binding ligands that are promising for further applications.

Introduction

A variety of engineered proteins have proven effective for molecularly targeted therapeutics (Leader, et al., *Nat. Rev. Drug Discov.* 2008, 7 (1), 21-39) and diagnostics (James, M. L.; Gambhir, S. S. *Physiol. Rev.* 2012, 92 (2), 897-965) for numerous disease states. The ever-growing landscape of clinically relevant cellular biomarkers motivates continued development of new agents to diagnose and treat newly characterized conditions.

To meet this demand, several high-throughput methods for selecting engineered proteins with novel binding functionality have been developed. One such method involves selections of yeast surface displayed ligands against mammalian cell monolayers (Wang, X. X.; Shusta, E. V., *J. Immunol. Methods* 2005, 304 (1-2), 30-42; Tillotson, et al., *Methods* 2013, 60 (1), 27-37), which has been successfully implemented to isolate antibody fragments against brain endothelial cells (Wang, et al., *Nat. Methods* 2007, 4 (2), 2006-2008), B7-H4 (Dangaj, et al., *Cancer Res.* 2013, 73 (15), 4820-4829), and androgen-dependent prostate cancer (Williams, et al., *BMC Biotechnol.* 2014, 14 (1), 81). Ligands discovered through this method are selected against full length, extracellularly-expressed transmembrane proteins, which differs from traditional selection methods using immobilized (Ackerman, et al., *Biotechnol. Prog.* 2009, 25 (3), 774-783; McCafferty, et al., *Nature* 1990, 348 (6301), 552-554) or fluorescently-labeled (Boder, et al., *Nat. Biotechnol.* 1997, 15, 553-557) recombinant extracellular domains. This exposure to cellular target from the initial selection stage increases the ability to isolate translatable binding interactions relative to ligands selected using recombinant extracellular domains, which motivates the use of intact cellular targets for selections of engineered proteins.

Recent advances to yeast-displayed cell panning allow for the recovery of ligands with even micromolar binding affinity (Stern, et al., *Biotechnol. Bioeng.* 2016, 113 (11), 2328-2341). While such modest affinities can be drastically improved by recursive mutagenesis (Joyce, G. F., *Sci. Am.* 1992, 267 (6), 90-97; Beaudry, A. A.; Joyce, G. F., *Science* 1992, 257 (5070), 635-641; Chen, K.; Arnold, F. H., *Proc. Natl. Acad. Sci. USA* 1993, 90 (12), 5618-5622; Stemmer, W. P., *Nature.* 1994, pp 389-391), an efficient cellular panning method has not yet been demonstrated for discrimination of higher affinity ligands from their weaker counterparts. One alternative method for affinity selection against full length transmembrane proteins is fluorescence activated cell sorting (FACS) with detergent solubilized cell lysates (Tillotson, et al., *Methods* 2013, 60 (1), 27-37; Cho, Y. K.; Shusta, E. V., *Protein Eng. Des. Sel.* 2010, 23 (7), 567-577; Tillotson, et al., *Protein Eng. Des. Sel.* 2013, 26 (2), 101-112). This method utilizes amphiphilic detergent molecules to stabilize the hydrophobic transmembrane domain, allowing these proteins to be used in selection in a concentration dependent manner. In cell panning, it has been shown that decreasing the target expression of mammalian cells from $1.5 \pm 0.6 \times 10^6$ targets per cell to $1.9 \pm 0.6 \times 10^5$ targets per cell drastically decreases the recovery of $17 \pm 4$ nM and micromolar affinity variants while still allowing measurable but reduced recovery of a $2 \pm 2$ nM variant in an epidermal growth factor receptor (EGFR) expressing system (Stern, et al., *Biotechnol. Bioeng.* 2016, 113 (11), 2328-2341). This suggests that avidity between yeast and mammalian cell is much less requisite to the recovery of stronger binding interactions. However, it is not always easy to generate cell lines with target expression ranging over several orders of magnitude. Further, expression variation cannot be achieved in cases where the biomarker's identity is not known or where the target cells are not stably cultured (e.g. patient biopsy samples). The same study showed that decreasing the ligand expression of the yeast cell over a 3.5-fold range did not adversely affect recovery of either the $2 \pm 2$ nM or $17 \pm 4$ nM affinity variants. However, the weakest protein expression tested was still near 10,000 ligands per yeast cell, which still has high avidity potential.

The experiments described below focused on the discovery and affinity selection of hydrophilic fibronectin domains engineered to bind epithelial cell adhesion molecule (EpCAM). Specifically, a further decrease in yeast valency was used to yield affinity discrimination in yeast-displayed cell panning selections. As ligands are tethered to the yeast surface by two disulfide linkages between yeast mating proteins agglutinin 1 (Aga1p) and agglutinin 2 (Aga2p), controlled avidity reduction is achieved by titration with dithiothreitol (DTT).

Results and Discussion

Yeast surface display selections against mammalian cell monolayers have shown success in the past, but their inability to preferentially select for high affinity ligands has been shown. The lead published scFvs isolated using this method have affinities of $82 \pm 15$ nM for rat brain endothelial (RBE4)

cells (Wang, et al., *Nat. Methods* 2007, 4 (2), 2006-2008) and 27±16 nM (determined multivalently) for androgen-dependent prostate cancer cells (Williams, et al., *BMC Biotechnol.* 2014, 14 (1), 81). In both studies, numerous isolated scFvs required dimerization to assess binding character, suggesting clones with weaker affinities were isolated. Moreover, this aforementined model system experiment yielded minimal differentiation of 2±2 nM versus 17±4 nM affinity (Stern, et al., *Biotechnol. Bioeng.* 2016, 113 (11), 2328-2341). Although functional for in vitro studies, preferential selection of stronger binders can aid in vivo imaging and therapeutic applications (Schmidt, M. M.; Wittrup, K. D. *Mol. Cancer Ther.* 2009, 8 (10), 2861-2871). This was sought to be solved by shifting from avidity-driven interaction to affinity-driven interaction by decreasing yeast-displayed ligand expression in a controlled manner.

Affinity Maturation of EpCAM-Binding Fibronectin Domains

EpCAM is an attractive cancer target due to its overexpression in many different carcinomas including those of the breast, pancreas, esophagus, colon, and prostate (Went, et al., *Hum. Pathol.* 2004, 35 (1), 122-128). Many ligands have been evolved for EpCAM binding including antibodies and their fragments (Eder, et al., *Eur. J. Nucl. Med. Mol. Imaging* 2010, 37 (7), 1397-1407), shark vNARs (Zielonka, et al., *J. Biotechnol.* 2014, 191, 236-245), DARPins (Martin-Killias, et al., *Clin. Cancer Res.* 2011, 17 (1), 100-110; Stefan, et al., *J. Mol. Biol.* 2011, 413 (4), 826-843), and small cyclic peptides (Iwasaki, et al., *J. Mol. Evol.* 2015, 81 (5-6), 210-217). Fibronectin domains (Koide, et al., *J. Mol. Biol.* 1998, 284 (4), 1141-1151; Lipovsek, D. et al., *Protein Eng. Des. Sel.* 2011, 24 (1-2), 3-9) have never been applied to EpCAM binding, but their evolvability for high affinity and specificity, small size, and ease of production and downstream handling could provide an advantage over established ligands.

Figure 6A:
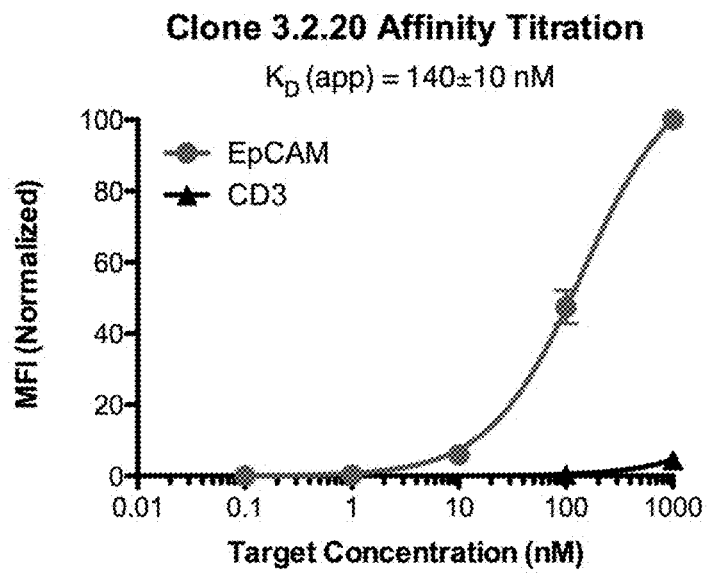
FIGS. 6A-B. Affinity estimations for intermediate anti-EpCAM fibronectin clones. The affinity of yeast-displayed clones from the population matured without DTT towards soluble EpCAM ectodomain was assessed via flow cytometry. Apparent dissociation constants ($K_D$) were estimated by fitting the mean fluorescence intensity values to a non-linear regression model assuming a single binding site.
Figure 6B:
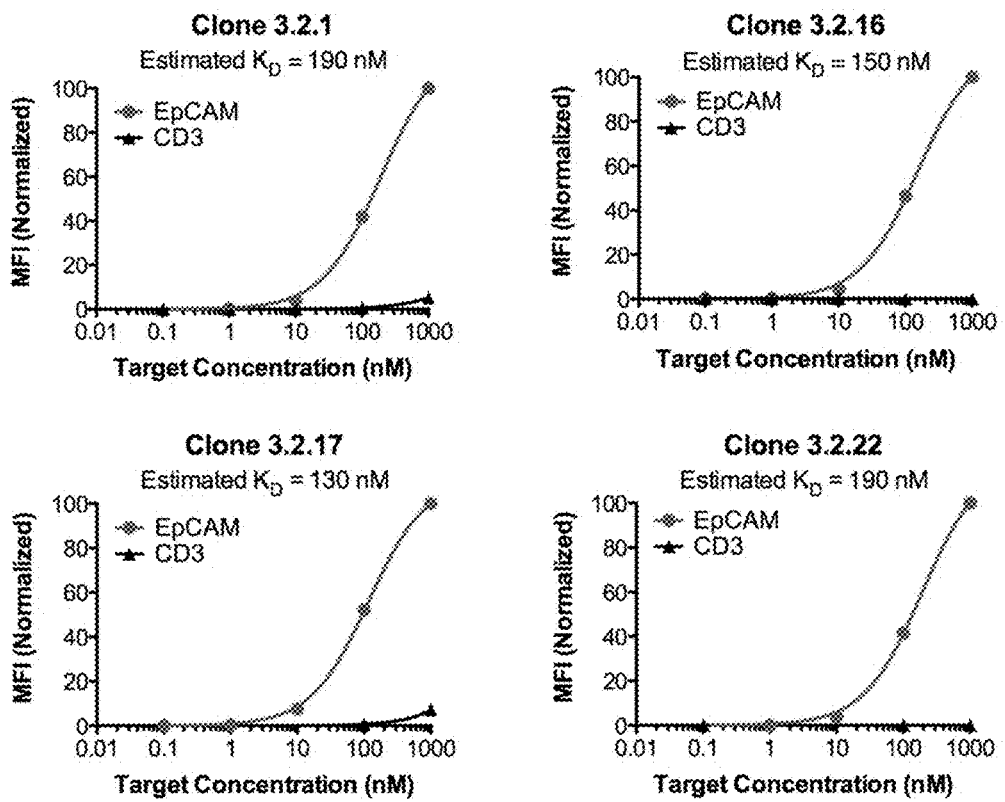

A population of EpCAM-specific fibronectin domains was selected through a combination of magnetic bead sorting and FACS sorting with soluble EpCAM extracellular domain and cellular based selection using MCF-7 and LnCAP cells. Two rounds of mutagenesis and selection were carried out to seek improved affinity. Clones isolated at this stage exhibited only moderate affinity for soluble EpCAM extracellular domain ($K_d$~130-190 nM; FIGS. 6A-B) and weak binding to EpCAM-expressing human cell lines. Therefore, isolating higher affinity clones from the population via this avidity reduction approach was sought.

Figure 1B:
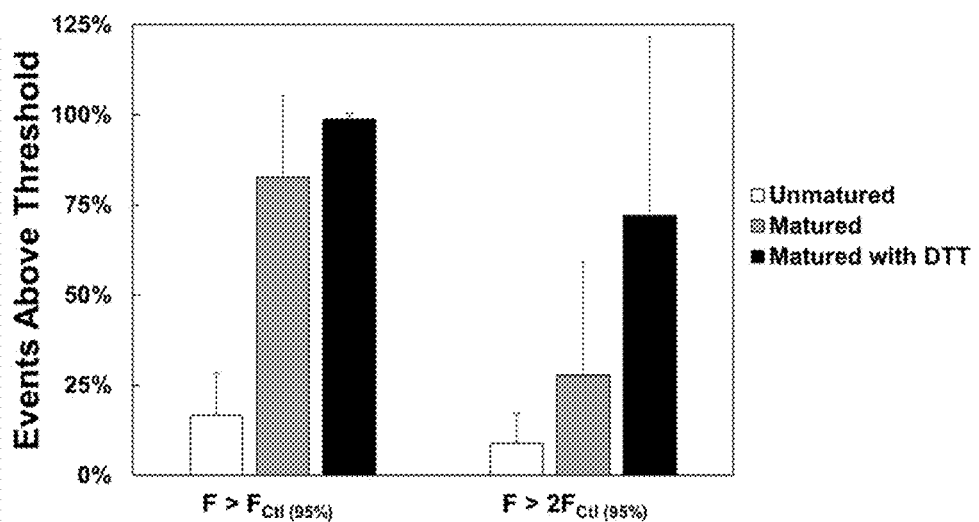

Three populations of EpCAM-binding fibronectin domains are compared: an enriched pool of fibronectins obtained after three rounds of selection with avidity reduction (matured population with DTT), a population from the same round of directed evolution sorted by standard cell panning methods (matured population without DTT), and the population from the previous round of directed evolution (unmatured population). Fibronectin domains from each population were produced as a polyclonal mixture and tested for binding to EpCAM positive MCF-7 cells (FIG. 1A). For analysis of this data, binding is considered detectable for all events with fluorescence above the 95$^{th}$ percentile of the negative control. Binding is considered strong for events lying 2-fold above the 95$^{th}$ percentile of the negative control (FIG. 1B). The unmatured population contains 16±11% detectable events and 9±8% strongly binding events. Upon mutagenesis and additional cell panning, the matured population distribution shifts to include more variants with stronger binding to MCF-7 cells, with 83±22% of events detectable and 28±30% appearing strong. When the mutated population is instead panned using yeast valency reduction with DTT, the resultant variants essentially all bind (99±2% of events detectable) and are predominantly strong binders (72±49%). To further examine this difference in affinity, individual clones from each population were titrated (FIG. 1C). The affinities of clones isolated from the matured population with DTT (median: 24 nM) were significantly higher (p=0.04) than those of clones isolated from the matured population without DTT (median: 1,600 nM). Importantly, none of the tested clones with strong affinities bind appreciably to EpCAM negative U87 cells (FIG. 1D) (Shibata, et al., *Gene Ther.* 2016, 23 (6), 479-488; MacArthur, et al., *Cancer Res.* 2014, 74 (8), 2152-2159). While all isolated clones appear to be from the same family based on upstream convergence of the lead molecule, four out of five of the clones tested from the matured population with DTT show a P87L/S mutation that may be beneficial for stronger binding (FIG. 2).

The knowledge gained from the aforementioned experiments allows for tuning yeast-displayed cellular selections to preferentially recover higher affinity ligands in a robust, facile way without the need of decreasing target expression on the mammalian cells. This is especially important for affinity maturation of engineered ligands. After mutagenesis, it is expected that an overwhelming majority of ligands either retain or decrease their binding affinity while only a small percentage improve (Tokuriki, et al., *J. Mol. Biol.* 2007, 369 (5), 1318-1332; Daugherty, et al., *Proc. Natl. Acad. Sci. U.S.A* 2000, 97 (5), 2029-2034). The ability to modify yeast-displayed cellular selections for the enrichment of that small percentage of clones ensures that ligands can be selected against full length, cellular target molecules. This avoids the use of traditional affinity discrimination methods that use soluble extracellular domains, which may not be available or may not translate to affinity maturation against genuine cellular target.

Conclusions

In conclusion, yeast-displayed cellular selections can be modified for affinity discrimination by decreasing ligand expression with DTT treatment. Ligand expression decreases titratably with increased concentration of DTT. Reduction of displayed ligand to 3,000-6,000 per cell allows 16-fold selectivity of a high-affinity (2 nM) binder from mid-affinity (17 nM) ligand. Further reduction in ligand expression decreases the overall effectiveness of selection. These considerations are applied to affinity maturation of EpCAM-binding fibronectin domains, where a small percentage of clones have a stronger target affinity than the majority of the pool, but selection would not be possible using standard protocols. These findings should ultimately increase the success of ligand engineering by aiding the isolation of strongly functional proteins that interact with full length cellular target.

Materials and Methods

Cells and Cell Culture

MCF-7, LnCAP, and U87 were purchased from ATCC. MCF-7, and U87 cell lines were grown at 37° C. in a humidified atmosphere with 5% $CO_2$ in Dulbecco's modified Eagle's medium with 4.5 g/L glucose, sodium pyruvate, and glutamine supplemented with 10% (v/v) fetal bovine serum and 1% (v/v) penicillin streptomycin. LnCAP cells were grown at 37° C. in a humidified atmosphere with 5% $CO_2$ in Roswell Park Memorial Institute (RPMI) medium with 4.5 g/L glucose, sodium pyruvate, and glutamine supplemented with 10% (v/v) fetal bovine serum and 1% (v/v) penicillin streptomycin.

Yeast surface display was performed essentially as described (Chen, et al., *Methods in Enzymology;* 2013; Vol. 523, pp 303-326). EBY100 yeast harboring expression plasmids were grown in SD-CAA medium (16.8 g/L sodium citrate dihydrate, 3.9 g/L citric acid, 20.0 g/L dextrose, 6.7 g/L yeast nitrogen base, 5.0 g/L casamino acids) at 30° C. with shaking. Protein expression was induced by transferring yeast cells in logarithmic phase ($OD_{600}$ nm<6) into SG-CAA medium (10.2 g/L sodium phosphate dibasic heptahydrate, 8.6 g/L sodium phosphate monobasic monohydrate, 19.0 g/L galactose, 1.0 g/L dextrose, 6.7 g/L yeast nitrogen base, 5.0 g/L casamino acids) and growing at 30° C. with shaking for at least 8 h. EBY100 without plasmid were grown in YPD medium (10.0 g/L yeast extract, 20.0 g/L peptone, 20.0 g/L dextrose) at 30° C. with shaking.

Expression Plasmids

The pCT-40 plasmid (Stern, et al., *Biotechnol. Bioeng.* 2016, 113 (11), 2328-2341) was used as the expression vector for yeast surface display. This vector encodes for Aga2p followed by an 80-amino acid linker—including a Factor Xa cleavage site, an HA epitope, a 40-mer linker with two repeats of the PAS #1 peptide (Schlapschy, et al., *Protein Eng. Des. Sel.* 2013, 26 (8), 489-501), and a glycine-rich peptide—followed by the fibronectin domain with a C-terminal MYC epitope.

Affinity Selection of EpCAM-Binding Engineered Fibronectin Domains EpCAM-binding fibronectin domains were selected via yeast surface display essentially as described (Chen, et al., *Methods in Enzymology;* 2013; Vol. 523, pp 303-326). Briefly, a yeast-display library of fibronectin domains (Woldring, et al., *PLoS One* 2015, 10 (9), e0138956) was subjected to negative selection against avidin-coated magnetic beads followed by magnetic beads functionalized with the irrelevant protein lysozyme to remove any non-specific binding interactions. Remaining yeast were then exposed to magnetic beads functionalized with biotinylated recombinant human EpCAM (Acro Biosystems, Cat: EPM-H8223) and bound yeast were selected. Incubations were performed at 4° C. and recovered beads were washed once in PBSA (PBS with 0.1% w/v bovine serum albumin) prior to culture in SD-CAA media.

Figure 3:
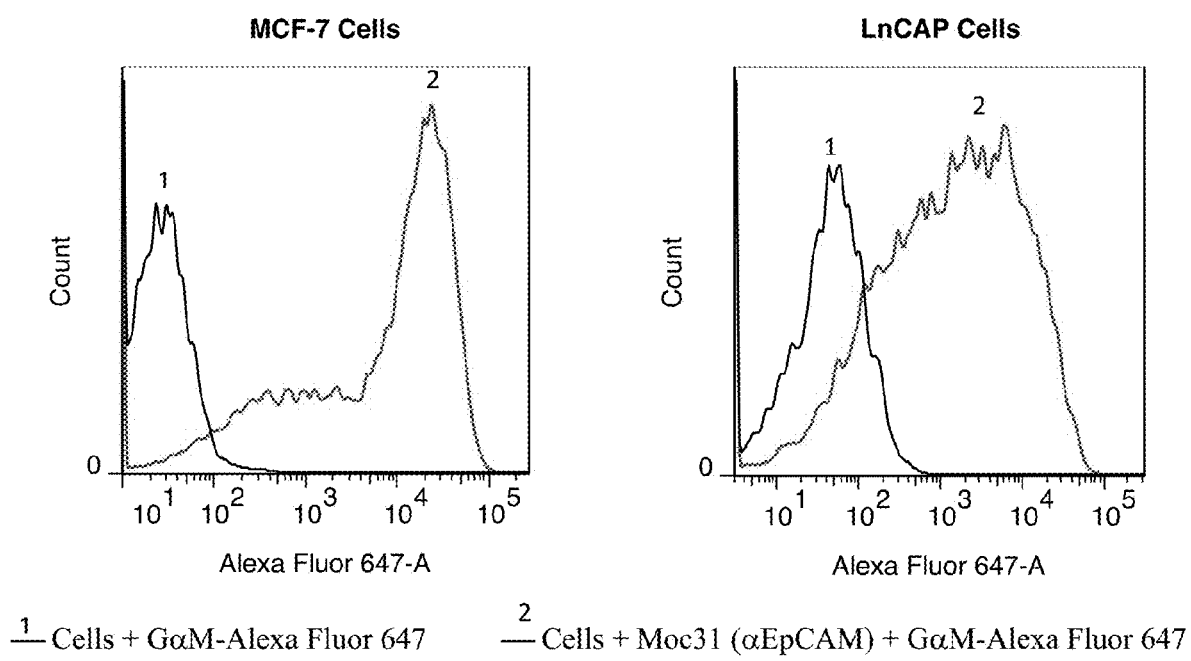
FIG. 3. EpCAM expression of MCF-7 and LnCAP cells. The EpCAM expression levels of MCF-7 and LnCAP cells lines were quantified via flow cytometry by comparing the mean fluorescence intensities to a calibration curve (generated by concurrently staining and analyzing known calibration beads). MCF-7 cells were found to have approximately $7.9 \times 10^5$ EpCAMs per cell. LnCAP cells were found to have approximately $2.7 \times 10^5$ EpCAMs per cell.

After three rounds of magnetic selection, full-length (MYC positive) fibronectin clones were selected via FACS using 9E10 and goat anti-mouse Alexa Fluor 647 conjugate. Isolated clones were subject to whole-gene and loop-focused error-prone PCR using mutagenic nucleotide analogs (Zaccolo, et al., An Approach to Random Mutagenesis of DNA Using Mixtures of Triphosphate Derivatives of Nucleoside Analogues. 1996, 589-603) and genetic loop shuffling between sequences (Hackel, et al., *J. Mol. Biol.* 2008, 381 (5), 1238-1252). After transformation of the mutants into EBY100 yeast, the resulting population was subject to one additional round of magnetic selection at 4° C.; recovered beads were washed twice with PBSA prior to culture in SD-CAA media. Yeast were then subject to two rounds of mammalian cell selections against adherent monolayers of the EpCAM-overexpressing cell lines MCF-7 and LNCaP (FIG. 3), as previously described (Stern et al., 2016). Full length clones that bound biotinylated target, detected with a streptavidin Alexa Fluor 488 conjugate (Thermo Fisher Scientific, Cat: S 11223), were then isolated via FACS and diversified as before.

After three additional rounds of panning against MCF-7 and LNCaP cell lines, target binding yeast were again isolated by FACS and diversified before panning against the same cell lines once more. This population was then subjected to three rounds of cell panning against MCF-7 cells in two parallel strategies: via the standard approach outlined above or with yeast valency reduction. For valency reduction, yeast were washed twice with 10 mM Tris pH 7.5 and pelleted at 8,000 g for 1 min. Yeast were resuspended in 800 µL 10 mM Tris buffer pH 7.5 with 0-15 mM DTT, incubated at 30° C. for 20 min without shaking, then washed twice with PBSACM and pelleted at 8,000 g for 1 min. Yeast were then used for selections on adherent mammalian cells.

Protein Production and Analysis

Figure 4:
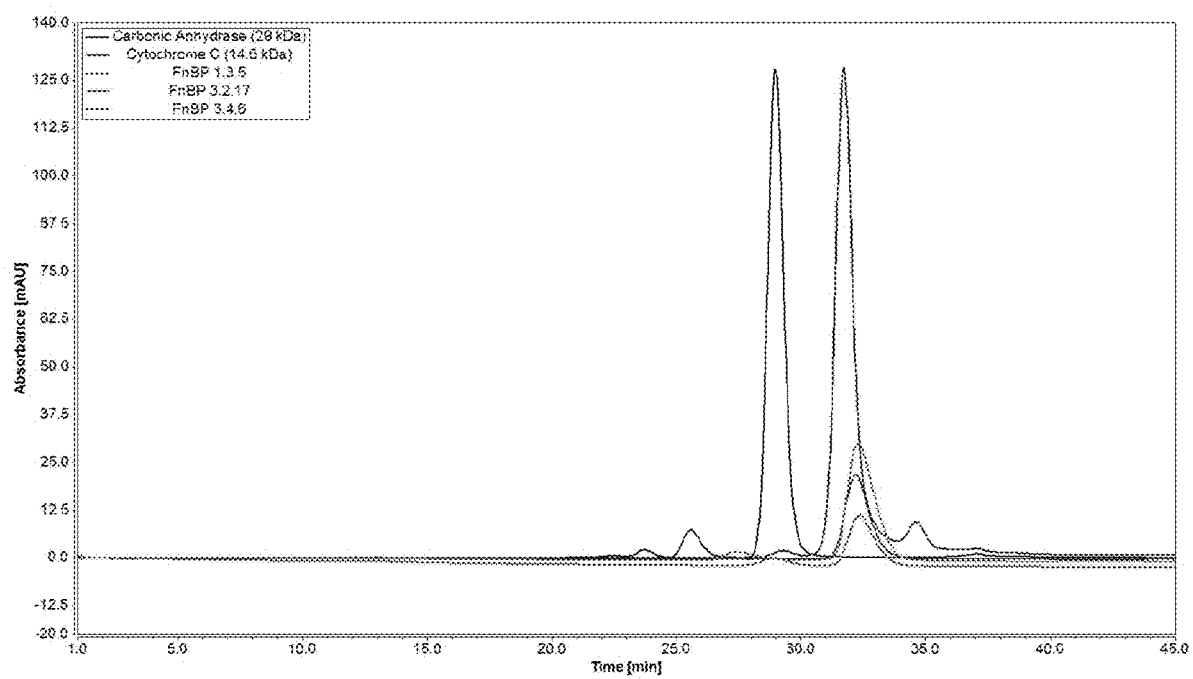
FIG. 4. Characterization of soluble fibronectin clones by size exclusion chromatography. Soluble fibronectin domains were produced, buffer exchanged into PBS, and diluted to 1 µM. SEC analyses were performed on a Dionex UltiMate 3000 UHPLC (Thermo Scientific) equipped with a Superdex 200 Increase 10/300 gel filtration column (GE Healthcare Life Sciences) by injecting 80 µL of the 1 µM protein solution; phosphate buffered saline (PBS), pH 7.4, was used as running buffer. Data analysis was performed in the associated Chromeleon 7 software package (Thermo Fisher Scientific), and peak integration confirms that all clones are ≥80% monomeric. One representative clone from each population (unmatured (FnBP 1.3.5); matured without DTT (FnBP 3.2.17); matured with DTT (FnBP 3.4.6)) is compared to the commercial molecular weight standards cytochrome C (14.6 kDa) and carbonic anhydrase (29.0 kDa) (Sigma Aldrich).
Figure 5:
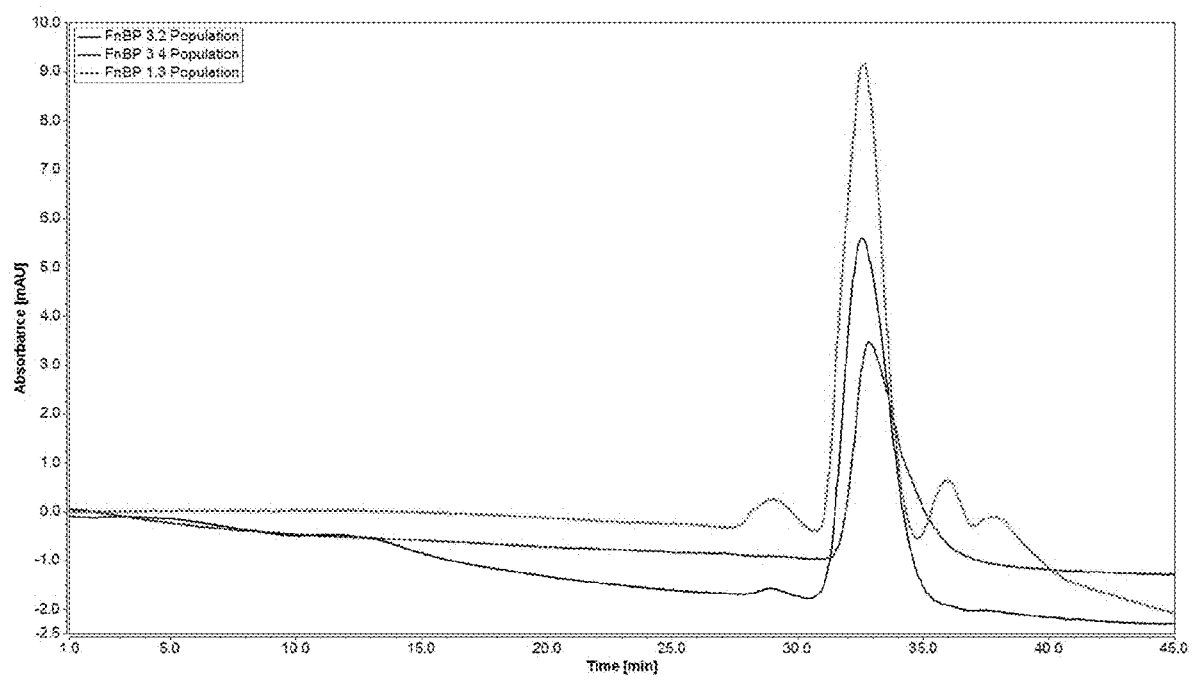
FIG. 5. Characterization of soluble fibronectin populations by size exclusion chromatography. Soluble fibronectin domains were produced, buffer exchanged into PBS, and diluted to 1 µM. SEC analyses were performed on a Dionex UltiMate 3000 UHPLC (Thermo Scientific) equipped with a Superdex 200 Increase 10/300 gel filtration column (GE Healthcare Life Sciences) by injecting 80 µL of the 1 µM protein solution; phosphate buffered saline (PBS), pH 7.4, was used as running buffer. Data analysis was performed in the associated Chromeleon 7 software package (Thermo Fisher Scientific), and peak integration confirms that the populations are comprised of ≥80% monomers. The three soluble fibronectin populations were compared to each other (unmatured (FnBP 1.3); matured without DTT (FnBP 3.2); matured with DTT (FnBP 3.4)) and to the same commercial molecular weight standards as before (see FIG. 4).

BL21(DE3) *Escherichia coli* (New England Biolabs, Cat: C2566I) were transformed with plasmid and grown overnight (37° C., 250 rpm) in lysogeny broth (LB) medium with kanamycin. Approximately 4 mL of overnight culture was added to 100 mL LB medium without antibiotics, grown until the optical density at 600 nm ($OD_{600}$) reached 0.65-1.0 (about 2 h), and induced with 1.0 mM isopropyl β-D-1-thiogalactopyranoside (IPTG) for 3 h. Cells were pelleted (3,500 rcf, 15 min, 4° C.), frozen in a dry ice/ethanol bath, and resuspended in 8 mL SoluLyse protein extraction reagent (Genlantis Inc., Cat: L100125) supplemented with EDTA-free protease inhibitor (Thermo Fisher Scientific, Cat: 88266). Cell lysates were centrifuged (27,000 rcf, 15 min, 4° C.) to separate soluble and insoluble protein fractions, and the supernatant was filtered through a 0.22 µm membrane. Fibronectin domains were purified by immobilized metal affinity chromatography on a gravity column packed with HisPur cobalt resin (Thermo Fisher Scientific, Cat: 89964), and eluted fractions were analyzed by SDS-PAGE. Fractions containing visibly pure fibronectin domains were pooled and buffer exchanged into phosphate buffered saline (PBS), pH 7.4, with Zeba spin desalting columns (Thermo Fisher Scientific, Cat: 89893). Protein concentration was determined via Bradford Protein Assay (Bio-Rad Laboratories, Cat: 500-0201) and diluted to 1 µM in additional PBS. Purified protein was analyzed by size-exclusion chromatography (SEC) on a Superdex 200 Increase 10/300 gel filtration column (GE Healthcare Life Sciences) in PBS running buffer. Retention times of fibronectin domains were compared to those of commercial molecular weight standards (Sigma Aldrich, Cat: C7150 and C7025, respectively) cytochrome C (14.6 kDa) and carbonic anhydrase (29 kDa) and found to be ≥80% monomeric (FIGS. 4 and 5).

Affinity Titration of Fibronectin Domains

Detached MCF-7 cells were washed and labeled with varying concentrations of each fibronectin clone for 90 min at 4° C. with rotation. Cells were pelleted at 300 g for 3 min and washed with 1 mL ice cold PBSACM, then labeled with 20 µL anti-$His_6$ FITC conjugate ("$His_6$" disclosed as SEQ ID NO: 65) (ab1206, Abcam, 13 µg/mL) for 20 min at 4° C. Cells were again pelleted and washed with 1 mL ice cold PBSACM. Fluorescence was analyzed using an Accuri C6 or BD LSRII.

Quantification of EpCAM Expression for Mammalian Cell Lines

Cells were grown to approximately 80% confluence as described in the main text and then detached with non-enzymatic cell dissociation buffer (Thermo Fisher Scientific, Cat: 13151014). Cells were aliquoted to 1×$10^6$ cells/sample, pelleted (300 g, 5 min), and washed with 1 mL ice cold PBSA. Cells were labeled with 50 µL mouse anti-human EpCAM monoclonal antibody (clone MOC31, Abnova, Cat: MAB 13332, resuspended to 1 µM in PBSA) on ice for 30 min, washed once in 1 mL PBSA, and then labeled with 50

µL goat anti-mouse Alexa Fluor 647 conjugate (1:200 dilution) in the dark on ice for 20 min. Cells were then washed three times with 1 mL PBSA before immediate analysis on a BD LSR II. EpCAM expression was quantified by comparing the mean fluorescence intensity to a calibration curve from concurrently analyzed anti-mouse IgG beads (Bangs Laboratories, Inc.) prepared as described in the main text.

Affinity Estimation for Yeast Displayed Ligands

Clones isolated from a population matured without DTT were grown overnight in SG-CAA media at 30° C. to induce fibronectin display. After induction, 1×10$^6$ yeast were pelleted (2,000 rcf, 2 min), washed with 1 mL PBSA, and resuspended in 50 µL of biotinylated antigen in PBSA at various concentrations (0-1,000 nM) plus 1 µL 9E10 (1:4 dilution, BioLegend). Yeast were labeled at 4° C. for ≥18 h, pelleted, washed with 1 mL PBSA, and labeled with 50 µL streptavidin Alexa Fluor 488 conjugate plus goat anti-mouse Alexa Fluor 647 conjugate (1:200 dilution each, Thermo Fisher Scientific) for 20 minutes at 4° C. in the dark. After a final wash in 1 mL PBSA, samples were analyzed on a BD LSR II. Mean fluorescence intensities were fitted to a nonlinear regression binding model assuming a single binding site (GraphPad Prism).

Example 2. Single Cysteine Mutants of EpCAM-Binding Fibronectin Domains for Site-Specific Conjugation Having developed anti-EpCAM fibronectins (Stern et al., *ACS Combinatorial Science.* 2017, 19, 315-323), an attempt to marry them with multiple downstream applications was made, including PET imaging, modular introduction to streptavidin-functionalized CSANs, and self-assembling hydrogels. Though many options for conjugating proteins to substrates exist—including both chemical and enzymatic (e.g., sortase, transglutaminase, "Q-tag", etc.) approaches—the lack of any natural cysteine residues in the fibronectin scaffold creates a unique opportunity for site-specific conjugation. It was hypothesized that by introducing a single cysteine residue into a non-paratopic region of the fibronectin, it would be possible to site-specifically conjugate the proteins onto other species, such as a PET imaging reagent chelator, biotin, or maleimide functionalized hydrogel matrix. Endeavors in these areas are described below.

Sites for Cysteine Mutation were Identified Rationally

Recently, Goldberg et al. detailed the individual reversion of each amino acid in the Centyrin® scaffold (a fibronectin-based scaffold; Janssen R&D) to a cysteine (Goldberg et al., *Protein Eng Des Sel.* 2016, 29, 563-572). Further, they tested the expression, target recognition, and conjugation capabilities of each cysteine mutant. Ultimately, they identified 26 positions suitable for cysteine mutation and subsequent conjugation.

However, the backbone of the Centyrin® scaffold differs from the Fn3HP scaffold that was used herein (Hackel et al., *Protein Eng Des Sel.* 2012, 25, 639-647). In order to identify which of the 26 mutable positions may still be applicable to the instant scaffold, the Centyrin® sequence was aligned to that of the anti-EpCAM Fn 3.4.5 clone (also known as clone C5 in the publication by Stern et al., *ACS Combinatorial Science.* 2017, 19, 315-323) (FIG. 7).

As shown, the alignment identified two homologous amino acid regions: LTVPGS (SEQ ID NO: 66) and GLKPG (SEQ ID NO: 67). The LTVPGS sequence (SEQ ID NO: 66) extends into the BC loop; because this loop is suspected to be paratopic and important for binding, cysteine mutation and conjugation in this region is likely to be detrimental. The GLKPG motif (SEQ ID NO: 67), however, is located in the EF loop, which is positioned on the opposite face of the fibronectin relative to the binding paratope (FIG. 8).

Of the five amino acids in the GLKPG motif (SEQ ID NO: 67), both of the glycine residues (called G61 and G65 based upon their position in the Centyrin® scaffold) were identified as sites amenable for cysteine mutation (Stern et al., *ACS Combinatorial Science.* 2017, 19, 315-323). Relative to a mutant with a cysteine residue added to the C-terminus, these mutations: 1) did not reduce expression in *E. coli;* 2) did not reduce binding to the target; 3) demonstrated >80% conjugation efficiency to the tubulin inhibitor monomethyl auristatin F (MMAF); 4) possessed melting temperatures of 66° C. and 70° C., respectively; 5) demonstrated reversible denaturing; and 6) demonstrated in vitro efficacy in cytotoxicity assays (IC$_{50}$ values ranged from 0.5-1.4 nM). Thus, it was hypothesized that there are at least three potential positions for cysteine-mutation in the Fn 3.4.5 clone: 1) at the C-terminus; 2) G61C; and 3) G65C.

Of the two mutations, G65C appeared superior in every aspect (higher expression, superior target binding, greater thermal stability, etc.). Therefore, G65C was prioritized over G61C for initial tests. The K63 residue located in the same motif is also often amenable to cysteine mutation, and this mutant may also be tested using methods and assays described herein.

Site-Directed Mutagenesis Successfully Introduces Single Cysteine Mutations

The cysteine modification was performed by site-directed mutagenesis, using the parent Fn 3.4.5 pET construct as the template. Currently, Fn clones are expressed with a C-terminal polyhistidine (His ×6) tag (SEQ ID NO: 65) for purification. Thus, a "C-terminal" cysteine was introduced after the final residue in the evolved fibronectin sequence (Q) but prior to the BamHI restriction site used for cloning.

A TGT codon was introduced at the C-terminus using primers specific for this region, but including the additional codon. Similarly, a mutagenic primer was used to convert the current G65 codon GGC to TGC. Using the NEBaseChanger tool, suitable primers were designed wherein the mutagenic region is shown in bold italics (Table 3).

TABLE 3

Mutagenic Primers for Introducing Engineered Cysteine Residues.

| Mutation | Direction | Sequence | Length (bp) | % GC | $T_m$ (° C.) | $T_a$ (° C.) |
|---|---|---|---|---|---|---|
| C-Terminal Insertion | Forward (5') | *TGT*GGATCCCACCATCACCAT (SEQ ID NO: 43) | 21 | 52 | 64 | 64 |
|  | Reverse (3') | CTGAGACGGTTTGTCGATTTC (SEQ ID NO: 44) | 21 | 48 | 63 |  |

TABLE 3-continued

Mutagenic Primers for Introducing Engineered Cysteine Residues.

| Mutation | Direction | Sequence | Length (bp) | % GC | $T_m$ (°C.) | $T_a$ (°C.) |
|---|---|---|---|---|---|---|
| G65C | Forward (5') | GTCTGAAACCG*T*GCCAGGATTATATC (SEQ ID NO: 45) | 26 | 46 | 63 | 64 |
|  | Reverse (3') | CGCTGATGGTCGCATTATAA (SEQ ID NO: 46) | 20 | 45 | 63 |  |

These primers were used alongside the NEB Q5 Site-Directed Mutagenesis Kit to make the desired mutations. The specific protocol is described below. First, the mutagenic primers were prepared. The proper 5' and 3' primers were designed for the desired mutation using the NEBaseChanger Tool and then ordered from IDT. Primers were resuspended to 100 µM in ultrapure water. A working stock was prepared, which consisted of 10 µM of each of the 5' and 3' primers in ultrapure water. The manufacturer's stock and working stock were stored at −20° C. until needed, minimizing freeze/thaw cycles. Subsequently, mutagenic PCR was performed. The following mixture was prepared for each sample:

| Component | "Amount" | Volume |
|---|---|---|
| Q5 Hot Start High Fidelity Master Mix | 2x | 12.5 µL |
| Template DNA | 1-25 ng/µL | 1 µL |
| 5' + 3' Primer Mix | 10 µM each | 1.25 µL |
| H₂O | to 25 µL | 10.25 µL |
| Total | — | 25 L |

The PCR thermal cycle was as follows:

| # | Step | Temperature | Time | Cycles |
|---|---|---|---|---|
| 1 | Initial Denaturation | 98° C. | 30 sec |  |
| 2 | Denaturation | 98° C. | 10 sec | 30 cycles |
| 3 | Primer Annealing | 50-72° C. | 30 sec |  |
| 4 | Extension | 72° C. | 20-30 sec/kbp |  |
| 5 | Final Extension | 72° C. | 2 min |  |
| 6 | Hold | 4° C. | ∞ |  |

PCR products were stored at −20° C. until needed for further experiments (e.g., KLD treatment and transformation).

Kinase, Ligase, and DpnI (KLD) treatments were then performed as described below. Specifically, the following mixture was prepared for each sample.

| Component | "Amount" | Volume |
|---|---|---|
| PCR Product | — | 1 µL |
| KLD Reaction Buffer | 2x | 5 µL |
| KLD Enzyme Mix | 10x | 1 µL |
| H₂O | to 10 µL | 3 µL |
| Total | — | 10 L |

The mixture was mixed well by pipetting up and down several times and then incubated at room temperature for 5 minutes. The material was then directly transformed into competent cells according to the manufacturer's protocol. Sequencing confirmed the introduction of the desired mutations. After transformation into Novagen Rosetta 2 pLysS cells or NEB T7 Express cells, protein expression was initiated.

Cysteine mutant fibronectin clones are shown below. Paratopic loops (BC, DE, and FG) are underlined and designed mutations shown in bold, italics.

Fn_C5_G65C:

EpCAM-binding scaffold derived from published clone C5 (Stern et al., *ACS Combinatorial Science*. 2017, 19, 315-323) with the G65C mutation.

Protein:
(SEQ ID NO: 47)
SSDSPRNLEVTNATPNSLTISW<u>DNSNYASY</u>YRITYGETGGNSPSQELTVP <u>GSTYN</u>ATISGLKPCQDYIITVYAV<u>TYRDNYSYS</u>NLISINYRSEIDKPSQ

DNA:
(SEQ ID NO: 48)
TCCTCCGACTCTCCGCGTAACCTGGAGGTTACCAACGCAACTCCGAACTC

TCTGACTATTTCTTGGG<u>ACAATTCTAACTATGCTTCGT</u>ATTACCGTATCA

CCTACGGCGAAACCGGTGGTAACTCCCCGAGCCAGGAACTCACTGTTCCG

<u>GGAAGTACTTATAAT</u>GCGACCATCAGCGGTCTGAAACCG*TGC*CAGGATTA

TATCATTACCGTGTACGCTGTA<u>ACCTATCGTGACAATTATTCCTATTCAA</u>

<u>AT</u>CTAATCAGCATCAATTATCGCTCCGAAATCGACAAACCGTCTCAG

Fn_C5_CtermC:

EpCAM-binding scaffold derived from published clone C5 (Stern et al., *ACS Combinatorial Science*. 2017, 19, 315-323) with an insertional cysteine mutation at the "C-terminus" of the fibronectin-coding sequence (but prior to the polyhistidine tag, as described above).

Protein:
(SEQ ID NO: 49)
SSDSPRNLEVTNATPNSLTISW<u>DNSNYASY</u>YRITYGETGGNSPSQELTVP <u>GSTYN</u>ATISGLKPGQDYIITVYAV<u>TYRDNYSYS</u>NLISINYRSEIDKPSQC

DNA:
(SEQ ID NO: 50)
TCCTCCGACTCTCCGCGTAACCTGGAGGTTACCAACGCAACTCCGAACTC

TCTGACTATTTCTTGGG<u>ACAATTCTAACTATGCTTCGT</u>ATTACCGTATCA

CCTACGGCGAAACCGGTGGTAACTCCCCGAGCCAGGAACTCACTGTTCCG

<u>GGAAGTACTTATAAT</u>GCGACCATCAGCGGTCTGAAACCGGGCCAGGATTA

TATCATTACCGTGTACGCTGTA<u>ACCTATCGTGACAATTATTCCTATTCAA</u>

<u>AT</u>CTAATCAGCATCAATTATCGCTCCGAAATCGACAAACCGTCTCAG*TGT*

Fn_NT_G65C:

Non-targeted scaffold derived from wild-type fibronectin with two modifications: (1) G65C mutation for downstream conjugation; and (2) the naturally-existing RGD motif in the FG loop has been revised to RDG to ablate integrin binding. To the inventors' knowledge, this scaffolds binds to nothing.

Protein:

(SEQ ID NO: 51)
SSDSPRNLEVTNATPNSLTISW<u>DAPAVTVRY</u>YRITYGETGGNSPSQEFTV

PG<u>SKSTATISGLKP</u>CQDYTITVYAVT<u>G*RDG*SPASSK</u>PISINYRTEIDKPS

Q

DNA:

(SEQ ID NO: 52)
TCCTCCGACTCTCCGCGTAACCTGGAGGTTACCAACGCAACTCCGAACTC

TCTGACTATTTCTTGG<u>GATGCTCCTGCTGTCACAGTGAGATAT</u>TACCGTA

TCACCTACGGCGAAACTGGTGGTAACTCCCCGAGCCAGGAATTCACTGTT

CCG<u>GGGAGCAAGTCTACAGCGACCATCAGC</u>GGTCTGAAACCG*TGC*CAGGA

TTATACCATTACCGTGTACGCTGTA<u>ACTGGC*CGTGACGGA*</u>AGCCCCGCAA

<u>GCAGCAAG</u>CCAATCAGCATCAATTATCGCACCGAAATCGACAAACCGTCT

CAG

Cysteine Mutants Express Solubly in *E. coli*

The expression capabilities of the newly transformed Rosetta clones were then tested. A small-scale "test expression" was performed (induced with 1 mM IPTG at 30° C., 250 rpm for 2 h) and the pre- and post-induction whole-cell lysates were analyzed by SDS-PAGE (FIG. 9). There appeared to be successful production of both the G65C and CtermC mutants, with some dimerization showing on the SDS-PAGE gel. Therefore, large-scale production and purification of the Fn 3.4.5 G65C mutant was performed.

Figure 10:
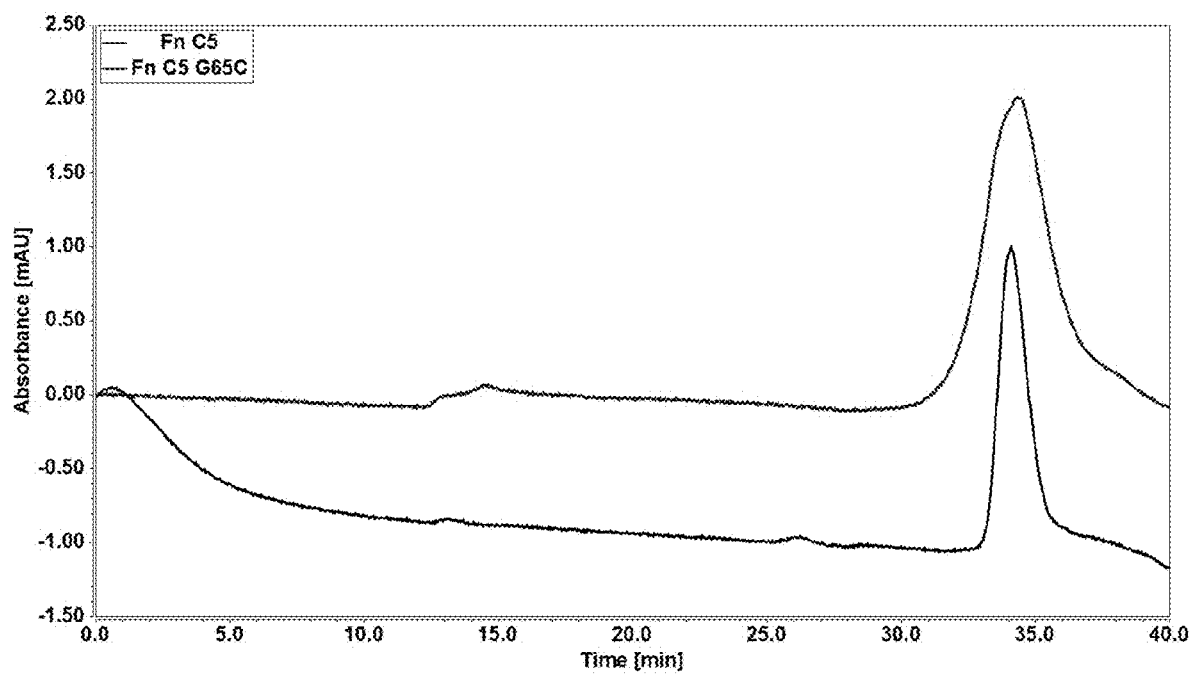
FIG. 10. SEC analysis of purified Fn C5 and Fn C5 G65C clones.
Figure 11:
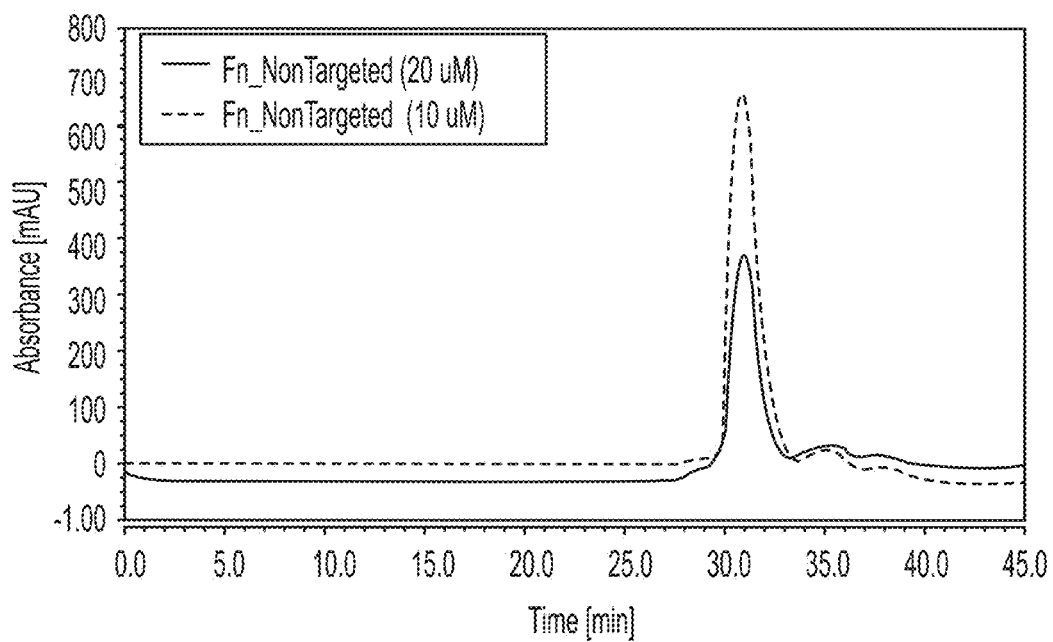
FIG. 11. SEC analysis of non-targeted control, Fn-NT (20 μM and 10 μM).

Fn 3.4.5 G65C and Fn-NT are Produced Solubly and can be Readily Purified from *E. coli* Lysates as Monomers Soluble fibronectin domains were produced and purified as described by Stern et al., *ACS Combinatorial Science*. 2017, 19, 315-323. Purified clones were analyzed by SEC (FIG. 10). The chromatogram topography for the G65C mutant matches that of the parent Fn 3.4.5 construct, suggesting successful production of the mutant clone as a monomer. The non-targeted control, Fn-NT, was produced and purified similarly. It also exists as a soluble monomer by SEC (above) (FIG. 11).

These experiments indicated that the fibronectin domains described herein are amenable to cysteine mutation at several locations, including (but not limited to) G65, the C-terminus, and colloquially, K63. Additionally, these cysteine-mutant domains can be readily and solubly produced in *E. coli*, which is a distinct advantage over some other scaffolds.

Applying Cysteine-Mutant Fibronectin Domains to PET Imaging of Cancer

Cysteine-Mutant Fibronectin Domains can be Conjugated to Maleimide-NODAGA

Figure 12:
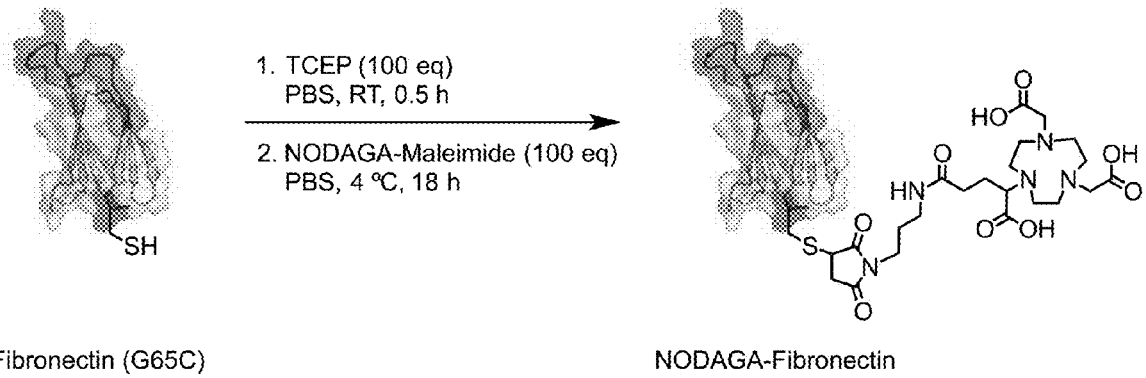
FIG. 12. Conjugation of radiochelator NODAGA to the fibronectin domains using sulfhydryl/maleimide chemistry, as well as reaction conditions.

To evaluate these ligands as positron emission tomography (PET) imaging agents, the radiochelator NODAGA was conjugated to the fibronectin domains using sulfhydryl/maleimide chemistry. Typical reaction conditions for this conjugation are shown; however, the procedure has also been done in 100 mM sodium acetate buffer at pH 6.0 (FIG. 12).

Specifically, TCEP-HCl was added to a solution of purified fibronectin in PBS, and the mixture was incubated at room temperature for 30 min with rotation. Then, NODAGA-maleimide was added and the mixture was incubated at 4° C. overnight with rotation. The completed reaction was then purified on a PD-10 Desalting column (GE Healthcare, Cat. 17085101) in 100 mM sodium acetate buffer (pH 6.0).

Figure 13:
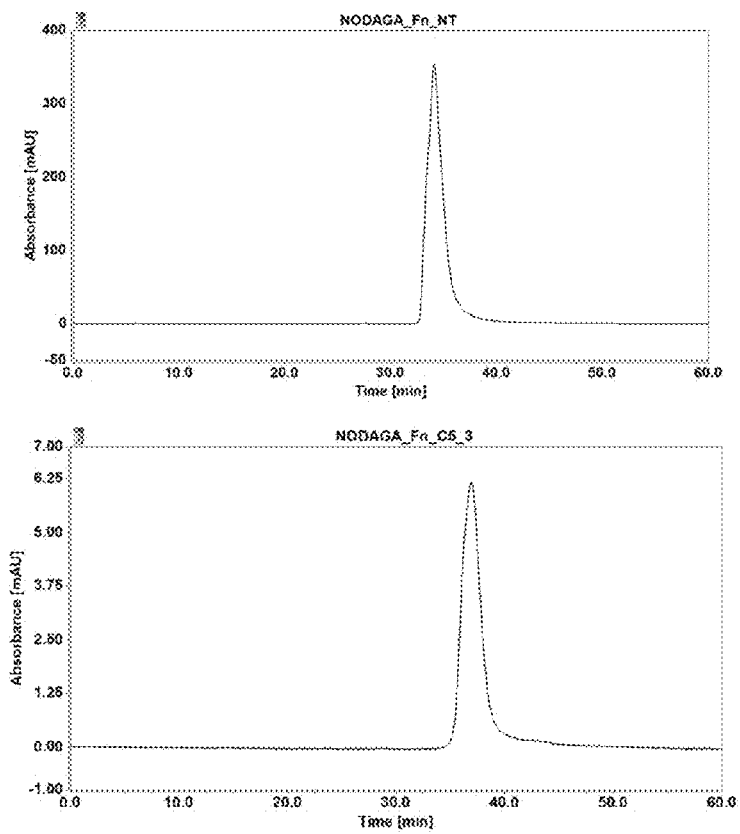
FIG. 13. SEC analysis of NODAGA-Fn-NT and NODAGA-Fn-C5.
Figure 14:
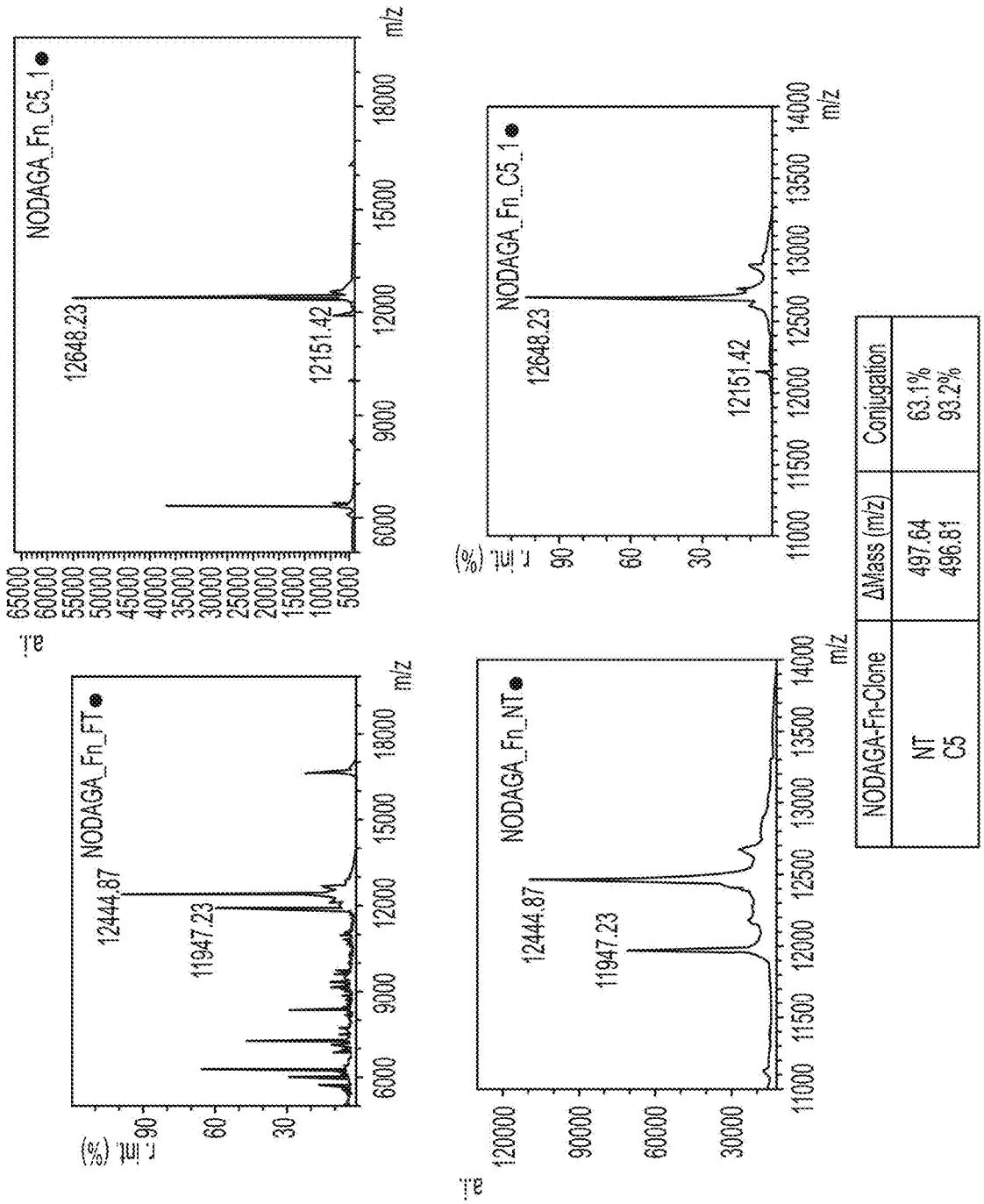
FIG. 14. MALDI-MS analysis of NODAGA-Fn-NT and NODAGA-Fn-C5.

Conjugated ligands were evaluated by SEC and demonstrated to be 100% monomeric following conjugation (FIG. 13). Conjugated ligands were also submitted to the Center for Mass Spectroscopy and Proteomics (CMSP) for MALDI-MS analysis to confirm single NODAGA-conjugation (FIG. 14).

Figure 15:
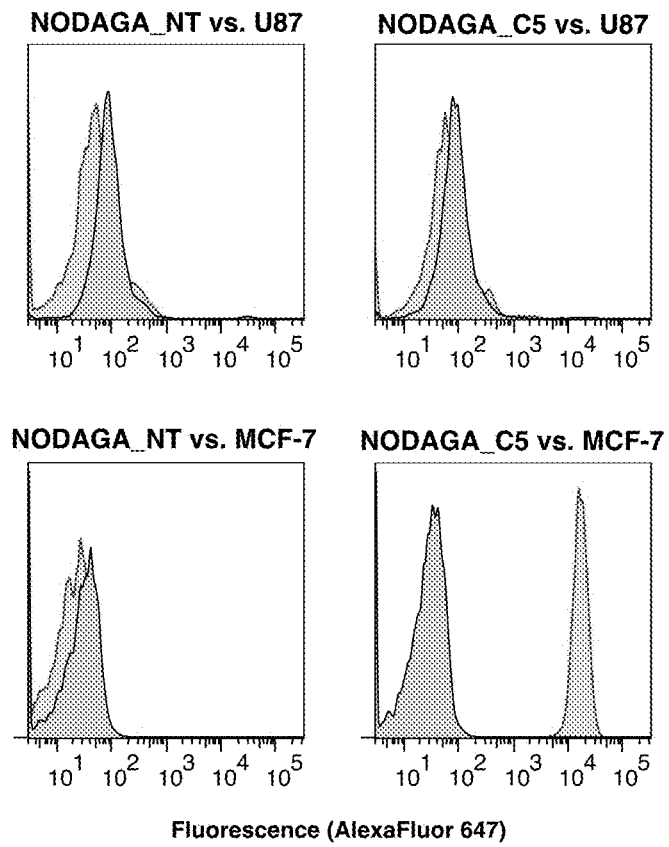
FIG. 15. NODAGA-conjugated ligands against EpCAM+ MCF-7 and EpCAM-U87 cells. The data shows the selectivity of the NODAGA-Fn-C5 ligand for the intended target (i.e., EpCAM+ MCF-7 cells).

NODAGA Conjugation does not Affect the Binding Affinity or Target Selectivity of the Fibronectin Domains To further validate the quality of the NODAGA-conjugated ligands, they were titrated against EpCAM+ MCF-7 and EpCAM-U87 cells (as described in Stern et al., *ACS Combinatorial Science*. 2017, 19, 315-323). As expected, only NODAGA-Fn-C5 binds to MCF-7 cells (FIG. 15).

Figure 16:
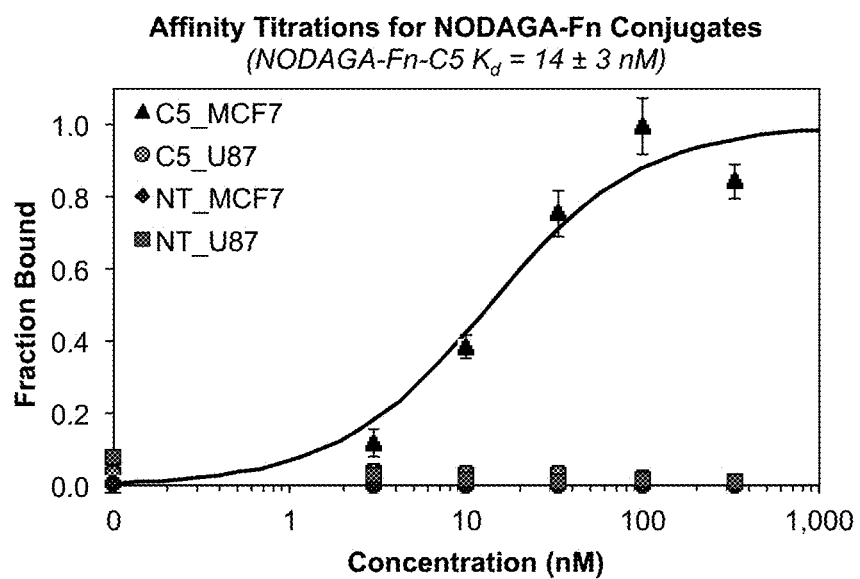
FIG. 16. Affinity titrations for NODAGA-Fn conjugates.

A summary analysis is shown in FIG. 16, which is based on multiple affinity titrations. The EpCAM-targetedd NODAGA_Fn_C5 conjugate binds to the EpCAM+ MCF-7 cells with a $K_d$ value of 14±3 nM, which resembles that of the parent clone (unmutated Fn C5 has a $K_d$ of 17±1 nM, as described in Stern et al., *ACS Combinatorial Science*. 2017, 19, 315-323). Furthermore, it exhibits no off-target binding to the EpCAM-U87 cells. Finally, the non-targeted control, NODAGA_Fn_NT binds to neither cell line, as expected.

Cysteine Mutation and Subsequent NODAGA Conjugation does not Alter Fibronectin Protein Structure To ascertain whether the NODAGA conjugations impacted the structure of the fibronectin ligands, the mutants and conjugates were evaluated by circular dichroism (FIG. 17). As shown, the cysteine mutants maintain their β-sheet structure, and this is not impacted by NODAGA conjugation.

These data indicate that the fibronectin domains appear to be amenable to cysteine mutation and subsequent conjugation at several locations, including (but not limited to) G65, the C-terminus, and colloquially, K63. The G65C mutation and subsequent conjugation does not affect the binding affinity, target selectivity, or structure of the scaffold. Additionally, the mutated and conjugated fibronectin domains may be highly valuable for a broad range of scientific, diagnostic, and therapeutic applications.

Site-Specific Biotinylation and Screening in an Immunotherapy Platform

Maleimide-Biotin can be Site-Specifically Conjugated to Cysteine Mutant Fibronectin Domains A biotin moiety was site-specifically coupled to the lone cysteine residue in fibronectin clone 3.4.5 G65C using maleimide chemistry. Reaction conditions were the same as shown above for the NODAGA conjugation. Chemically self-assembled nanorings (CSAN) functionalized with monovalent streptavidin (mSA (Lim et al., *Biotechnol Bioeng*. 2013, 110, 57-67)) domains were then labeled with the biotinylated fibronectin ligands. CSANs are a protein-based scaffold developed by the Wagner lab with potential use as a T cell directing immunotherapy platform (Carlson et al., *J Am Chem Soc*. 2006, 128, 7630-7638; Gabrielse et al., *Angew Chem Int Ed*. 2014, 53, 5112-5116; Shah et al., *Mol Pharm*. 2016, 13, 2193-2203; Shen et al., *J Am Chem Soc*. 2015, 137, 10108-10111).

The goal of these experiments was to show that targeting ligands—such as the fibronectin domains (Stern et al., *ACS Combinatorial Science*. 2017, 19, 315-23)—could be non-covalently bound to the CSAN scaffold for screening purposes prior to undertaking the more laborious process of directly fusing the ligand into the CSAN scaffold (as discussed in Examples 4 and 5 below). In this manner, libraries of targeting ligands could be screened in binding and T cell activation assays to identify only the useful clones. This would avoid the more costly approach of fusing, producing, and testing each combination individually.

Figure 18:
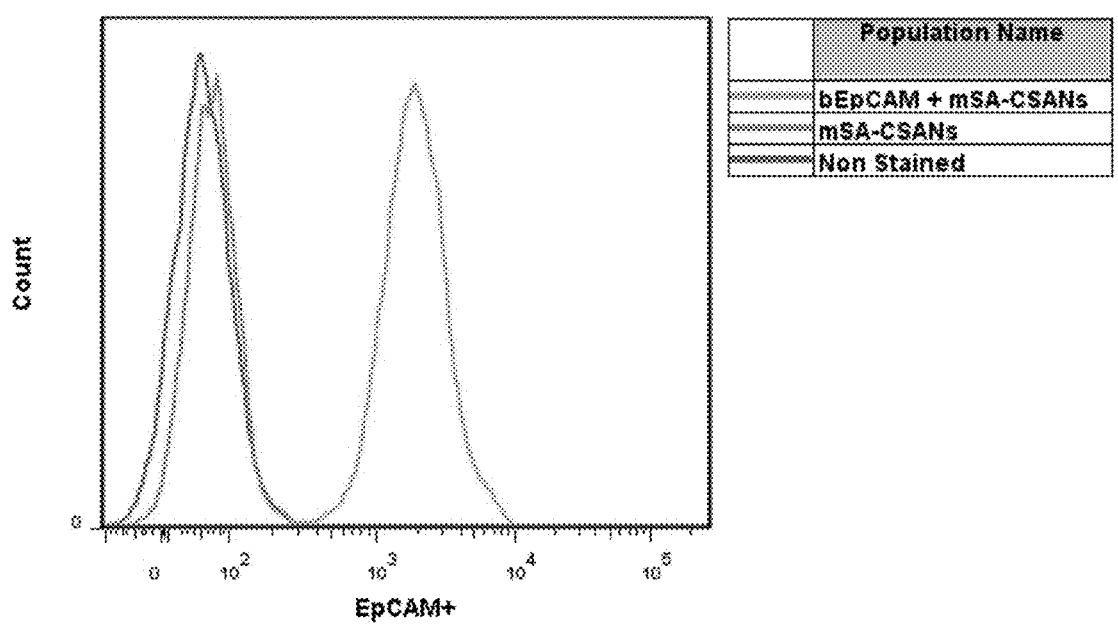
FIG. 18. Labeling of EpCAM+ cells with the biotin-fibronectin domains labeled with the mSA-CSANs, as assessed by flow cytometry.

Biotinylated Fibronectin Domains can be Installed on mSA-CSANs and Retain their Cell-Binding Efficacy Similar to the NODAGA-conjugated ligands, the biotinyated fibronectins retain their ability to recognize cellular EpCAM, as assessed by flow cytometry. In this case, the mSA-CSANs were labeled with the biotin-fibronectin domains and then used to label EpCAM+ cells; the assay detects the presence of these targeted CSANs on the cell surface (FIG. 18).

Figure 19:
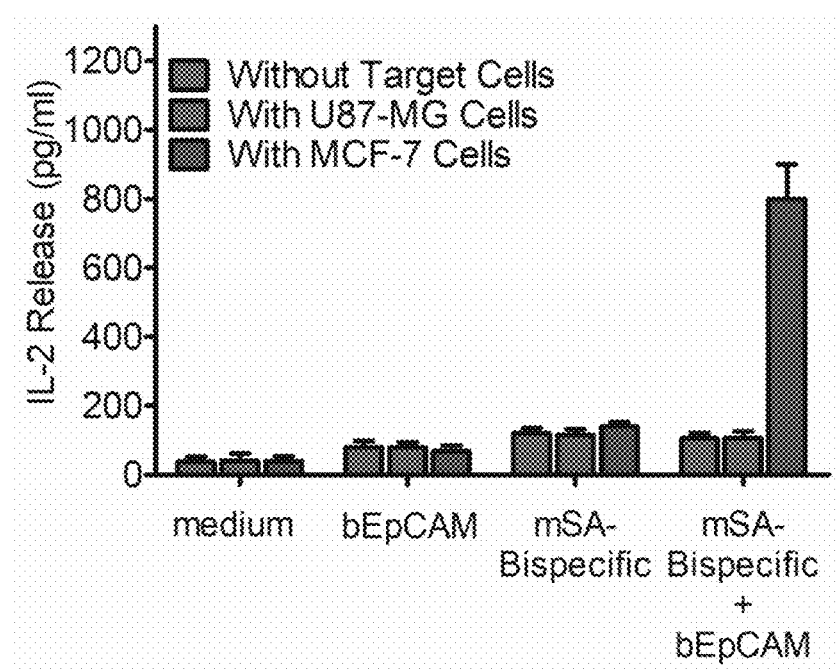
FIG. 19. IL-2 release. For each grouping, without target cells is shown in the left, with U87-MG cells is shown in the middle and with MCF-7 cells is shown on the right.

Bispecific CSANs Targeting both CD3 and EpCAM Drive Selective Activation of T Cells Unactivated PBMC cells from donor 11 were treated with biotinylated EpCAM fibronectins (bEpCAM), anti-mSA/anti-CD3 CSANs (at a final 50 nM), 50 nM bEpCAM plus anti-mSA/anti-CD3, or not treated. Pre-plated MCF-7 or U87-MG cells (either as a single CD4/CD8 population or a ratio of the two) were treated with these PBMCs for 24 h at 37° C., 5% CO2. The plate was then spun down and the supernatant was obtained for analysis by IL-2 BD Bioscience beads. All tests samples were performed at a 10:1 effector:target cell ratio. The experiment was repeated to provide replicate data (see, FIG. 19).

This data shows that the epitope recognized by the EpCAM-binding fibronectin domains is suitable for T cell activation, as indicated by the release of IL-2. This makes these ligands useful as targeting elements in T cell directing immunotherapy applications.

In summary, these experiments demonstrate that the fibronectin domains incorporating a single cysteine mutation can be site-specifically biotinylated. The biotinylated fibronectin domains can also be conjugated to streptavidin-based scaffolds and retain their EpCAM-binding efficacy. At least one (if not all) of these EpCAM-binding domains recognize an epitope suitable for T cell activation and subsequent immunotherapy.

Example 3. Non-Specific Conjugation of EpCAM-Binding Fibronectin Domains

Though useful, site-specific conjugation is not required for many applications. Indeed, non-specific conjugation approaches are arguably faster and easier to execute as they do not require prior modification of the parent protein (e.g., such as designed cysteine mutations). Perhaps the most popular non-specific conjugation method is the use of activated esters to react with the primary amines located on the polypeptide's N-terminus and lysine side chains. Therefore, it was hypothesized that the fibronectin domains described herein could be non-specifically conjugated to NHS-biotin and retain their EpCAM-binding affinity and selectivity.

Biotinylated Fibronectin Domains Retain their EpCAM-Binding Affinity and Selectivity Three of the published (Stern et al., *ACS Combinatorial Science.* 2017, 19, 315-23) fibronectin clones—B22, C8, and C10—were non-specifically biotinyalted using EZ-Link Sulfo-NHS-Biotin (Thermo Fisher Scientific, Cat. 21217). Specifically, a 10-fold molar excess of the biotin reagent was combined with a single fibronectin clone in PBS and incubated on ice for 30 min. The reaction was purified using a PD-10 Desalting column (GE Healthcare, Cat. 17085101) in PBS.

Figure 20:
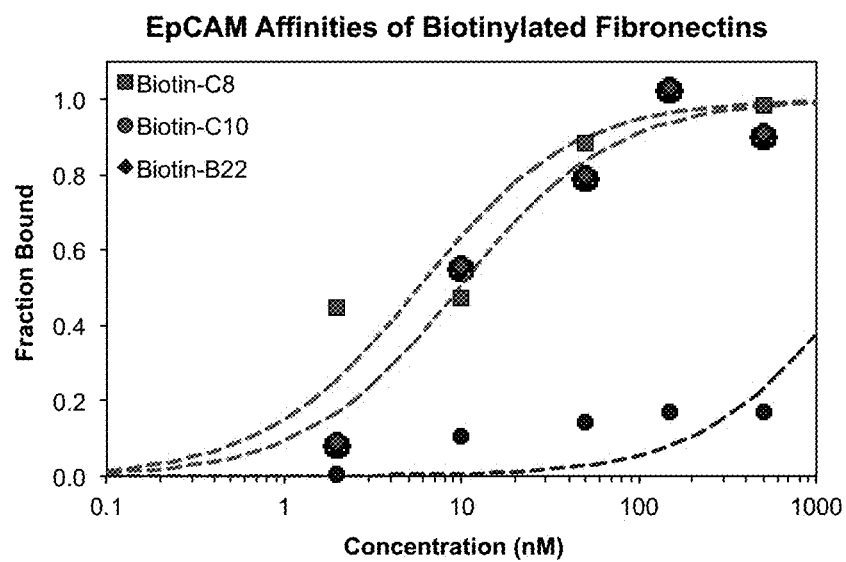
FIG. 20. EpCAM affinity of biotinylated fibronectin domains, as assessed by flow cytometry.

The biotinylated fibronectin domains were then titrated against EpCAM+ MCF-7 cells and analyzed by flow cytometry to estimate their $K_d$ values (FIG. 20). The $K_d$ values of the biotinylated ligands is compared to that of the parent ligand in the table below. As shown, biotinylation does not appear to significantly alter the affinity of the ligands.

| EpCAM Affinity Comparison for Non-Specifically Biotinylated and Unmodified Fibronectin Domains | | |
|---|---|---|
| Clone[1] | $K_d$ of Biotinylated Ligand (nM) | $K_d$ of Parent Ligand[1] (nM) |
| B22 | 1,700 | 1,100 ± 200 |
| C8 | 5.7 | 11 ± 4 |
| C10 | 9.7 | 25 ± 9 |

Figure 21:
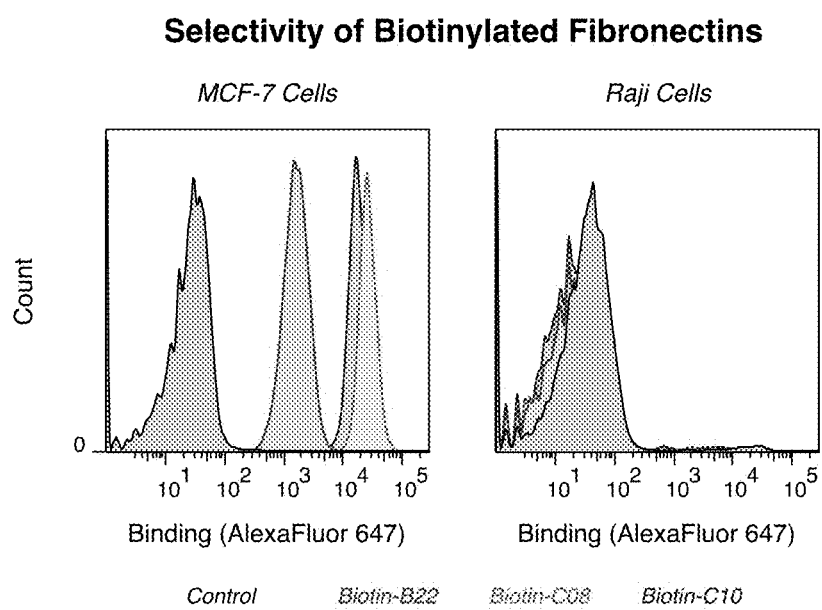
FIG. 21. Selectivity of biotinylated fibronectins, as assessed by flow cytometry. For the panel on the left, the peaks are shown from left to right in the following order: control, biotin-B22, biotin-C10 and biotin-C08.

A similar experiment was performed to assess the selectivity of the biotinylated ligands. As shown in FIG. 21, the biotinylated fibronectins do not bind to the EpCAM-negative Raji cells by flow cytometry.

Similar to the experiments described in Example 2, these biotinylated ligands can be loaded on mSA-CSANs to provide EpCAM-targeting capabilities to the CSAN scaffold (data not shown).

In summary, the fibronectin domains described herein can be non-specifically conjugated without affecting their EpCAM affinity or selectivity.

Example 4. Affinity/Avidity Relationships and Immunotherapeutic Target Discrimination Emerging data suggests that the ability of a targeting construct to discriminate between cells that express high and low levels of the target antigen can be tuned by varying the affinity and avidity of the construct (Caruso et al., *Cancer Res.* 2015, 75, 3305-3518; Liu et al., *Cancer Res.* 2015, 75, 3596-3607; Arcangeli et al., *Mol Ther.* 2017, 25, 1933-1945; Drent et al., *Mol Ther.* 2017, 25, 1946-1958). Preliminary data using the anti-EpCAM fibronectin based chemically self-assembled nanorings (CSANs) suggests that this may also be true for the scaffold described herein. It is hypothesized that, by varying the affinity and avidity of the CSAN's fibronectin domain, constructs can be generated that selectively target EpCAM-overexpressing tissues (i.e., neoplastic tissue) while sparing low-EpCAM expressing tissue (i.e., healthy tissue). To accomplish this, a new 1DD-fibronectin monomer was designed that more closely mimics the apparent affinity of the parent fibronectin clone.

Design and Construction of 1DD-Fn-v4

The fourth generation fusion protein resembles that of the previous generation, with the only difference being the lengthening of the GS linker between the C-terminal DHFR subunit and the fibronectin domain.

As shown in FIG. 22 and below, three such constructs have been made, each incorporating one of either a "high-affinity" EpCAM-binding domain (using clone C5), "low-affinity" EpCAM-binding domain (using clone B22), or "non-targeted" fibronectin domain (using control clone NT). Fibronectin sequences are shown bold.

```
1DD-FnC5-v4: fusion protein incorporating EpCAM-
binding fibronectin clone C5.
Protein (497 amino acids, calc. 52.89 kDa):
                                          (SEQ ID NO: 53)
MGEQKLISEEDLGGSGGGSGGGISLIAALAVDRVIGMENAMPWNLPADLAWFKRNTLNKP

VIMGRHTWESIGRPLPGRKNIILSSQPGTDDRVTWVKSVDEAIAAAGDVPEIMVIGGGRVYE
```

-continued

QFLPKAQKLYLTHIDAEVEGDTHFPDYEPDDWESVFSEFHDADAQNSHSYSFEILERRGGISL

IAALAVDRVIGMENAMPWNLPADLAWFKRNTLNKPVIMGRHTWESIGRPLPGRKNIILSSQP

GTDDRVTWVKSVDEAIAAAGDVPEIMVIGGGRVYEQFLPKAQKLYLTHIDAEVEGDTHFPD

YEPDDWESVFSEFHDADAQNSHSYSFEILERRGELGGSGGGGSGGGGSGGGGSGGGGSGG

GGSGGGGSGGGGSGGGGSGGASSSDSPRNLEVTNATPNSLTISWDNSNYASYYRITYGET

GGNSPSQELTVPGSTYNATISGLKPGQDYIITVYAVTYRDNYSYSNLISINYRSEIDKPSQ

GSHHHHHH

DNA (1,505 base pairs)

(SEQ ID NO: 54)

CCATGGGCGAACAAAAGCTTATTTCTGAAGAGGACTTGGGCGGTTCAGGTGGTGGCTC

GGGAGGCGGCATCAGTCTGATTGCGGCGTTAGCGGTAGATCGCGTTATCGGCATGGAA

AACGCCATGCCGTGGAACCTGCCTGCCGATCTCGCCTGGTTTAAACGCAACACCTTAAA

TAAACCCGTGATTATGGGCCGCCATACCTGGGAATCAATCGGTCGTCCGTTGCCAGGAC

GCAAAATATTATCCTCAGCAGTCAACCGGGTACGGACGATCGCGTAACGTGGGTGAA

GTCGGTGGATGAAGCCATCGCGGCGGCTGGTGACGTACCAGAAATCATGGTGATTGGC

GGCGGTCGCGTTTATGAACAGTTCTTGCCAAAAGCGCAAAAACTGTATCTGACGCATAT

CGACGCAGAAGTGGAAGGCGACACCCATTTCCCGGATTACGAGCCGGATGACTGGGAA

TCGGTATTCAGTGAATTCCACGATGCTGATGCGCAGAACTCTCACAGCTATAGCTTTGA

GATTCTGGAGCGGCGGGGCGGCATTAGCCTTATTGCCGCCTTAGCGGTTGATCGCGTGA

TCGGAATGGAGAACGCAATGCCCTGGAATCTTCCGGCAGACCTTGCCTGGTTCAAACGC

AACACTTTAAACAAGCCTGTCATTATGGGCCGTCACACATGGGAGTCAATTGGTCGTCC

CCTGCCTGGGCGCAAAAATATCATCTTGTCCTCGCAGCCTGGACAGATGATCGCGTTA

CATGGGTGAAGTCCGTAGACGAAGCGATTGCCGCTGCCGGCGATGTGCCCGAGATTAT

GGTAATCGGGGAGGGCGTGTTTACGAACAATTTCTGCCCAAAGCTCAGAAATTATAC

CTGACGCACATCGACGCGGAGGTCGAAGGTGACACACACTTTCCAGATTATGAGCCTG

ATGATTGGGAATCCGTTTTCTCAGAATTTCATGACGCGGATGCTCAAAACTCGCACTCG

TACTCTTTTGAAATTTTAGAGCGCCGTGGCGAGCTCGGAGGTTCCGGCGGGGCGGAA

GCGGAGGTGGAGGCTCAGGGGCGGAGGGTCGGGCGGTGGAGGTTCGGGGGGAGGCG

GGAGCGGTGGCGGTGGTTCAGGAGGAGGGGGTTCCGGGGGTGGTGGATCGGGCGGTGC

TAGCTCCTCCGACTCTCCGCGTAACCTGGAGGTTACCAACGCAACTCCGAACTCTC

TGACTATTTCTTGGGACAATTCTAACTATGCTTCGTATTACCGTATCACCTACGGC

GAAACCGGTGGTAACTCCCCGAGCCAGGAACTCACTGTTCCGGGAAGTACTTATA

ATGCGACCATCAGCGGTCTGAAACCGGGCCAGGATTATATCATTACCGTGTACGC

TGTAACCTATCGTGACAATTATTCCTATTCAAATCTAATCAGCATCAATTATCGCTC

CGAAATCGACAAACCGTCTCAGGGATCCCATCATCATCATCATCACTAGTAACTGA

1DD-FnB22-v4: Fusion protein incorporating EpCAM-binding
fibronectin clone B22.
Protein (497 amino acids, calc. 52.95 kDa):

(SEQ ID NO: 55)

MGEQKLISEEDLGGSGGGSGGGISLIAALAVDRVIGMENAMPWNLPADLAWFKRNTLNKP

VIMGRHTWESIGRPLPGRKNIILSSQPGTDDRVTWVKSVDEAIAAAGDVPEIMVIGGGRVYE

QFLPKAQKLYLTHIDAEVEGDTHFPDYEPDDWESVFSEFHDADAQNSHSYSFEILERRGGISL

IAALAVDRVIGMENAMPWNLPADLAWFKRNTLNKPVIMGRHTWESIGRPLPGRKNIILSSQP

GTDDRVTWVKSVDEAIAAAGDVPEIMVIGGGRVYEQFLPKAQKLYLTHIDAEVEGDTHFPD

-continued

YEPDDWESVFSEFHDADAQNSHSYSFEILERRGELGGSGGGGSGGGGSGGGGSGGGGSGG

GGSGGGGSGGGGSGGGGSGGASSSDSPRNLEVTNATPNSLTISWDDYTSASYYRITYGET

GGNSPSQEFTVPGNTYNATVSGLRPGQDYIITVYAVTYRDNYSYSNPISINYRTEIDKPS

QGSHHHHHH

DNA (1,505 base pairs)
(SEQ ID NO: 56)
CCATGGGCGAACAAAAGCTTATTTCTGAAGAGGACTTGGGCGGTTCAGGTGGTGGCTC

GGGAGGCGGCATCAGTCTGATTGCGGCGTTAGCGGTAGATCGCGTTATCGGCATGGAA

AACGCCATGCCGTGGAACCTGCCTGCCGATCTCGCCTGGTTTAAACGCAACACCTTAAA

TAAACCCGTGATTATGGGCCGCCATACCTGGGAATCAATCGGTCGTCCGTTGCCAGGAC

GCAAAAATATTATCCTCAGCAGTCAACCGGGTACGGACGATCGCGTAACGTGGGTGAA

GTCGGTGGATGAAGCCATCGCGGCGGCTGGTGACGTACCAGAAATCATGGTGATTGGC

GGCGGTCGCGTTTATGAACAGTTCTTGCCAAAAGCGCAAAAACTGTATCTGACGCATAT

CGACGCAGAAGTGGAAGGCGACACCCATTTCCCGGATTACGAGCCGGATGACTGGGAA

TCGGTATTCAGTGAATTCCACGATGCTGATGCGCAGAACTCTCACAGCTATAGCTTTGA

GATTCTGGAGCGGCGGGGCGGCATTAGCCTTATTGCCGCCTTAGCGGTTGATCGCGTGA

TCGGAATGGAGAACGCAATGCCCTGGAATCTTCCGGCAGACCTTGCCTGGTTCAAACGC

AACACTTTAAACAAGCCTGTCATTATGGGCCGTCACACATGGGAGTCAATTGGTCGTCC

CCTGCCTGGGCGCAAAAATATCATCTTGTCCTCGCAGCCTGGGACAGATGATCGCGTTA

CATGGGTGAAGTCCGTAGACGAAGCGATTGCCGCTGCCGGCGATGTGCCCGAGATTAT

GGTAATCGGGGAGGGCGTGTTTACGAACAATTTCTGCCCAAAGCTCAGAAATTATAC

CTGACGCACATCGACGCGGAGGTCGAAGGTGACACACACTTTCCAGATTATGAGCCTG

ATGATTGGGAATCCGTTTTCTCAGAATTTCATGACGCGGATGCTCAAAACTCGCACTCG

TACTCTTTTGAAATTTTAGAGCGCCGTGGCGAGCTCGGAGGTTCCGGCGGGGCGGAA

GCGGAGGTGGAGGCTCAGGGGCGGAGGGTCGGGCGGTGGAGGTTCGGGGGGAGGCG

GGAGCGGTGGCGGTGGTTCAGGAGGAGGGGGTTCCGGGGGTGGTGGATCGGGCGGTGC

TAGCTCCTCCGACTCTCCGCGTAACCTGGAGGTTACCAACGCTACTCCGAACTCTC

TGACTATCTCTTGGGACGATTATACTTCCGCTTCTTATTACCGTATCACCTACGGC

GAAACTGGTGGTAACTCCCCGAGCCAGGAATTCACTGTTCCGGGAAATACTTATAA

TGCGACCGTCAGCGGCCTGAGACCGGGCCAGGATTATATCATTACCGTGTACGCT

GTAACCTATCGTGACAATTATTCCTATTCAAACCCAATCAGCATCAATTATCGCAC

CGAAATCGACAAACCGTCTCAGGGATCCCATCATCATCATCATCACTAGTAACTCGAG

1DD-FnNT-v4: Fusion protein incorporating a non-binding
control fibronectin termed clone NT.
Protein (499 amino acids, calc. 52.68 kDa)
(SEQ ID NO: 57)
MGEQKLISEEDLGGSGGGSGGGISLIAALAVDRVIGMENAMPWNLPADLAWFKRNTLNKP

VIMGRHTWESIGRPLPGRKNIILSSQPGTDDRVTWVKSVDEAIAAAGDVPEIMVIGGGRVYE

QFLPKAQKLYLTHIDAEVEGDTHFPDYEPDDWESVFSEFHDADAQNSHSYSFEILERRGGISL

IAALAVDRVIGMENAMPWNLPADLAWFKRNTLNKPVIMGRHTWESIGRPLPGRKNIILSSQP

GTDDRVTWVKSVDEAIAAAGDVPEIMVIGGGRVYEQFLPKAQKLYLTHIDAEVEGDTHFPD

YEPDDWESVFSEFHDADAQNSHSYSFEILERRGELGGSGGGGSGGGGSGGGGSGGGGSGG

GGSGGGGSGGGGSGGGGSGGASSSDSPRNLEVTNATPNSLTISWDAPAVTVRYYRITYG

-continued

ETGGNSPSQEFTVPGSKSTATISGLKPGQDYTITVYAVTGRDGSPASSKPISINYRTEIDK

PSQGSHHHHHH

DNA (1,511 base pairs)

(SEQ ID NO: 58)

CCATGGGCGAACAAAAGCTTATTTCTGAAGAGGACTTGGGCGGTTCAGGTGGTGGCTC

GGGAGGCGGCATCAGTCTGATTGCGGCGTTAGCGGTAGATCGCGTTATCGGCATGGAA

AACGCCATGCCGTGGAACCTGCCTGCCGATCTCGCCTGGTTTAAACGCAACACCTTAAA

TAAACCCGTGATTATGGGCCGCCATACCTGGGAATCAATCGGTCGTCCGTTGCCAGGAC

GCAAAATATTATCCTCAGCAGTCAACCGGGTACGGACGATCGCGTAACGTGGGTGAA

GTCGGTGGATGAAGCCATCGCGGCGGCTGGTGACGTACCAGAAATCATGGTGATTGGC

GGCGGTCGCGTTTATGAACAGTTCTTGCCAAAAGCGCAAAAACTGTATCTGACGCATAT

CGACGCAGAAGTGGAAGGCGACACCCATTTCCCGGATTACGAGCCGGATGACTGGGAA

TCGGTATTCAGTGAATTCCACGATGCTGATGCGCAGAACTCTCACAGCTATAGCTTTGA

GATTCTGGAGCGGCGGGGCGGCATTAGCCTTATTGCCGCCTTAGCGGTTGATCGCGTGA

TCGGAATGGAGAACGCAATGCCCTGGAATCTTCCGGCAGACCTTGCCTGGTTCAAACGC

AACACTTTAAACAAGCCTGTCATTATGGGCCGTCACACATGGGAGTCAATTGGTCGTCC

CCTGCCTGGGCGCAAAATATCATCTTGTCCTCGCAGCCTGGGACAGATGATCGCGTTA

CATGGGTGAAGTCCGTAGACGAAGCGATTGCCGCTGCCGGCGATGTGCCCGAGATTAT

GGTAATCGGGGAGGGCGTGTTTACGAACAATTTCTGCCCAAAGCTCAGAAATTATAC

CTGACGCACATCGACGCGGAGGTCGAAGGTGACACACACTTTCCAGATTATGAGCCTG

ATGATTGGGAATCCGTTTTCTCAGAATTTCATGACGCGGATGCTCAAAACTCGCACTCG

TACTCTTTTGAAATTTTAGAGCGCCGTGGCGAGCTCGGAGGTTCCGGCGGGGCGGAA

GCGGAGGTGGAGGCTCAGGGGGCGGAGGGTCGGGCGGTGGAGGTTCGGGGGGAGGCG

GGAGCGGTGGCGGTGGTTCAGGAGGAGGGGGTTCCGGGGGTGGTGGATCGGGCGGTGC

TAGCTCCTCCGACTCTCCGCGTAACCTGGAGGTTACCAACGCAACTCCGAACTCTC

TGACTATTTCTTGGGATGCTCCTGCTGTCACAGTGAGATATTACCGTATCACCTAC

GGCGAAACTGGTGGTAACTCCCCGAGCCAGGAATTCACTGTTCCGGGGAGCAAGT

CTACAGCGACCATCAGCGGTCTGAAACCGGGCCAGGATTATACCATTACCGTGTA

CGCTGTAACTGGCCGTGACGGAAGCCCCGCAAGCAGCAAGCCAATCAGCATCAAT

TATCGCACCGAAATCGACAAACCGTCTCAGGGATCCCATCATCATCATCATCACTAG

TAACTCGAG

Expression, Purification, and Characterization

Figure 23:
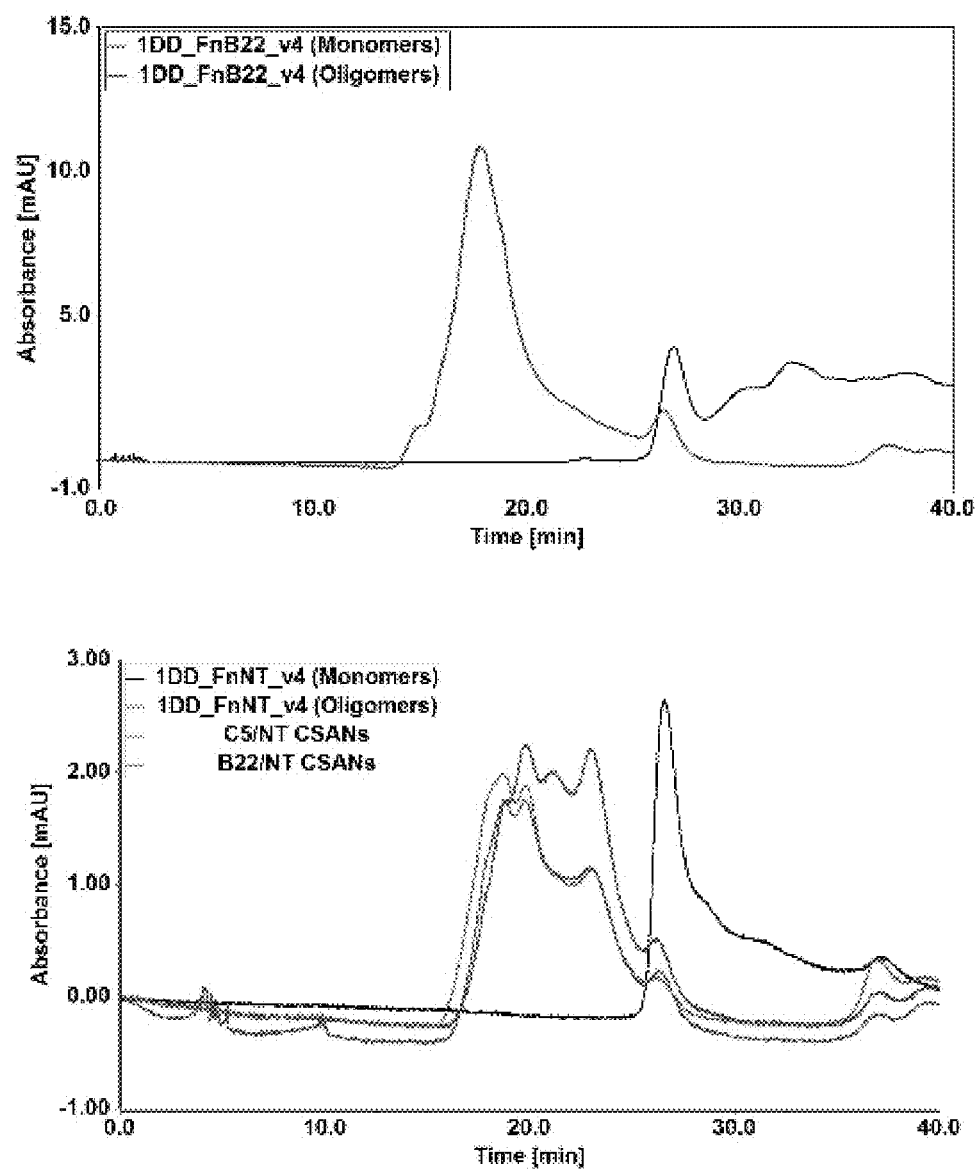
FIG. 23. SEC analysis of the 1DD-Fn fusion proteins.

All three fusion proteins express solubly in E. coli and can be readily purified from cell lysates via IMAC on a cobalt resin. SEC demonstrates monomeric production and successful oligomerization into CSANs in the presence of the chemical dimerzer, bis-methotrexate (FIG. 23).

Affinity and Selectivity of Fusion Proteins

Figure 25:
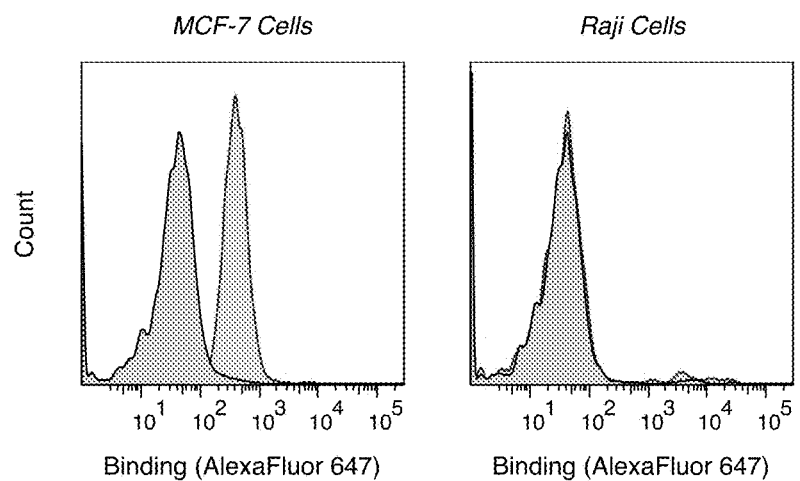
FIG. 25. EpCAM selectivity of 1DD-Fn-v4 monomers.

To ascertain whether the longer linker actually improves the apparent affinity of the monomeric ligand, 1DD-Fn-v4 was titrated against EpCAM+ MCF-7 cells. Affinity titrations were performed as described in Stern L A, et al. 2017 (full reference above) (FIG. 24). Another experiment, performed similarly, demonstrated the retained EpCAM selectivity of the construct (FIG. 25)

As shown, the longer linker helps maintain the binding efficacy of the fibronectin domain (relative to the shorter linker used in the previous generation construct, which is described below in Example 5). EpCAM selectivity is also maintained.

Figure 26:
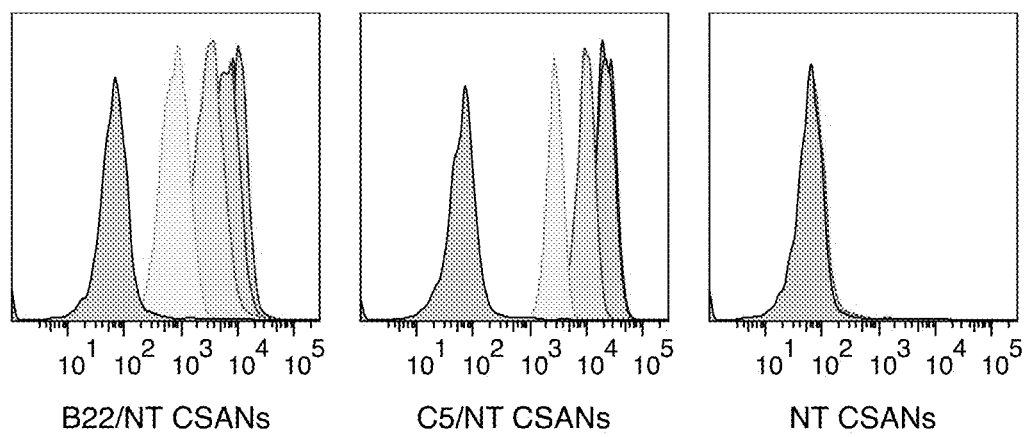
FIG. 26. Titration of mixed, reduced valency CSANs against EpCAM+ MCF-7 cells.

As demonstrated by the fourth SEC trace in FIG. 23, the fusion protein subunits can be co-assembled into CSANs that display two distinct fibronectin domains. When subunits displaying an EpCAM-binding Fn domain are co-assembled with subunits displaying the non-binding control Fn domain, CSANs with a "reduced valency" for EpCAM are produced. These mixed, reduced valency CSANs still bind to EpCAM+ MCF-7 cells, albeit with reduced apparent affinity (see, below; FIG. 26). Finally, CSANs displaying only the non-binding control domain do not bind to EpCAM+ cells, as expected.

Figure 27:
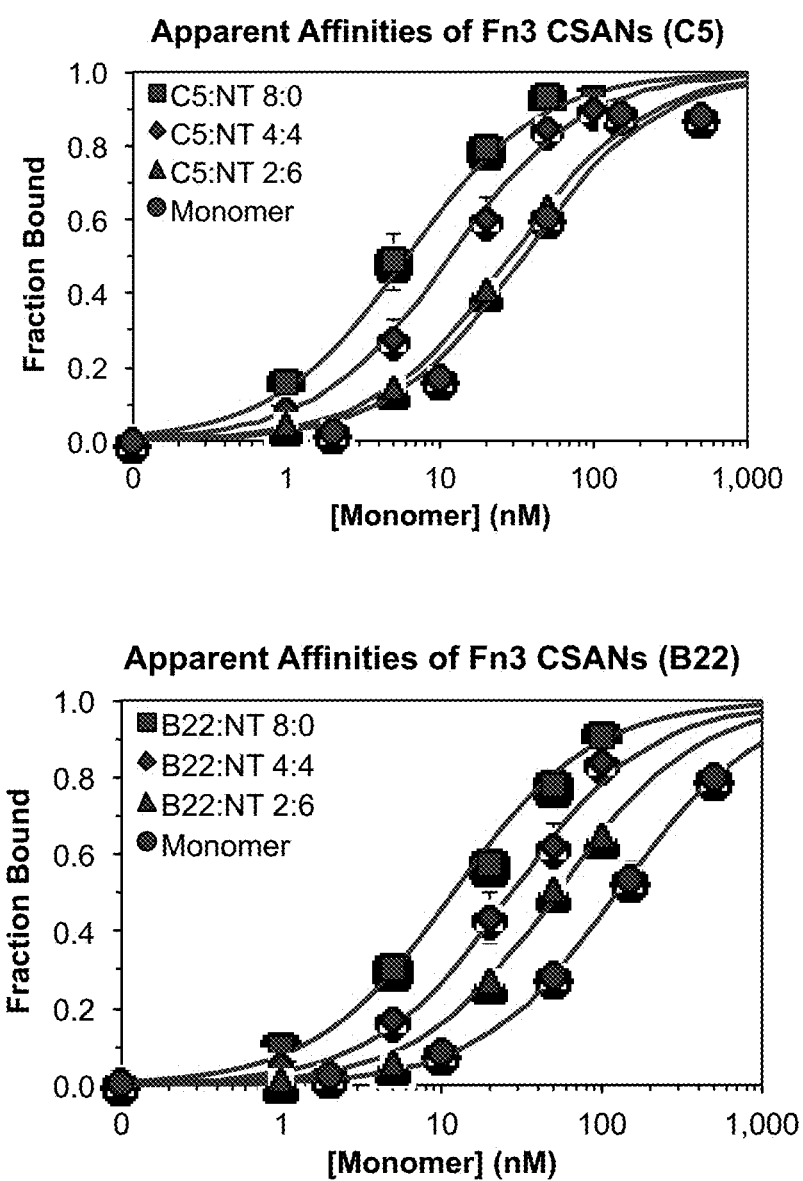
FIG. 27. Affinities of CSANs displaying either (1) only an EpCAM-binding Fn domain; or (2) a mixture of binding (either C5 or B22) and non-binding domains.

Affinity Titrations for CSANs Displaying Different Affinities and Valencies of EpCAM-Binding Fn Domains CSANs displaying either (1) only an EpCAM-binding Fn domain, or (2) a mixture of binding (either C5 or B22) and non-binding domains were titrated against MCF-7 cells to ascertain the apparent affinity of both "full" and "reduced" valency CSANs, respectively (FIG. 27).

Figure 28:
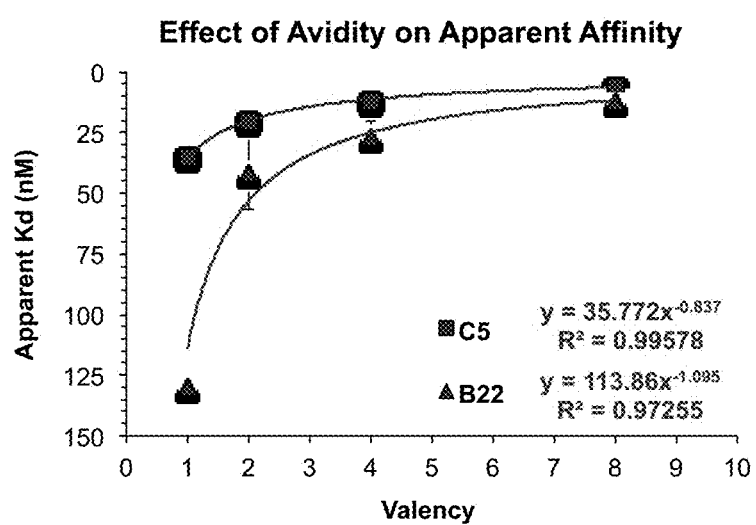
FIG. 28. Effect of avidity on apparent affinity.

As expected, the apparent affinity directly correlates with the valency of the targeting ligand. Furthermore, the effect of valency on the apparent $K_d$ value can be quantified by comparing the two parameters (FIG. 28).

Therefore, the panel of fibronectin ligands described herein are highly useful as a tool for elucidating fundamental properties of multivalent binding interactions. Ultimately, it is hypothesized that this ability to tune affinity/avidity can be taken advantage of to develop an CSAN-based immunotherapy that can discriminate between malignant cells that overexpress EpCAM and healthy cells that only express basal, low levels of EpCAM.

In summary, these data demonstrate that the fibronectin domains described herein can be fused to other functional proteins and still maintain their stability and EpCAM-binding efficacy/selectivity. Because the fibronectin clones span a range of affinities, the collection becomes useful as a tool for studying fundamental properties of binding interactions.

Example 5. Engineering Reversible Cell-Cell Interactions with Lipid Anchored Prosthetic Receptors

ABSTRACT

Membrane-engineered cells displaying antigen-targeting ligands are useful as both scientific tools and clinical therapeutics. While genetically-encoded artificial receptors have proven efficacious, their scope remains limited as this approach is not amenable to all cell types and the modification is often permanent. As described herein, a non-genetic method to rapidly, stably, and reversibly modify any cell membrane with a chemically self-assembled nanoring (CSAN) that can function as a prosthetic receptor as been developed. Bifunctional CSANs displaying epithelial cell adhesion molecule (EpCAM)-targeted fibronectin domains were installed on the cell membrane through hydrophobic insertion and remained stably bound for ≥72 h in vitro. These CSAN-labeled cells were capable of recognizing EpCAM-expressing target cells, forming intercellular interactions that were subsequently reversed by disassembling the nanoring with the FDA-approved antibiotic, trimethoprim. This study demonstrates the use of this system to engineer cell surfaces with prosthetic receptors capable of directing specific and reversible cell-cell interactions.

Introduction

The ability to direct cell-cell interactions has tremendous value across numerous fields—including tissue engineering (Gartner, et al., Proc Natl Acad Sci USA 2009, 106 (12), 4606-10; Rogozhnikov, et al., Sci Rep 2016, 6, 39806), regenerative medicine (Kean, et al., J Drug Target 2012, 20 (1), 23-32; Sarkar, et al., Blood 2011, 118 (25), e184-91), adoptive immunotherapy (Shi, et al., Nat Commun 2016, 7, 13088; Gabrielse, et al., Angew Chem Int Ed Engl 2014, 53 (20), 5112-6)—and as a tool for elucidating fundamental biology (Merzaban, et al., Glycobiology 2015, 25 (12), 1392-409; Zhao, et al., Faseb j 2011, 25 (9), 3045-56). To this end, several approaches for modifying cell surfaces have been developed, perhaps the most notable being that of chimeric antigen receptor (CAR) T cells (Sadelain, et al., Nature 2017, 545, 423). Though clinically efficacious, the genetic engineering underlying the CAR T cell platform makes it irreversible and yields several limitations that hinder its use for alternative applications (Fesnak, et al., Nat Rev Cancer 2016, 16 (9), 566-81). Specifically, not all cell types—such as regenerative stem cells—are amenable to such modification, and the permanence of the genetically encoded receptor has led to significant adverse events in the clinic, including B cell aplasia (Maude, et al., New England Journal of Medicine 2014, 371 (16), 1507-1517), solid organ damage (Lamers, et al., Molecular Therapy 21 (4), 904-912), and neurotoxicity (Gust, et al., Cancer Discov 2017).

To address these limitations and expand the use of cell-directing therapies, many groups have sought non-genetic approaches to introduce artificial receptors and targeting elements to the cell surface. Liposome fusion has been used to integrate bioorthogonal functional groups into the cell membrane, which can either be paired with complementarily modified cells or reacted with appropriately-conjugated targeting ligands (Dutta, et al., Bioconjug Chem 2011, 22 (12), 2423-33; Luo, et al., ACS Chem Biol 2015, 10 (10), 2219-26). Reactive groups can be introduced to the cell surface through metabolic engineering, wherein cells are grown in media supplemented with chemically-functionalized sugar analogs that get incorporated into membrane glycoproteins; similarly, these functional groups can then be conjugated to antigen targeting elements (Gartner, et al., Proc Natl Acad Sci USA 2009, 106 (12), 4606-10; Shi, et al., Nat Commun 2016, 7, 13088). Others have taken advantage of naturally existing cell-surface amines (primarily lysine side chains) to bind activated esters tethered to a variety of species to the cell surface nonspecifically (Sarkar, et al., Blood 2011, 118 (25), e184-91; Cheng, et al., Biomaterials 2012, 33 (20), 5004-12). Finally, various alkyl-, lipid-, and glycophosphatidylinositol (GPI)-tagged species have been hydrophobically inserted and anchored into the cell membrane (Ko, et al., Biomaterials 2009, 30 (22), 3702-10; Jeong, et al., J Am Chem Soc 2013, 135 (24), 8770-3; Todhunter, et al., Nat Methods 2015, 12 (10), 975-81; Hamdy, et al., J Immunol Methods 2005, 297 (1-2), 109-24).

While many of these non-genetic approaches have demonstrated the ability to direct specific cell-cell interactions, relatively few do so in a reversible fashion. Additionally, reversal mechanisms employed thus far—including irradiation with ultraviolet (UV) light (Shi, et al., Nat Commun 2016, 7, 13088; Luo, et al., Scientific Reports 2014, 4, 6313), changes in electrochemical redox potential (Pulsipher, et al., Angew Chem Int Ed Engl 2014, 53 (36), 9487-92), alterations in temperature (Altman, et al., Sci Rep 2013, 3, 3343; Amaral, et al., Chem Commun (Camb) 2015, 51 (99), 17556-9), and enzymatic cleavage of the tethering species (Xiong, et al., Angewandte Chemie International Edition 2013, 52 (5), 1472-1476)—are unfit for in vivo applications, especially when surface-modified cells are distributed throughout an organism.

Expanding upon this body of prior work, a cell membrane engineering methodology was designed that would be broadly applicable to a variety of cell types and possess a reversal mechanism suitable for in vivo use. To accomplish this, a protein scaffold called the chemically self-assembled nanoring (CSAN; FIG. 29A) was utilized (Carlson, et al., Journal of the American Chemical Society 2006, 128 (23), 7630-7638). CSANs are formed when bivalent dihydrofolate reductase (DHFR$^2$) fusion proteins are spontaneously oligomerized by a chemical dimerizer, bis-methotrexate (bisMTX) (Carlson, et al., Journal of the American Chemical Society 2006, 128 (23), 7630-7638). CSANs can be further functionalized by fusing various binding entities to the DHFR[2] subunits (Li, et al., *Journal of the American Chemical Society* 2010, 132 (48), 17247-17257; Shah, et al., *Mol Pharm* 2016, 13 (7), 2193-203)—in this case, either a monovalent streptavidin (mSA (Lim, et al., *Biotechnol Bioeng* 2013, 110 (1), 57-67)) unit or a fibronectin (Fn3) domain with engineered specificity for epithelial cell adhesion molecule (EpCAM) was fused (Stern, et al., *ACS Combinatorial Science* 2017, 19 (5), 315-323). Similarly, the bisMTX moiety can be chemically modified to incorporate a bioorthogonal ligation handle, such as an azide group (Shah, et al., *Mol Pharm* 2016, 13 (7), 2193-203; Fegan, et al., *Molecular Pharmaceutics* 2012, 9 (11), 3218-3227). Using stochastic combinations of the fusion proteins and the bisMTX, one can form multivalent, heterobifunctional CSANs capable of targeting multiple distinct antigens (Shen, et al., *J Am Chem Soc* 2015, 137 (32), 10108-11). Importantly, the CSAN scaffold can be disassembled through exposure to the FDA-approved antibiotic trimethoprim, providing a pharmacologic mechanism for removing the targeting ligands from the cell surface (Gabrielse, et al., *Angew Chem Int Ed Engl* 2014, 53 (20), 5112-6; Fegan, et al., *Molecular Pharmaceutics* 2012, 9 (11), 3218-3227; Shen, et al., *J Am Chem Soc* 2015, 137 (32), 10108-11).

Consistent with the aim to develop a surface engineering approach that would be applicable to multiple cell types, a system based upon the spontaneous hydrophobic insertion of commercially available phospholipid conjugates was designed (FIG. 29B-C). Using either 1,2-distearoyl-sn-glycero-3-phosphoethanolamine-N-{biotinyl(polyethylene glycol)-2000}(DSPE-PEG$_{2000}$-biotin) or 1,2-distearoyl-sn-glycero-3-phosphoethanolamine-N-{dibenzocyclooctyl (polyethylene glycol)-2000} (DSPE-PEG$_{2000}$-DBCO), cell surfaces can be decorated with biotin and DBCO moieties, respectively. Targeted CSANs are then attached to the lipid-modified cells via a non-covalent biotin/mSA interaction or a copper-free, strain-promoted alkyne/azide cycloaddition (SPAAC) involving the DBCO/azide groups, thereby functionalizing the cell with the EpCAM-binding domains. As demonstrated herein, the CSAN-functionalized cells are capable of interacting with EpCAM+ target cells, and these intercellular interactions are readily reversed with trimethoprim.

As such, this study details a non-genetic, two-component strategy to functionalize cells with antigen-binding ligands capable of directing targeted cell-cell interactions in a pharmacologically reversible fashion.

Results and Discussion

Functionalized Phospholipids Hydrophobically Insert into Cell Membranes

The spontaneous membrane insertion of hydrophobic species—including alkyl chains, phospholipids, and GPI-conjugated proteins—has been demonstrated in numerous cell types (Lim, et al., *Biochem Biophys Res Commun* 2017, 482 (4), 1042-1047; de Kruif, et al., *Nat Med* 2000, 6 (2), 223-7), including mesenchymal stem cells (MSCs) (Kean, et al., *J Drug Target* 2012, 20 (1), 23-32; Ko, et al., *Biomaterials* 2009, 30 (22), 3702-10; Lo, et al., *Biomaterials* 2013, 34 (33), 8213-22). These results have shown that this insertion is innocuous to the modified cell, having no effect on cell viability, proliferation, or differentiation. Furthermore, this approach is facile, requiring no specialized reagents or techniques, and is universally applicable to essentially any cell type. Therefore, hydrophobic insertion was used to tether CSANs to the cell surface (FIG. 29B-C).

The commercially available phospholipid conjugates DSPE-PEG$_{2000}$-biotin and DSPE-PEG$_{2000}$-DBCO were selected for this study. These species were chosen because it was hypothesized that the hydrophobic lipid would enable membrane insertion while the long, flexible PEG linker would improve the accessibility of the biotin and DBCO groups. Two approaches to labeling the cells with the phospholipids were envisioned: (1) resuspending the cells ex vitro in buffer supplemented with the phospholipids; and (2) actively culturing the cells in vitro in phospholipid-supplemented media. Importantly, cell viability was not affected by either lipid-modification approach, even when concentrations of up to 100 µM of DSPE-PEG$_{2000}$-biotin or DSPE-PEG$_{2000}$-DBCO were used (FIG. 36A-B). This was true for both of the model cell lines, adherent MCF-7 and suspensive Raji cells.

To simultaneously assess the membrane insertion of phospholipids and ensure that the biotin and DBCO groups were accessible, cells were analyzed via flow cytometry using streptavidin- and azide-conjugated fluorophores, respectively. Both MCF-7 and Raji cells were modified with increasing concentrations of DSPE-PEG$_{2000}$-biotin or DSPE-PEG$_{2000}$-DBCO through both the buffer (ex vitro) and culture (in vitro) methods. In all instances, the biotin and DBCO moieties were readily detected on the cell surface after lipid modification, indicating both successful membrane insertion and availability of the functional groups for subsequent labeling (FIGS. 30A-H and 378A-B). Furthermore, the extent of the modification could be easily modulated by varying the concentration of the phospholipid conjugate that was used.

Seemingly, the DSPE-PEG$_{2000}$-biotin species affords a more tunable modification than DSPE-PEG$_{2000}$-DBCO (FIG. 30A-H). However, this observation is likely an artifact of the relatively short time (1 hour) and low temperature (4° C.) for which the lipid-modified cells were incubated with the secondary reagent, as the biotin/streptavidin interaction forms more rapidly (Srisa-Art, et al., *Analytical Chemistry* 2008, 80 (18), 7063-7067) than the slower azide/alkyne ligation (Karver, et al., *Angewandte Chemie* (International ed. in English) 2012, 51 (4), 920-922) necessary to detect the DBCO species. Indeed, extending this incubation time to ≥3 h and raising the temperature to 37° C. enhances conjugation to surface DBCO groups (FIG. 38A-B). Therefore, it is possible that both DSPE-PEG$_{2000}$-biotin and DSPE-PEG$_{2000}$-DBCO insert into the cell membrane to a similar extent, and that the discrepancies between the labeling observed in FIGS. 30A-H and 37A-B are due to the inherent differences between the subsequent binding and ligation efficiencies. Additionally, the hydrophobicity of the DBCO group itself may enable it to interact with hydrophobic membrane components, further slowing the azide ligation reaction.

Lastly, the Raji cells appear to become saturated with DSPE-PEG$_{2000}$-biotin following incubation with 10 µM of the phospholipid, as incubation with 100 µM does not afford an increase in the fluorescent signal. Across the concentration range tested, no such saturation was observed for the MCF-7 cells. This observation is most likely explained by the difference in size between the two cell types—the Raji cells are smaller and thus their membranes cannot support the same quantity of the DSPE-PEG$_{2000}$-biotin as the larger MCF-7 cells.

Collectively, this data shows that a variety of cell types can be effectively modified with phospholipid conjugates via hydrophobic insertion into the cell membrane without effecting cell viability. These results are consistent with those obtained by others performing similar hydrophobic insertions and further validates this approach as a universal method for cell surface modification (Kean, et al., *J Drug Target* 2012, 20 (1), 23-32; Sarkar, et al., *Blood* 2011, 118 (25), e184-91; Ko, et al., *Biomaterials* 2009, 30 (22), 3702-10; Lim, et al., *Biochem Biophys Res Commun* 2017, 482 (4), 1042-1047; de Kruif, et al., *Nat Med* 2000, 6 (2), 223-7; Lo, et al., *Biomaterials* 2013, 34 (33), 8213-22).

Production and Characterization of Cell-Binding CSANs
EpCAM is a cell surface antigen that is overexpressed by numerous carcinomas and several cancer stem cells (Patriarca, et al., *Cancer Treat Rev* 2012, 38 (1), 68-75). The development of EpCAM-binding Fn3 ligands, based upon the human tenth type III fibronectin domain, is described herein (Stern, et al., *ACS Combinatorial Science* 2017, 19 (5), 315-323). To impart EpCAM-targeting capabilities to CSANs, the Fn3 clone C5 ($K_d$=17±1 nM) was fused to the C-terminus of DHFR$^2$ fusion proteins. When these DHFR$^2$-Fn3 monomers were exposed to a molar excess of the chemical dimerizer, bisMTX, they rapidly and completely oligomerized into Fn3 CSANs, as demonstrated by size exclusion chromatography (FIG. 39A-B). Importantly, the Fn3 CSANs continued to bind to EpCAM-expressing MCF-7 cells with high affinity (apparent $K_d$=21±6 nM and selectivity (FIGS. 40A-B).

Methods were then developed for binding these Fn3 CSANs to cells that had been modified with DSPE-PEG$_{2000}$-biotin or DSPE-PEG$_{2000}$-DBCO. To recognize the biotin-decorated cells, a monovalent streptavidin domain (mSA) was fused to the N-terminus of the DHFR$^2$ fusion proteins. In the presence of bisMTX, these mSA-DHFR$^2$ monomers readily oligomerized into biotin-binding CSANs (FIG. 39C). Furthermore, stochastic mixtures of the mSA- and Fn3-fused monomers could be co-assembled into CSANs with bispecificty for both biotin and cellular EpCAM (FIG. 39D). Importantly, these bispecific mSA/Fn3 CSANs retained their apparent affinity for EpCAM+ cells (apparent $K_d$=24±6 nM; FIG. 40A).

Figure 41B:
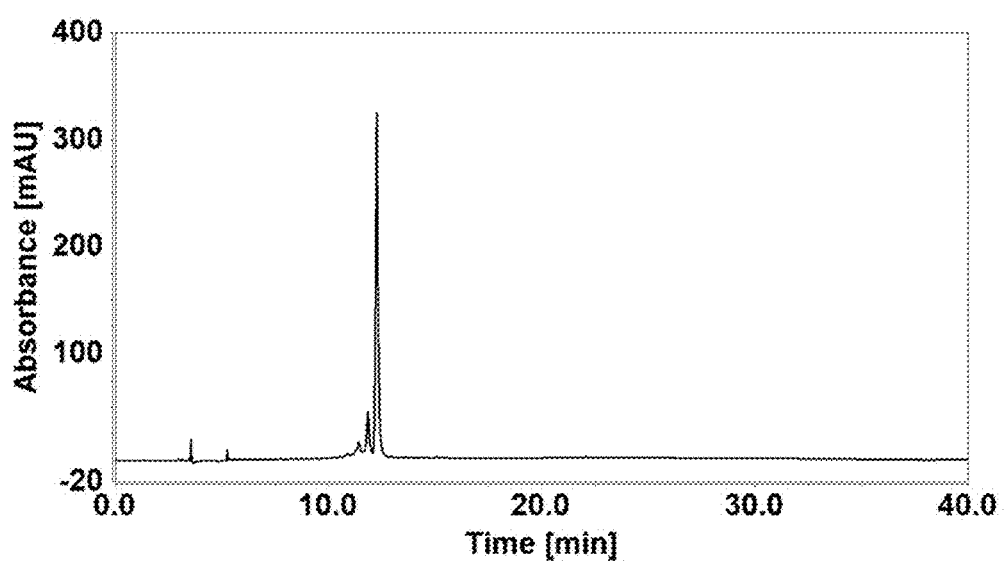

The synthesis and use of a bisMTX analog that incorporates a free amine suitable for further conjugation and additional functionalization has previously been reported (Shah, et al., *Mol Pharm* 2016, 13 (7), 2193-203; Fegan, et al., *Molecular Pharmaceutics* 2012, 9 (11), 3218-3227). To produce CSANs capable of binding to the DBCO-decorated cells, a PEG$_4$-azide moiety was coupled to this amine via N-hydroxysuccinimide (NHS) chemistry, generating an azide-bisMTX analog that contains a free azide group (FIG. 41A-B). As with the parent bisMTX dimerizer, DHFR$^2$-Fn3 fusion proteins exposed to azide-bisMTX oligomerized into azide/Fn3-CSANs (FIG. 39B).

The formation of the mSA, Fn3, and mSA/Fn3 bispecific CSAN species was further verified via cryo-electron microscopy (cryo-EM). Nanoring structures were readily visualized for all three species (FIGS. 31A-C, respectively), and analysis of multiple samples indicated similar sizes for the mSA (18±3 nm), Fn3 (19±4 nm), and mSA/Fn3 bispecific (19±4 nm) CSANs (FIG. 31D). These diameters are in close agreement to dynamic light scattering (DLS) measurements of the hydrodynamic radii of these species (FIG. 42).

CSANs are Readily Installed on Phospholipid-Modified Cells
After confirming the membrane insertion of the phospholipid conjugates, the associated functional groups were used as handles for the attachment of the nanoring platform. Cells were first modified with DSPE-PEG$_{2000}$-biotin or DSPE-PEG$_{2000}$-DBCO ex vitro. They were subsequently incubated with CSANs of various functionalities at 4° C. for 1 h, or in the case of the Fn3 CSANs oligomerized with azide-bisMTX, 37° C. for 3 h. Specifically: (1) mSA CSANs were successfully bound to biotin-modified MCF-7 cells (FIG. 32A); (2) Fn3 CSANs oligomerized with azide-bisMTX were conjugated to DBCO-modified Raji cells (FIG. 32B); and (3) Fn3 CSANs were bound to EpCAM-expressing MCF-7 cells (FIG. 32C). Additionally, mSA/Fn3 bispecific CSANs could be installed on both biotin-modified Raji cells (FIG. 32D) and unmodified MCF-7 cells (FIG. 32E), demonstrating the retained biofunctionality of these co-assembled CSANs. These experiments also verified the presence of both the mSA-DHFR$^2$ and DHFR$^2$-Fn3 subunits within a single CSAN, as the analyzed events were positive for both the FLAG and MYC epitope tags present on the respective fusion proteins (FIG. 43A). Finally, in preparation for future cell-targeting experiments, the optimal labeling concentration of mSA/Fn3 CSANs on Raji cells modified with DSPE-PEG$_{2000}$-biotin was assayed by flow cytometry and found to be 100 nM (FIG. 43B).

In Vitro Stability of Phospholipid-Anchored CSANs
While the insertion of hydrophobic anchors into the lipid bilayer is an enthalpically-favored process (Jeong, et al., *J Am Chem Soc* 2013, 135 (24), 8770-3), it is typically a transient modification with a half-life on the order of hours for cells in active culture (Kean, et al., *J Drug Target* 2012, 20 (1), 23-32; de Kruif, et al., *Nat Med* 2000, 6 (2), 223-7). Additionally, because the lipids can insert into essentially any cell membrane, it was conceivable that a lipid-anchored species could dissociate from the membrane into which it was principally installed and subsequently label a neighboring cell, essentially "hopping" from the intended cell to a bystander cell. However, it was hypothesized that by engaging multiple lipid anchors per nanoring, the multivalency of the CSAN would portend an improved surface stability relative to single lipid species and keep the CSANs localized to the principally modified cell.

To test both the surface stability of lipid-anchored CSANs and their potential to transfer amongst cells, two populations of Raji cells were differentially labeled. The first population was labeled only with CellTrace Violet (CTV) dye. The second population was modified with DSPE-PEG$_{2000}$-biotin in vitro and then labeled with "reduced valency" mSA CSANs. To more accurately recapitulate the valency of mSA domains that would be present in a bifunctional mSA/targeted CSAN, the CSANs used in this study were co-assembled with an equal ratio of mSA-DHFR$^2$ monomers and non-targeted DHFR$^2$ monomers. In this manner, the reduced valency CSANs used in this experiment serve as a surrogate for any bispecific mSA/targeted CSAN, including the mSA/Fn3 CSANs previously introduced.

The CTV-labeled and CSAN-labeled Raji cell populations were combined and co-cultured for 72 h; every 24 h, the culture media was refreshed (to partially simulate the effect of clearance) and a sample of the pooled population was analyzed for CTV and CSAN presence by flow cytometry. For comparison, the same analysis was performed for a mixed population of CTV-labeled Raji cells and Raji cells only modified with the DSPE-PEG$_{2000}$-biotin (no CSANs). As shown in FIG. 33A, the lipid-anchored CSANs remained stably bound to the cell surface for ≥72 h. In contrast, significant loss of the monomeric phospholipid conjugates was observed over this same time frame (p<0.0025). This indicates that, through the engagement of multiple phospholipid conjugates, the multivalent CSANs possess an increased avidity for the cell surface and thus an enhanced surface stability relative to species that are anchored by only a single lipid. Furthermore, the CSANs exhibited a surface half-life of approximately 24 h when incubated in mouse plasma (FIG. 44), making them considerably more stable than previously-reported phospholipid-anchored constructs and thus potentially useful for future in vivo applications. Furthermore, FIG. 33C demonstrates that there is minimal migration of a lipid-anchored CSAN from one cell to another. Specifically, the percentage of CTV+/CSAN+ Raji cells in the population increases only marginally over the course of three days, from 0.9±0.3% of the population on day zero to 2.9±0.9% on day three; this correlates to a decrease in the number of CTV+/CSAN− Raji cells from 27.1±0.9% to 24.5±0.4% over the same time period. A similar effect is observed for the monomeric DSPE-PEG$_{2000}$-biotin moieties (FIG. 33D), with an increase in the number of CTV+/lipid+ cells from 0.6±0.6% to 4.1±0.8% and a corresponding decrease in the number of CTV+/lipid− cells from 26.9±0.5% to 23.3±0.5% over three days. This data suggests that, while the phospholipid conjugates and their tethered cargo can dissociate from the cell surface, very few of the dissociated species re-insert themselves into the membranes of neighboring cells. This is likely due to the low concentration of the dissociated species in the media and the frequent refreshing of the cell media (every 24 h), thus reducing the accumulation of free phospholipid conjugates.

Trimethoprim Removes Targeting Elements from the Cell Surface

To date, relatively few cell surface engineering approaches—either genetic or non-genetic in origin—possess mechanisms for removing the artificial receptors from the cell surface. Furthermore, many of those reversal stimuli are not currently suited for in vivo applications (Luo, et al., *Scientific Reports* 2014, 4, 6313; Pulsipher, et al., *Angew Chem Int Ed Engl* 2014, 53 (36), 9487-92; Altman, et al., *Sci Rep* 2013, 3, 3343; Amaral, et al., *Chem Commun* (Camb) 2015, 51 (99), 17556-9; Xiong, et al., *Angewandte Chemie International Edition* 2013, 52 (5), 1472-1476). Accordingly, the trimethoprim-induced disassembly of the CSAN scaffold was used as a pharmacologic mechanism for removing the targeting ligands from the surface of a CSAN-functionalized cell. To demonstrate this, Raji cells were sequentially modified with DSPE-PEG$_{2000}$-biotin in vitro and labeled with mSA/Fn3 bispecific CSANs. The CSAN-functionalized Raji cells were then resuspended in culture media supplemented with a clinically-relevant concentration of trimethoprim (2 μM; serum concentrations of trimethoprim have been shown to reach peak concentrations of ~6-15 μM within 2 h of oral dosing (Eatman, et al., *Journal of Pharmacokinetics and Biopharmaceutics* 1977, 5 (6), 615-624; Watson, et al., *European Journal of Clinical Pharmacology* 1986, 30 (4), 457-461)) and incubated at 37° C. for up to 2 h. An aliquot of cells was analyzed by flow cytometry at 0, 1, and 2 h. As shown in FIG. 33B, the targeting ligands were dissociated from the cell surface in a time-dependent manner, with 95% of the EpCAM-targeted Fn3 domains removed within 2 h.

CSANs Direct Reversible Cell-Cell Interactions In Vitro

The ability of CSANs to direct reversible intercellular interactions in vitro was assessed by fluorescence microscopy (FIG. 34A-C). CFSE-labeled Raji cells were sequentially modified with DSPE-PEG$_{2000}$-biotin, labeled with mSA/Fn3 bispecific CSANs, and then incubated with a monolayer of EpCAM-expressing target cells (MCF-7) adhered to glass coverslips. The CSAN-functionalized Raji cells readily bound to the culturing monolayer of target cells (FIG. 34B), and these cell-cell interactions were readily reversed via a brief (1 h) exposure to trimethoprim (FIG. 34C). Importantly, phospholipid-modified cells that were not functionalized with the mSA/Fn3 CSANs were not able to interact with the target cells (FIG. 34A), indicating that the observed interactions were induced by the CSANs and not non-specific adherence.

A similar experiment was conducted via flow cytometry. In this case, CTV-labeled Raji cells were again modified with DSPE-PEG$_{2000}$-biotin and labeled with mSA/Fn3 bispecific CSANs. They were then combined with detached, CFSE-labeled MCF-7 cells and incubated together on a rotating platform for 1 h. Samples were subsequently resuspended in either standard culture media or media supplemented with 2 μM trimethoprim. After another 1 h incubation with rotation, samples were thoroughly washed and analyzed on a flow cytometer. Similar to the microscopy results, very few non-specific cell-cell interactions are observed in the absence of the CSANs (FIG. 34D). However, the CSAN-functionalized Raji cells were able to form targeted cell clusters with the MCF-7 cells (FIG. 34E); again, nearly all of the targeted interactions were dissociated with trimethoprim treatment (FIG. 34F). Even under the high-flow conditions of the cytometer (an instrument designed for single cell analyses), the CSAN− functionalized Raji cells were able to form significantly more interactions with the MCF-7 cells relative to the non-functionalized Raji cells (7.3±1.1% vs. 0.8±0.1%; p<0.001). Brief exposure to trimethoprim drove significant dissociation of these clusters (p<0.01), returning nearly the baseline number of non-specific interactions (1.9±0.3%). As demonstrated above, the trimethoprim-induced dissociation of the CSAN scaffold is time-dependent; therefore, it is conceivable that prolonging the trimethoprim incubation in this experiment beyond 1 h would drive further reversal of the cell-cell interactions.

Bioorthogonal CSANs Enable Formation of Multicellular Interactions

Taking advantage of the modular nature of the CSAN platform, a combination of multifunctional CSANs was used to induce controlled interactions between three different model cell populations (FIG. 35A-D). MCF-7 cells were again adhered to glass coverslips to form a monolayer of EpCAM-positive target cells. Then, CFSE-labeled Raji cells that had been sequentially modified with DSPE-PEG$_{2000}$-biotin and mSA/Fn3 CSANs were bound to the MCF-7 cells, as before. To introduce a third cell population, a separate aliquot of Raji cells was labeled with CellTrace Far Red, modified with DSPE-PEG$_{2000}$-DBCO and functionalized with azide/mSA bispecific CSANs capable of targeting the unoccupied biotin moieties on the surface of the preceding CFSE-labeled Raji population. After washing the cell layer to remove unbound CFSE-Raji cells, the functionalized FarRed-Raji cell population was added and incubated in an analogous fashion. After washing, fixation, and mounting on glass slides using DAPI-containing mountant, the coverslips were analyzed by fluorescence microscopy. In the absence of CSANs, it was again observed that the phospholipid-modified Raji cells were unable to interact with the MCF-7 cells (FIG. 35A). However, the CSAN-functionalized Raji cells were able to form targeted cell arrangements, adhering to the monolayer of EpCAM-expressing cells and to each other (FIG. 35B). Many of these interactions were reversed after a one-hour incubation in trimethoprim-containing media (FIG. 35C). Finally, when the FarRed-Raji cells that had been functionalized with the azide/mSA CSANs were incubated with just the primary MCF-7 cell layer, they were not able to adhere as these cells did not express the target "antigen", in this case, biotin (FIG. 35D). These results indicate that by exchanging the various targeting domains utilized in the CSAN platform, diverse cell populations can be driven to interact with one another in a controlled and pharmacologically reversible fashion.

CONCLUSIONS

In conclusion, the CSAN platform offers a modular approach for reversibly functionalizing cell membranes with targeting ligands. Through the spontaneous membrane insertion of phospholipids conjugated to biotin and DBCO groups, CSANs can be installed on essentially any cell surface and function as prosthetic receptors. In contrast to genetic engineering approaches, which require both manipulation of the target cell's genome and extensive culturing to expand the modified cells, the method described here is rapid, scalable to large cell numbers, and broadly applicable to diverse cell types.

Once installed on cell surfaces, EpCAM-targeting CSANs were capable of inducing specific intercellular interactions between the CSAN-functionalized cells and EpCAM-expressing target cells in vitro. Due to the modularity of the CSAN platform, this approach was further expanded to direct targeted interactions between three different cell populations. Additionally, these interactions were rapidly reversed through exposure to trimethoprim.

The capacity to remove CSAN-based surface modifications pharmacologically with trimethoprim makes them distinct from other reversal approaches developed thus far. While photoirradiation, enzymatic degradation, and changes in redox potential or temperature have all been demonstrated, none of the mechanisms are currently applicable in an in vivo setting, especially when the modified cells are broadly distributed throughout an organism (as would be the case for immunotherapy and some regenerative medicine applications). Because trimethoprim is an FDA-approved antibiotic that is used systemically, CSAN-directed cell-cell interactions could conceivably be readily reversed in vivo via trimethoprim administration, providing a safe mechanism for deactivating the targeted cells in the case of adverse events or initiating processes dependent on the loss of intercellular interactions. Ultimately, this work demonstrates that lipid-anchored prosthetic receptors provide a broadly-applicable approach to cell surface engineering that could be used to expand the formation of targeted, reversible cell-cell interactions across diverse fields.

Materials & Methods

Cells and Cell Culture

The MCF-7, U-87 MG, and Raji cell lines were previously purchased from the American Type Culture Collection (ATCC). MCF-7 and U-87 MG cells were grown at 37° C. in a humidified atmosphere with 5% $CO_2$ in Dulbecco's Modified Eagle's Medium (DMEM) with 4.5 g/L glucose, L-glutamine, and supplemented with 10% fetal bovine serum (FBS), 100 U/mL penicillin, and 100 µg/mL streptomycin. Raji cells were grown at 37° C. in a humidified atmosphere with 5% $CO_2$ in Roswell Park Memorial Institute (PRMI) media with L-glutamine and supplemented with 10% FBS, 100 U/mL penicillin, and 100 µg/mL streptomycin. When needed for passaging or harvesting, adherent cell lines MCF-7 and U-87 MG were detached via trypsin. Cell count and viability was determined via trypan blue staining/exclusion using a Bio Rad TC20 automated cell counter (Bio Rad Laboratories, Inc.).

Expression Plasmids gBlock Gene Fragments coding for the $DHFR^2$-Fn3 and mSA-$DHFR^2$ fusion proteins were ordered from Integrated DNA Technologies (IDT) and cloned into the Novagen pET28a(+) vector (EMD Millipore, Cat: 69864-3) via NcoI and XhoI restriction sites. Notably, the $DHFR^2$-Fn3 fusion proteins contain an N-terminal MYC epitope tag and C-terminal polyhistidine tag to facilitate detection via flow cytometry and purification via immobilized metal affinity chromatography (IMAC), respectively. Similarly, the mSA-$DHFR^2$ fusion proteins contain a C-terminal FLAG epitope tag to enable flow cytometric detection.

Protein Sequences of $DHFR^2$ Fusion Proteins $DHFR^2$-Fn3 (487 amino acids; calculated MW 51.1 kDa)
(SEQ ID NO: 59)
MGEQKLISEEDLGGSGGGSGGGISLIAALAVDRVIGMENAMPWNLPADLA

WFKRNTLNKPVIMGRHTWESIGRPLPGRKNIILSSQPGTDDRVTWVKSVD

EAIAAAGDVPEIMVIGGGRVYEQFLPKAQKLYLTHIDAEVEGDTHFPDYE

PDDWESVFSEFHDADAQNSHSYSFEILERRGGISLIAALAVDRVIGMENA

MPWNLPADLAWFKRNTLNKPVIMGRHTWESIGRPLPGRKNIILSSQPGTD

DRVTWVKSVDEAIAAAGDVPEIMVIGGGRVYEQFLPKAQKLYLTHIDAEV

EGDTHFPDYEPDDWESVFSEFHDADAQNSHSYSFEILERRGELGGGGSGG

GGSGGGGSASSSDSPRNLEVTNATPNSLTISWDNSNYASYYRITYGETGG

NSPSQELTVPGSTYNATISGLKPGQDYIITVYAVTYRDNYSYSNLISINY

RSEIDKPSQGSHHHHHH mSA-$DHFR^2$ (471 amino acids; calculated MW 51.4 kDa)
(SEQ ID NO: 60)
MAEAGITGTWYNQSGSTFTVTAGADGNLTGQYENRAQGTGCQNSPYTLTG

RYNGTKLEWRVEWNNSTENCHSRTEWRGQYQGGAEARINTQWNLTYEGGS

GPATEQGQDTFTKVKELGGSGGGSGGGSGGMISLIAALAVDRVIGMENAM

PWNLPADLAWFKRNTLNKPVIMGRHTWESIGRPLPGRKNIILSSQPGTDD

RVTWVKSVDEAIAAAGDVPEIMVIGGGRVYEQFLPKAQKLYLTHIDAEVE

GDTHFPDYEPDDWESVFSEFHDADAQNSHSYSFEILERRGMISLIAALAV

DRVIGMENAMPWNLPADLAWFKRNTLNKPVIMGRHTWESIGRPLPGRKNI

ILSSQPGTDDRVTWVKSVDEAIAAAGDVPEIMVIGGGRVYEQFLPKAQKL

YLTHIDAEVEGDTHFPDYEPDDWESVFSEFHDADAQNSHSYSFEILERRG

GSGGGSGGGSGGDYKDDDDK

Protein Expression and Purification

The $DHFR^2$-Fn3 fusion proteins were produced in Escherichia coli (E. coli) and purified from the soluble fraction of the cell lysates by IMAC according to the methods previously reported for the parent Fn3 clones (Stern, et al., ACS Combinatorial Science 2017, 19 (5), 315-323). The mSA-$DHFR^2$ fusion proteins produced in E. coli and purified from the insoluble inclusion bodies of the cell lysates according to previously reported refolding methods (Gabrielse, et al., Angew Chem Int Ed Engl 2014, 53 (20), 5112-6; Li, et al., Angew Chem Int Ed Engl 2008, 47 (52), 10179-82). Purified proteins were analyzed by SEC on a Superdex 200 Increase 10/300 gel filtration column (GE Healthcare Life Sciences, Cat: 28990944) in phosphate buffered saline (PBS, pH 7.4) running buffer (FIG. 39A-D). Fusion protein retention times were compared to those of commercial molecular weight standards (Sigma Aldrich, Cat: MWGF1000-1KT).

CSAN Formation and Characterization

CSANs were formed by adding a 1.1-3.0 fold molar excess of the desired chemical dimerizer—either bisMTX or aizde-bisMTX—to a solution of targeted DHFR[2] fusion protein monomers in PBS. Consistent with previous studies, CSAN oligomerization occurs within minutes of adding the dimerizer (Carlson, et al., *Journal of the American Chemical Society* 2006, 128 (23), 7630-7638). Cryo-EM samples were prepared using a Vitrobot Mark IV (FEI). Briefly, 3 μL of CSANs in PBS was applied to a lacey formvar/carbon grid (Ted Pella, Inc.; Cat: 01883) in a humidified chamber, blotted, and plunged into liquid ethane for vitrification. Grids were imaged on a Tecnai Spirit G2 BioTWIN (FEI) equipped with an Eagle 2k CCD camera (FEI) under a high tension of 120 kV. Images were analyzed in ImageJ and, for the size distribution analysis, only nanoparticles with ≥70% circularity were included. For DLS, 60 μL of CSANs in PBS was loaded into a cuvette and analyzed on a Punk DLS unit (Unchained Labs). Hydrodynamic diameter values represent the mean±standard deviation of at least three measurements.

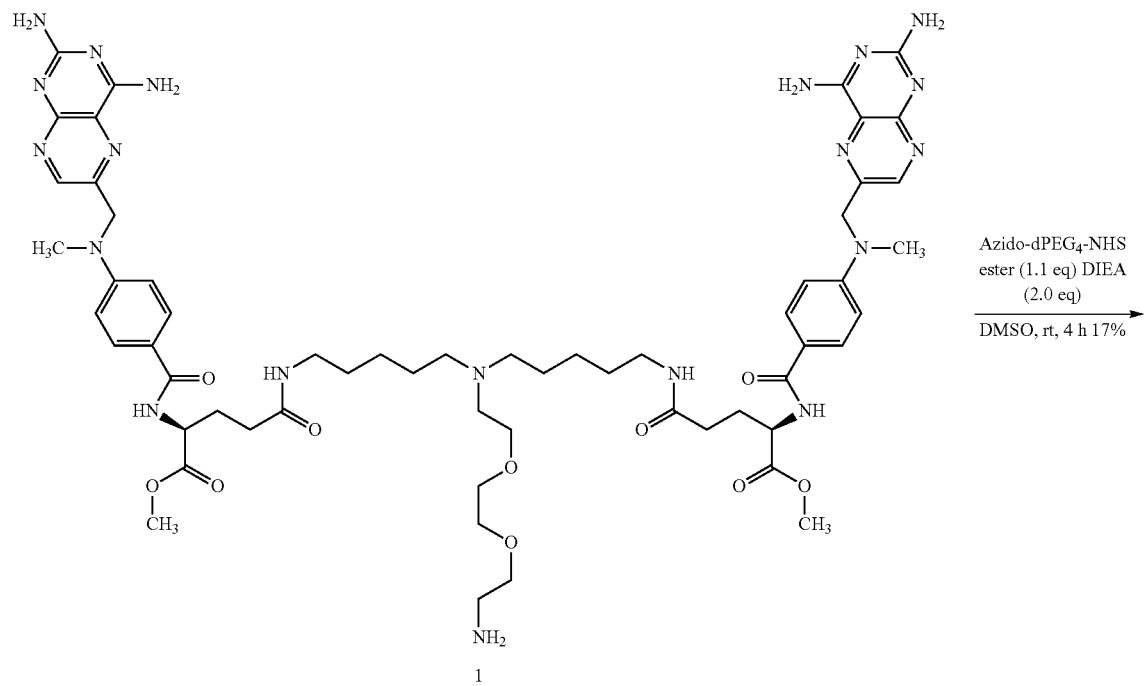

1
Chemical Formula: $C_{58}H_{82}N_{20}O_{10}$
Exact Mass: 1218.65

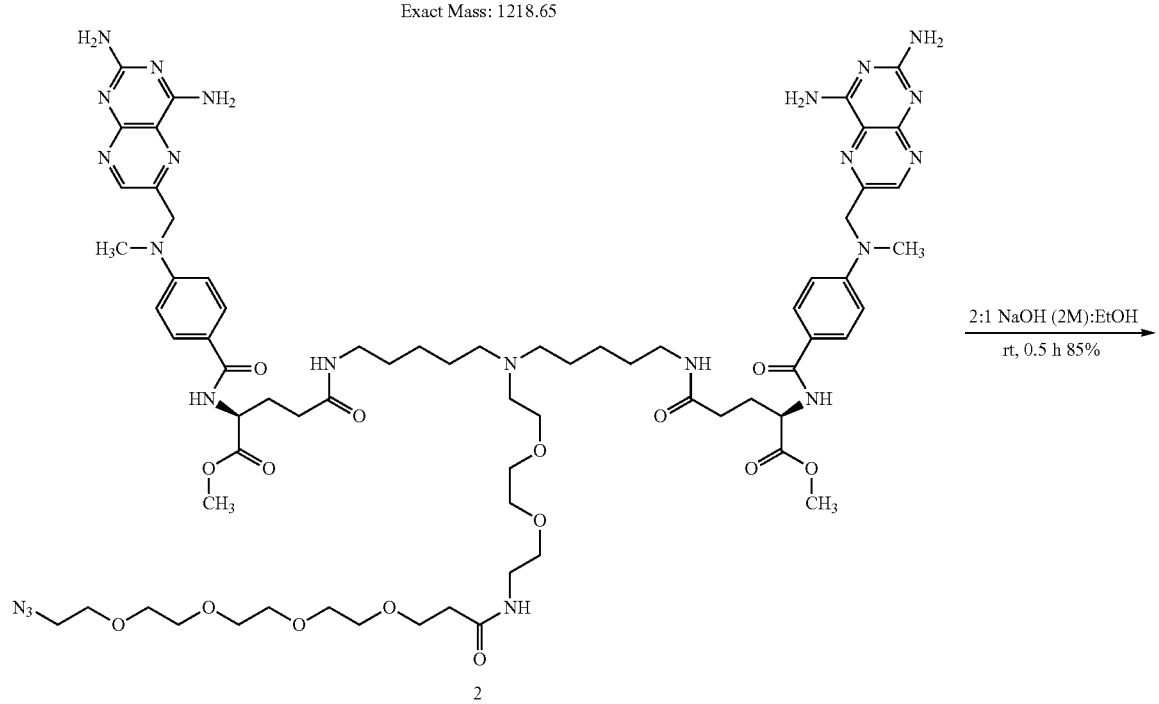

2
Chemical Formula: $C_{69}H_{101}N_{23}O_{15}$
Exact Mass: 1491.78

-continued

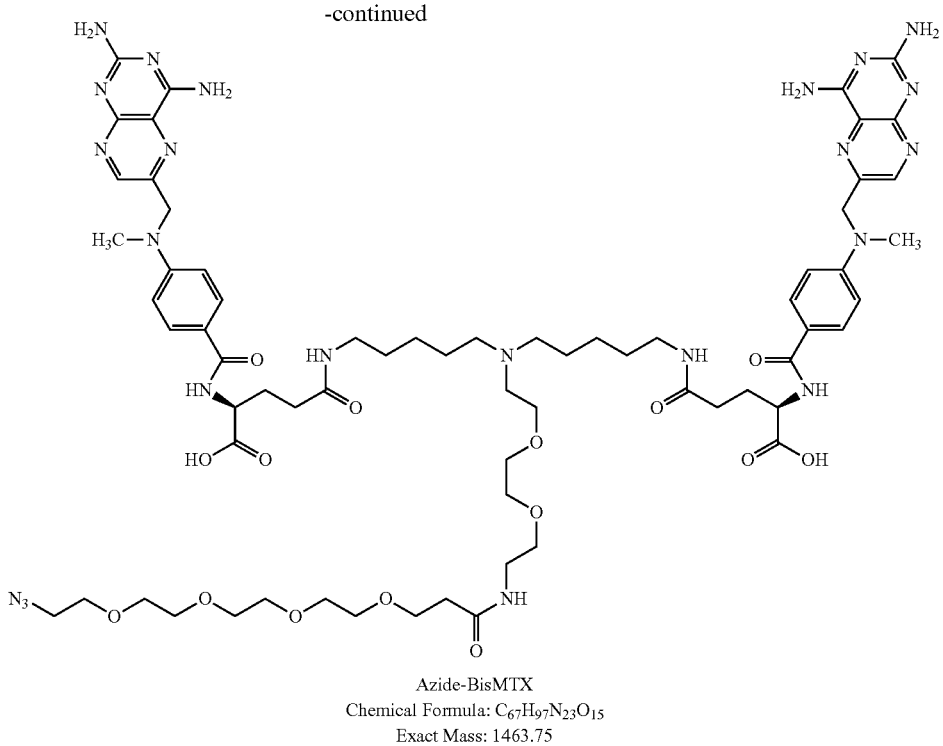

Azide-BisMTX
Chemical Formula: $C_{67}H_{97}N_{23}O_{15}$
Exact Mass: 1463.75

Synthesis of the Azide-BisMTX Dimerizer

The azide-bisMTX dimerizer was prepared in two steps, starting from the previously-reported compound 1 (Fegan, et al., *Mol Pharm* 2012, 9 (11), 3218-27, which is incorporated by reference in its entirety for all purposes).

Preparation of 2

Compound 1 (59 mg, 0.048 mmol) and azido-dPEG4-NHS ester (Quanta Biodesign, Cat: 10501; 20 mg, 0.053 mmol) were dissolved in 2.0 mL DMSO and purged under argon. DIEA (20 uL, 0.10 mmol) was added and the solution was stirred for 4 h at rt. The reaction mixture was then purified via reverse-phase chromatography on a 40 g C18 column using 25% acetonitrile (0.1% TFA) in water to obtain 12 mg (17%). Low resolution ESI-MS: calculated $[(M+H)^+]$ for $C_{69}H_{102}N_{23}O_{15}$ is 1492.8. found 1492.6. Calculated $[(M+2H)^{2+}/2]C_{69}H_{103}N_{23}O_{15}$ is 746.9. found 746.8. Calculated $[(M+3H)^{3+}/3]$ $C_{69}H_{104}N_{23}O_{15}$ is 498.2. found 498.3.

Preparation of Azide-bisMTX

Compound 2 was dissolved in 0.5 mL ethanol followed by 1.0 mL 2 M NaOH. After stirring for 0.5 h, the ethanol was evaporated and the aqueous solution diluted two-fold and neutralized with glacial acetic acid. The mixture was then purified via reverse-phase chromatography using 40% acetonitrile (0.1% TFA) in water to obtain 10 mg (85%). Low resolution ESI-MS: Calculated $[(M+H)^+]$ for $C_{67}H_{98}N_{23}O_{15}$ is 1464.8. found 1465.7. Calculated $[(M+2H)^{2+}/2]$ $C_{67}H_{99}N_{23}O_{15}$ is 732.9. found 732.9. Calculated $[(M+3H)^{3+}/3]C_{67}H_{100}N_{23}O_{15}$ is 488.9. found 489.0.

Affinity Determination of Fn3 and mSA/Fn3 CSANs

The apparent affinity and selectivity of the Fn3 and mSA/Fn3 CSANs was determined by flow cytometry, as previously described (Stern, et al., *ACS Combinatorial Science* 2017, 19 (5), 315-323). Briefly, EpCAM-expressing MCF-7 cells and EpCAM-negative U-87 MG cells were cultured to approximately 80% confluency, detached, and counted, as described above. Aliquots of $5 \times 10^4$ cells were washed with PBSA (PBS with 0.1% w/v bovine serum albumin) and labeled with varying concentrations of Fn3 or mSA/Fn3 CSANs for ≥90 min at 4° C. Cells were then pelleted (500 g, 5 min, 4° C.) and resuspended in 50 μL anti-MYC (clone 9E10) Alexa Fluor 647 conjugate (Thermo Fisher Scientific, Cat: MA1-980-A647; 5 μg/mL in PBSA). After incubating at 4° C. for ≥30 min in the dark, cells were again pelleted and washed thrice with 1 mL cold PBSA before the fluorescence was analyzed on an LSR II flow cytometer (BD Biosciences).

Hydrophobic Insertion of Phospholipid Conjugates

DSPE-PEG$_{2000}$-biotin and DSPE-PEG$_{2000}$-DBCO were purchased from Avanti Polar Lipids (Cat: 880129P and 880229P, respectively) and resuspended in PBS at pH 7.4. Cells were modified with DSPE-PEG$_{2000}$-biotin and DSPE-PEG$_{2000}$-DBCO via one of two methods: (1) through resuspension in phospholipid-containing PBS (ex vitro), or (2) through active culture in media supplemented with the phospholipid (in vitro).

For the ex vitro (buffer) method, cells were harvested from culture, pelleted at 300 g for 5 min, and washed with 1 mL PBS. Cells were then resuspended in PBS containing the desired concentration of phospholipid (0-100 μM) at a ratio of $2.5 \times 10^6$ cells/mL. The cell suspension was then placed on a rotating platform and incubated at room temperature for 1 h. Cells were then pelleted at 300 g for 5 min, and washed thrice with 1 mL cold PBS to remove uninserted DSPE-PEG$_{2000}$-biotin or DSPE-PEG$_{2000}$-DBCO. Cells were then used directly for subsequent applications.

For the in vitro (culture) method, cells were grown in culture media (DMEM or RPMI, as above) supplemented with the desired concentration (0-100 μM) of DSPE-PEG$_{2000}$-biotin or DSPE-PEG$_{2000}$-DBCO for 24-48 h. Cells were then harvested from culture (adherent cells were detached with trypsin), pelleted at 300 g for 5 min, and washed thrice with 1 mL cold PBS to remove uninserted DSPE-PEG$_{2000}$-biotin or DSPE-PEG$_{2000}$-DBCO. Cells were then used directly for subsequent applications.

Following each modification, flow cytometry was used to determine whether the DSPE-PEG$_{2000}$-biotin or DSPE-PEG$_{2000}$-DBCO conjugates had inserted into the cell membrane. To probe for the biotin and DBCO moieties on the cell surface, the phospholipid-modified cells were washed as above and resuspended in 50 μL of either streptavidin Alexa Fluor 488 conjugate (Thermo Fisher Scientific, Cat: S32354; 10 μg/mL in PBS) or azide Alexa Fluor 488 conjugate (Thermo Fisher Scientific, Cat: A10266; 5 μM in PBS), respectively. After incubating at 4° C. for 1 h, the cells were pelleted (500 g, 5 min, 4° C.) and washed thrice with 1 mL cold PBS before the fluorescence was analyzed on an LSR II flow cytometer (BD Biosciences). For data analysis, the maximum MFI obtained within each experimental series is normalized to 1.0, with the other samples in that series scaled relative to this value.

Functionalizing Phospholipid-Modified Cells with CSANs

Cells were cultured, harvested, and modified with 10 μM of either DSPE-PEG$_{2000}$-biotin or DSPE-PEG$_{2000}$-DBCO ex vitro, as described above. Generally, 0.5×10$^6$ cells were then labeled with 500 μL of 100 nM CSANs of the desired functionality (FIG. 33A-D) in PBS at 4° C. for 1 h. However, to install the Fn3 CSANs formed with azide-bisMTX onto DBCO-modified Raji cells, 100 μL of 500 nM CSANs in PBS was used and the cells were incubated at 37° C. for 3 h. After the primary incubation, cells were washed once with 1 mL cold PBS to remove unbound CSANs. The cells were then resuspended in 50 μL of either anti-MYC (clone 9E10) Alexa Fluor 647 conjugate (Thermo Fisher Scientific, Cat: MA1-980-A647; 5 μg/mL in PBS) or anti-FLAG PE conjugate (Biolegend, Cat: 637309; 1 μg/mL in PBS) to probe for the MYC epitope tag present on the DHFR$^2$-Fn3 subunits or the FLAG epitope tag present on the mSA-DHFR$^2$ subunits, respectively. After incubating at 4° C. for 1 h, the cells were pelleted (500 g, 5 min, 4° C.) and washed thrice with 1 mL cold PBS before the fluorescence was analyzed on an LSR II flow cytometer.

Stability Studies

The in vitro longevity of the phospholipid-anchored CSANs on the cell surface was assessed by flow cytometry. Briefly, Raji cells were modified with 10 μM DSPE-PEG$_{2000}$-biotin in vitro, labeled with 100 nM "reduced-avidity" mSA CSANs (CSANs formed with a 1:1 ratio of mSA-DHFR$^2$ subunits and non-targeted DHFR$^2$ subunits), and then returned to culture for 0-72 h. At 24 h intervals, an aliquot of 0.5×10$^6$ cells was taken, labeled with an anti-FLAG PE conjugate (1 μg/mL in PBS) to detect cell surface CSANs, and analyzed on an LSR II flow cytometer, as described above. To compare the surface longevity of the CSANs to that of the individual DSPE-PEG$_{2000}$-biotin moieties themselves, a separate population of Raji cells was modified with only 10 μM DSPE-PEG$_{2000}$-biotin in vitro (no CSANs) and returned to culture for 0-72 h. An aliquot of these cells was taken, labeled with streptavidin Alexa Fluor 488 conjugate (10 μg/mL in PBS) to detect cell surface biotin moieties, and analyzed on an LSR II flow cytometer in parallel with the CSAN-labeled samples. To determine the number of cell divisions over the course of the experiment, a third aliquot of Raji cells was labeled with CellTrace Violet (CTV; Thermo Fisher Scientific, Cat: C34571) according to the manufacturer's instructions and cultured/analyzed in parallel with the CSAN and phospholipid samples. For data analysis, the MFI of the samples at t=0 was normalized to 1.0, representing maximum labeling, and the MFI on subsequent days was scaled relative to this value. Because cell division reduces the MFI value through dilution of the CSANs/phospholipids across daughter cell membranes and not due to loss of the constructs, the MFI values of subsequent analyses were corrected for the number of cell divisions, as determined by the CTV labeling.

To ascertain whether the phospholipid-anchored CSANs could "migrate" from the principally modified cell to an unmodified neighbor cell, two populations of Raji cells were prepared. The first population was labeled only with CTV. The second population was modified with 10 μM DSPE-PEG$_{2000}$-biotin in vitro and then labeled with "reduced valency" mSA CSANs (see above). The CTV-labeled and CSAN-labeled Raji cell populations were combined at a 3:7 ratio and co-cultured in RPMI for 72 h; every 24 h, the culture media was refreshed (to partially simulate the effect of clearance) and a 0.5×10$^6$ cell sample of the pooled population was analyzed for CTV and CSAN presence by flow cytometry. CSANs were detected by labeling the cells with anti-FLAG PE conjugate (1 μg/mL in PBS), as above. At each time point, the percentage of CTV+/CSAN− (original CTV-modified population), CTV+/CSAN+(CTV cells that had acquired a "migrating" CSAN), CTV−/CSAN+ (original CSAN-functionalized population), and CTV−/CSAN− (cell that has lost their CSAN functionalization) cells was quantified by flow cytometry. For comparison, the same analysis was performed for a mixed population of CTV-labeled Raji cells and Raji cells modified with only the 10 μM DSPE-PEG$_{2000}$-biotin (no CSANs).

Trimethoprim-Induced CSAN Dissociation

Raji cells (0.5×10$^6$) were modified with 10 μM DSPE-PEG$_{2000}$-biotin ex vitro and then labeled with 100 nM mSA/Fn3 CSANs, as above. The CSAN-labeled cells were then divided into two equal aliquots, one of which was resuspended in 200 μL of RPMI and the other in 200 L of RPMI supplemented with 2 μM trimethoprim (Fisher Scientific, Cat: AAJ66646MD). Cells were then incubated at 37° C. for 1-2 h, labeled with anti-FLAG PE conjugate (1 μg/mL in PBS) to detect cell surface CSANs, and analyzed on an LSR II flow cytometer, as described above. For data analysis, the MFI of the samples in plain RPMI was normalized to 1.0, representing maximum labeling, and the MFI of the samples in RPMI with was scaled relative to this value.

Formation of Intercellular Interactions

To form intercellular interactions between two cell types (FIG. 35A-D), a monolayer of MCF-7 cells was adhered to glass coverslips (Thermo Scientific, Cat: 12-541-B) via overnight culture in a 6-well plate. Separately, a population of Raji cells was labeled with CFSE (Biolegend, Cat: 423801) according to the manufacturer's protocol and returned to culture overnight. The following day, the CFSE-labeled Raji cells were sequentially modified with 10 M DSPE-PEG$_{2000}$-biotin ex vitro and 100 nM mSA/Fn3 CSANs, as above. The CSAN− functionalized, and thus EpCAM-targeted, Raji cells were then washed once in 1 mL PBS, resuspended in 1 mL DMEM, and added to the wells containing the MCF-7 cells on the coverslips. The two cell populations were then incubated static at 4° C. for 1 h. Media and unbound cells were then removed via aspiration, and the cell layers were washed thrice with 1 mL PBS. Then, 1 mL of DMEM with or without 2 μM trimethoprim was added to the wells and the cell layers were incubated for another 1 h at 4° C. Media and unbound cells were again removed via aspiration, and the cell layers were washed thrice with 1 mL PBS. The cell layers were then fixed in 4% paraformaldehyde in PBS at room temperature for 15 min before washing thrice with 1 mL PBS. Coverslips were then rinsed twice in ultrapure water, blotted to remove excess liquid, and mounted on glass coverslips using ProLong Gold Antifade Reagent with DAPI (Thermo Fisher Scientific, Cat: P36935). After curing for ≥24 h in the dark, slides were imaged on an Eclipse Ti-E Wide Field Deconvolution Inverted Microscope (Nikon Instruments, Inc.).

Intercellular interactions between three different cell populations were formed similarly; however, the CFSE-labeled Raji cells were modified with only 50 nM mSA/Fn3 CSANs instead of 100 nM. Then, a third cell population was prepared by sequentially labeling Raji cells with CellTrace Far Red (Thermo Fisher Scientific, Cat: 34572) according to the manufacturer's protocols, 100 μM DSPE-PEG$_{2000}$-DBCO ex vitro, and 500 nM mSA CSANs oligomerized with azide-bisMTX, as above. This population of Raji cells—now capable of targeting the unoccupied biotin moieties on the CFSE-labeled Raji cell layer—was added to the wells after the incubation with the CFSE-labeled Raji cells (but before the addition of the DMEM with trimethoprim). After incubating the cell layers with this third cell population at 4° C. for 1 h, the coverslips were washed, fixed, mounted, and imaged on an Eclipse Ti-E Wide Field Deconvolution Inverted Microscope, as above.

For the flow cytometry analysis of cell pairing, target MCF-7 cells were labeled with CFSE, cultured for 24 h, and detached, as above. Separately, a population of Raji cells were sequentially labeled with CTV, cultured for 24 h, modified with 10 μM DSPE-PEG$_{2000}$-biotin, and functionalized with mSA/Fn3 CSANs, as above. The two cell populations were resuspended in PBS, combined at a 1:1 ratio, and incubated at 4° C. in the dark with rotation for 1 h. Cells were then pelleted (500 g, 5 min, 4° C.), washed once with 1 mL cold PBS, and resuspended in PBS with or without 2 μM trimethoprim. After incubating at 4° C. in the dark with rotation for 1 h, the cells were washed thrice with PBS and analyzed on an LSR II flow cytometer to ascertain the number of CTV+/CFSE+ cell clusters. As controls, unmodified Raji cells, unmodified MCF-7 cells, CTV-labeled Raji cells, CFSE-labeled MCF-7 cells, and CTV-Raji cells modified with only 10 μM DSPE-PEG$_{2000}$-biotin (no CSANs) plus CFSE-MCF-7 cells were all prepared and analyzed in parallel.

Statistical Considerations

Unless otherwise stated, experiments were performed in triplicate and data is presented as the mean±standard deviation of three independent trials. Differences between means are compared using a two-tailed Student's t-test, and a p-value <0.05 is denoted in graphics with an (*), p<0.01 is denoted with (), and p<0.001 is denoted with (*).

ABBREVIATIONS

CFSE (carboxyfluorescein succinimidyl ester); CSAN (chemically self-assembled nanoring); CTV (CellTrace Violet); DBCO (dibencocyclooctyne); DHFR (dihydrofolate reductase); DSPE (1,2-distearoyl-sn-glycero-3-phosphoethanolamine); EpCAM (epithelial cell adhesion molecule); Fn3 (tenth type III fibronectin domain); mSA (monovalent streptavidin domain); MTX (methotrexate); PEG (polyethylene glycol); TMP (trimethoprim).

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A polypeptide comprising an amino acid sequence having at least about 95% sequence identity to a sequence selected from the group consisting of SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:47, SEQ ID NO:49, SEQ ID NO:61, and SEQ ID NO:62, wherein the polypeptide is capable of binding to epithelial cell adhesion molecule (EpCAM).

2. The polypeptide of claim 1, comprising an amino acid sequence having at least about 97% sequence identity to a sequence selected from the group consisting of SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:47, SEQ ID NO:49, SEQ ID NO:61, and SEQ ID NO:62.

3. The polypeptide of claim 1, comprising an amino acid sequence having at least about 99% sequence identity to a sequence selected from the group consisting of SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:47, SEQ ID NO:49, SEQ ID NO:61, and SEQ ID NO:62.

4. The polypeptide of claim 1, comprising a non-paratopic cysteine variation.

5. The polypeptide of claim 1, comprising an amino acid sequence selected from the group consisting of SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:47, SEQ ID NO:49, SEQ ID NO:61, and SEQ ID NO:62.

6. A polypeptide comprising an amino acid sequence, wherein 1) the amino acid sequence has at least about 85% sequence identity to a sequence selected from the group consisting of SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:47, SEQ ID NO:49, SEQ ID NO:61, and SEQ ID NO:62; and 2) the amino acid sequence comprises a combination of three loop regions selected from the group consisting of:
1) DYPNSASY (SEQ ID NO:16), GNTYN (SEQ ID NO:17), and TYRDNYSYSN (SEQ ID NO:18);
2) DYPNSASY (SEQ ID NO:16), GNTYN (SEQ ID NO:17), and TSRDNYSWSN (SEQ ID NO:32);
3) DYPNSASY (SEQ ID NO:16), GNTYN (SEQ ID NO:17), and TSRDNYSYLN (SEQ ID NO:33);
4) DDYTSASY (SEQ ID NO:34), GNTYN (SEQ ID NO:17), and TYRDNYSYSN (SEQ ID NO:18);
5) DYPNSASY (SEQ ID NO:16), GNTYN (SEQ ID NO:17), and TSRDNYSYSN (SEQ ID NO:35);
6) DNSNYASY (SEQ ID NO:36), GSTYN (SEQ ID NO:37), and TYRDNYSYSN (SEQ ID NO:18);
7) DDPDFASY (SEQ ID NO:39), GNTYS (SEQ ID NO:40), and TYRDNYSYSN (SEQ ID NO:18);
8) DYPNSASY (SEQ ID NO:16), GDTYN (SEQ ID NO:38), and TYRDNYSYSN (SEQ ID NO:18);
9) DYPNSASY (SEQ ID NO:16), GSKST (SEQ ID NO:3), and TGRGDSPASSK (SEQ ID NO:4);
10) DAPAVTVRY (SEQ ID NO:2), GNTYN (SEQ ID NO:17), and TGRGDSPASSK (SEQ ID NO:4); and
11) DAPAVTVRY (SEQ ID NO:2), GSKST (SEQ ID NO:3), and TYRDNYSYSN (SEQ ID NO:18); and
wherein the polypeptide is capable of binding to epithelial cell adhesion molecule (EpCAM).

7. The polypeptide of claim 5, comprising an amino acid sequence selected from the group consisting of SEQ ID NO:6, SEQ ID NO:11, SEQ ID NO:12, SEQ ID NO:13, SEQ ID NO:14 and SEQ ID NO:15, SEQ ID NO:47, SEQ ID NO:49, SEQ ID NO:61, and SEQ ID NO:62.

8. A nucleic acid encoding a polypeptide of claim 1.

9. A vector comprising an expression cassette, wherein the expression cassette comprises a nucleic acid sequence as described in claim 8 and a promoter operably linked to the nucleic acid.

10. A conjugate of formula (I):

P-(L-A)$_n$     (I)

wherein:
P is a polypeptide as described in claim 1 that binds to epithelial cell adhesion molecule (EpCAM);
each L is independently a direct bond or a linking group;
each A is independently a detectable agent or a biologically active agent; and
n is 1 to 5.

11. The conjugate of claim 10, wherein at least one A is a detectable agent.

12. The conjugate of claim 11, wherein the detectable agent comprises a chelating group selected from the group consisting of p-SCN-Bn-TCMC, p-NO2-Bn-Cyclen, p-NO2-Bn-DOTA, p-NH2-Bn-DOTA, p-NH2-Bn-DOTA-tetra(t-Bu-ester), p-SCN-Bn-DOTA, DOTA-tris (t-Bu ester), DOTA-mono-NHS-tris(t-Bu ester), Maleimido-mono-amide-DOTA-tris (t-Bu ester), Maleimido-mono-amide-DOTA, Fmoc-L-Lys-mono-amide-DOTA-tris(t-Bu ester), 2-Aminoethyl-mono-amide-DOTA-tris(t-Bu ester), Azido-mono-amide-DOTA-tris(t-butyl ester), DOTA-NHS-ester, Azido-mono-amide-DOTA, p-NH2-Bn-DTPA, p-NH2-Bn-DTPA-penta (t-Bu ester), p-SCN-Bn-DTPA, p-NH2-CHX-A"-DTPA, CHX-A"-DTPA, DTPA-tetra (t-Bu ester), Maleimido-mono-amide-DTPA, p-NH2-Bn-PCTA, p-SCN-Bn-PCTA, p-NH2-Bn-oxo-DO3A, p-SCN-Bn-oxo-DO3A, p-NH2-Bn-NOTA, p-SCN-Bn-NOTA, NOTA-bis(t-Bu ester), Maleimido-mono-amide-NOTA, Deferoxamine-p-SCN, Deferoxamine-maleimide, DOTA-Biotin-Sarcosine, DO3A-Serotonin, Cyclen, Cyclam, DO2A, DO3A, DOTA, DOTA-NHS, DOTP, DOTMA, TETA, DOTAM, DiAmSar, CB-Cyclam, CB-TE2A, NOTA, TACN, Tm-DOTA, Gd-DOTA, Tm[DOTP]5-, Tm-DOTMA, Eu-DOTA-4AmC, Tm-p-SCN-Bn-DOTA, Gd-p-SCN-Bn-DOTA, Ho-p-SCN-Bn-DOTA, Tm-Maleimido-DOTA, Ho-Maleimido-DOTA, BisCBZ-Cyclen, TrisBOC-Cyclen, NO2A-(t-Bu ester), DO2A-t-Bu-ester, DO3A-t-Bu-ester and NODAGA.

13. The conjugate of claim 12, wherein the chelating group is labeled with one or more radionuclides selected from the group consisting of Fluorine-18, Antimony-124, Antimony-125, Arsenic-74, Barium-103, Barium-140, Beryllium-7, Bismuth-206, Bismuth-207, Cadmium-109, Cadmium-115m, Calcium-45, Cerium-139, Cerium-141, Cerium-144, Cesium-137, Chromium-51, Cobalt-55, Cobalt-56, Cobalt-57, Cobalt-58, Cobalt-60, Cobalt-64, Copper-64, Copper-67, Erbium-169, Europium-152, Gallium-64, Gallium-68, Gadolinium-153, Gadolinium-157 Gold-195, Gold-199, Hafnium-175, Hafnium-175-181, Holmium-166, Indium-110, Indium-111, Iridium-192, Iron-55, Iron-59, Krypton-85, Lead-210, Manganese-54, Mercury-197, Mercury-203, Molybdenum-99, Neodymium-147, Neptunium-237, Nickel-63, Niobium-95, Osmium-185+191, Palladium-103, Platinum-195m, Praseodymium-143, Promethium-147, Protactinium-233, Radium-226, Rhenium-186, Rhenium-188, Rubidium-86, Ruthenium-103, Ruthenium-106, Scandium-44, Scandium-46, Selenium-75, Silver-110m, Silver-111, Sodium-22, Strontium-85, Strontium-89, Strontium-90, Sulfur-35, Tantalum-182, Technetium-99m, Tellurium-125, Tellurium-132, Thallium-204, Thorium-228, Thorium-232, Thallium-170, Tin-113, Tin-114, Tin-117m, Titanium-44, Tungsten-185, Vanadium-48, Vanadium-49, Ytterbium-169, Yttrium-86, Yttrium-88, Yttrium-90, Yttrium-91, Zinc-65, and Zirconium-95.

14. The conjugate of claim 11, wherein the detectable agent comprises a fluorescent group.

15. The conjugate of claim 10, wherein at least one A is a biologically active agent selected from the group consisting of biotin, a peptide, an antibody, chemotherapeutic agent, and an immunotherapeutic agent.

16. The conjugate of claim 10, wherein L is a divalent, branched or unbranched, saturated or unsaturated, hydrocarbon chain, having from 1 to 25 carbon atoms, wherein one or more of the carbon atoms is optionally replaced by (—O—) or a divalent ring of formula:

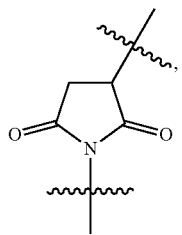 [SMILES: *C1CC(=O)N(*)C1=O]

and wherein the chain or ring is optionally substituted on carbon with one or more substituents selected from $(C_1-C_6)$ alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo (=O), carboxy, aryl, aryloxy, heteroaryl, and heteroaryloxy.

17. The conjugate of claim 10, wherein,
P is a polypeptide as described in claim 1 that binds to epithelial cell adhesion molecule (EpCAM);
L is a peptide linking group;
A is a polypeptide comprising a first dihydrofolate reductase (DHFR) peptide operably linked to a second DHFR peptide; and optionally, a tag peptide operably linked to either the first or second DHFR peptide; and
n is 1.

18. The conjugate of claim 17, selected from the group consisting of SEQ ID NO: 53, SEQ ID NO: 55 and SEQ ID NO: 59.

19. A pharmaceutical composition comprising a conjugate of claim 10 and a pharmaceutically acceptable excipient.

20. A method for targeting a detectable agent or a biologically active agent to an EpCAM positive cell in an animal comprising administering a conjugate of claim 10 to the animal.

21. A method of detecting cancer in an animal, comprising administering a conjugate of claim 10 to the animal, wherein the conjugate binds to an EpCAM molecule; and detecting a signal from the detectable agent, wherein a signal greater than a signal from a control animal without cancer indicates the animal has cancer.

22. A chemically self-assembled nanoring (CSAN) comprising a plurality of conjugates as described in claim 17 and a plurality of bisMTX compounds.

23. The CSAN of claim 22, operably linked to a biologically active agent or an immune cell.

24. A method for targeting a biologically active agent or an immune cell to an EpCAM positive cell in an animal comprising administering a CSAN as described in claim 23 to the animal.

25. The polypeptide of claim 5, comprising SEQ ID NO:12.

26. The polypeptide of claim 5, comprising SEQ ID NO:10.

27. A method for activating a T cell comprising contacting an EpCAM positive cell with a CSAN as described in claim 23, wherein the CSAN is operably linked to an immune cell via CD3, and wherein the immune cell is a T cell.

* * * * *